(12) United States Patent
Miller et al.

(10) Patent No.: US 11,623,922 B2
(45) Date of Patent: Apr. 11, 2023

(54) COMPOUNDS

(71) Applicant: INFLAZOME LIMITED, Dublin (IE)

(72) Inventors: David Miller, Cambridge (GB);
Stephen Thom, Nottingham (GB);
Stephen St-Gallay, Nottingham (GB);
Jonathan Shannon, Nottingham (GB);
Paul Leeson, Leicestershire (GB)

(73) Assignee: INFLAZOME LIMITED, Dublin (IE)

( * ) Notice: Subject to any disclaimer, the term of this patent is extended or adjusted under 35 U.S.C. 154(b) by 0 days.

(21) Appl. No.: 16/753,239

(22) PCT Filed: Oct. 3, 2018

(86) PCT No.: PCT/EP2018/076922
§ 371 (c)(1),
(2) Date: Apr. 2, 2020

(87) PCT Pub. No.: WO2019/068772
PCT Pub. Date: Apr. 11, 2019

(65) Prior Publication Data
US 2020/0331886 A1    Oct. 22, 2020

(30) Foreign Application Priority Data

Oct. 3, 2017 (GB) .................................. 1716131
Apr. 5, 2018 (GB) .................................. 1805602

(51) Int. Cl.
| C07D 401/12 | (2006.01) |
| C07C 381/10 | (2006.01) |
| C07D 205/04 | (2006.01) |
| C07D 231/18 | (2006.01) |

(52) U.S. Cl.
CPC .......... C07D 401/12 (2013.01); C07C 381/10 (2013.01); C07D 205/04 (2013.01); C07D 231/18 (2013.01)

(58) Field of Classification Search
CPC .... C07D 401/12; C07D 231/18; C07C 381/10
See application file for complete search history.

(56) References Cited

U.S. PATENT DOCUMENTS

| 4,666,506 A | 5/1987 | Hillemann |
| 5,258,406 A * | 11/1993 | Toth ...................... C07C 381/10 514/593 |
| 2002/0077486 A1 | 6/2002 | Scarborough et al. |

FOREIGN PATENT DOCUMENTS

| EP | 0552553 A1 | 7/1993 |
| EP | 2927214 A1 | 10/2015 |
| IN | 201721020305 | 6/2017 |
| WO | WO 1998/032733 A1 | 7/1998 |
| WO | WO 2001/19390 A1 | 3/2001 |
| WO | WO 2016/131098 A1 | 8/2016 |
| WO | WO 2017/129897 A1 | 8/2017 |
| WO | WO 2017/140778 A1 | 8/2017 |
| WO | WO 2018/225018 A1 | 12/2018 |
| WO | WO 2019/023145 A1 | 1/2019 |
| WO | WO 2019/023147 A1 | 1/2019 |
| WO | WO 2019/211463 A1 | 11/2019 |
| WO | WO 2020/010118 A1 | 1/2020 |
| WO | WO 2020/018975 A1 | 1/2020 |
| WO | WO 2020/035465 A1 | 2/2020 |
| WO | WO 2020/035466 A1 | 2/2020 |
| WO | WO 2020/104657 A1 | 5/2020 |
| WO | WO 2020/208249 A1 | 10/2020 |
| WO | WO 2021/032588 A1 | 2/2021 |
| WO | WO 2021/032591 A1 | 2/2021 |
| WO | WO 2021/165245 A1 | 8/2021 |

OTHER PUBLICATIONS

WIPO Application No. PCT/EP2018/076922, PCT International Search Report and Written Opinion of the International Searching Authority dated Nov. 13, 2018.
WIPO Application No. PCT/EP2018/076922, PCT International Preliminary Report on Patentability dated Apr. 16, 2020.
U.S. Appl. No. 62/573,894, filed Oct. 18, 2017, Glick et al.
U.S. Appl. No. 62/693,879, filed Jul. 3, 2018, Glick et al.
U.S. Appl. No. 62/693,886, filed Jul. 3, 2018, Glick et al.
U.S. Appl. No. 62/702,602, filed Jul. 24, 2018, Glick et al.
U.S. Appl. No. 62/702,621, filed Jul. 24, 2018, Glick et al.
U.S. Appl. No. 62/536,271, filed Jul. 24, 2017, Glick et al.
Agarwal, et al., Discovery of N-Cyano-sulfoximineurea Derivatives as Potent and Orally Bioavailable NLRP3 Inflammasome Inhibitors, ACS Medicinal Chemistry Letters, 11(4): 414-418, (Feb. 2020).
Balant, ed in Wolff et al. Burger's Medicinal Chemistry and drug discovery, 5th Ed., vol. 1. Principles and practice, pp. 949-982, (1995).

(Continued)

*Primary Examiner* — Kamal A Saeed
(74) *Attorney, Agent, or Firm* — Alston & Bird LLP

(57) ABSTRACT

The present invention relates to compounds of formula (I): wherein Q is selected from O or S; $R^1$ is a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; and $R^2$ is a cyclic group substituted at the a-position, wherein $R^2$ may optionally be further substituted. The present invention further relates to salts, solvates and prodrugs of such compounds, to pharmaceutical compositions comprising such compounds, and to the use of such compounds in the treatment and prevention of medical disorders and diseases, most especially by the inhibition of $NLRP_3$.

(I)

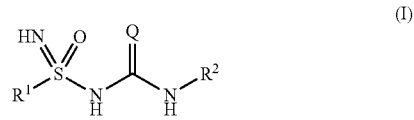

16 Claims, No Drawings

(56) References Cited

OTHER PUBLICATIONS

Banker, et al., Prodrugs, Modern Pharmaceutics, 3rd edition, Revised and Expanded, pp. 451 and 596,(1995).
Belikov, "Pharmaceutical chemistry", chapter 2.6 "The interconnection between chemical structure, properties of substances and their effect on the body", MEDpress-inform, Moscow, p. 27-29, (2007), Brief statement of relevance.
Bundgaard, Design of Prodrugs, Chapter 1, p. 1, (1985).
CAS 1027831-60-2; date unavailable.
Coll, et al., "A small-molecule inhibitor of the NLRP3 inflammasome for the treatment of inflammatory diseases", Nature Medicine, 21(3): 248-255, (2015).
Disease—Wikipedia, retrieved from the internet on Mar. 4, 2022 at: https://en.wikipedia.org/wiki/Disease.
Ettmayer, et al., "Lessons learned from marketed and investigational prodrugs" J. Med. Chem., 47(10):2394-2404 (2004).
GB1716131.6 Search Report dated Jul. 3, 2018.
Han, "Targeted prodrug design to optimize drug delivery" AAPS Pharmsci. 2(1) Article 6: 1-11, (2000).
Himiceskij, Chemical Encyclopedia, p. 130-131, (1983), Brief statement of relevance.
Nandi, et al., "Direct Synthesis of N-Acyl Sulfonimidamides and N-Sulfonimidoyl Amindines from Sulfonimidoyl Azides," Advanced Synthesis & Catalysis, vol. 360(13), pp. 2465-2469, (2018).
Parajuli, et al., "Prodrug as a Novel Approach of Drug Deiivery—a Review," Journal of Drug Delivery & Therapeutics, 5(3):5-9, (2015).
PubChem 10787134: 1-[(4-Chloroanilino)-(4-methylphenyl)-oxo-lambda6-sulfanylidene]-3-phenylurea; created Oct. 26, 2006; modified Jan. 8, 2022.

Scozzafava, et al., "Arylsulfonyl-N,N-diethyl-dithiocarbamates: a novel class of antitumor agents" Bioorganic & Medicinal Chemistry Letters, vol. 10(16), pp. 1887-1991, (2000).
Silverman, Prodrugs and drug delivery systems, the organic chemistry of drug design and drug action, Chapters, pp. 352-400, (1992).
So, et al., "Evaluation of designed ligands by a multiple screening method: Application to glycogen phosphorylase inhibitors constructed with a variety of approaches," Journal of Computer Aided Molecular Design, 613-647, (2001).
Solvation—Wikipedia, retrieved from the internet on Mar. 4, 2022 at: https://en.wikipedia.org/wiki/Solvation.
Stella, "Prodrugs as theraputics" Expert Opinion of theraputic patents, 14(3): 277-280 (2004).
Supuran, et al., "Carbonic anhydrase inhibitors—Part 94. 1,3,4-Thiadiazole-2-sulfonamide derivatives as antitumor agents?" European Journal of Medicinal Chemistry, vol. 35(9), pp. 867-874, (2000).
Testa, "Prodrug Research: futile or fertile?" Biochemical Pharmacology, 68, 2097-2106, (2004).
Toth, et al., "Sulfonimidamide Analogs of Oncolytic Sulfonylureas" Journal of Medicinal Chemistry, vol. 40(6), pp. 1018-1025, (1997).
Toth, et al., "Synthesis and resolution of sulfonimidamide analogs of sulfonylureas" Journal of Organic Chemistry, vol. 58(12), pp. 3469-3472. (1993).
Zawilska, et al., Prodrugs: a challenge for the drug development, Pharmacological Reports, vol. 65, No. 1, pp. 1-14 (2013).
EP 20180782720 Third Party Observation filed Sep. 8, 2021.
EP 20180782720 Third Party Observation filed Jan. 31, 2022.
EP 20180782720 Third Party Observation filed Jan. 28, 2022.

* cited by examiner

COMPOUNDS

CROSS-REFERENCE TO RELATED APPLICATION

This application is the US national stage of PCT/EP2018/076922 filed Oct. 3, 2018, which claims priority to GB 1716131.6 filed Oct. 3, 2017 and GB 1805602.8 filed Apr. 5, 2018.

FIELD OF THE INVENTION

The present invention relates to sulfoximine ureas and sulfoximine thioureas comprising a cyclic group substituted at the α-position, and to associated salts, solvates, prodrugs and pharmaceutical compositions. The present invention further relates to the use of such compounds in the treatment and prevention of medical disorders and diseases, most especially by NLRP3 inhibition.

BACKGROUND

The NOD-like receptor (NLR) family, pyrin domain-containing protein 3 (NLRP3) inflammasome is a component of the inflammatory process, and its aberrant activity is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular signalling molecule that senses many pathogen-derived, environmental and host-derived factors. Upon activation, NLRP3 binds to apoptosis-associated speck-like protein containing a caspase activation and recruitment domain (ASC). ASC then polymerises to form a large aggregate known as an ASC speck. Polymerised ASC in turn interacts with the cysteine protease caspase-1 to form a complex termed the inflammasome. This results in the activation of caspase-1, which cleaves the precursor forms of the proinflammatory cytokines IL-1β and IL-18 (termed pro-IL-1 and pro-IL-18 respectively) to thereby activate these cytokines. Caspase-1 also mediates a type of inflammatory cell death known as pyroptosis. The ASC speck can also recruit and activate caspase-8, which can process pro-IL-1 and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the pro-inflammatory cytokines IL-6 and TNF. IL-1β and IL-18 synergise with IL-23 to induce IL-17 production by memory CD4 Th17 cells and by γδ T cells in the absence of T cell receptor engagement. IL-18 and IL-12 also synergise to induce IFN-γ production from memory T cells and NK cells driving a Th1 response.

The inherited CAPS diseases Muckle-Wells syndrome (MWS), familial cold autoinflammatory syndrome (FCAS) and neonatal-onset multisystem inflammatory disease (NO-MID) are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using Nlrp3$^{-/-}$ mice, but there have also been insights into the specific activation of NLRP3 in these diseases. In type 2 diabetes mellitus (T2D), the deposition of islet amyloid polypeptide in the pancreas activates NLRP3 and IL-1β signaling, resulting in cell death and inflammation.

Several small molecules have been shown to inhibit the NLRP3 inflammasome. Glyburide inhibits IL-1β production at micromolar concentrations in response to the activation of NLRP3 but not NLRC4 or NLRP1. Other previously characterised weak NLRP3 inhibitors include parthenolide, 3,4-methylenedioxy-p-nitrostyrene and dimethyl sulfoxide (DMSO), although these agents have limited potency and are nonspecific.

Current treatments for NLRP3-related diseases include biologic agents that target IL-1. These are the recombinant IL-1 receptor antagonist anakinra, the neutralizing IL-1β antibody canakinumab and the soluble decoy IL-1 receptor rilonacept. These approaches have proven successful in the treatment of CAPS, and these biologic agents have been used in clinical trials for other IL-1β-associated diseases.

Some diarylsulfonylurea-containing compounds have been identified as cytokine release inhibitory drugs (CRIDs) (Perregaux et al.; J. Pharmacol. Exp. Ther. 299, 187-197, 2001). CRIDs are a class of diarylsulfonylurea-containing compounds that inhibit the post-translational processing of IL-1β. Post-translational processing of IL-1β is accompanied by activation of caspase-1 and cell death. CRIDs arrest activated monocytes so that caspase-1 remains inactive and plasma membrane latency is preserved.

Certain sulfonylurea-containing compounds are also disclosed as inhibitors of NLRP3 (see for example, Baldwin et al., J. Med. Chem., 59(5), 1691-1710, 2016; and WO 2016/131098 A1, WO 2017/129897 A1, WO 2017/140778 A1, WO 2017/184604 A1, WO 2017/184623 A1, WO 2017/184624 A1, WO 2018/015445 A1 and WO 2018/136890 A1).

There is a need to provide compounds with improved pharmacological and/or physiological and/or physicochemical properties and/or those that provide a useful alternative to known compounds.

SUMMARY OF THE INVENTION

A first aspect of the invention provides a compound of formula (I):

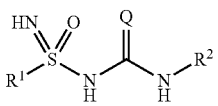

Formula (I)

wherein:
Q is selected from O or S;
R$^1$ is a saturated or unsaturated hydrocarbyl group, wherein the hydrocarbyl group may be straight-chained or branched, or be or include cyclic groups, wherein the hydrocarbyl group may optionally be substituted, and wherein the hydrocarbyl group may optionally include one or more heteroatoms N, O or S in its carbon skeleton; and
R$^2$ is a cyclic group substituted at the α-position, wherein R$^2$ may optionally be further substituted.

In one embodiment, the compound of formula (I) is not:

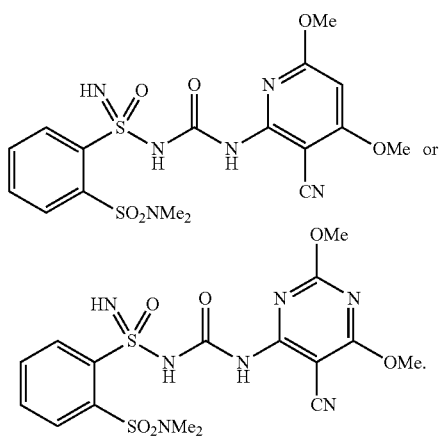

In one embodiment, the α-substituent on the cyclic group of R$^2$ is not —CN.

In the context of the present specification, a "hydrocarbyl" substituent group or a hydrocarbyl moiety in a substituent group only includes carbon and hydrogen atoms but, unless stated otherwise, does not include any heteroatoms, such as N, O or S, in its carbon skeleton. A hydrocarbyl group/moiety may be saturated or unsaturated (including aromatic), and may be straight-chained or branched, or be or include cyclic groups wherein, unless stated otherwise, the cyclic group does not include any heteroatoms, such as N, O or S, in its carbon skeleton. Examples of hydrocarbyl groups include alkyl, alkenyl, alkynyl, cycloalkyl, cycloalkenyl and aryl groups/moieties and combinations of all of these groups/moieties. Typically a hydrocarbyl group is a $C_1$-$C_{20}$ hydrocarbyl group. More typically a hydrocarbyl group is a $C_1$-$C_{15}$ hydrocarbyl group. More typically a hydrocarbyl group is a $C_1$-$C_{10}$ hydrocarbyl group. A "hydrocarbylene" group is similarly defined as a divalent hydrocarbyl group.

An "alkyl" substituent group or an alkyl moiety in a substituent group may be linear (i.e. straight-chained) or branched. Examples of alkyl groups/moieties include methyl, ethyl, n-propyl, i-propyl, n-butyl, i-butyl, t-butyl and n-pentyl groups/moieties. Unless stated otherwise, the term "alkyl" does not include "cycloalkyl". Typically an alkyl group is a $C_1$-$C_{12}$ alkyl group. More typically an alkyl group is a $C_1$-$C_6$ alkyl group. An "alkylene" group is similarly defined as a divalent alkyl group.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl groups/moieties. Unless stated otherwise, the term "alkenyl" does not include "cycloalkenyl". Typically an alkenyl group is a $C_2$-$C_{12}$ alkenyl group. More typically an alkenyl group is a $C_2$-$C_6$ alkenyl group. An "alkenylene" group is similarly defined as a divalent alkenyl group.

An "alkynyl" substituent group or an alkynyl moiety in a substituent group refers to an unsaturated alkyl group or moiety having one or more carbon-carbon triple bonds. Examples of alkynyl groups/moieties include ethynyl, propargyl, but-1-ynyl and but-2-ynyl groups/moieties. Typically an alkynyl group is a $C_2$-$C_{12}$ alkynyl group. More typically an alkynyl group is a $C_2$-$C_6$ alkynyl group. An "alkynylene" group is similarly defined as a divalent alkynyl group.

A "cyclic" substituent group or a cyclic moiety in a substituent group refers to any hydrocarbyl ring, wherein the hydrocarbyl ring may be saturated or unsaturated (including aromatic) and may include one or more heteroatoms, e.g. N, O or S, in its carbon skeleton. Examples of cyclic groups include cycloalkyl, cycloalkenyl, heterocyclic, aryl and heteroaryl groups as discussed below. A cyclic group may be monocyclic, bicyclic (e.g. bridged, fused or spiro), or polycyclic. Typically, a cyclic group is a 3- to 12-membered cyclic group, which means it contains from 3 to 12 ring atoms. More typically, a cyclic group is a 3- to 7-membered monocyclic group, which means it contains from 3 to 7 ring atoms.

A "heterocyclic" substituent group or a heterocyclic moiety in a substituent group refers to a cyclic group or moiety including one or more carbon atoms and one or more (such as one, two, three or four) heteroatoms, e.g. N, O or S, in the ring structure. Examples of heterocyclic groups include heteroaryl groups as discussed below and non-aromatic heterocyclic groups such as azetidinyl, azetinyl, tetrahydrofuranyl, pyrrolidinyl, tetrahydrothiophenyl, tetrahydropyranyl, piperidinyl, piperazinyl, morpholinyl and thiomorpholinyl groups and such as oxetanyl, thietanyl, pyrazolidinyl, imidazolidinyl, dioxolanyl, oxathiolanyl, thianyl and dioxanyl groups.

A "cycloalkyl" substituent group or a cycloalkyl moiety in a substituent group refers to a saturated hydrocarbyl ring containing, for example, from 3 to 7 carbon atoms, examples of which include cyclopropyl, cyclobutyl, cyclopentyl and cyclohexyl. Unless stated otherwise, a cycloalkyl substituent group or moiety may include monocyclic, bicyclic or polycyclic hydrocarbyl rings.

A "cycloalkenyl" substituent group or a cycloalkenyl moiety in a substituent group refers to a non-aromatic unsaturated hydrocarbyl ring having one or more carbon-carbon double bonds and containing, for example, from 3 to 7 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic or polycyclic hydrocarbyl rings.

An "aryl" substituent group or an aryl moiety in a substituent group refers to an aromatic hydrocarbyl ring. The term "aryl" includes monocyclic aromatic hydrocarbons and polycyclic fused ring aromatic hydrocarbons wherein all of the fused ring systems (excluding any ring systems which are part of or formed by optional substituents) are aromatic. Examples of aryl groups/moieties include phenyl, naphthyl, anthracenyl and phenanthrenyl. Unless stated otherwise, the term "aryl" does not include "heteroaryl".

A "heteroaryl" substituent group or a heteroaryl moiety in a substituent group refers to an aromatic heterocyclic group or moiety. The term "heteroaryl" includes monocyclic aromatic heterocycles and polycyclic fused ring aromatic heterocycles wherein all of the fused ring systems (excluding any ring systems which are part of or formed by optional substituents) are aromatic. Examples of heteroaryl groups/moieties include the following:

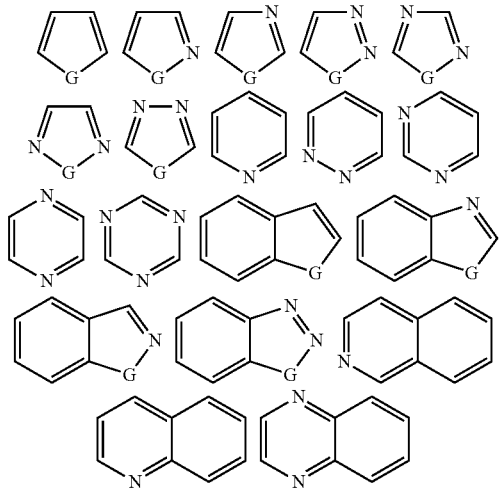

wherein G=O, S or NH.

For the purposes of the present specification, where a combination of moieties is referred to as one group, for example, arylalkyl, arylalkenyl, arylalkynyl, alkylaryl, alkenylaryl or alkynylaryl, the last mentioned moiety contains the atom by which the group is attached to the rest of the molecule. An example of an arylalkyl group is benzyl.

For the purposes of the present specification, in an optionally substituted group or moiety:
(i) each hydrogen atom may optionally be replaced by a group independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^3$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR$^\beta$)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR)R$^\beta$; —R$^\alpha$—C(=NR$^\beta$)NHR$^\beta$; —R$^\alpha$—C(=NR)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; or —N$^+$(R$^\beta$)$_2$—R$^\alpha$—N(O)(R$^\beta$)$_2$; and/or
(ii) any two hydrogen atoms attached to the same atom may optionally be replaced by a π-bonded substituent independently selected from oxo (=O), =S, =NH or =NR$^\beta$; and/or
(iii) any two hydrogen atoms attached to the same or different atoms, within the same optionally substituted group or moiety, may optionally be replaced by a bridging substituent independently selected from —O—, —S—, —NH—, —N=N—, —N(R$^\beta$)—, —N(O)(R$^\beta$)—, —N$^+$(R$^\beta$)$_2$— or —R$^\alpha$—;
   wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and
   wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, or wherein any two or three —R$^\beta$ attached to the same nitrogen atom may, together with the nitrogen atom to which they are attached, form a C$_2$-C$_7$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, C$_3$-C$_7$ halocycloalkyl, —O(C$_1$-C$_4$ alkyl), —O(C$_1$-C$_4$ haloalkyl), —O(C$_3$-C$_7$ cycloalkyl), —O(C$_3$-C$_7$ halocycloalkyl), —CO(C$_1$-C$_4$ alkyl), —CO(C$_1$-C$_4$ haloalkyl), —COO(C$_1$-C$_4$ alkyl), —COO(C$_1$-C$_4$ haloalkyl), halo, —OH, —NH$_2$, —CN, —C≡CH, oxo (=O), or 4- to 6-membered heterocyclic group.

Typically, the compounds of the present invention comprise at most one quaternary ammonium group such as —N$^+$(R$^\beta$)$_3$ or —N$^+$(R$^\beta$)$_2$—.

Where reference is made to a —R$^\alpha$—C(N$_2$)R$^\beta$ group, what is intended is:

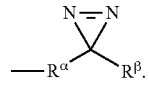

Typically, in an optionally substituted group or moiety:
(i) each hydrogen atom may optionally be replaced by a group independently selected from halo; —CN; —NO$_2$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; or —NR$^\beta$—R$^\alpha$—N(R$^\beta$)$_2$; and/or
(ii) any two hydrogen atoms attached to the same carbon atom may optionally be replaced by a π-bonded substituent independently selected from oxo (=O), =S, =NH or =NR$^\beta$; and/or
(iii) any two hydrogen atoms attached to the same or different atoms, within the same optionally substituted group or moiety, may optionally be replaced by a bridging substituent independently selected from —O—, —S—, —NH—, —N(R$^\beta$)— or —R$^\alpha$—;
   wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and
   wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

Typically, in an optionally substituted group or moiety:
(i) each hydrogen atom may optionally be replaced by a group independently selected from halo; —CN; —NO$_2$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$; and/or
(ii) any two hydrogen atoms attached to the same carbon atom may optionally be replaced by a π-bonded substituent independently selected from oxo (=O), =S, =NH or =NR$^\beta$; and/or
(iii) any two hydrogen atoms attached to the same or different atoms, within the same optionally substituted group or moiety, may optionally be replaced by a bridging substituent independently selected from —O—, —S—, —NH—, —N(R$^\beta$)— or —R$^\alpha$—;
   wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and
   wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_4$ alkyl, C$_1$-C$_4$ haloalkyl, C$_3$-C$_7$ cycloalkyl, —O(C$_1$-C$_4$ alkyl), —O(C$_1$-C$_4$ haloalkyl), —O(C$_3$-C$_7$ cycloalkyl), halo, —OH, —NH$_2$, —CN, —C≡CH, oxo (=O), or 4- to 6-membered heterocyclic group.

Typically, in an optionally substituted group or moiety:
(i) each hydrogen atom may optionally be replaced by a group independently selected from halo; —CN; —NO$_2$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$; and/or
(ii) any two hydrogen atoms attached to the same carbon atom may optionally be replaced by a π-bonded substituent independently selected from oxo (=O), =S, =NH or =NR$^\beta$; and/or
(iii) any two hydrogen atoms attached to the same or different atoms, within the same optionally substituted group or moiety, may optionally be replaced by a bridging substituent independently selected from —O—, —S—, —NH—, —N(R$^\beta$)— or —R$^\alpha$—;
   wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and
   wherein each —R$^\beta$ is independently selected from a C$_1$-C$_6$ alkyl, C$_2$-C$_6$ alkenyl, C$_2$-C$_6$ alkynyl or C$_2$-C$_6$ cyclic group, and wherein any —R$^\beta$ may optionally be substituted with one or more C$_1$-C$_4$ alkyl, halo, —OH, or 4- to 6-membered heterocyclic group.

Typically a substituted group comprises 1, 2, 3 or 4 substituents, more typically 1, 2 or 3 substituents, more typically 1 or 2 substituents, and even more typically 1 substituent.

Unless stated otherwise, any divalent bridging substituent (e.g. —O—, —S—, —NH—, —N(R$^\beta$)—, —N(O)(R$^\beta$)—, —N$^+$(R$^\beta$)$_2$— or —R$^\alpha$—) of an optionally substituted group or moiety (e.g. R$^1$) must only be attached to the specified group or moiety and may not be attached to a second group or moiety (e.g. R$^2$), even if the second group or moiety can itself be optionally substituted.

The term "halo" includes fluoro, chloro, bromo and iodo.

Unless stated otherwise, where a group is prefixed by the term "halo", such as a haloalkyl or halomethyl group, it is to be understood that the group in question is substituted with one or more halo groups independently selected from fluoro, chloro, bromo and iodo. Typically, the maximum number of halo substituents is limited only by the number of hydrogen atoms available for substitution on the corresponding group without the halo prefix. For example, a halomethyl group may contain one, two or three halo substituents. A haloethyl or halophenyl group may contain one, two, three, four or five halo substituents. Similarly, unless stated otherwise, where a group is prefixed by a specific halo group, it is to be understood that the group in question is substituted with one or more of the specific halo groups. For example, the term "fluoromethyl" refers to a methyl group substituted with one, two or three fluoro groups.

Unless stated otherwise, where a group is said to be "halo-substituted", it is to be understood that the group in question is substituted with one or more halo groups independently selected from fluoro, chloro, bromo and iodo. Typically, the maximum number of halo substituents is limited only by the number of hydrogen atoms available for substitution on the group said to be halo-substituted. For example, a halo-substituted methyl group may contain one, two or three halo substituents. A halo-substituted ethyl or halo-substituted phenyl group may contain one, two, three, four or five halo substituents.

Unless stated otherwise, any reference to an element is to be considered a reference to all isotopes of that element. Thus, for example, unless stated otherwise any reference to hydrogen is considered to encompass all isotopes of hydrogen including deuterium and tritium.

Where reference is made to a hydrocarbyl or other group including one or more heteroatoms N, O or S in its carbon skeleton, or where reference is made to a carbon atom of a hydrocarbyl or other group being replaced by an N, O or S atom, what is intended is that:

—CH—
| is replaced by

—N—;
|

—CH$_2$— is replaced by —NH—, —O— or —S—;
—CH$_3$ is replaced by —NH$_2$, —OH or —SH;
—CH= is replaced by —N=;
CH$_2$= is replaced by NH=, O= or S=; or
CH≡ is replaced by N≡;

provided that the resultant group comprises at least one carbon atom. For example, methoxy, dimethylamino and aminoethyl groups are considered to be hydrocarbyl groups including one or more heteroatoms N, O or S in their carbon skeleton.

Where reference is made to a —CH$_2$— group in the backbone of a hydrocarbyl or other group being replaced by a —N(O)(R$^\beta$)— or —N$^+$(R$^\beta$)$_2$— group, what is intended is that:

—CH$_2$— is replaced by

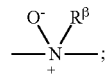

or

—CH$_2$— is replaced by

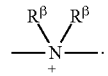

In the context of the present specification, unless otherwise stated, a $C_x$-$C_y$ group is defined as a group containing from x to y carbon atoms. For example, a $C_1$-$C_4$ alkyl group is defined as an alkyl group containing from 1 to 4 carbon atoms. Optional substituents and moieties are not taken into account when calculating the total number of carbon atoms in the parent group substituted with the optional substituents and/or containing the optional moieties. For the avoidance of doubt, replacement heteroatoms, e.g. N, O or S, are to be counted as carbon atoms when calculating the number of carbon atoms in a $C_x$-$C_y$ group. For example, a morpholinyl group is to be considered a $C_6$ heterocyclic group, not a $C_4$ heterocyclic group.

For the purposes of the present specification, where it is stated that a first atom or group is "directly attached" to a second atom or group it is to be understood that the first atom or group is covalently bonded to the second atom or group with no intervening atom(s) or group(s) being present. So, for example, for the group (C=O)N(CH$_3$)$_2$, the carbon atom of each methyl group is directly attached to the nitrogen atom and the carbon atom of the carbonyl group is directly attached to the nitrogen atom, but the carbon atom of the carbonyl group is not directly attached to the carbon atom of either methyl group.

R$^1$ is a saturated or unsaturated (including aromatic) hydrocarbyl group, such as a $C_1$-$C_{30}$ or $C_2$-$C_{20}$ or $C_3$-$C_{17}$ hydrocarbyl group, wherein the hydrocarbyl group may be straight-chained or branched, or be or include cyclic groups, wherein the hydrocarbyl group may optionally be substituted, and wherein the hydrocarbyl group may optionally include one or more (such as one, two, three or four) heteroatoms N, O or S in its carbon skeleton.

For the avoidance of doubt it is noted that R$^1$ comprises at least one carbon atom. In one embodiment, the atom of R$^1$ which is attached to the sulfur atom of the sulfoximine group is a carbon atom.

In one embodiment, R$^1$ is a 4- to 10-membered cyclic group, wherein the cyclic group may optionally be substituted. Typically, the cyclic group is a cycloalkyl, cycloalkenyl, non-aromatic heterocyclic, aryl or heteroaryl group. In one embodiment, R$^1$ is a saturated or unsaturated, optionally substituted, 4-, 5- or 6-membered heterocyclic group. In one embodiment, R$^1$ is an optionally substituted heteroaryl group. In one embodiment, R$^1$ is an optionally substituted non-aromatic heterocyclic group. In one embodiment, R$^1$ is a phenyl, naphthyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, cyclopropyl, cyclobutyl, cyclopentyl, cyclohexyl, cycloheptyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, $R^1$ is a pyrazolyl, imidazolyl, triazolyl, pyrrolyl, azetidinyl, pyrrolidinyl or piperidinyl group, all of which may optionally be substituted. In one embodiment, $R^1$ is a pyrazolyl, imidazolyl, triazolyl, azetidinyl, pyrrolidinyl or piperidinyl group, all of which may optionally be substituted. In one embodiment, $R^1$ is an optionally substituted pyrazolyl or optionally substituted azetidinyl group. In one embodiment, $R^1$ is optionally substituted with one or more (such as one, two, three or four) substituents independently selected from a halo or $C_1$-$C_5$ alkyl group, wherein the $C_1$-$C_5$ alkyl group itself is optionally substituted with one or more (such as one, two, three or four) substituents independently selected from a —O($C_1$-$C_4$ alkyl), —O($C_1$-$C_4$ haloalkyl), —O($C_3$-$C_7$ cycloalkyl), —NH($C_1$-$C_4$ alkyl), —N($C_1$-$C_4$ alkyl)$_2$, halo, —OH, —NH$_2$, —CN, oxo (=O), or 4- to 6-membered heterocyclic group. Typically, when $R^1$ is a substituted, 4- to 10-membered, nitrogen-containing cyclic group, at least one substituent on $R^1$ is attached to a ring nitrogen atom.

In another embodiment, $R^1$ is a $C_1$-$C_{15}$ alkyl, $C_2$-$C_{15}$ alkenyl or $C_2$-$C_{15}$ alkynyl group, all of which may optionally be substituted, and all of which may optionally include one or more (such as one, two or three) heteroatoms N, O or S in their carbon skeleton. $R^1$ may be a $C_1$-$C_{10}$ alkyl, $C_2$-$C_{10}$ alkenyl or $C_2$-$C_{10}$ alkynyl group, all of which may optionally be substituted, and all of which may optionally include one or more (such as one, two or three) heteroatoms N, O or S in their carbon skeleton. In one embodiment, $R^1$ is a $C_1$-$C_5$ alkyl, $C_2$-$C_5$ alkenyl or $C_2$-$C_5$ alkynyl group, all of which may optionally be substituted. In one embodiment, $R^1$ is a $C_1$-$C_5$ alkyl or $C_2$-$C_5$ alkenyl group, both of which may optionally be substituted. In one embodiment, $R^1$ is optionally substituted with one or more (such as one, two, three or four) substituents independently selected from a —O($C_1$-$C_4$ alkyl), —O($C_1$-$C_4$ haloalkyl), —O($C_3$-$C_7$ cycloalkyl), —NH($C_1$-$C_4$ alkyl), —N($C_1$-$C_4$ alkyl)$_2$, halo, —OH, —NH$_2$, —CN, oxo (=O), or 4- to 6-membered heterocyclic group.

In another embodiment, $R^1$ is an optionally substituted phenyl or optionally substituted benzyl group.

In another embodiment, $R^1$ is a hydrocarbyl group, wherein the hydrocarbyl group may be straight-chained or branched, or be or include cyclic groups, wherein the hydrocarbyl group may optionally be substituted, and wherein the hydrocarbyl group includes one or more (such as one, two, three or four) heteroatoms N or O in its carbon skeleton or is substituted with one or more (such as one, two, three or four) heteroatoms N or O. Typically the hydrocarbyl group contains 1-15 carbon atoms and 1-4 nitrogen or oxygen atoms. In one embodiment, $R^1$ is a $C_1$-$C_6$ alkyl group substituted with one or more (such as one, two, three or four) substituents independently selected from a —O($C_1$-$C_4$ alkyl), —O($C_1$-$C_4$ haloalkyl), —O($C_3$-$C_7$ cycloalkyl), —NH($C_1$-$C_4$ alkyl), —N($C_1$-$C_4$ alkyl)$_2$, —OH, —NH$_2$, —CN, oxo (=O), or 4- to 6-membered heterocyclic group, wherein the heterocyclic group comprises one or more (such as one, two, three or four) heteroatoms N or O.

In the above embodiments, $R^1$ may be substituted with one or more (such as one, two, three or four) substituents independently selected from halo; —CN; —NO$_2$; —N$_3$; —R$^\beta$; —OH; —OR$^\beta$; —R$^\alpha$-halo; —R$^\alpha$—CN; —R$^\alpha$—NO$_2$; —R$^\alpha$—N$_3$; —R$^\alpha$—R$^\beta$; —R$^\alpha$—OH; —R$^\alpha$—OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —Si(R$^\beta$)$_3$; —O—Si(R$^\beta$)$_3$; —R$^\alpha$—Si(R$^\beta$)$_3$; —R$^\alpha$—O—Si(R$^\beta$)$_3$; —NH$_2$; —NHR$^\beta$; —N(R$^\beta$)$_2$; —N(O)(R$^\beta$)$_2$; —N$^+$(R$^\beta$)$_3$; —R$^\alpha$—NH$_2$; —R$^\alpha$—NHR$^\beta$; —R$^\alpha$—N(R$^\beta$)$_2$; —R$^\alpha$—N(O)(R$^\beta$)$_2$; —R$^\alpha$—N$^+$(R$^\beta$)$_3$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —C(=NH)R$^\beta$; —C(=NH)NH$_2$; —C(=NH)NHR$^\beta$; —C(=NH)N(R$^\beta$)$_2$; —C(=NR)R$^\beta$; —C(=NR$^\beta$)NHR$^\beta$; —C(=NR$^\beta$)N(R$^\beta$)$_2$; —C(=NOH)R$^\beta$; —C(N$_2$)R$^\beta$; —R$^\alpha$—C(=NH)R$^\beta$; —R$^\alpha$—C(=NH)NH$_2$; —R$^\alpha$—C(=NH)NHR$^\beta$; —R$^\alpha$—C(=NH)N(R$^\beta$)$_2$; —R$^\alpha$—C(=NR$^\beta$)R$^\beta$; —R$^\alpha$—C(=NR$^\beta$)NHR$^\beta$; —R$^\alpha$—C(=NR$^\beta$)N(R$^\beta$)$_2$; —R$^\alpha$—C(=NOH)R$^\beta$; —R$^\alpha$—C(N$_2$)R$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —O—R$^\alpha$—N(O)(R$^\beta$)$_2$; —O—R$^\alpha$—N$^+$(R$^\beta$)$_3$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NH—R$^\alpha$—N(O)(R$^\beta$)$_2$; —NH—R$^\alpha$—N$^+$(R$^\beta$)$_3$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; —NR$^\beta$—R$^\alpha$—N(O)(R$^\beta$)$_2$; —NR$^\beta$—R$^\alpha$—N$^+$(R$^\beta$)$_3$; —N(O)R$^\beta$—R$^\alpha$—OH; —N(O)R$^\beta$—R$^\alpha$—OR$^\beta$; —N(O)R$^\beta$—R$^\alpha$—NH$_2$; —N(O)R$^\beta$—R$^\alpha$—NHR$^\beta$; —N(O)R$^\beta$—R$^\alpha$—N(R$^\beta$)$_2$; —N(O)R$^\beta$—R$^\alpha$—N(O)(R$^\beta$)$_2$; —N(O)R$^\beta$—R$^\alpha$—N$^+$(R$^\beta$)$_3$; —N$^+$(R$^\beta$)$_2$—R$^\alpha$—OH; —N$^+$(R$^\beta$)$_2$—R$^\alpha$—OR$^\beta$; —N$^+$(R$^\beta$)$_2$—R$^\alpha$—NH$_2$; —N$^+$(R$^\beta$)$_2$—R$^\alpha$—NHR$^\beta$; —N$^+$(R$^\beta$)$_2$—R$^\alpha$—N(R$^\beta$)$_2$; —N$^+$(R$^\beta$)$_2$—R$^\alpha$—N(O)(R$^\beta$)$_2$; a $C_3$-$C_7$ cycloalkyl group optionally substituted with one or more $C_1$-$C_3$ alkyl or $C_1$-$C_3$ haloalkyl groups; a $C_3$-$C_7$ cycloalkenyl group optionally substituted with one or more $C_1$-$C_3$ alkyl or $C_1$-$C_3$ haloalkyl groups; a 3- to 7-membered non-aromatic heterocyclic group optionally substituted with one or more $C_1$-$C_6$ alkyl or $C_1$-$C_3$ haloalkyl groups; oxo (=O); or a $C_1$-$C_4$ alkylene bridge;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, wherein one or more —CH$_2$— groups in the backbone of the alkylene, alkenylene or alkynylene group may optionally be replaced by one or more —N(O)(R$^\beta$)— or —N$^+$(R$^\beta$)$_2$— groups, and wherein the alkylene, alkenylene or alkynylene group may optionally be substituted with one or more halo and/or —R$^\beta$ groups; and wherein each —R$^\beta$ is independently selected from a $C_1$-$C_6$ alkyl, $C_2$-$C_6$ alkenyl, $C_2$-$C_6$ alkynyl or $C_2$-$C_6$ cyclic group, or wherein any two or three —R$^\beta$ attached to the same nitrogen atom may, together with the nitrogen atom to which they are attached, form a $C_2$-$C_7$ cyclic group, and wherein any —R$^\beta$ may optionally be substituted with one or more $C_1$-$C_4$ alkyl, $C_1$-$C_4$ haloalkyl, $C_3$-$C_7$ cycloalkyl, $C_3$-$C_7$ halocycloalkyl, —O($C_1$-$C_4$ alkyl), —O($C_1$-$C_4$ haloalkyl), —O($C_3$-$C_7$ cycloalkyl), —O($C_3$-$C_7$ halocycloalkyl), —CO($C_1$-$C_4$ alkyl), —CO($C_1$-$C_4$ haloalkyl), —COO($C_1$-$C_4$ alkyl), —COO($C_1$-$C_4$ haloalkyl), halo, —OH, —NH$_2$, —CN, —C≡CH, oxo (=O), or 4- to 6-membered heterocyclic group.

Alternatively, $R^1$ may be substituted with one or more (such as one, two, three or four) substituents independently selected from halo; —CN; —NO$_2$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta\beta$; —SO$_2$N(R$^\beta\beta$)$_2$; —R$^\beta\alpha$—SH; —R$^\beta\alpha$—SR$^\beta\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; —R$^\alpha$—OCOR$^\beta$; —NH—CHO; —NR$^\beta$—CHO; —NH—COR$^\beta$; —NR$^\beta$—COR$^\beta$; —CONH$_2$; —CONHR$^\beta$; —CON(R$^\beta$)$_2$; —R$^\alpha$—NH—CHO; —R$^\alpha$—NR$^\beta$—CHO; —R$^\alpha$—NH—COR$^\beta$; —R$^\alpha$—NR$^\beta$—COR$^\beta$; —R$^\alpha$—CONH$_2$; —R$^\alpha$—CONHR$^\beta$; —R$^\alpha$—CON(R$^\beta$)$_2$; —O—R$^\alpha$—OH; —O—R$^\alpha$—OR$^\beta$; —O—R$^\alpha$—NH$_2$; —O—R$^\alpha$—NHR$^\beta$; —O—R$^\alpha$—N(R$^\beta$)$_2$; —NH—R$^\alpha$—OH; —NH—R$^\alpha$—OR$^\beta$; —NH—R$^\alpha$—NH$_2$; —NH—R$^\alpha$—NHR$^\beta$; —NH—R$^\alpha$—N(R$^\beta$)$_2$; —NR$^\beta$—R$^\alpha$—OH; —NR$^\beta$—R$^\alpha$—OR$^\beta$; —NR$^\beta$—R$^\alpha$—NH$_2$; —NR$^\beta$—R$^\alpha$—NHR$^\beta$; —NR$^\beta$—R$^\alpha$—N(R$^\beta$)$_2$; a $C_3$-$C_7$ cycloalkyl group optionally substituted with one or more $C_1$-$C_3$ alkyl or $C_1$-$C_3$ haloalkyl groups; a $C_3$-$C_7$ cycloalkenyl group optionally substituted with one or more $C_1$-$C_3$ alkyl or $C_1$-$C_3$ haloalkyl groups; a 3- to 7-membered non-aromatic heterocyclic group optionally substituted with one or more $C_1$-$C_6$ alkyl or $C_1$-$C_3$ haloalkyl groups; oxo (=O); or a $C_1$-$C_4$ alkylene bridge;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —R$^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH$_2$, —CN, —C≡CH, oxo (=O), or 4- to 6-membered heterocyclic group.

Alternatively, $R^1$ may be substituted with one or more (such as one, two, three or four) substituents independently selected from halo; —CN; —NO$_2$; —R$^\beta$; —OH; —OR$^\beta$; —SH; —SR$^\beta$; —SOR$^\beta$; —SO$_2$H; —SO$_2$R$^\beta$; —SO$_2$NH$_2$; —SO$_2$NHR$^\beta$; —SO$_2$N(R$^\beta$)$_2$; —R$^\alpha$—SH; —R$^\alpha$—SR$^\beta$; —R$^\alpha$—SOR$^\beta$; —R$^\alpha$—SO$_2$H; —R$^\alpha$—SO$_2$R$^\beta$; —R$^\alpha$—SO$_2$NH$_2$; —R$^\alpha$—SO$_2$NHR$^\beta$; —R$^\alpha$—SO$_2$N(R$^\beta$)$_2$; —NH$_2$; —NHR$^\beta$; —N(R$^\beta$)$_2$; —R$^\alpha$—NH$_2$; —R$^\alpha$—NHR$^\beta$; —R$^\alpha$—N(R$^\beta$)$_2$; —CHO; —COR$^\beta$; —COOH; —COOR$^\beta$; —OCOR$^\beta$; —R$^\alpha$—CHO; —R$^\alpha$—COR$^\beta$; —R$^\alpha$—COOH; —R$^\alpha$—COOR$^\beta$; or —R$^\alpha$—OCOR$^\beta$;

wherein each —R$^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —R$^\beta$ groups; and wherein each —R$^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —R$^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —NH$_2$, —CN, —C≡CH, oxo (=O), or 4- to 6-membered heterocyclic group.

Alternatively still, $R^1$ may be substituted with one or more (such as one, two, three or four) substituents independently selected from halo; —CN; —NO$_2$; —R$^\beta$; —OH; —OR$^\beta$; —R$^\alpha$—OH; —R$^\alpha$—OR$^\beta$; —NH$_2$; —NHR$^\beta$; —N(R$^\beta$)$_2$; —R$^\alpha$—NH$_2$; —R$^\alpha$—NHR$^\beta$; or —R$^\alpha$—N(R$^\beta$)$_2$;

wherein each —R$^\alpha$— is independently selected from an alkylene, alkenylene or alkynylene group, wherein the alkylene, alkenylene or alkynylene group contains from 1 to 6 carbon atoms in its backbone; and wherein each —R$^\beta$ is independently selected from a $C_1$-$C_6$ alkyl, $C_2$-$C_6$ alkenyl, $C_2$-$C_6$ alkynyl or $C_3$-$C_7$ cycloalkyl group, and wherein any —R$^\beta$ may optionally be substituted with one or more (such as one, two, three or four) substituents independently selected from a $C_1$-$C_4$ alkyl, halo, —OH or 4- to 6-membered heterocyclic group.

In one aspect of any of the above embodiments, $R^1$ contains from 1 to 30 atoms other than hydrogen. More typically, $R^1$ contains from 1 to 25 atoms other than hydrogen. More typically, $R^1$ contains from 2 to 20 atoms other than hydrogen. More typically, $R^1$ contains from 4 to 17 atoms other than hydrogen.

$R^2$ is a cyclic group substituted at the α-position, wherein $R^2$ may optionally be further substituted. For the avoidance of doubt, it is noted that it is a ring atom of the cyclic group of $R^2$ that is directly attached to the nitrogen atom of the urea or thiourea group, not any substituent.

As used herein, the nomenclature α, β, α', β' refers to the position of the atoms of a cyclic group, such as —R$^2$, relative to the point of attachment of the cyclic group to the remainder of the molecule. For example, where —R$^2$ is a 1,2,3,5,6,7-hexahydro-s-indacen-4-yl moiety, the α, β, α' and β' positions are as follows:

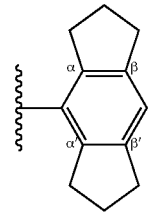 [SMILES: *c1c2c(cc3c1CCC3)CCC2]

For the avoidance of doubt, where it is stated that a cyclic group, such as an aryl or a heteroaryl group, is substituted at the α and/or α' positions, it is to be understood that one or more hydrogen atoms at the α and/or α' positions respectively are replaced by one or more substituents, such as any optional substituent as defined above. Unless stated otherwise, the term 'substituted' does not include the replacement of one or more ring carbon atoms by one or more ring heteroatoms.

In one embodiment of the first aspect of the invention, $R^2$ is an aryl or a heteroaryl group, wherein the aryl or the heteroaryl group is substituted at the α-position, and wherein $R^2$ may optionally be further substituted. Typically, $R^2$ is a phenyl or a 5- or 6-membered heteroaryl group, wherein the phenyl or the heteroaryl group is substituted at the α-position, and wherein $R^2$ may optionally be further substituted. Typically, $R^2$ is an aryl or a heteroaryl group, wherein the aryl or the heteroaryl group is substituted at the α and α' positions, and wherein $R^2$ may optionally be further substituted. Typically, $R^2$ is a phenyl or a 5- or 6-membered heteroaryl group, wherein the phenyl or the heteroaryl group is substituted at the α and α' positions, and wherein $R^2$ may optionally be further substituted. For example, $R^2$ may be a phenyl group substituted at the 2- and 6-positions or a phenyl group substituted at the 2-, 4- and 6-positions.

In one embodiment, the parent phenyl or 5- or 6-membered heteroaryl group of $R^2$ may be selected from phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl. Typically, the parent phenyl or 5- or 6-membered heteroaryl group of $R^2$ may be selected from phenyl, pyridinyl, pyridazinyl, pyrimidinyl, pyrrolyl, pyrazolyl, imidazolyl or triazolyl. Typically, the parent phenyl or 5- or 6-membered heteroaryl group of $R^2$ may be selected from phenyl, pyridinyl, pyridazinyl, pyrimidinyl or pyrazolyl.

In another embodiment, $R^2$ is a cyclic group substituted at the α and α' positions, wherein $R^2$ may optionally be further substituted. For example, $R^2$ may be a cycloalkyl, cycloalkenyl or non-aromatic heterocyclic group substituted at the α and α' positions.

In any of the above embodiments, typical substituents at the α and/or α' positions of the parent cyclic group of $R^2$ comprise a carbon atom. For example, typical substituents at the α and/or α' positions may be independently selected from —$R^4$, —$OR^4$ and —$COR^4$ groups, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. More typically, the substituents at the α and/or α' positions are independently selected from alkyl and cycloalkyl groups, such as $C_3$-$C_6$ branched alkyl and $C_3$-$C_6$ cycloalkyl groups, e.g. isopropyl, cyclopropyl, cyclohexyl or t-butyl groups, wherein the alkyl and cycloalkyl groups are optionally further substituted with one or more fluoro and/or chloro groups.

In one aspect of any of the above embodiments, each substituent at the α and α' positions comprises a carbon atom.

Other typical substituents at the α and/or α' positions of the parent cyclic group of $R^2$ may include cycloalkyl, cycloalkenyl, non-aromatic heterocyclic, aryl or heteroaryl rings which are fused to the parent cyclic group across the α,β and/or α',β' positions respectively. Such fused cyclic groups are described in greater detail below.

In one embodiment, $R^2$ is a fused aryl or a fused heteroaryl group, wherein the aryl or heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the aryl or heteroaryl group across the α,β positions. Typically, the aryl or heteroaryl group is also substituted at the α' position, for example with a substituent selected from —$R^4$, —$OR^4$ and —$COR^4$, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. Typically in such an embodiment, $R^2$ is bicyclic or tricyclic.

More typically, $R^2$ is a fused phenyl or a fused 5- or 6-membered heteroaryl group, wherein the phenyl or the 5- or 6-membered heteroaryl group is fused to one or more cycloalkyl, cycloalkenyl, non-aromatic heterocyclic, aryl or heteroaryl rings, wherein $R^2$ may optionally be further substituted. Typically, a cycloalkyl, cycloalkenyl, non-aromatic heterocyclic, aryl or heteroaryl ring is fused to the phenyl or the 5- or 6-membered heteroaryl group across the α,β positions so as to form a 4- to 6-membered fused ring structure. Typically, the phenyl or the 5- or 6-membered heteroaryl group is also substituted at the α' position, for example with a substituent selected from —$R^4$, —$OR^4$ and —$COR^4$, wherein each $R^4$ is independently selected from a $C_1$-$C_6$ alkyl, $C_2$-$C_6$ alkenyl, $C_2$-$C_6$ alkynyl or $C_2$-$C_6$ cyclic group and wherein each $R^4$ is optionally further substituted with one or more halo groups. Typically in such an embodiment, $R^2$ is bicyclic or tricyclic.

In another embodiment, $R^2$ is a fused aryl or a fused heteroaryl group, wherein the aryl or heteroaryl group is fused to two or more independently selected cycloalkyl, cycloalkenyl, non-aromatic heterocyclic, aryl or heteroaryl rings, wherein $R^2$ may optionally be further substituted. Typically, the two or more cycloalkyl, cycloalkenyl, non-aromatic heterocyclic, aryl or heteroaryl rings are each ortho-fused to the aryl or heteroaryl group, i.e. each fused cycloalkyl, cycloalkenyl, non-aromatic heterocyclic, aryl or heteroaryl ring has only two atoms and one bond in common with the aryl or heteroaryl group. Typically in such an embodiment, $R^2$ is tricyclic.

In yet another embodiment, $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α,β positions and a second cycloalkyl, cycloalkenyl, non-aromatic heterocyclic, aryl or heteroaryl ring is fused to the aryl or heteroaryl group across the α',β' positions, wherein $R^2$ may optionally be further substituted. Typically in such an embodiment, $R^2$ is tricyclic.

More typically, $R^2$ is a fused phenyl or a fused 5- or 6-membered heteroaryl group, wherein a first cycloalkyl, cycloalkenyl, non-aromatic heterocyclic, aryl or heteroaryl ring is fused to the phenyl or the 5- or 6-membered heteroaryl group across the α,β positions so as to form a first 4- to 6-membered fused ring structure, and a second cycloalkyl, cycloalkenyl, non-aromatic heterocyclic, aryl or heteroaryl ring is fused to the phenyl or the 5- or 6-membered heteroaryl group across the α',β' positions so as to form a second 4- to 6-membered fused ring structure, wherein $R^2$ may optionally be further substituted. Typically in such an embodiment, $R^2$ is tricyclic.

In one embodiment, —$R^2$ has a formula selected from:

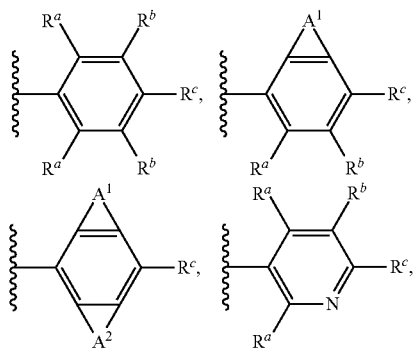

-continued

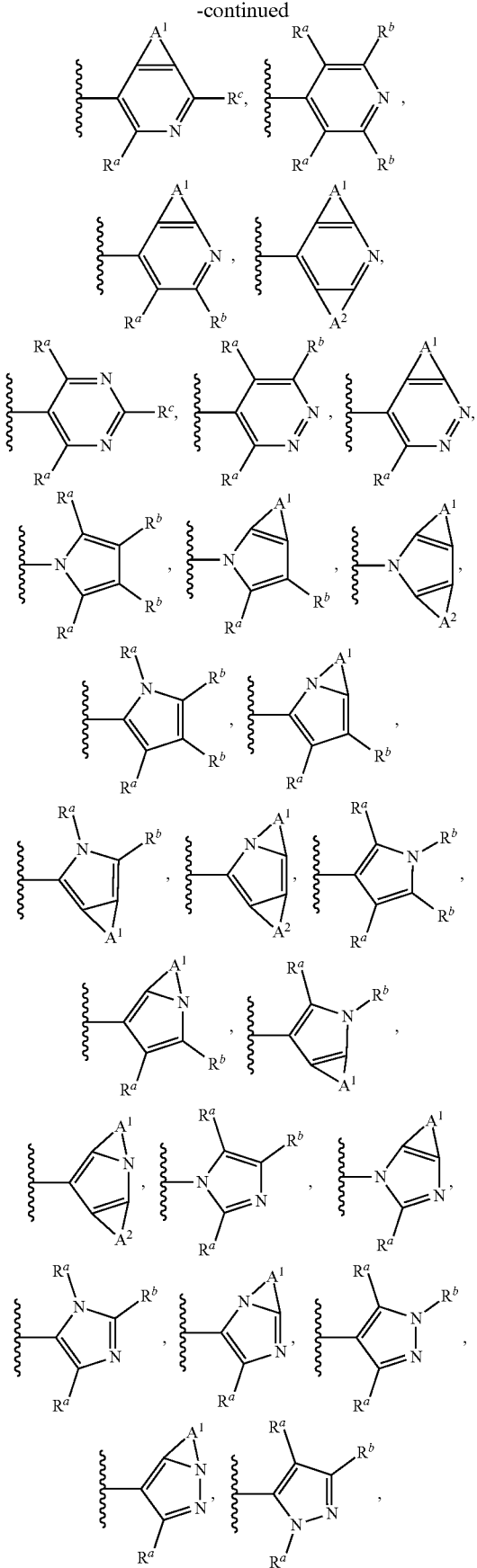
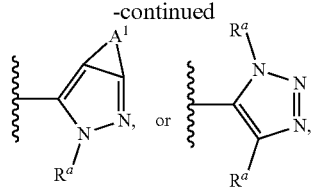

wherein:
A¹ and A² are each independently selected from an optionally substituted alkylene or alkenylene group, wherein one or more carbon atoms in the backbone of the alkylene or alkenylene group may optionally be replaced by one or more heteroatoms N, O or S;

each $R^a$ is independently selected from —$R^{aa}$, —$OR^{aa}$ or —$COR^{aa}$;

each $R^b$ is independently selected from hydrogen, halo, —$NO_2$, —CN, —$R^{aa}$, —$OR^{aa}$ or —$COR^{aa}$;

provided that any $R^a$ or $R^b$ that is directly attached to a ring nitrogen atom is not halo, —$NO_2$, —CN, or —$OR^{aa}$;

each $R^c$ is independently selected from hydrogen, halo, —OH, —$NO_2$, —CN, —$R^{cc}$—, —$OR^{cc}$, —$COR^{cc}$, —$COOR^{cc}$, —$CONH_2$, —$CONHR^{cc}$ or —$CON(R^{cc})_2$;

each $R^{aa}$ is independently selected from a $C_1$-$C_6$ alkyl, $C_2$-$C_6$ alkenyl, $C_2$-$C_6$ alkynyl or a 3- to 7-membered cyclic group, wherein each $R^{aa}$ is optionally substituted; and each $R^{cc}$ is independently selected from a $C_1$-$C_6$ alkyl, $C_2$-$C_6$ alkenyl, $C_2$-$C_6$ alkynyl or a 3- to 7-membered cyclic group, or any two $R^c$ attached to the same nitrogen atom may, together with the nitrogen atom to which they are attached, form a 3- to 7-membered heterocyclic group, wherein each R is optionally substituted.

Typically, any ring containing A¹ or A² is a 5- or 6-membered ring. Typically, A¹ and A² are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, A¹ and A² are each independently selected from an optionally substituted straight-chained alkylene group, wherein one carbon atom in the backbone of the alkylene group may optionally be replaced by an oxygen atom. Typically, no heteroatom in A¹ or A² is directly attached to another ring heteroatom. Typically, A¹ and A² are unsubstituted or substituted with one or more substituents independently selected from halo, —OH, —CN, —$NO_2$, $C_1$-$C_4$ alkyl, $C_1$-$C_4$ haloalkyl, —O($C_1$-$C_4$ alkyl) or —O($C_1$-$C_4$ haloalkyl). More typically, A¹ and A² are unsubstituted or substituted with one or more fluoro and/or chloro groups. Where $R^2$ contains both A and A² groups, A¹ and A² may be the same or different. Typically, A¹ and A² are the same.

Where $R^{aa}$ is a substituted $C_1$-$C_6$ alkyl, $C_2$-$C_6$ alkenyl or $C_2$-$C_6$ alkynyl group, typically the $C_1$-$C_6$ alkyl, $C_2$-$C_6$ alkenyl or $C_2$-$C_6$ alkynyl group is substituted with one or more (e.g. one or two) substituents independently selected from halo, —OH, —CN, —$NO_2$, —O($C_1$-$C_4$ alkyl) or —O($C_1$-$C_4$ haloalkyl).

Where $R^{aa}$ is a substituted 3- to 7-membered cyclic group, typically the 3- to 7-membered cyclic group is substituted with one or more (e.g. one or two) substituents independently selected from halo, —OH, —$NH_2$, —CN, —$NO_2$, —B$^1$, —OB$^1$, —NHB$^1$, —N(B$^1$)$_2$, —CONH$_2$, —CONHB$^1$, —CON(B$^1$)$_2$, —NHCOB$^1$, —NB$^1$COB$^1$, or —B$^{11}$—;

wherein each B$^1$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^1$ together with the nitrogen atom to which they are attached may form a 4- to 6-membered heterocyclic group containing one or two ring heteroatoms N and/or O, wherein any B may optionally be halo-substituted and/or substituted with one or two substituents independently selected from —OH, —NH$_2$, —OB$^{12}$, —NHB$^{12}$ or —N(B$^{12}$)$_2$;

wherein each B$^{11}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{12}$, —NHB$^{12}$ or —N(B$^{12}$)$_2$; and wherein each B$^{12}$ is independently selected from a C$_1$-C$_3$ alkyl or C$_1$-C$_3$ haloalkyl group. Typically, any divalent group —B$^{11}$— forms a 4- to 6-membered fused ring.

Typically, each R$^a$ is —R$^{aa}$. More typically, each R$^a$ is independently selected from a C$_1$-C$_6$ alkyl (in particular C$_3$-C$_6$ branched alkyl) or C$_3$-C$_6$ cycloalkyl group, wherein each R$^a$ is optionally further substituted with one or more halo groups. More typically, each R$^a$ is independently selected from a C$_1$-C$_4$ alkyl, C$_1$-C$_4$ haloalkyl, C$_3$-C$_4$ cycloalkyl or C$_3$-C$_4$ halocycloalkyl group. Where a group R$^a$ is present at both the α- and α'-positions, each R$^a$ may be the same or different. Typically, each R$^a$ is the same.

Typically, each R$^b$ is independently selected from hydrogen or halo. More typically, each R$^b$ is hydrogen.

Typically, each R$^c$ is independently selected from hydrogen, halo, —OH, —NO$_2$, —CN, —R$^{cc}$— or —OR$^{cc}$. More typically, each R$^c$ is independently selected from hydrogen, halo, —CN, C$_1$-C$_3$ alkyl, C$_1$-C$_3$ haloalkyl, cyclopropyl or halocyclopropyl. Most typically, each R is independently selected from hydrogen or halo.

Typically, each R$^{cc}$ is independently selected from a C$_1$-C$_4$ alkyl or C$_3$-C$_6$ cycloalkyl group, or any two R$^{cc}$ attached to the same nitrogen atom may, together with the nitrogen atom to which they are attached, form a 3- to 6-membered saturated heterocyclic group, wherein each R$^{cc}$ is optionally substituted. Where R$^{cc}$ is substituted, typically R$^{cc}$ is substituted with one or more halo, —OH, —CN, —NO$_2$, —O(C$_1$-C$_4$ alkyl) or —O(C$_1$-C$_4$ haloalkyl) groups. More typically, each R$^{cc}$ is independently selected from a C$_1$-C$_4$ alkyl, C$_1$-C$_4$ haloalkyl, C$_3$-C$_4$ cycloalkyl or C$_3$-C$_4$ halocycloalkyl group.

In one embodiment, —R$^2$ has a formula selected from:

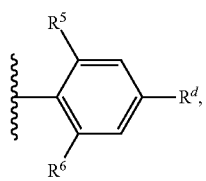

wherein R$^5$ and R$^6$ are independently selected from C$_1$-C$_4$ alkyl, C$_1$-C$_4$ haloalkyl, C$_3$-C$_4$ cycloalkyl and C$_3$-C$_4$ halocycloalkyl, and R$^d$ is hydrogen, halo, —OH, —NO$_2$, —CN, —R$^{dd}$, —OR$^{dd}$, —COR$^{dd}$, —COOR$^{dd}$, —CONH$_2$, —CONHR$^{dd}$ or —CON(R$^{dd}$)$_2$, wherein each —R$^{dd}$ is independently selected from C$_1$-C$_4$ alkyl, C$_1$-C$_4$ haloalkyl, C$_3$-C$_4$ cycloalkyl and C$_3$-C$_4$ halocycloalkyl. Typically, R$^5$ and R$^6$ are independently selected from C$_1$-C$_4$ alkyl, and R$^d$ is hydrogen, halo, —CN, C$_1$-C$_3$ alkyl, C$_1$-C$_3$ haloalkyl, cyclopropyl or halocyclopropyl. More typically, R$^5$ and R$^6$ are independently selected from C$_1$-C$_4$ alkyl, and R$^d$ is hydrogen or halo.

Typically, —R$^2$ has a formula selected from:

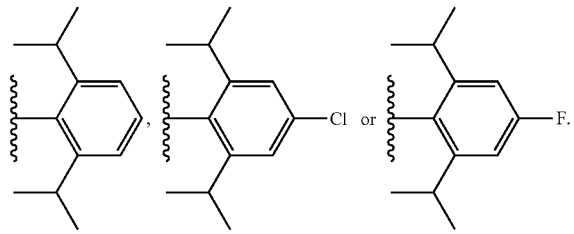

In one embodiment, —R$^2$ has a formula selected from:

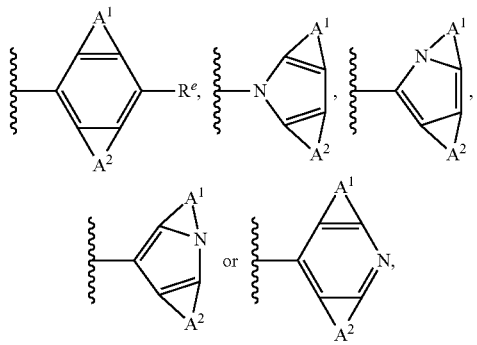

wherein A$^1$ and A$^2$ are each independently selected from an optionally substituted alkylene or alkenylene group, wherein one or more carbon atoms in the backbone of the alkylene or alkenylene group may optionally be replaced by one or more heteroatoms N, O or S, and wherein R$^e$ is hydrogen or any optional substituent. R$^e$ and any optional substituent attached to A$^1$ or A$^2$ may together with the atoms to which they are attached form a further fused cycloalkyl, cycloalkenyl, non-aromatic heterocyclic, aryl or heteroaryl ring which may itself be optionally substituted. Similarly, any optional substituent attached to A$^1$ and any optional substituent attached to A$^2$ may also together with the atoms to which they are attached form a further fused cycloalkyl, cycloalkenyl, non-aromatic heterocyclic, aryl or heteroaryl ring which may itself be optionally substituted.

In one embodiment, R$^e$ is hydrogen, halo, —OH, —NO$_2$, —CN, —R$^{ee}$, —OR$^{ee}$, —COR$^{ee}$, —COOR$^{ee}$, —CONH$_2$, —CONHR$^{ee}$ or —CON(R$^{ee}$)$_2$, wherein each —R$^{ee}$ is independently selected from C$_1$-C$_4$ alkyl, C$_1$-C$_4$ haloalkyl, C$_3$-C$_4$ cycloalkyl and C$_3$-C$_4$ halocycloalkyl. Typically, R$^e$ is hydrogen or a halo, hydroxyl, —CN, —NO$_2$, —R$^{ee}$ or —OR$^{ee}$ group, wherein R$^{ee}$ is a C$_1$-C$_4$ alkyl group which may optionally be halo-substituted. More typically, R$^e$ is hydrogen or halo.

Typically, any ring containing A$^1$ or A$^2$ is a 5- or 6-membered ring.

Typically, $A^1$ and $A^2$ are each independently selected from an optionally substituted straight-chained alkylene group or an optionally substituted straight-chained alkenylene group, wherein one or two carbon atoms in the backbone of the alkylene or alkenylene group may optionally be replaced by one or two heteroatoms independently selected from nitrogen and oxygen. More typically, $A^1$ and $A^2$ are each independently selected from an optionally substituted straight-chained alkylene group, wherein one carbon atom in the backbone of the alkylene group may optionally be replaced by an oxygen atom. Typically, no heteroatom in $A^1$ or $A^2$ is directly attached to another ring heteroatom. Typically, $A^1$ and $A^2$ are unsubstituted or substituted with one or more halo, hydroxyl, —CN, —NO$_2$, —B$^3$ or —OB$^3$ groups, wherein B$^3$ is a C$_1$-C$_4$ alkyl group which may optionally be halo-substituted. More typically, $A^1$ and $A^2$ are unsubstituted or substituted with one or more fluoro and/or chloro groups. Where R$^2$ contains both $A^1$ and $A^2$ groups, $A^1$ and $A^2$ may be the same or different. Typically, $A^1$ and $A^2$ are the same.

In a further embodiment, —R$^2$ has a formula selected from:

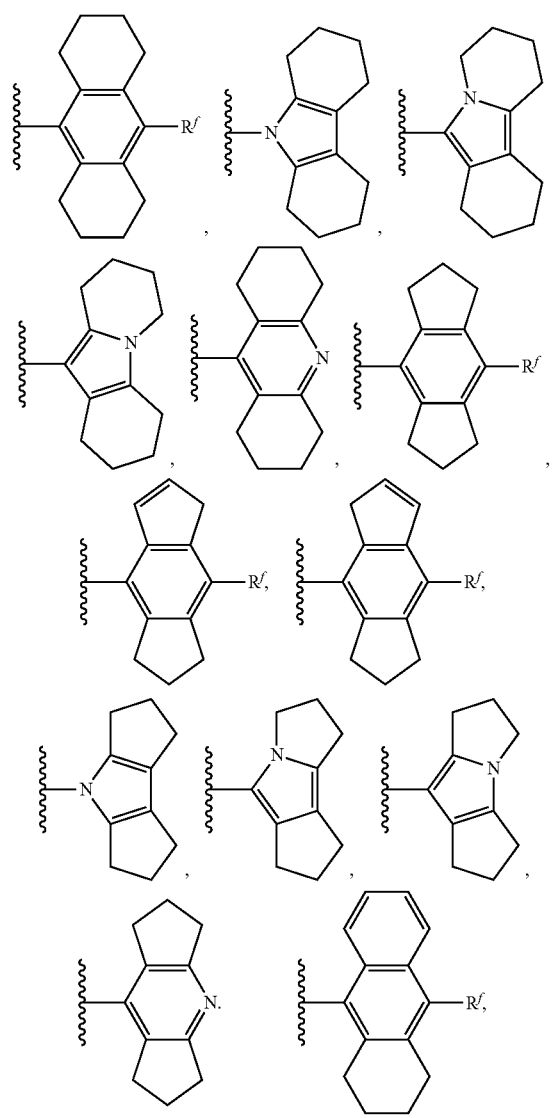

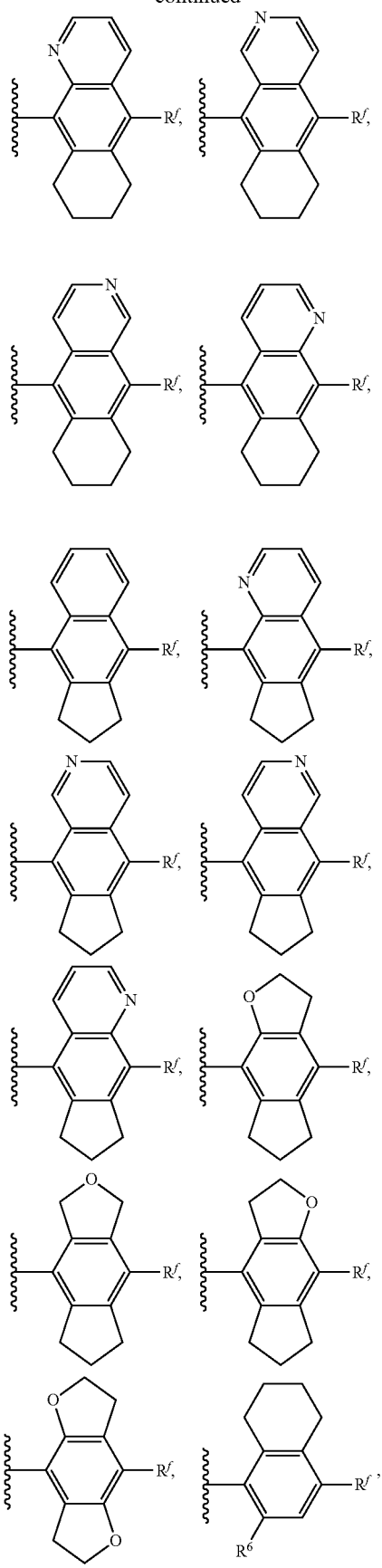

-continued

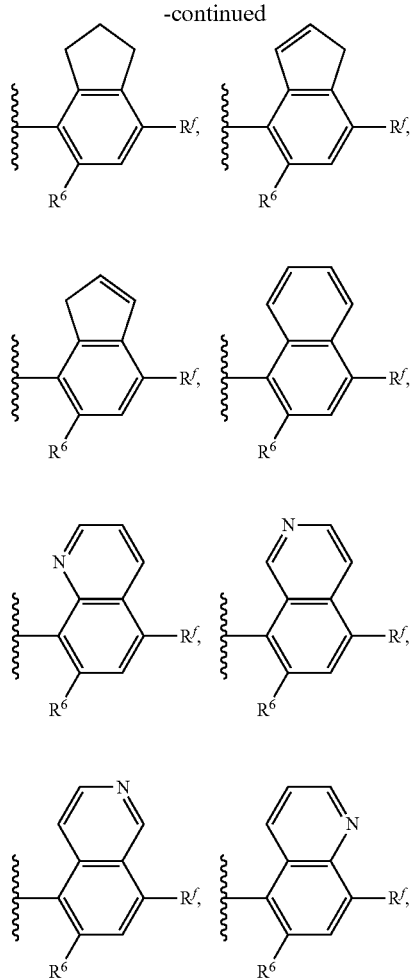

Typically, —R² has the formula:

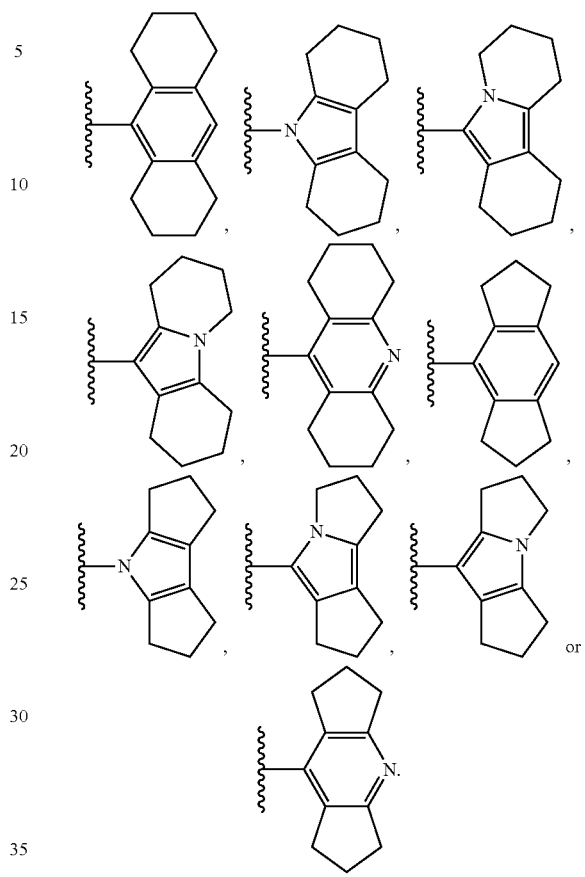

More typically, —R² has the formula:

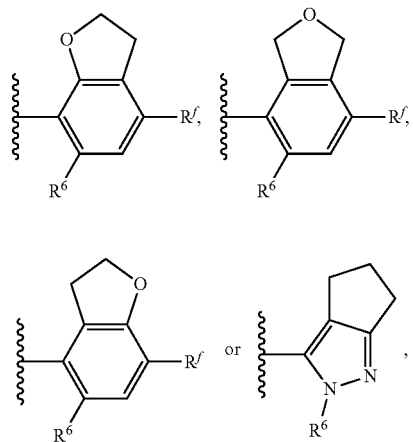

wherein R⁶ is $C_1$-$C_4$ alkyl, $C_1$-$C_4$ haloalkyl, $C_3$-$C_4$ cycloalkyl or $C_3$-$C_4$ halocycloalkyl, and $R^f$ is hydrogen, halo, —OH, —NO₂, —CN, —$R^{ff}$, —$OR^{ff}$, —$COR^{ff}$, —$COOR^{ff}$, —CONH₂, —$CONHR^{ff}$ or —$CON(R^{ff})_2$, wherein each —$R^{ff}$ is independently selected from $C_1$-$C_4$ alkyl, $C_1$-$C_4$ haloalkyl, $C_3$-$C_4$ cycloalkyl and $C_3$-$C_4$ halocycloalkyl. Typically, R⁶ is $C_1$-$C_4$ alkyl, and $R^f$ is hydrogen, halo, —CN, $C_1$-$C_3$ alkyl, $C_1$-$C_3$ haloalkyl, cyclopropyl or halocyclopropyl. Typically, R⁶ is $C_1$-$C_4$ alkyl, and $R^f$ is hydrogen or halo.

Yet other typical substituents at the α-position of the parent cyclic group of R² may include monovalent heterocyclic groups and monovalent aromatic groups, wherein a ring atom of the heterocyclic or aromatic group is directly attached via a single bond to the α-ring atom of the parent cyclic group, wherein the heterocyclic or aromatic group may optionally be substituted, and wherein the parent cyclic group may optionally be further substituted. Such R² groups are described in greater detail below.

In one embodiment, the α-substituted parent cyclic group of R² is a 5- or 6-membered cyclic group, wherein the cyclic group may optionally be further substituted. In one embodiment, the α-substituted parent cyclic group of R² is an aryl or a heteroaryl group, all of which may optionally be further substituted. In one embodiment, the α-substituted parent cyclic group of R² is a phenyl or a 5- or 6-membered heteroaryl group, all of which may optionally be further substituted. In one embodiment, the α-substituted parent cyclic group of $R^2$ is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl or oxadiazolyl group, all of which may optionally be further substituted. In one embodiment, the α-substituted parent cyclic group of $R^2$ is a phenyl or pyrazolyl group, both of which may optionally be further substituted. In a further embodiment, the α-substituted parent cyclic group of $R^2$ is a phenyl group, which may optionally be further substituted.

In one embodiment, the α-substituted parent cyclic group of $R^2$ is substituted at the α and α' positions, and may optionally be further substituted. For example, the α-substituted parent cyclic group of $R^2$ may be a phenyl group substituted at the 2- and 6-positions or a phenyl group substituted at the 2-, 4- and 6-positions.

In one embodiment, $R^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, the monovalent heterocyclic or aromatic group at the α-position is a phenyl or a 5- or 6-membered heterocyclic group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, piperazinyl, 1,4-dioxanyl, thianyl, morpholinyl, thiomorpholinyl or 1-methyl-2-oxo-1,2-dihydropyridinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, triazolyl, oxadiazolyl, azetinyl, azetidinyl, oxetanyl, thietanyl, pyrrolidinyl, tetrahydrofuranyl, tetrahydrothiophenyl, pyrazolidinyl, imidazolidinyl, 1,3-dioxolanyl, 1,2-oxathiolanyl, 1,3-oxathiolanyl, piperidinyl, tetrahydropyranyl, thianyl, piperazinyl, 1,4-dioxanyl, morpholinyl or thiomorpholinyl group, all of which may optionally be substituted. In one embodiment, the monovalent heterocyclic or aromatic group at the α-position is a phenyl, pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, piperidinyl or tetrahydropyranyl group, all of which may optionally be substituted. In one embodiment, the monovalent heterocyclic or aromatic group at the α-position is a phenyl, pyridinyl, pyridazinyl, pyrimidinyl, pyrazolyl, imidazolyl, isoxazolyl, thiazolyl, tetrahydropyranyl or 1-methyl-2-oxo-1,2-dihydropyridinyl group, all of which may optionally be substituted. In one embodiment, the monovalent heterocyclic or aromatic group at the α-position is a phenyl, pyridinyl, pyrimidinyl, pyrazolyl, imidazolyl, isoxazolyl, thiazolyl or tetrahydropyranyl group, all of which may optionally be substituted. In one embodiment, the monovalent heterocyclic or aromatic group at the α-position is a phenyl, pyridinyl, pyrimidinyl or pyrazolyl group, all of which may optionally be substituted. In one embodiment, the monovalent heterocyclic or aromatic group at the α-position is an unsubstituted phenyl, pyridinyl, pyrimidinyl or pyrazolyl group. In one embodiment, the monovalent heterocyclic group at the α-position is a pyridin-2-yl, pyridin-3-yl or pyridin-4-yl group, all of which may optionally be substituted. In one embodiment, the monovalent heterocyclic group at the α-position is an unsubstituted pyridin-3-yl group or an optionally substituted pyridin-4-yl group.

For any of these monovalent heterocyclic or aromatic groups at the α-position mentioned in the immediately preceding paragraph, the monovalent heterocyclic or aromatic group may optionally be substituted with one or two substituents independently selected from halo, —OH, —NH₂, —CN, —NO₂, —B⁴, —OB⁴, —NHB⁴, —N(B⁴)₂, —CONH₂, —CONHB⁴, —CON(B⁴)₂, —NHCOB⁴, —NB⁴COB⁴, or —B⁴⁴—;

wherein each $B^4$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^4$ together with the nitrogen atom to which they are attached may form a 4- to 6-membered heterocyclic group containing one or two ring heteroatoms N and/or O, wherein any $B^4$ may optionally be halo-substituted and/or substituted with one or two substituents independently selected from —OH, —NH₂, —OB⁴⁵, —NHB⁴⁵ or —N(B⁴⁵)₂;

wherein each $B^{44}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH₂, —OB⁴⁵, —NHB⁴⁵ or —N(B⁴⁵)₂; and wherein each $B^{45}$ is independently selected from a $C_1$-$C_3$ alkyl or $C_1$-$C_3$ haloalkyl group.

Typically, any divalent group —B⁴⁴— forms a 4- to 6-membered fused ring.

In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH₂, —CN, —NO₂, —B⁴, —OB⁴, —NHB⁴ or —N(B⁴)₂, wherein each $B^4$ is independently selected from a $C_1$-$C_4$ alkyl, $C_2$-$C_4$ alkenyl or $C_2$-$C_4$ alkynyl group all of which may optionally be halo-substituted. In one embodiment, the monovalent heterocyclic or aromatic group at the α-position is a phenyl, pyridinyl, pyrimidinyl or pyrazolyl group, all of which may optionally be substituted with one or two substituents independently selected from halo, —OH, —NH₂, —CN, $C_1$-$C_3$ alkyl or —O($C_1$-$C_3$ alkyl). In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH₂, —CN, —NO₂, —B⁴, —OB⁴, —NHB⁴ or —N(B⁴)₂, wherein each $B^4$ is independently selected from a $C_1$-$C_4$ alkyl, $C_2$-$C_4$ alkenyl or $C_2$-$C_4$ alkynyl group all of which may optionally be halo-substituted. In one embodiment, the monovalent heterocyclic group at the α-position is a pyridin-2-yl, pyridin-3-yl or pyridin-4-yl group, all of which may optionally be substituted with one or two substituents independently selected from halo, —OH, —NH₂, —CN, $C_1$-$C_3$ alkyl or —O($C_1$-$C_3$ alkyl). In one embodiment, the monovalent heterocyclic group at the α-position is an unsubstituted pyridin-3-yl group or a pyridin-4-yl group optionally substituted with one or two substituents independently selected from halo, —OH, —NH₂, —CN, —NO₂, —B⁴, —OB⁴, —NHB⁴ or —N(B⁴)₂, wherein each $B^4$ is independently selected from a $C_1$-$C_4$ alkyl, $C_2$-$C_4$ alkenyl or $C_2$-$C_4$ alkynyl group all of which may optionally be halo-substituted. In one embodiment, the monovalent heterocyclic group at the α-position is an unsubstituted pyridin-3-yl group or a pyridin-4-yl group optionally substituted with one or two substituents independently selected from halo, —OH, —$NH_2$, —CN, $C_1$-$C_3$ alkyl or —O($C_1$-$C_3$ alkyl).

In one embodiment, $R^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. In one embodiment, such further substituents are in the α' position of the α-substituted parent cyclic group of $R^2$. Such further substituents may be independently selected from halo, —R, —$OR^6$ or —$COR^6$ groups, wherein each $R^6$ is independently selected from a $C_1$-$C_6$ alkyl, $C_2$-$C_6$ alkenyl, $C_2$-$C_6$ alkynyl or $C_2$-$C_6$ cyclic group and wherein each $R^6$ is optionally further substituted with one or more halo groups. Typically, such further substituents on the α-substituted parent cyclic group of $R^2$ are independently selected from halo, $C_1$-$C_6$ alkyl (in particular $C_3$-$C_6$ branched alkyl) or $C_3$-$C_6$ cycloalkyl groups, e.g. fluoro, chloro, isopropyl, cyclopropyl, cyclohexyl or t-butyl groups, wherein the alkyl and cycloalkyl groups are optionally further substituted with one or more fluoro and/or chloro groups.

In one embodiment, —$R^2$ has a formula selected from:

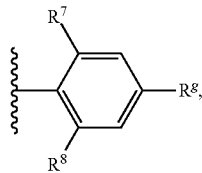

wherein $R^7$ is $C_1$-$C_4$ alkyl, $C_1$-$C_4$ haloalkyl, $C_3$-$C_6$ cycloalkyl or $C_3$-$C_6$ halocycloalkyl, $R^8$ is a 5- or 6-membered, optionally substituted heterocyclic or aromatic group, and $R^g$ is hydrogen, halo, —OH, —$NO_2$, —CN, —$R^{gg}$, —$OR^{gg}$, —$COR^{gg}$, —$COOR^{gg}$, —$CONH_2$, —$CONHR^{gg}$ or —CON($R^{gg}$)$_2$, wherein each —$R^{gg}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group are independently selected from halo, —OH, —$NH_2$, —CN, —$NO_2$, —$B^5$, —$OB^5$, —$NHB^5$, —$N(B^5)_2$, —$CONH_2$, —$CONHB^5$, —$CON(B^5)_2$, —$NHCOB^5$, —$NB^5COB^5$, or —$B^{55}$—;
wherein each $B^5$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^5$ together with the nitrogen atom to which they are attached may form a 4- to 6-membered heterocyclic group containing one or two ring heteroatoms N and/or O, wherein any $B^5$ may optionally be halo-substituted and/or substituted with one or two substituents independently selected from —OH, —$NH_2$, —$OB^{56}$, —$NHB^{56}$ or —$N(B^{56})$
wherein each $B^{55}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —$NH_2$, —$OB^{56}$, —$NHB^{56}$ or —$N(B^{56})_2$; and
wherein each $B^{56}$ is independently selected from a $C_1$-$C_3$ alkyl or $C_1$-$C_3$ haloalkyl group.

Typically, any divalent group —$B^{55}$— forms a 4- to 6-membered fused ring. Typically, $R^7$ is $C_1$-$C_4$ alkyl, $R^8$ is a 5- or 6-membered, optionally substituted heterocyclic or aromatic group, and $R^g$ is hydrogen, halo, —CN, $C_1$-$C_3$ alkyl, $C_1$-$C_3$ haloalkyl, cyclopropyl or halocyclopropyl. More typically, $R^7$ is $C_1$-$C_4$ alkyl, $R^8$ is a 5- or 6-membered, optionally substituted heterocyclic or aromatic group, and $R^g$ is hydrogen or halo. In one embodiment, the optional substituents on the heterocyclic or aromatic group are independently selected from halo, —OH, —$NH_2$, —CN, —$NO_2$, —$B^5$, —$OB^5$, —$NHB^5$ or —$N(B^5)_2$, wherein each $B^5$ is independently selected from a $C_1$-$C_4$ alkyl, $C_1$-$C_4$ alkenyl or $C_1$-$C_4$ alkynyl group all of which may optionally be halo-substituted. In another embodiment, the optional substituents on the heterocyclic or aromatic group are independently selected from halo, hydroxyl, —CN, —$NH_2$, —$B^5$ or —$OB^5$, wherein $B^5$ is a $C_1$-$C_4$ alkyl group which may optionally be halo-substituted.

Typically, —$R^2$ has a formula selected from:

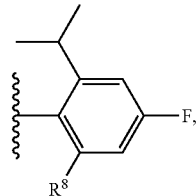

wherein $R^8$ is a 5- or 6-membered, optionally substituted heterocyclic or aromatic group. In one embodiment, the optional substituents on the heterocyclic or aromatic group are independently selected from halo, —OH, —$NH_2$, —CN, —$NO_2$, —$B^6$, —$OB^6$, —$NHB^6$, —$N(B^6)_2$, —$CONH_2$, —$CONHB^6$, —$CON(B^6)_2$, —$NHCOB^6$, —$NB^6COB^6$, or —$B^{66}$—;
wherein each $B^6$ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two $B^6$ together with the nitrogen atom to which they are attached may form a 4- to 6-membered heterocyclic group containing one or two ring heteroatoms N and/or O, wherein any $B^6$ may optionally be halo-substituted and/or substituted with one or two substituents independently selected from —OH, —$NH_2$, —$OB^{67}$, —$NHB^{67}$ or —$N(B^{67})_2$;
wherein each $B^{66}$ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —$NH_2$, —$OB^{67}$, —$NHB^{67}$ or —$N(B^{67})_2$; and
wherein each $B^{67}$ is independently selected from a $C_1$-$C_3$ alkyl or $C_1$-$C_3$ haloalkyl group.

Typically, any divalent group —$B^{66}$— forms a 4- to 6-membered fused ring. Typically, the optional substituents on the heterocyclic or aromatic group are independently selected from halo, —OH, —$NH_2$, —CN, —$NO_2$, —$B^6$, —OB⁶, —NHB⁶ or —N(B⁶)₂, wherein each B⁶ is independently selected from a $C_1$-$C_4$ alkyl, $C_2$-$C_4$ alkenyl or $C_2$-$C_4$ alkynyl group all of which may optionally be halo-substituted. In another embodiment, the optional substituents on the heterocyclic or aromatic group are independently selected from halo, hydroxyl, —CN, —NH₂, —B⁶ or —OB⁶, wherein B⁶ is a $C_1$-$C_4$ alkyl group which may optionally be halo-substituted. In another embodiment, the optional substituents on the heterocyclic or aromatic group are independently selected from halo, hydroxyl, —CN, —NH₂, —B⁶ or —OB⁶, wherein B⁶ is a $C_1$-$C_3$ alkyl group.

In one embodiment, $R^2$ is a parent cyclic group substituted at the α-position with a monovalent heterocyclic group or a monovalent aromatic group, wherein the heterocyclic or aromatic group may optionally be substituted, and wherein the parent cyclic group may optionally be further substituted. The further substituents on the α-substituted parent cyclic group of $R^2$ also include cycloalkyl, cycloalkenyl, non-aromatic heterocyclic, aryl or heteroaryl rings which are fused to the α-substituted parent cyclic group of $R^2$. Typically, the cycloalkyl, cycloalkenyl, non-aromatic heterocyclic, aryl or heteroaryl rings are ortho-fused to the α-substituted parent cyclic group of $R^2$, i.e. each fused cycloalkyl, cycloalkenyl, non-aromatic heterocyclic, aryl or heteroaryl ring has only two atoms and one bond in common with the α-substituted parent cyclic group of $R^2$. Typically, the cycloalkyl, cycloalkenyl, non-aromatic heterocyclic, aryl or heteroaryl rings are ortho-fused to the α-substituted parent cyclic group of $R^2$ across the α',β' positions.

In one embodiment, —$R^2$ has a formula selected from:

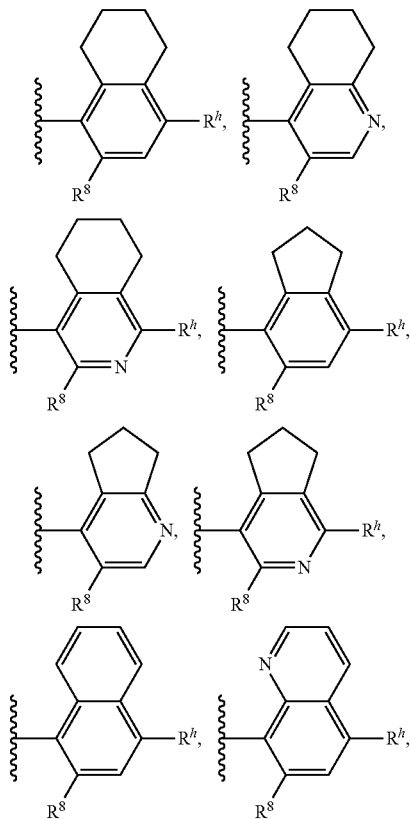

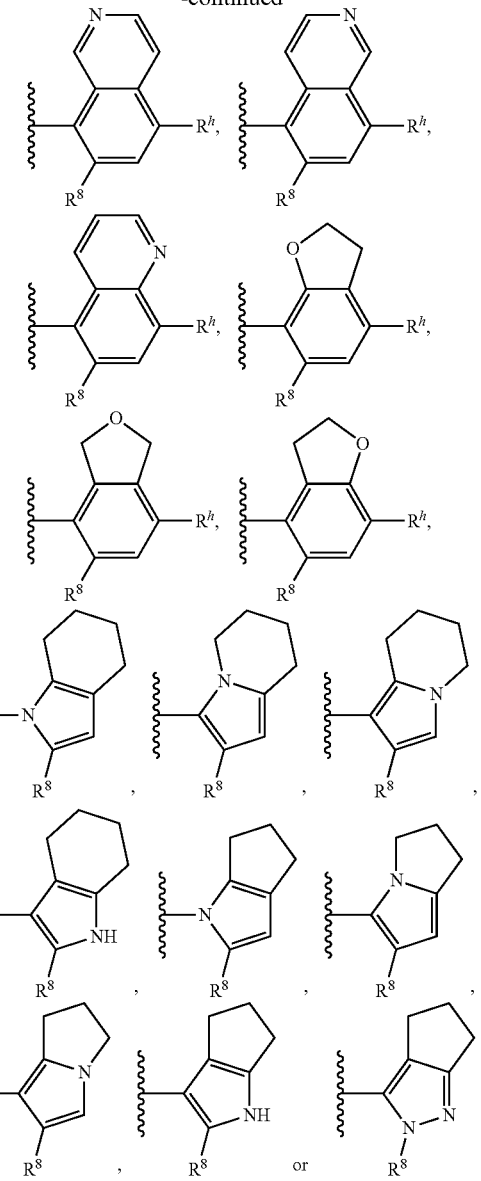

wherein $R^8$ is a 5- or 6-membered, optionally substituted heterocyclic or aromatic group, and $R^h$ is hydrogen, halo, —OH, —NO₂, —CN, —$R^{hh}$, —$OR^{hh}$, —$COR^{hh}$, —CO-$OR^{hh}$, —CONH₂, —$CONHR^{hh}$ or —$CON(R^{hh})_2$, wherein each —$R^{hh}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group are independently selected from halo, —OH, —NH₂, —CN, —NO₂, —B⁷, —OB⁷, —NHB⁷, —N(B⁷)₂, —CONH₂, —CONHB⁷, —CON(B⁷)₂, —NHCOB⁷, —NB⁷COB⁷, or —B⁷⁷—;

wherein each B⁷ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B⁷ together with the nitrogen atom to which they are attached may form a 4- to 6-membered heterocyclic group containing one or two ring heteroatoms N and/or O, wherein any B⁷ may optionally be halo-substituted and/or substituted with one or two substituents independently selected from —OH, —NH$_2$, —OB$^{78}$, —NHB$^{78}$ or —N(B$^{78}$)

wherein each B$^{77}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{78}$, —NHB$^{78}$ or —N(B$^{78}$)$_2$; and wherein each B$^{78}$ is independently selected from a C$_1$-C$_3$ alkyl or C$_1$-C$_3$ haloalkyl group.

Typically, any divalent group —B$^{77}$— forms a 4- to 6-membered fused ring. Typically, R$^h$ is hydrogen, halo, —CN, C$_1$-C$_3$ alkyl, C$_1$-C$_3$ haloalkyl, cyclopropyl or halocyclopropyl. More typically, R$^h$ is hydrogen or halo. Typically, the optional substituents on the heterocyclic or aromatic group are independently selected from halo, —OH, —NH$_2$, —CN, —NO$_2$, —B$^7$, —OB$^7$, —NHB$^7$ or —N(B$^7$)$_2$, wherein each B$^7$ is independently selected from a C$_1$-C$_4$ alkyl, C$_2$-C$_4$ alkenyl or C$_2$-C$_4$ alkynyl group all of which may optionally be halo-substituted. In another embodiment, the optional substituents on the heterocyclic or aromatic group are independently selected from halo, hydroxyl, —CN, —NH$_2$, —B$^7$ or —OB$^7$, wherein B$^7$ is a C$_1$-C$_4$ alkyl group which may optionally be halo-substituted.

In one embodiment, —R$^2$ has a formula selected from:

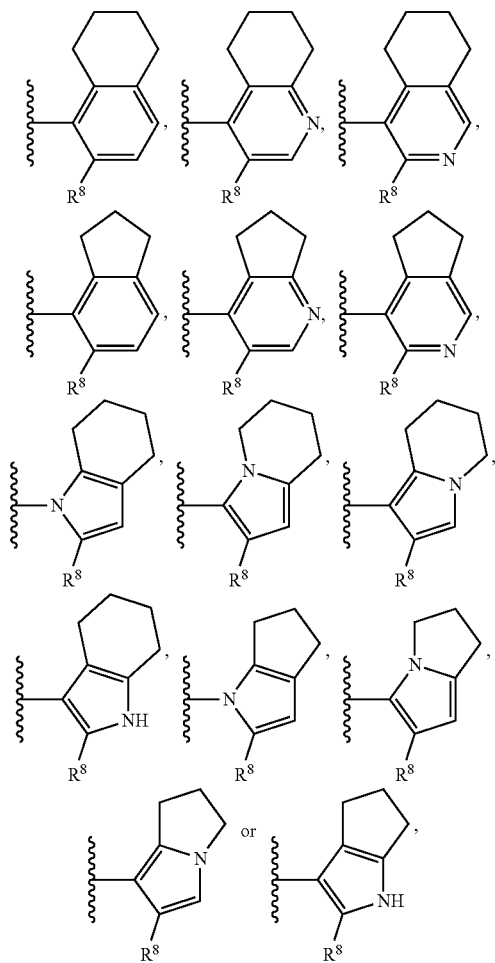

wherein R$^8$ is a 5- or 6-membered, optionally substituted heterocyclic or aromatic group. In one embodiment, the optional substituents on the heterocyclic or aromatic group are independently selected from halo, —OH, —NH$_2$, —CN, —NO$_2$, —B$^8$, —OB$^8$, —NHB$^8$, —N(B$^8$)$_2$, —CONH$_2$, —CONHB$^8$, —CON(B$^8$)$_2$, —NHCOB$^8$, —NB$^8$COB$^8$, or —B$^{88}$—;

wherein each B$^8$ is independently selected from a C$_1$-C$_4$ alkyl, C$_2$-C$_4$ alkenyl, C$_2$-C$_4$ alkynyl, C$_3$-C$_6$ cycloalkyl or phenyl group, or a 4- to 6-membered heterocyclic group containing one or two ring heteroatoms N and/or O, or two B$^8$ together with the nitrogen atom to which they are attached may form a 4- to 6-membered heterocyclic group containing one or two ring heteroatoms N and/or O, wherein any B$^8$ may optionally be halo-substituted and/or substituted with one or two substituents independently selected from —OH, —NH$_2$, —OB$^{89}$, —NHB$^{89}$ or —N(B$^{89}$)$_2$;

wherein each B$^{88}$ is independently selected from a C$_1$-C$_8$ alkylene or C$_2$-C$_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH$_2$, —OB$^{89}$, —NHB$^{89}$ or —N(B$^{89}$)$_2$; and wherein each B$^{89}$ is independently selected from a C$_1$-C$_3$ alkyl or C$_1$-C$_3$ haloalkyl group.

Typically, any divalent group —B$^{88}$— forms a 4- to 6-membered fused ring. Typically, the optional substituents on the heterocyclic or aromatic group are independently selected from halo, —OH, —NH$_2$, —CN, —NO$_2$, —B$^8$, —OB$^8$, —NHB$^8$ or —N(B$^8$)$_2$, wherein each B$^8$ is independently selected from a C$_1$-C$_4$ alkyl, C$_2$-C$_4$ alkenyl or C$_2$-C$_4$ alkynyl group all of which may optionally be halo-substituted. In another embodiment, the optional substituents on the heterocyclic or aromatic group are independently selected from halo, hydroxyl, —CN, —NH$_2$, —B$^8$ or —OB$^8$, wherein B$^8$ is a C$_1$-C$_4$ alkyl group which may optionally be halo-substituted.

Typically, —R$^2$ has a formula selected from:

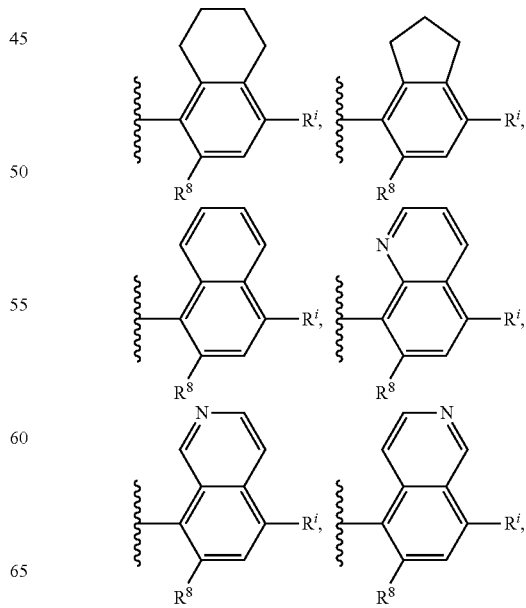

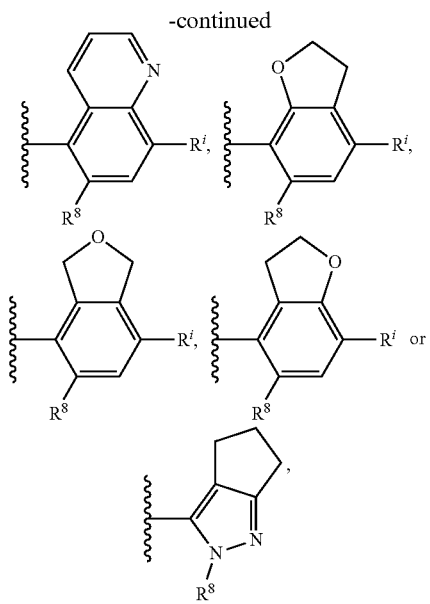

wherein R⁸ is a 5- or 6-membered, optionally substituted heterocyclic or aromatic group, and $R^i$ is hydrogen, halo, —OH, —NO₂, —CN, —$R^{ii}$, —$OR^{ii}$, —$COR^{ii}$, —$COOR^{ii}$, —CONH₂, —$CONHR^{ii}$ or —$CON(R^{ii})_2$, wherein each —$R^{ii}$ is independently selected from $C_1$-$C_4$ alkyl, $C_1$-$C_4$ haloalkyl, $C_3$-$C_4$ cycloalkyl and $C_3$-$C_4$ halocycloalkyl. In one embodiment, the optional substituents on the heterocyclic or aromatic group are independently selected from halo, —OH, —NH₂, —CN, —NO₂, —B⁹, —OB⁹, —NHB⁹, —N(B⁹)₂, —CONH₂, —CONHB⁹, —CON(B⁹)₂, —NHCOB⁹, —NB⁹COB⁹, or —B⁹⁹—;

wherein each B⁹ is independently selected from a $C_1$-$C_4$ alkyl, $C_2$-$C_4$ alkenyl, $C_2$-$C_4$ alkynyl, $C_3$-$C_6$ cycloalkyl or phenyl group, or a 4- to 6-membered heterocyclic group containing one or two ring heteroatoms N and/or O, or two B⁹ together with the nitrogen atom to which they are attached may form a 4- to 6-membered heterocyclic group containing one or two ring heteroatoms N and/or O, wherein any B⁹ may optionally be halo-substituted and/or substituted with one or two substituents independently selected from —OH, —NH₂, —OB⁹⁸, —NHB⁹⁸ or —N(B⁹⁸)

wherein each B⁹⁹ is independently selected from a $C_1$-$C_8$ alkylene or $C_2$-$C_8$ alkenylene group, wherein one or two carbon atoms in the backbone of the alkylene or alkenylene group may optionally be replaced by one or two heteroatoms N and/or O, and wherein the alkylene or alkenylene group may optionally be halo-substituted and/or substituted with one or two substituents independently selected from —OH, —NH₂, —OB⁹⁸, —NHB⁹⁸ or —N(B⁹⁸)₂; and wherein each B⁹⁸ is independently selected from a $C_1$-$C_3$ alkyl or $C_1$-$C_3$ haloalkyl group.

Typically, any divalent group —B⁹⁹— forms a 4- to 6-membered fused ring. Typically, $R^i$ is hydrogen, halo, —CN, $C_1$-$C_3$ alkyl, $C_1$-$C_3$ haloalkyl, cyclopropyl or halocyclopropyl. More typically, $R^i$ is hydrogen or halo. Typically, the optional substituents on the heterocyclic or aromatic group are independently selected from halo, —OH, —NH₂, —CN, —NO₂, —B⁹, —OB⁹, —NHB⁹ or —N(B⁹)₂, wherein each B⁹ is independently selected from a $C_1$-$C_4$ alkyl, $C_2$-$C_4$ alkenyl or $C_2$-$C_4$ alkynyl group all of which may optionally be halo-substituted. In another embodiment, the optional substituents on the heterocyclic or aromatic group are independently selected from halo, hydroxyl, —CN, —NH₂, —B⁹ or —OB⁹, wherein B⁹ is a $C_1$-$C_4$ alkyl group which may optionally be halo-substituted.

In one embodiment, R² is phenyl or a 5- or 6-membered heteroaryl group (such as phenyl, pyridinyl, pyridazinyl, pyrimidinyl or pyrazinyl); wherein (i) the phenyl or 5- or 6-membered heteroaryl group is substituted at the α position with a substituent selected from —R⁴, —OR⁴ and —COR⁴, wherein R⁴ is selected from a $C_1$-$C_6$ alkyl, $C_2$-$C_6$ alkenyl, $C_2$-$C_6$ alkynyl or $C_2$-$C_6$ cyclic group and wherein R⁴ is optionally substituted with one or more halo groups; and optionally the phenyl or 5- or 6-membered heteroaryl group is further substituted at the α' position with a substituent selected from —R¹⁴, —OR¹⁴ and —COR¹⁴, wherein R¹⁴ is selected from a $C_1$-$C_6$ alkyl, $C_2$-$C_6$ alkenyl, $C_2$-$C_6$ alkynyl or $C_2$-$C_6$ cyclic group and wherein R¹⁴ is optionally substituted with one or more halo groups; and optionally the phenyl or 5- or 6-membered heteroaryl group is further substituted (typically with one, two or three substituents independently selected from halo, —NO₂, —CN, —COOR¹⁵, —CONH₂, —CONHR¹⁵ or —CON(R¹⁵)₂, wherein each —R¹⁵ is independently selected from a $C_1$-$C_4$ alkyl or $C_1$-$C_4$ haloalkyl group);
or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and optionally the phenyl or 5- or 6-membered heteroaryl group is further substituted at the α' position with a substituent selected from —R⁴, —OR⁴ and —COR⁴, wherein R⁴ is selected from a $C_1$-$C_6$ alkyl, $C_2$-$C_6$ alkenyl, $C_2$-$C_6$ alkynyl or $C_2$-$C_6$ cyclic group and wherein R⁴ is optionally substituted with one or more halo groups; and optionally the phenyl or 5- or 6-membered heteroaryl group is further substituted (typically with one or two substituents independently selected from halo, —NO₂, —CN, —COOR¹⁵, —CONH₂, —CONHR¹⁵ or —CON(R¹⁵)₂, wherein each —R¹⁵ is independently selected from a $C_1$-$C_4$ alkyl or $C_1$-$C_4$ haloalkyl group);
or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted (typically with a substituent selected from halo, —NO₂, —CN, —COOR¹⁵, —CONH₂, —CONHR¹⁵ or —CON($R^{15}$)$_2$, wherein each —$R^{15}$ is independently selected from a $C_1$-$C_4$ alkyl or $C_1$-$C_4$ haloalkyl group); or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{12}$—$OR^{13}$, —$R^{12}$—N($R^{13}$)$_2$, —$R^{12}$—CN or —$R^{12}$—C≡$CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and optionally the phenyl or 5- or 6-membered heteroaryl group is further substituted at the α' position with a substituent selected from —$R^4$, —$OR^4$ and —$COR^4$, wherein $R^4$ is selected from a $C_1$-$C_6$ alkyl, $C_2$-$C_6$ alkenyl, $C_2$-$C_6$ alkynyl or $C_2$-$C_6$ cyclic group and wherein $R^4$ is optionally substituted with one or more halo groups; and optionally the phenyl or 5- or 6-membered heteroaryl group is further substituted (typically with one, two or three substituents independently selected from halo, —$NO_2$, —CN, —$COOR^{15}$, —$CONH_2$, —$CONHR^{15}$ or —CON($R^{15}$)$_2$, wherein each —$R^{15}$ is independently selected from a $C_1$-$C_4$ alkyl or $C_1$-$C_4$ haloalkyl group); or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, $C_1$-$C_3$ alkyl, $C_1$-$C_3$ haloalkyl, —$R^{12}$—$OR^{13}$, —$R^{12}$—N($R^{13}$)$_2$, —$R^{12}$—CN or —$R^{12}$—C≡$CR^{13}$, and wherein a ring atom of the monovalent heterocyclic or aromatic group is directly attached to the α-ring atom of the parent phenyl or 5- or 6-membered heteroaryl group; wherein $R^{12}$ is independently selected from a bond or a $C_1$-$C_3$ alkylene group; and $R^{13}$ is independently selected from hydrogen or a $C_1$-$C_3$ alkyl or $C_1$-$C_3$ haloalkyl group; and optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —$NO_2$, —CN, —$COOR^{15}$, —$CONH_2$, —$CONHR^{15}$ or —CON($R^{15}$)$_2$, wherein each —$R^{15}$ is independently selected from a $C_1$-$C_4$ alkyl or $C_1$-$C_4$ haloalkyl group).

In the embodiment directly above, where a group or moiety is optionally substituted with one or more halo groups, it may be substituted for example with one, two, three, four, five or six halo groups.

In one aspect of any of the above embodiments, $R^2$ contains from 10 to 50 atoms other than hydrogen. More typically, $R^2$ contains from 10 to 40 atoms other than hydrogen. More typically, $R^2$ contains from 10 to 35 atoms other than hydrogen. Most typically, $R^2$ contains from 12 to 30 atoms other than hydrogen.

Q is selected from O or S. In one embodiment of the first aspect of the invention, Q is O.

In one specific embodiment, the invention provides a compound of formula (I), wherein:

Q is O;

$R^1$ is a saturated or unsaturated, optionally substituted, 4-, 5- or 6-membered heterocyclic group; or $R^1$ is an optionally substituted group selected from $C_1$-$C_5$ alkyl, $C_2$-$C_5$ alkenyl, $C_2$-$C_5$ alkynyl, $C_3$-$C_6$ cycloalkyl, phenyl or benzyl; or $R^1$ is a hydrocarbyl group, wherein the hydrocarbyl group may be straight-chained or branched, or be or include cyclic groups, wherein the hydrocarbyl group may optionally be substituted, and wherein the hydrocarbyl group includes one or more heteroatoms N or O in its carbon skeleton or is substituted with a substituent comprising one or more heteroatoms N or O (typically the hydrocarbyl group contains 1-15 carbon atoms and 1-4 nitrogen or oxygen atoms); and $R^2$ is phenyl or a 5- or 6-membered heteroaryl group; wherein (i) the phenyl or 5- or 6-membered heteroaryl group is substituted at the α position with a substituent selected from —$R^{30}$, —$OR^{30}$ and —$COR^{30}$, wherein $R^{30}$ is selected from a $C_1$-$C_6$ alkyl, $C_2$-$C_6$ alkenyl, $C_2$-$C_6$ alkynyl or $C_2$-$C_6$ cyclic group and wherein $R^{30}$ is optionally substituted with one or more halo groups; and optionally the phenyl or 5- or 6-membered heteroaryl group is further substituted at the α' position with a substituent selected from —$R^{33}$, —$OR^{33}$ and —$COR^{33}$, wherein $R^{33}$ is selected from a $C_1$-$C_6$ alkyl, $C_2$-$C_6$ alkenyl, $C_2$-$C_6$ alkynyl or $C_2$-$C_6$ cyclic group and wherein $R^{33}$ is optionally substituted with one or more halo groups; and optionally the phenyl or 5- or 6-membered heteroaryl group is further substituted (typically with one, two or three substituents independently selected from halo, —$NO_2$, —CN, —$COOR^{34}$, —$CONH_2$, —$CONHR^{34}$ or —CON($R^{34}$)$_2$, wherein each —$R^{34}$ is independently selected from a $C_1$-$C_4$ alkyl or $C_1$-$C_4$ haloalkyl group); or (ii) the phenyl or 5- or 6-membered heteroaryl group is substituted with a cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and optionally the phenyl or 5- or 6-membered heteroaryl group is further substituted at the α' position with a substituent selected from —$R^{30}$, —$OR^{30}$ and —$COR^{30}$, wherein $R^{30}$ is selected from a $C_1$-$C_6$ alkyl, $C_2$-$C_6$ alkenyl, $C_2$-$C_6$ alkynyl or $C_2$-$C_6$ cyclic group and wherein $R^{30}$ is optionally substituted with one or more halo groups; and optionally the phenyl or 5- or 6-membered heteroaryl group is further substituted (typically with one or two substituents independently selected from halo, —$NO_2$, —CN, —$COOR^{34}$, —$CONH_2$, —$CONHR^{34}$ or —CON(R$^{34}$)$_2$, wherein each —R$^{34}$ is independently selected from a C$_1$-C$_4$ alkyl or C$_1$-C$_4$ haloalkyl group); or (iii) the phenyl or 5- or 6-membered heteroaryl group is substituted with a first cycloalkyl, cycloalkenyl, non-aromatic heterocyclic, aryl or heteroaryl ring which is fused to the parent phenyl or 5- or 6-membered heteroaryl group across the α,β positions and which is optionally substituted with one or more halo groups; and the phenyl or 5- or 6-membered heteroaryl group is substituted with a second cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl group is further substituted (typically with a substituent selected from halo, —NO$_2$, —CN, —COOR$^{34}$, —CONH$_2$, —CONHR$^{34}$ or —CON(R$^{34}$)$_2$, wherein each —R$^{34}$ is independently selected from a C$_1$-C$_4$ alkyl or C$_1$-C$_4$ haloalkyl group); or (iv) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, C$_1$-C$_3$ alkyl, C$_1$-C$_3$ haloalkyl, —R$^{31}$—OR$^{32}$, —R$^{31}$—N(R$^{32}$)$_2$, —R$^{31}$—CN or —R$^{31}$—C≡CR$^{32}$, and wherein a ring atom of the monovalent heterocyclic or aromatic group is directly attached to the α-ring atom of the parent phenyl or 5- or 6-membered heteroaryl group; wherein R$^{31}$ is independently selected from a bond or a C$_1$-C$_3$ alkylene group; and R$^{32}$ is independently selected from hydrogen or a C$_1$-C$_3$ alkyl or C$_1$-C$_3$ haloalkyl group; and optionally the phenyl or 5- or 6-membered heteroaryl group is further substituted at the α' position with a substituent selected from —R$^{30}$, —OR$^{30}$ and —COR$^{30}$, wherein R$^{30}$ is selected from a C$_1$-C$_6$ alkyl, C$_2$-C$_6$ alkenyl, C$_2$-C$_6$ alkynyl or C$_2$-C$_6$ cyclic group and wherein R$^{30}$ is optionally substituted with one or more halo groups; and optionally the phenyl or 5- or 6-membered heteroaryl group is further substituted (typically with one, two or three substituents independently selected from halo, —NO$_2$, —CN, —COOR$^{34}$, —CONH$_2$, —CONHR$^{34}$ or —CON(R$^{34}$)$_2$, wherein each —R$^{34}$ is independently selected from a C$_1$-C$_4$ alkyl or C$_1$-C$_4$ haloalkyl group); or (v) the phenyl or 5- or 6-membered heteroaryl group is substituted at the α-position with a monovalent heterocyclic group or a monovalent aromatic group selected from phenyl, pyridinyl, pyrimidinyl, pyrazolyl, imidazolyl, triazolyl or tetrahydropyranyl, wherein the monovalent heterocyclic or aromatic group may optionally be substituted with one or two substituents independently selected from halo, C$_1$-C$_3$ alkyl, C$_1$-C$_3$ haloalkyl, —R$^{31}$—OR$^{32}$, —R$^{31}$—N(R$^{32}$)$_2$, —R$^{31}$—CN or —R$^{31}$—C≡CR$^{32}$, and wherein a ring atom of the monovalent heterocyclic or aromatic group is directly attached to the α-ring atom of the parent phenyl or 5- or 6-membered heteroaryl group; wherein R$^{31}$ is independently selected from a bond or a C$_1$-C$_3$ alkylene group; and R$^{32}$ is independently selected from hydrogen or a C$_1$-C$_3$ alkyl or C$_1$-C$_3$ haloalkyl group; and optionally the phenyl or 5- or 6-membered heteroaryl group is further substituted with a cycloalkyl, cycloalkenyl, non-aromatic heterocyclic, aryl or heteroaryl ring which is fused to the parent phenyl or 5- or 6-membered heteroaryl group across the α',β' positions and which is optionally substituted with one or more halo groups; and optionally the phenyl or 5- or 6-membered heteroaryl group is further substituted (typically with one or two substituents independently selected from halo, —NO$_2$, —CN, —COOR$^{34}$, —CONH$_2$, —CONHR$^{34}$ or —CON(R$^{34}$)$_2$, wherein each —R$^{34}$ is independently selected from a C$_1$-C$_4$ alkyl or C$_1$-C$_4$ haloalkyl group).

In this specific embodiment, R$^1$ may be a pyrazolyl, imidazolyl, triazolyl, pyrrolyl, azetidinyl, pyrrolidinyl or piperidinyl group, all of which may optionally be substituted; or R$^1$ may be an optionally substituted group selected from C$_1$-C$_5$ alkyl, C$_2$-C$_5$ alkenyl, C$_2$-C$_5$ alkynyl, C$_3$-C$_6$ cycloalkyl, phenyl or benzyl.

In this specific embodiment, R$^1$ may be substituted with one or more (such as one, two, three or four) substituents independently selected from halo; —CN; —NO$_2$; —R$^β$; —OH; —OR$^β$; —R$^α$—OH; —R$^α$—OR$^β$; —NH$_2$; —NHR$^β$; —N(R$^β$)$_2$; —R$^α$—NH$_2$; —R$^α$—NHR$^β$; or —R$^α$—N(R$^β$)$_2$;

wherein each —R$^α$— is independently selected from an alkylene, alkenylene or alkynylene group, wherein the alkylene, alkenylene or alkynylene group contains from 1 to 6 carbon atoms in its backbone; and wherein each —R$^β$ is independently selected from a C$_1$-C$_6$ alkyl, C$_2$-C$_6$ alkenyl, C$_2$-C$_6$ alkynyl or C$_3$-C$_7$ cycloalkyl group, and wherein any —R$^β$ may optionally be substituted with one or more (such as one, two, three or four) substituents independently selected from a C$_1$-C$_4$ alkyl, halo, —OH or 4- to 6-membered heterocyclic group.

In this specific embodiment, the parent phenyl or 5- or 6-membered heteroaryl group of R$^2$ may be selected from phenyl, pyridinyl, pyridazinyl, pyrimidinyl or pyrazinyl.

In this specific embodiment, where a group or moiety is optionally substituted with one or more halo groups, it may be substituted for example with one, two, three, four, five or six halo groups.

In one aspect of any of the above embodiments, the compound of formula (I) has a molecular weight of from 250 to 2000 Da. Typically, the compound of formula (I) has a molecular weight of from 280 to 900 Da. More typically, the compound of formula (I) has a molecular weight of from 310 to 600 Da.

A second aspect of the invention provides a compound selected from the group consisting of:

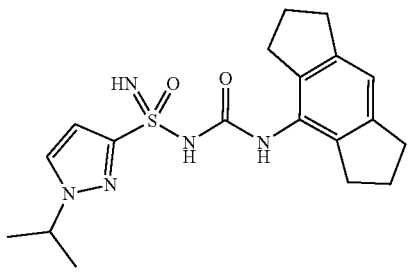

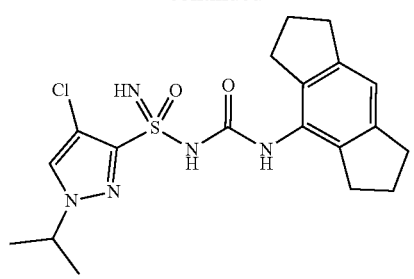
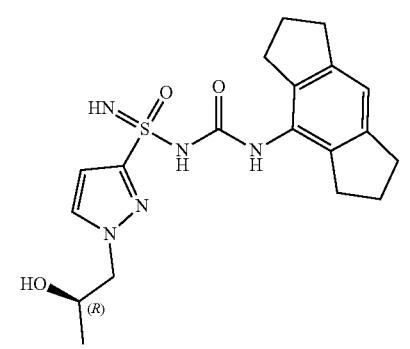
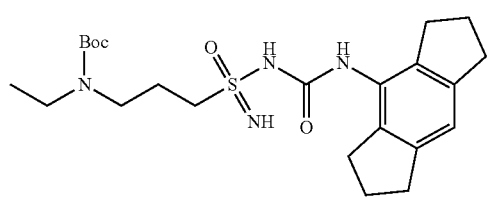
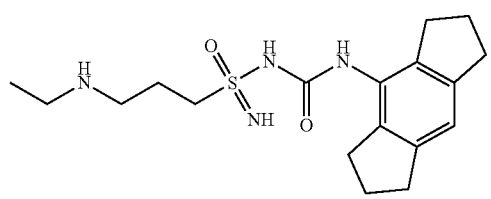
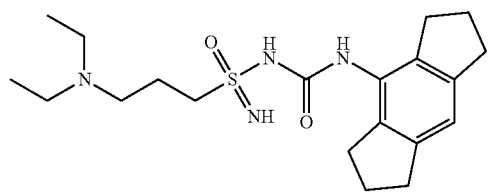
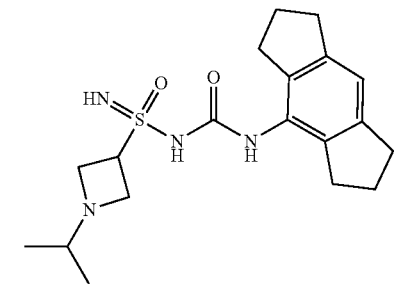
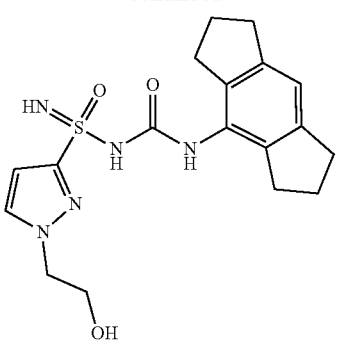
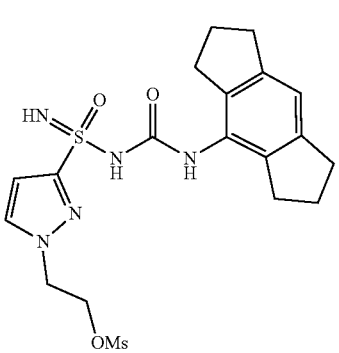
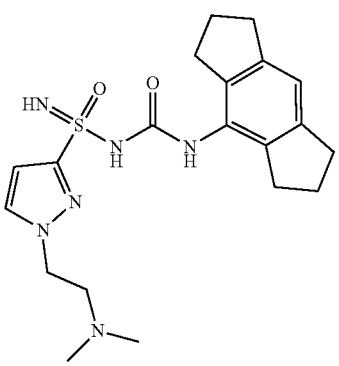
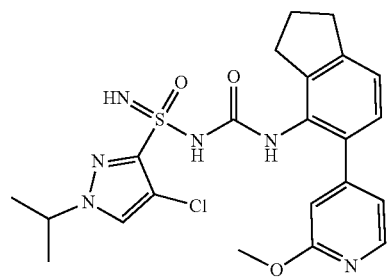
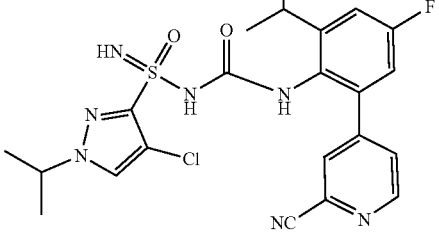

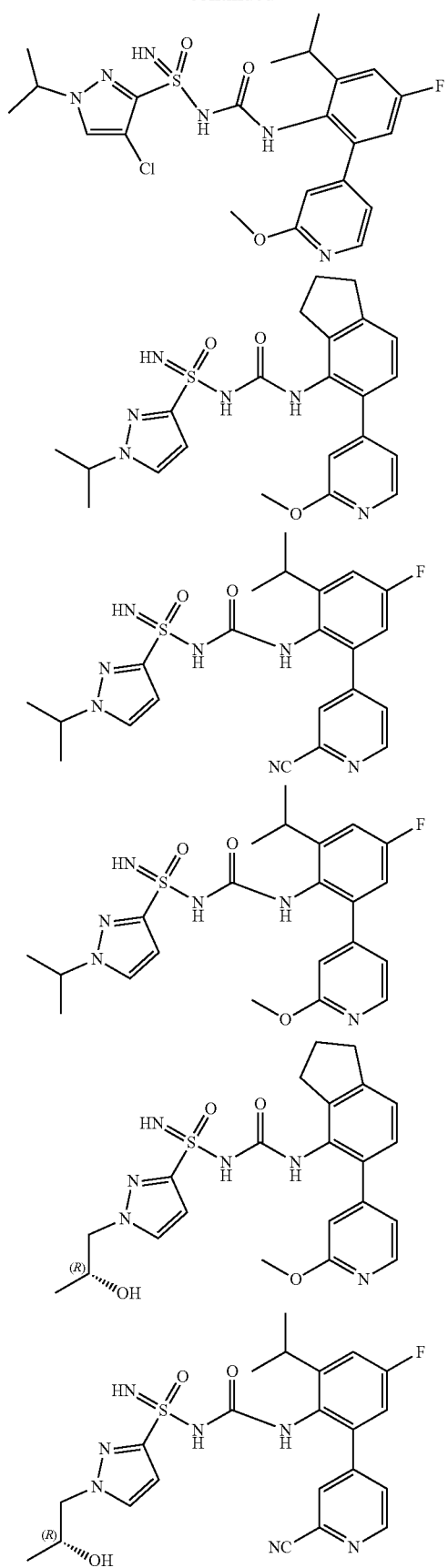
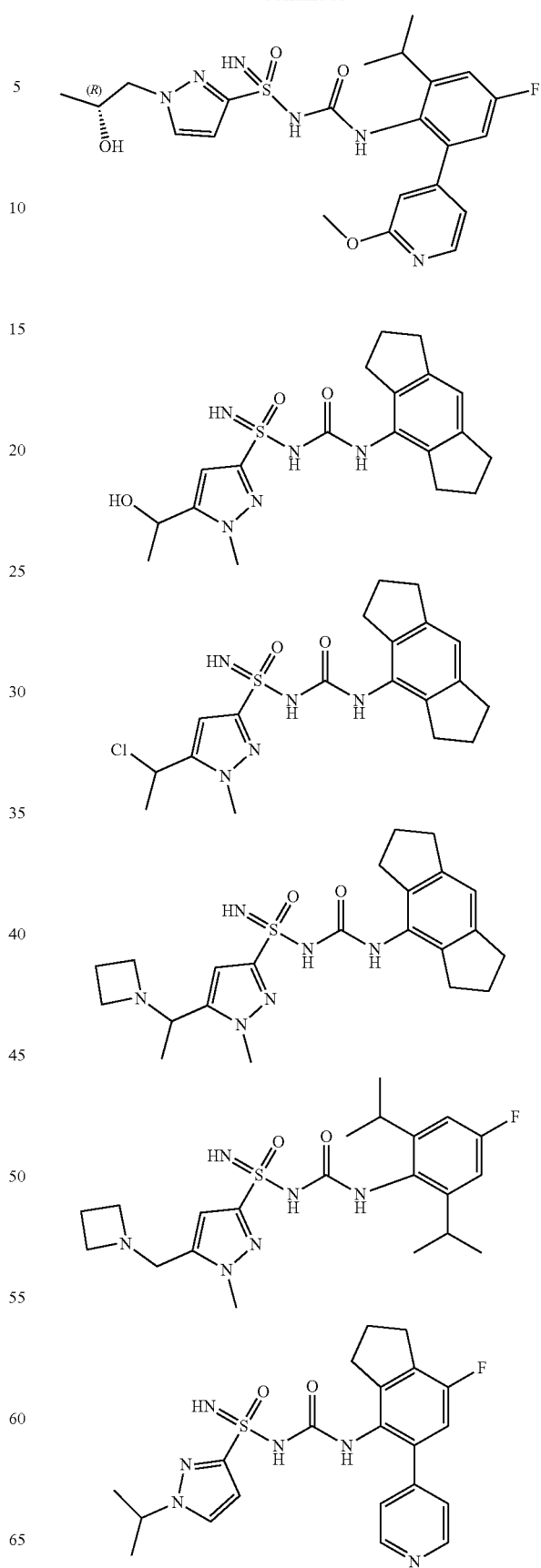

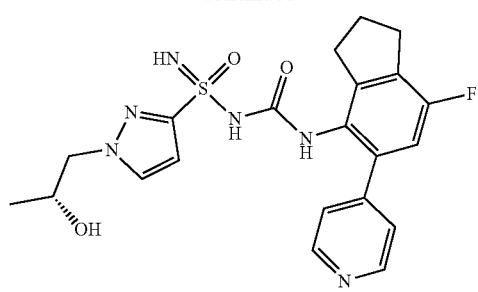
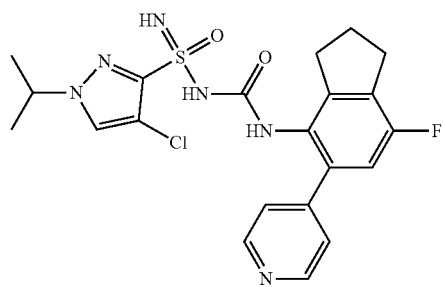
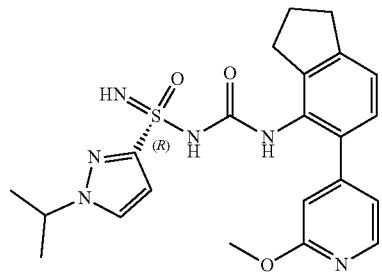
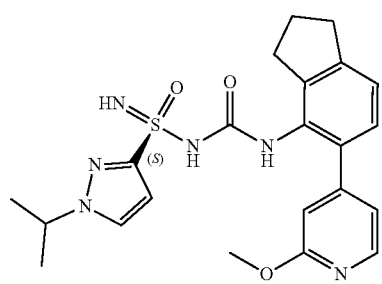
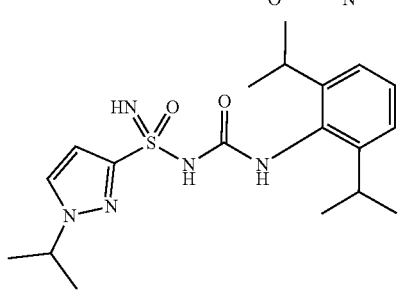
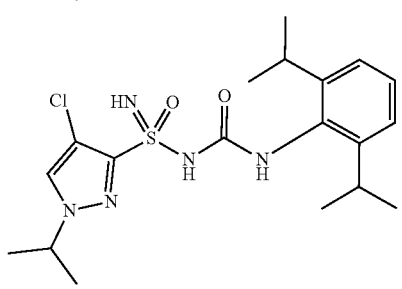
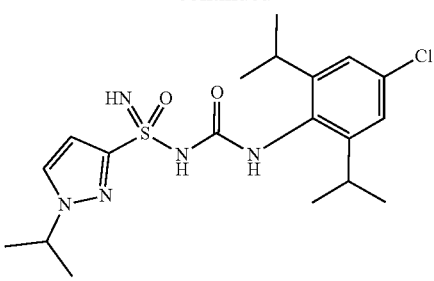
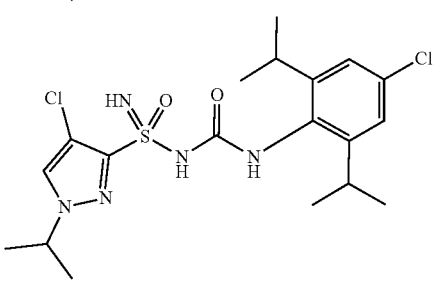
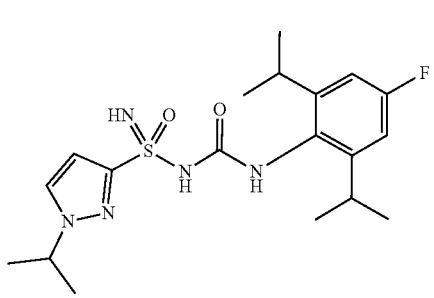
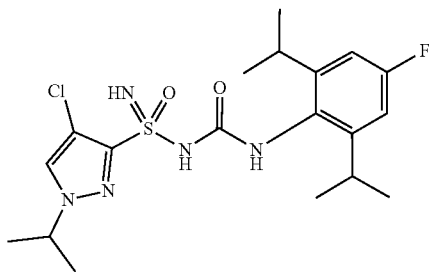
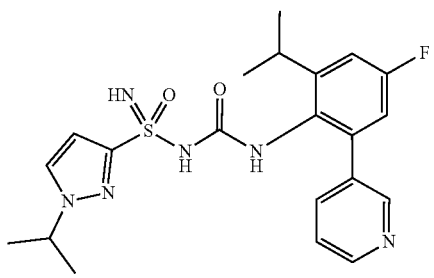
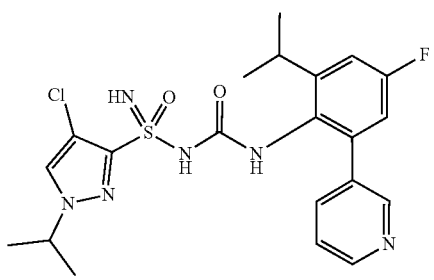

-continued
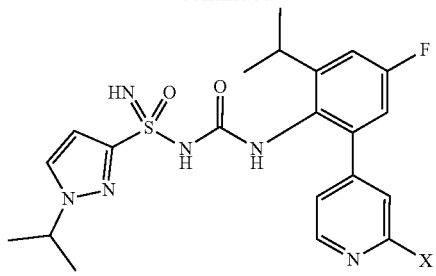
where X is H, Me, Et, $^n$Pr, $^i$Pr, OMe, OEt, O$^n$Pr, O$^i$Pr, OH, NH$_2$, CN, F, Cl or Br
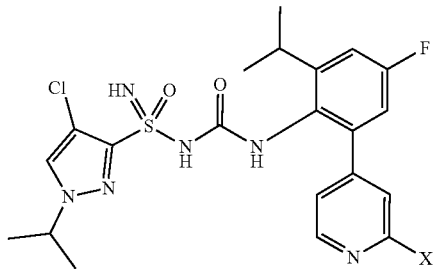
where X is H, Me, Et, $^n$Pr, $^i$Pr, OMe, OEt, O$^n$Pr, O$^i$Pr, OH, NH$_2$, CN, F, Cl or Br
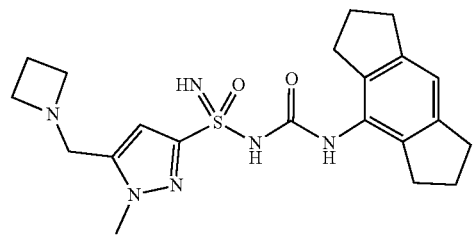
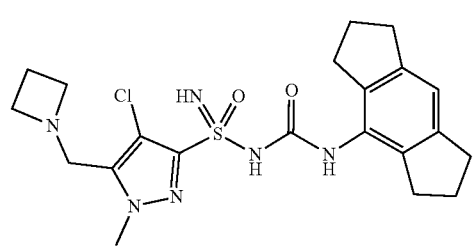
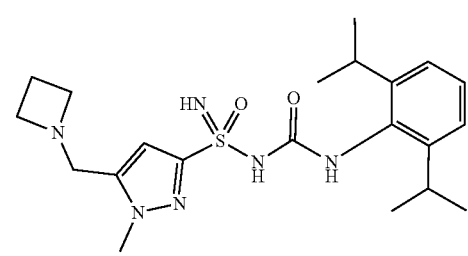
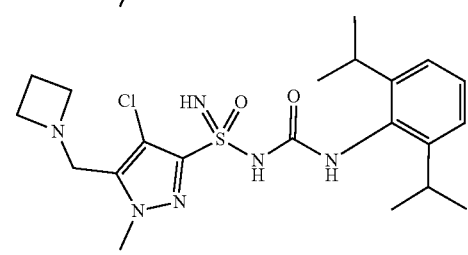
-continued
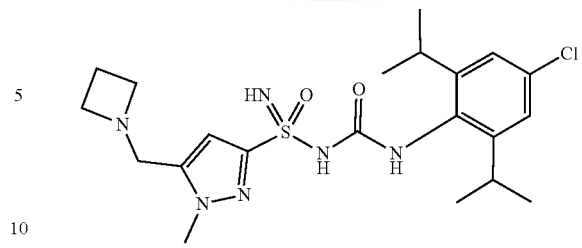
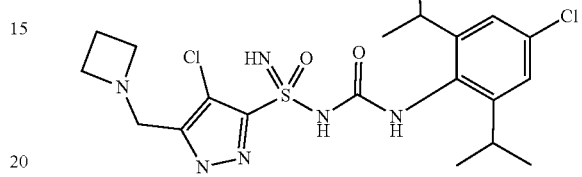
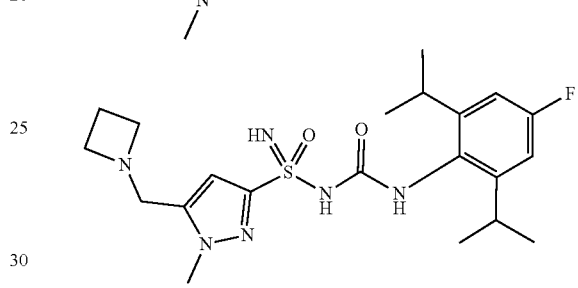
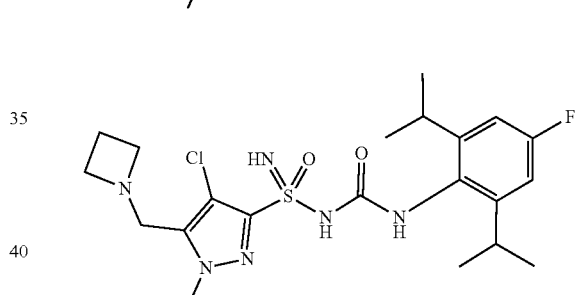
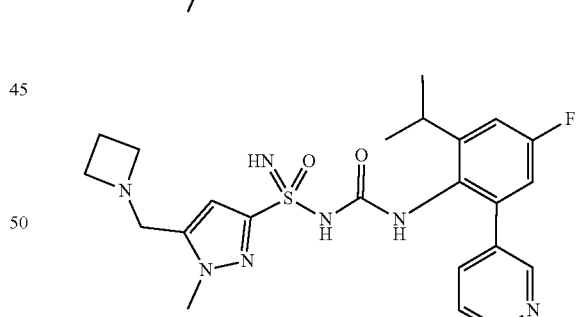
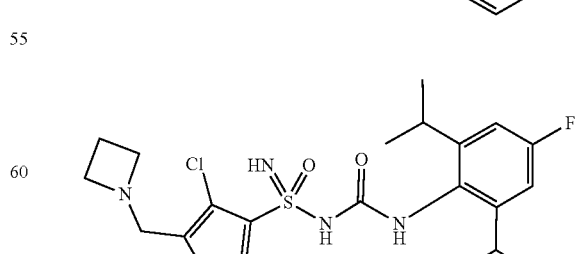

47
-continued
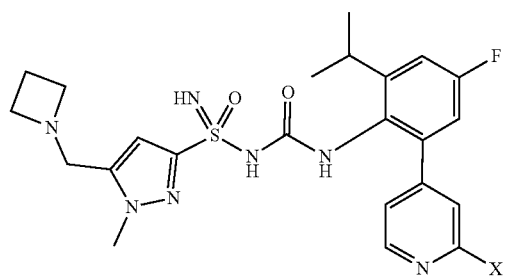
where X is H, Me, Et, $^n$Pr, $^i$PR, OMe, OEt, O$^n$Pr, O$^i$Pr, OH, NH$_2$, CN, F, Cl or Br
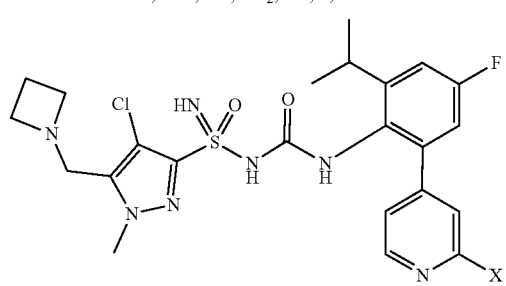
where X is H, Me, Et, $^n$Pr, $^i$PR, OMe, OEt, O$^n$Pr, O$^i$Pr, OH, NH$_2$, CN, F, Cl or Br
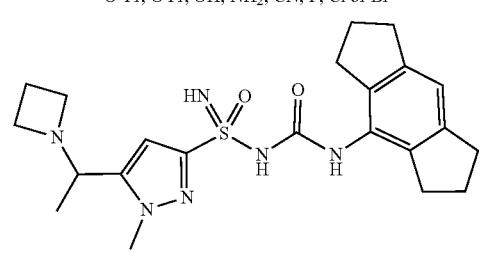
48
-continued
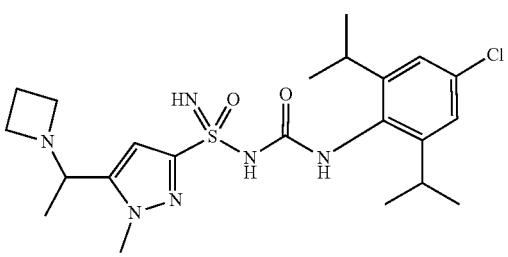
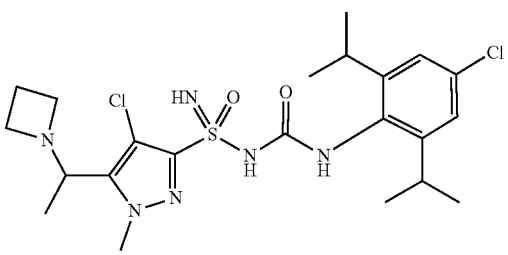
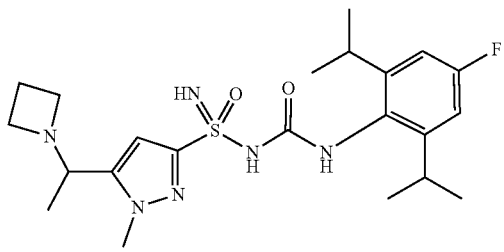
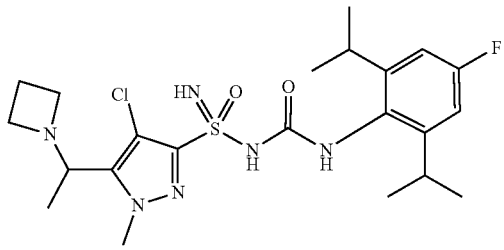
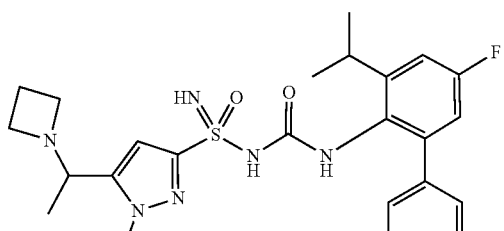
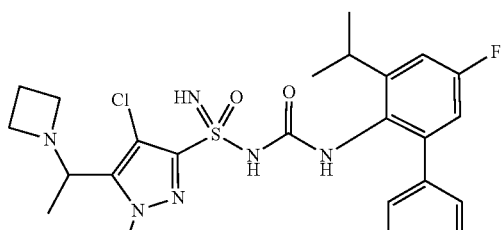

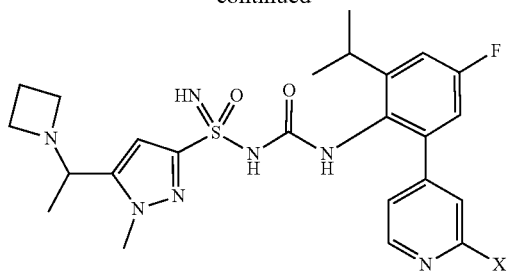
where X is H, Me, Et, <sup>n</sup>Pr, <sup>i</sup>Pr, OMe, OEt, O<sup>n</sup>Pr, O<sup>i</sup>Pr, OH, NH$_2$, CN, F, Cl or Br
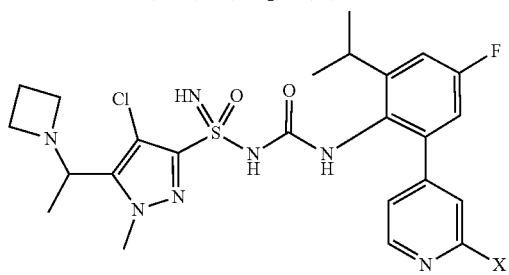
where X is H, Me, Et, <sup>n</sup>Pr, <sup>i</sup>Pr, OMe, OEt, O<sup>n</sup>Pr, O<sup>i</sup>Pr, OH, NH$_2$, CN, F, Cl or Br
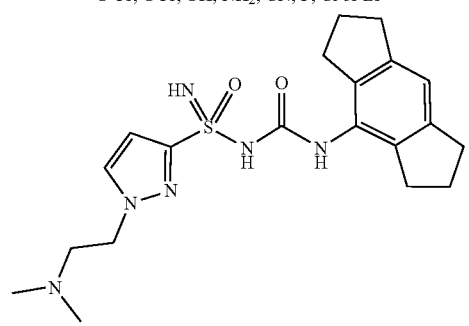
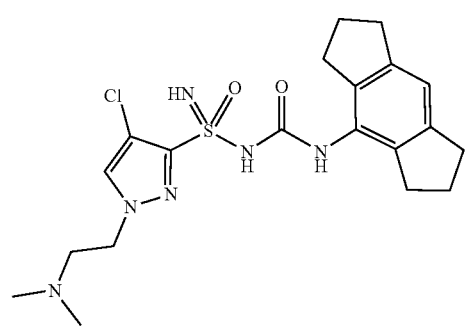
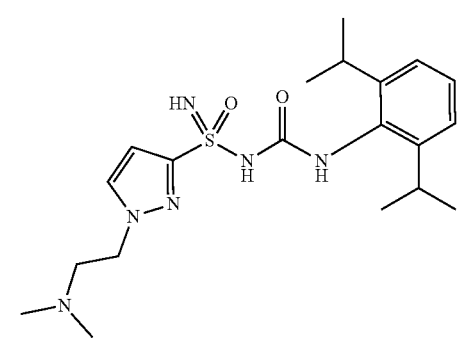
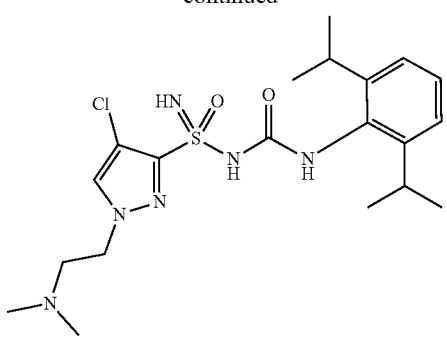
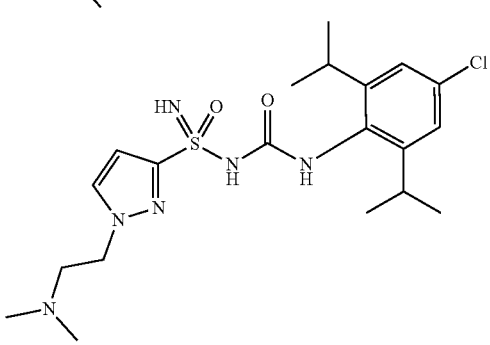
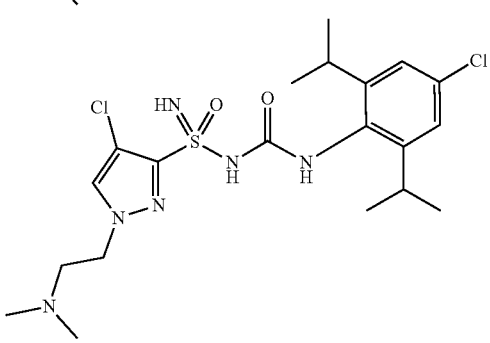
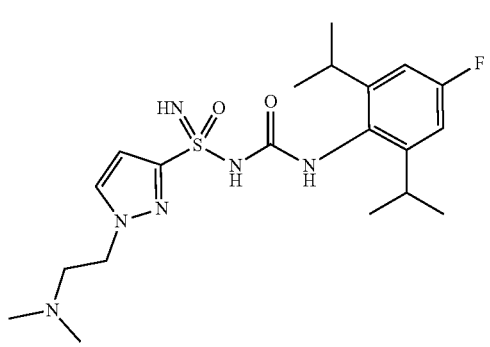
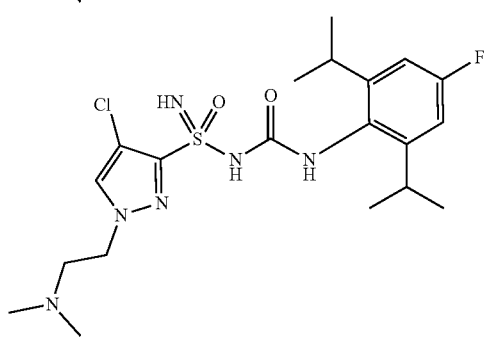

51
-continued
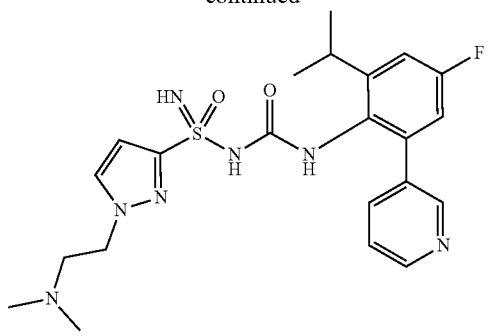
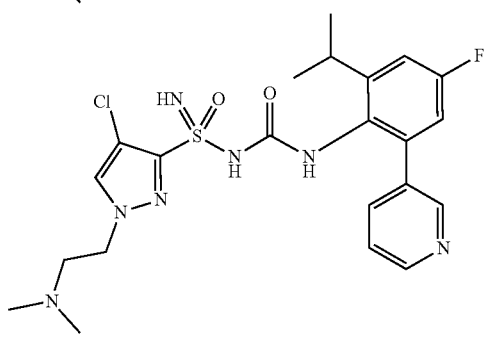
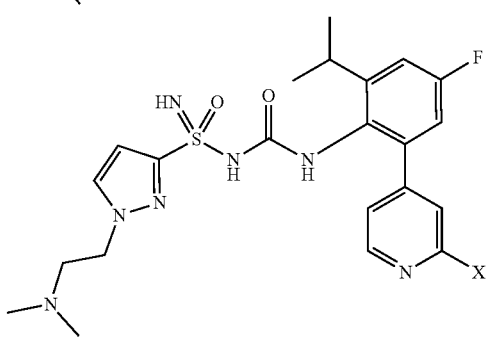
where X is H, Me, Et, $^n$Pr, OMe, OEt, O$^n$Pr, O$^i$Pr, OH, NH$_2$, CN, F, Cl, or Br
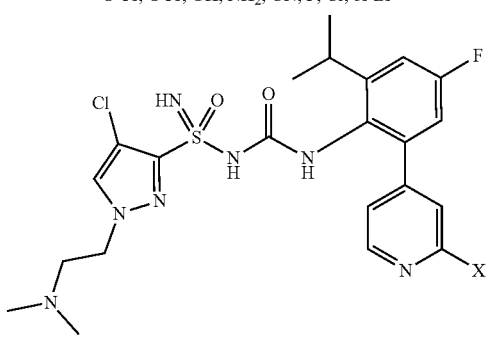
where X is H, Me, Et, $^n$Pr, OMe, OEt, O$^n$Pr, O$^i$Pr, OH, NH$_2$, CN, F, Cl, or Br
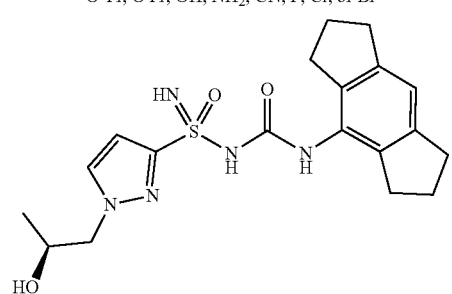
52
-continued
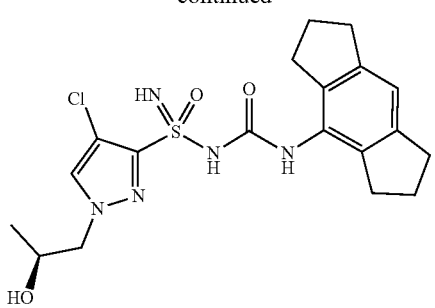
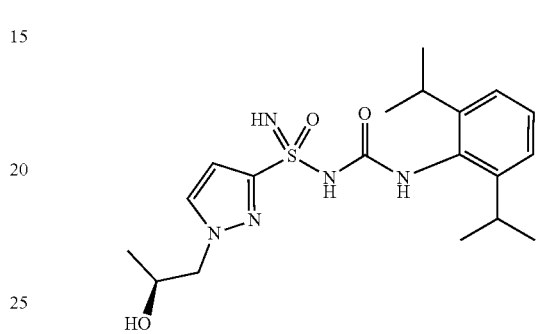
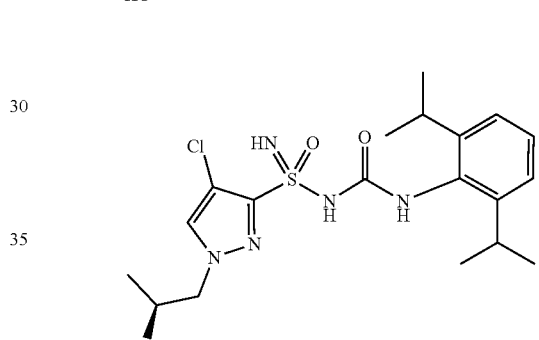
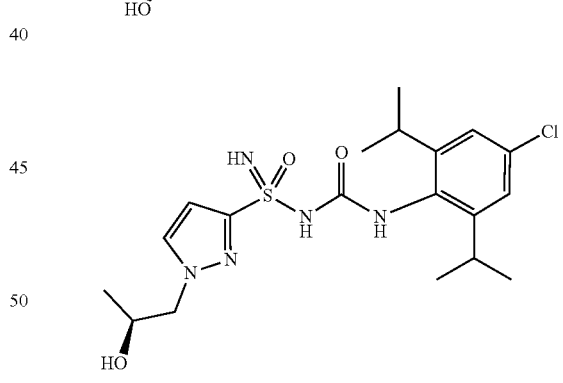
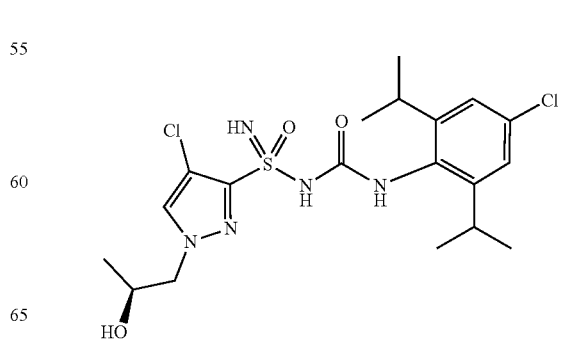

53
-continued
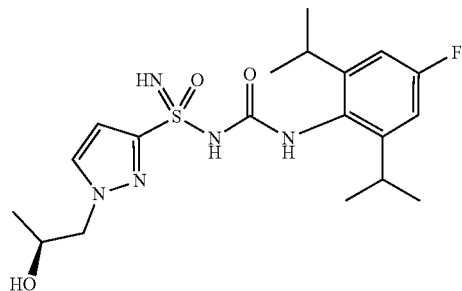
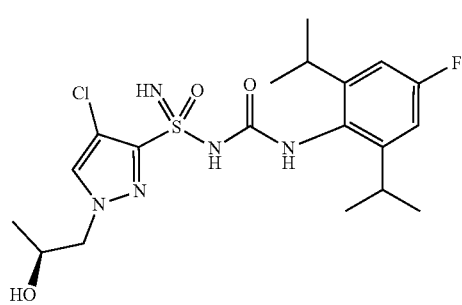
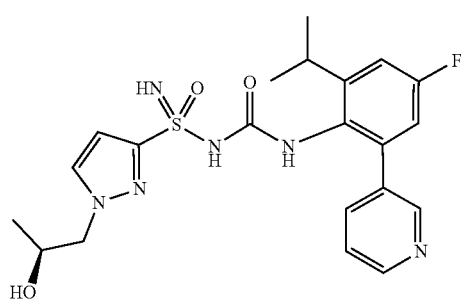
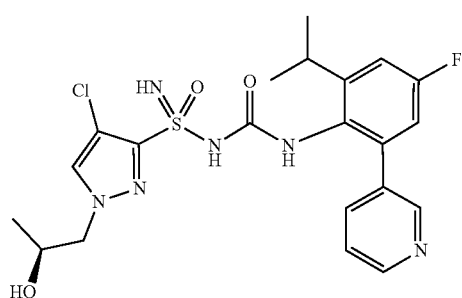
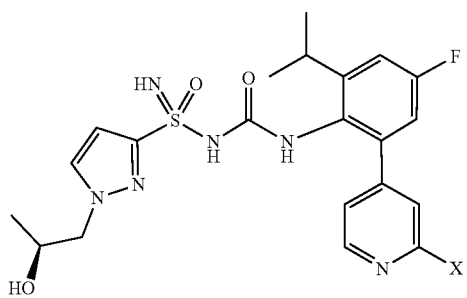
where X is H, Me, Et, $^n$Pr, $^i$Pr, OMe, OEt, O$^n$Pr, O$^i$Pr, OH, NH$_2$, CN, F, Cl or Br
54
-continued
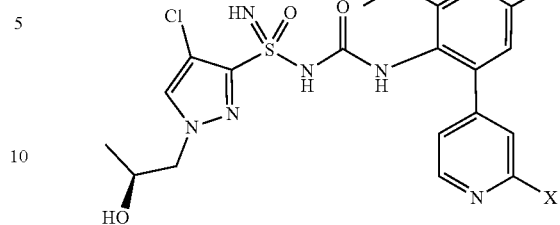
where X is H, Me, Et, $^n$Pr, $^i$Pr, OMe, OEt, O$^n$Pr, O$^i$Pr, OH, NH$_2$, CN, F, Cl or Br
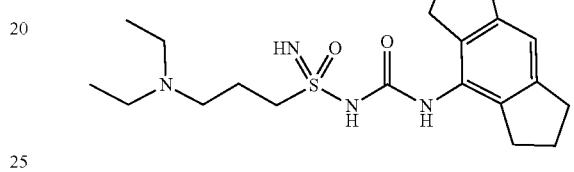
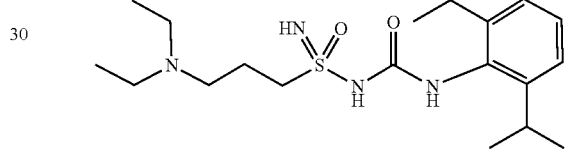
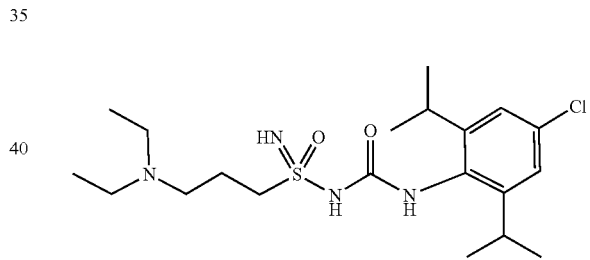
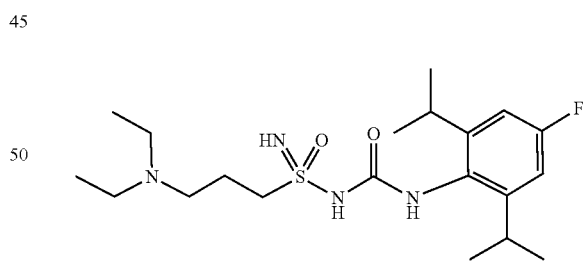
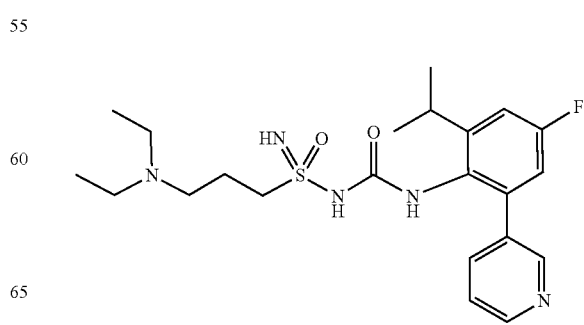

-continued

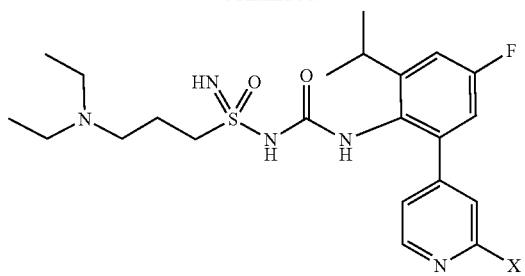

where X is H, Me, Et, $^n$Pr, $^i$Pr, OMe, OEt, O$^n$Pr, O$^i$Pr, OH, NH$_2$, CN, F, Cl or Br

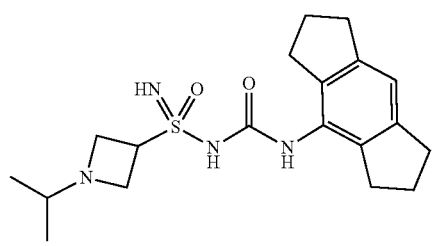

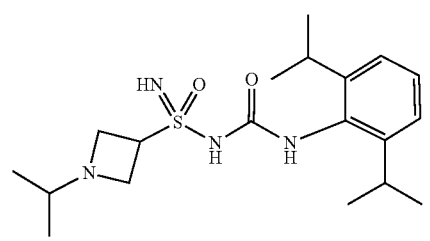

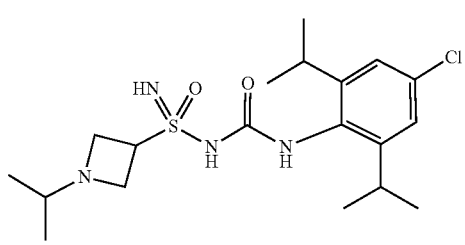

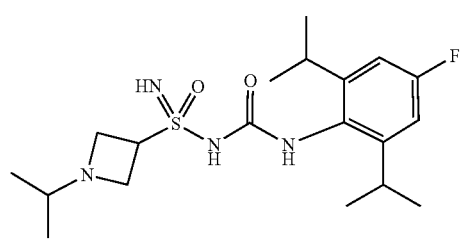

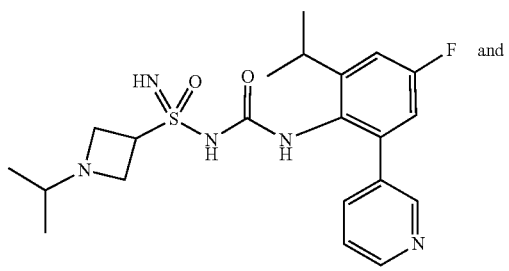

and

-continued

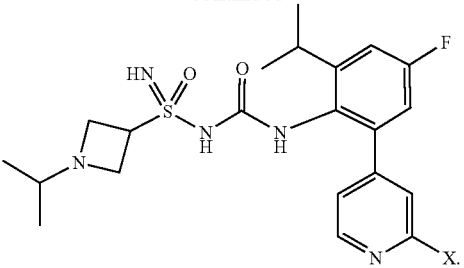

where X is H, Me, Et, $^n$Pr, $^i$Pr, OMe, OEt, O$^n$Pr, O$^i$Pr, OH, NH$_2$, CN, F, Cl or Br A third aspect of the invention provides a pharmaceutically acceptable salt, solvate or prodrug of any compound of the first or second aspect of the invention.

The compounds of the present invention can be used both in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulfuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulfonic acids (for example, methanesulfonic, trifluoromethanesulfonic, ethanesulfonic, 2-hydroxyethanesulfonic, benzenesulfonic, toluene-p-sulfonic, naphthalene-2-sulfonic or camphorsulfonic acid) or amino acids (for example, ornithinic, glutamic or aspartic acid). The acid addition salt may be a mono-, di-, tri- or multi-acid addition salt. A preferred salt is a hydrohalogenic, sulfuric, phosphoric or organic acid addition salt. A preferred salt is a hydrochloric acid addition salt.

Where a compound of the invention includes a quaternary ammonium group, typically the compound is used in its salt form. The counter ion to the quaternary ammonium group may be any pharmaceutically acceptable, non-toxic counter ion. Examples of suitable counter ions include the conjugate bases of the protic acids discussed above in relation to acid-addition salts.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt or a mono- or di-potassium salt.

Preferably any salt is a pharmaceutically acceptable non-toxic salt. However, in addition to pharmaceutically acceptable salts, other salts are included in the present invention, since they have potential to serve as intermediates in the purification or preparation of other, for example, pharmaceutically acceptable salts, or are useful for identification, characterisation or purification of the free acid or base.

The compounds and/or salts of the present invention may be anhydrous or in the form of a hydrate (e.g. a hemihydrate, monohydrate, dihydrate or trihydrate) or other solvate. Such solvates may be formed with common organic solvents, including but not limited to, alcoholic solvents e.g. methanol, ethanol or isopropanol.

In some embodiments of the present invention, therapeutically inactive prodrugs are provided. Prodrugs are compounds which, when administered to a subject such as a human, are converted in whole or in part to a compound of the invention. In most embodiments, the prodrugs are pharmacologically inert chemical derivatives that can be converted in vivo to the active drug molecules to exert a therapeutic effect. Any of the compounds described herein can be administered as a prodrug to increase the activity, bioavailability, or stability of the compound or to otherwise alter the properties of the compound. Typical examples of prodrugs include compounds that have biologically labile protecting groups on a functional moiety of the active compound. Prodrugs include, but are not limited to, compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound. The present invention also encompasses salts and solvates of such prodrugs as described above.

The compounds, salts, solvates and prodrugs of the present invention may contain at least one chiral centre. The compounds, salts, solvates and prodrugs may therefore exist in at least two isomeric forms. The present invention encompasses racemic mixtures of the compounds, salts, solvates and prodrugs of the present invention as well as enantiomerically enriched and substantially enantiomerically pure isomers. For the purposes of this invention, a "substantially enantiomerically pure" isomer of a compound comprises less than 5% of other isomers of the same compound, more typically less than 2%, and most typically less than 0.5% by weight.

The compounds, salts, solvates and prodrugs of the present invention may contain any stable isotope including, but not limited to $^{12}C$, $^{13}C$, $^{1}H$, $^{2}H$ (D), $^{14}N$, $^{15}N$, $^{16}O$, $^{17}O$, $^{18}O$, $^{19}F$ and $^{127}I$, and any radioisotope including, but not limited to $^{11}C$, $^{14}C$, $^{3}H$ (T), $^{13}N$, $^{15}O$, $^{18}F$, $^{123}I$, $^{124}I$, $^{125}I$ and $^{131}I$.

The compounds, salts, solvates and prodrugs of the present invention may be in any polymorphic or amorphous form.

A fourth aspect of the invention provides a pharmaceutical composition comprising a compound of the first or second aspect of the invention, or a pharmaceutically acceptable salt, solvate or prodrug of the third aspect of the invention, and a pharmaceutically acceptable excipient.

Conventional procedures for the selection and preparation of suitable pharmaceutical formulations are described in, for example, "Aulton's Pharmaceutics—The Design and Manufacture of Medicines", M. E. Aulton and K. M. G. Taylor, Churchill Livingstone Elsevier, 4$^{th}$ Ed., 2013.

Pharmaceutically acceptable excipients including adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

In one embodiment, the pharmaceutical composition of the fourth aspect of the invention additionally comprises one or more further active agents.

In a further embodiment, the pharmaceutical composition of the fourth aspect of the invention may be provided as a part of a kit of parts, wherein the kit of parts comprises the pharmaceutical composition of the fourth aspect of the invention and one or more further pharmaceutical compositions, wherein the one or more further pharmaceutical compositions each comprise a pharmaceutically acceptable excipient and one or more further active agents.

A fifth aspect of the invention provides a compound of the first or second aspect of the invention, or a pharmaceutically acceptable salt, solvate or prodrug of the third aspect of the invention, or a pharmaceutical composition of the fourth aspect of the invention, for use in medicine, and/or for use in the treatment or prevention of a disease, disorder or condition. Typically, the use comprises the administration of the compound, salt, solvate, prodrug or pharmaceutical composition to a subject. In one embodiment, the use comprises the co-administration of one or more further active agents.

The term "treatment" as used herein refers equally to curative therapy, and ameliorating or palliative therapy. The term includes obtaining beneficial or desired physiological results, which may or may not be established clinically. Beneficial or desired clinical results include, but are not limited to, the alleviation of symptoms, the prevention of symptoms, the diminishment of extent of disease, the stabilisation (i.e., not worsening) of a condition, the delay or slowing of progression/worsening of a condition/symptoms, the amelioration or palliation of the condition/symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering a compound, salt, solvate, prodrug or pharmaceutical composition of the present invention. The term "prevention" as used herein in relation to a disease, disorder or condition, relates to prophylactic or preventative therapy, as well as therapy to reduce the risk of developing the disease, disorder or condition. The term "prevention" includes both the avoidance of occurrence of the disease, disorder or condition, and the delay in onset of the disease, disorder or condition. Any statistically significant ($p \leq 0.05$) avoidance of occurrence, delay in onset or reduction in risk as measured by a controlled clinical trial may be deemed a prevention of the disease, disorder or condition. Subjects amenable to prevention include those at heightened risk of a disease, disorder or condition as identified by genetic or biochemical markers. Typically, the genetic or biochemical markers are appropriate to the disease, disorder or condition under consideration and may include for example, inflammatory biomarkers such as C-reactive protein (CRP) and monocyte chemoattractant protein 1 (MCP-1) in the case of inflammation; total cholesterol, triglycerides, insulin resistance and C-peptide in the case of NAFLD and NASH; and more generally IL1β and IL18 in the case of a disease, disorder or condition responsive to NLRP3 inhibition.

A sixth aspect of the invention provides the use of a compound of the first or second aspect, or a pharmaceutically effective salt, solvate or prodrug of the third aspect, in the manufacture of a medicament for the treatment or prevention of a disease, disorder or condition. Typically, the treatment or prevention comprises the administration of the compound, salt, solvate, prodrug or medicament to a subject. In one embodiment, the treatment or prevention comprises the co-administration of one or more further active agents.

A seventh aspect of the invention provides a method of treatment or prevention of a disease, disorder or condition, the method comprising the step of administering an effective amount of a compound of the first or second aspect, or a pharmaceutically acceptable salt, solvate or prodrug of the third aspect, or a pharmaceutical composition of the fourth aspect, to thereby treat or prevent the disease, disorder or condition. In one embodiment, the method further comprises the step of co-administering an effective amount of one or more further active agents. Typically, the administration is to a subject in need thereof.

An eighth aspect of the invention provides a compound of the first or second aspect of the invention, or a pharmaceutically acceptable salt, solvate or prodrug of the third aspect of the invention, or a pharmaceutical composition of the fourth aspect of the invention, for use in the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the use comprises the administration of the compound, salt, solvate, prodrug or pharmaceutical composition to the individual. In one embodiment, the use comprises the co-administration of one or more further active agents. The use may also comprise the diagnosis of an individual having a germline or somatic non-silent mutation in NLRP3, wherein the compound, salt, solvate, prodrug or pharmaceutical composition is administered to an individual on the basis of a positive diagnosis for the mutation. Typically, identification of the mutation in NLRP3 in the individual may be by any suitable genetic or biochemical means.

A ninth aspect of the invention provides the use of a compound of the first or second aspect, or a pharmaceutically effective salt, solvate or prodrug of the third aspect, in the manufacture of a medicament for the treatment or prevention of a disease, disorder or condition in an individual, wherein the individual has a germline or somatic non-silent mutation in NLRP3. The mutation may be, for example, a gain-of-function or other mutation resulting in increased NLRP3 activity. Typically, the treatment or prevention comprises the administration of the compound, salt, solvate, prodrug or medicament to the individual. In one embodiment, the treatment or prevention comprises the co-administration of one or more further active agents. The treatment or prevention may also comprise the diagnosis of an individual having a germline or somatic non-silent mutation in NLRP3, wherein the compound, salt, solvate, prodrug or medicament is administered to an individual on the basis of a positive diagnosis for the mutation. Typically, identification of the mutation in NLRP3 in the individual may be by any suitable genetic or biochemical means.

A tenth aspect of the invention provides a method of treatment or prevention of a disease, disorder or condition, the method comprising the steps of diagnosing of an individual having a germline or somatic non-silent mutation in NLRP3, and administering an effective amount of a compound of the first or second aspect, or a pharmaceutically acceptable salt, solvate or prodrug of the third aspect, or a pharmaceutical composition of the fourth aspect, to the positively diagnosed individual, to thereby treat or prevent the disease, disorder or condition. In one embodiment, the method further comprises the step of co-administering an effective amount of one or more further active agents. Typically, the administration is to a subject in need thereof.

In general embodiments, the disease, disorder or condition may be a disease, disorder or condition of the immune system, the cardiovascular system, the endocrine system, the gastrointestinal tract, the renal system, the hepatic system, the metabolic system, the respiratory system, the central nervous system, may be a cancer or other malignancy, and/or may be caused by or associated with a pathogen.

It will be appreciated that these general embodiments defined according to broad categories of diseases, disorders and conditions are not mutually exclusive. In this regard any particular disease, disorder or condition may be categorized according to more than one of the above general embodiments. A non-limiting example is type I diabetes which is an autoimmune disease and a disease of the endocrine system.

In one embodiment of the fifth, sixth, seventh, eighth, ninth or tenth aspect of the present invention, the disease, disorder or condition is responsive to NLRP3 inhibition. As used herein, the term "NLRP3 inhibition" refers to the complete or partial reduction in the level of activity of NLRP3 and includes, for example, the inhibition of active NLRP3 and/or the inhibition of activation of NLRP3.

There is evidence for a role of NLRP3-induced IL-1 and IL-18 in the inflammatory responses occurring in connection with, or as a result of, a multitude of different disorders (Menu et al., Clinical and Experimental Immunology, 166: 1-15, 2011; Strowig et al., Nature, 481: 278-286, 2012).

NLRP3 has been implicated in a number of autoinflammatory diseases, including Familial Mediterranean fever (FMF), TNF receptor associated periodic syndrome (TRAPS), hyperimmunoglobulinemia D and periodic fever syndrome (HIDS), pyogenic arthritis, pyoderma gangrenosum and acne (PAPA), Sweet's syndrome, chronic nonbacterial osteomyelitis (CNO), and acne vulgaris (Cook et al., Eur. J. Immunol., 40: 595-653, 2010). In particular, NLRP3 mutations have been found to be responsible for a set of rare autoinflammatory diseases known as CAPS (Ozaki et al., J. Inflammation Research, 8: 15-27, 2015; Schroder et al., Cell, 140: 821-832, 2010; and Menu et al., Clinical and Experimental Immunology, 166: 1-15, 2011). CAPS are heritable diseases characterized by recurrent fever and inflammation and are comprised of three autoinflammatory disorders that form a clinical continuum. These diseases, in order of increasing severity, are familial cold autoinflammatory syndrome (FCAS), Muckle-Wells syndrome (MWS), and chronic infantile cutaneous neurological articular syndrome (CINCA; also called neonatal-onset multisystem inflammatory disease, NOMID), and all have been shown to result from gain-of-function mutations in the NLRP3 gene, which leads to increased secretion of IL-1β.

A number of autoimmune diseases have been shown to involve NLRP3 including, in particular, multiple sclerosis, type-1 diabetes (T1D), psoriasis, rheumatoid arthritis (RA), Behcet's disease, Schnitzler syndrome, macrophage activation syndrome (Masters Clin. Immunol. 2013; Braddock et al. Nat. Rev. Drug Disc. 2004 3: 1-10; Inoue et al., Immunology 19: 11-18, Coll et al. Nat. Med. 2015 21(3): 248-55; and Scott et al. Clin. Exp. Rheumatol 2016 34(1): 88-93), systemic lupus erythematosus (Lu et al. J Immunol. 2017198 (3): 1119-29), and systemic sclerosis (Artlett et al. Arthritis Rheum. 2011; 63(11): 3563-74). NLRP3 has also been shown to play a role in a number of lung diseases including chronic obstructive pulmonary disorder (COPD), asthma (including steroid-resistant asthma), asbestosis, and silicosis (De Nardo et al., Am. J. Pathol., 184: 42-54, 2014 and Kim et al. Am J Respir Crit Care Med. 2017196(3): 283-97). NLRP3 has also been suggested to have a role in a number of central nervous system conditions, including Parkinson's disease (PD), Alzheimer's disease (AD), dementia, Huntington's disease, cerebral malaria, brain injury from pneumococcal meningitis (Walsh et al., Nature Reviews, 15: 84-97, 2014, and Dempsey et al. Brain. Behav. Immun. 2017 61: 306-316), intracranial aneurysms (Zhang et al. J. Stroke & Cerebrovascular Dis. 2015 24; 5: 972-979), and traumatic brain injury (Ismael et al. J Neurotrauma. 2018 Jan. 2). NRLP3 activity has also been shown to be involved in various metabolic diseases including type 2 diabetes (T2D), atherosclerosis, obesity, gout, pseudo-gout, metabolic syndrome (Wen et al., Nature Immunology, 13: 352-357, 2012; Duewell et al., Nature, 464: 1357-1361, 2010; Strowig et al., Nature, 481: 278-286, 2012), and non-alcoholic steatohepatitis (Mridha et al. J Hepatol. 2017 66(5): 1037-46). A role for NLRP3 via IL-1β has also been suggested in atherosclerosis, myocardial infarction (van Hout et al. Eur. Heart J. 2017 38(11): 828-36), heart failure (Sano et al. J AM. Coll. Cardiol. 2018 71(8): 875-66), aortic aneurysm and dissection (Wu et al. Arterioscler. Thromb. Vasc. Biol. 2017 37(4): 694-706), and other cardiovascular events (Ridker et al., N Engl J Med., doi: 10.1056/NEJMoa1707914, 2017). Other diseases in which NLRP3 has been shown to be involved include: ocular diseases such as both wet and dry age-related macular degeneration (Doyle et al., Nature Medicine, 18: 791-798, 2012 and Tarallo et al. Cell 2012149(4): 847-59), diabetic retinopathy (Loukovaara et al. Acta Ophthalmol. 2017; 95(8): 803-808) and optic nerve damage (Puyang et al. Sci Rep. 2016 Feb. 19; 6: 20998); liver diseases including non-alcoholic steatohepatitis (NASH) (Henao-Meija et al., Nature, 482: 179-185, 2012); inflammatory reactions in the lung and skin (Primiano et al. J Immunol. 2016 197(6): 2421-33) including contact hypersensitivity (such as bullous pemphigoid (Fang et al. J Dermatol Sci. 2016; 83(2): 116-23)), atopic dermatitis (Niebuhr et al. Allergy 2014 69(8): 1058-67), Hidradenitis suppurativa (Alikhan et al. 2009 J Am Acad Dermatol 60(4): 539-61), acne vulgaris (Qin et al. J Invest. Dermatol. 2014 142(2): 381-88), and sarcoidosis (Jager et al. Am J Respir Crit Care Med 2015 191: A5816); inflammatory reactions in the joints (Braddock et al., Nat. Rev. Drug Disc., 3: 1-10, 2004); amyotrophic lateral sclerosis (Gugliandolo et al. Inflammation 2018 41(1): 93-103); cystic fibrosis (Iannitti et al. Nat. Commun. 2016 7: 10791); stroke (Walsh et al., Nature Reviews, 15: 84-97, 2014); chronic kidney disease (Granata et al. PLoS One 2015 10(3): e0122272); and inflammatory bowel diseases including ulcerative colitis and Crohn's disease (Braddock et al., Nat. Rev. Drug Disc., 3: 1-10, 2004, Neudecker et al. J Exp. Med. 2017 214(6): 1737-52, and Lazaridis et al. Dig. Dis. Sci. 2017 62(9): 2348-56). The NLRP3 inflammasome has been found to be activated in response to oxidative stress, and UVB irradiation (Schroder et al., Science, 327: 296-300, 2010). NLRP3 has also been shown to be involved in inflammatory hyperalgesia (Dolunay et al., Inflammation, 40: 366-386, 2017).

The inflammasome, and NLRP3 specifically, has also been proposed as a target for modulation by various pathogens including viruses such as DNA viruses (Amsler et al., Future Virol. (2013) 8(4), 357-370).

NLRP3 has also been implicated in the pathogenesis of many cancers (Menu et al., Clinical and Experimental Immunology 166: 1-15, 2011; and Masters Clin. Immunol. 2013). For example, several previous studies have suggested a role for IL-1β in cancer invasiveness, growth and metastasis, and inhibition of IL-1β with canakinumab has been shown to reduce the incidence of lung cancer and total cancer mortality in a randomised, double-blind, placebo-controlled trial (Ridker et al. Lancet, S0140-6736(17)32247-X, 2017). Inhibition of the NLRP3 inflammasome or IL-1β has also been shown to inhibit the proliferation and migration of lung cancer cells in vitro (Wang et al. Oncol Rep. 2016; 35(4): 2053-64). A role for the NLRP3 inflammasome has been suggested in myelodysplastic syndromes (Basiorka et al. Blood. 2016 Dec. 22; 128(25): 2960-2975) and also in the carcinogenesis of various other cancers including glioma (Li et al. Am J Cancer Res. 2015; 5(1): 442-449), inflammation-induced tumours (Allen et al. J Exp Med. 2010; 207(5): 1045-56 and Hu et al. PNAS. 2010; 107(50): 21635-40), multiple myeloma (Li et al. Hematology 2016 21(3): 144-51), and squamous cell carcinoma of the head and neck (Huang et al. J Exp Clin Cancer Res. 2017 2; 36(1): 116). Activation of the NLRP3 inflammasome has also been shown to mediate chemoresistance of tumour cells to 5-Fluorouracil (Feng et al. J Exp Clin Cancer Res. 2017 21; 36(1): 81), and activation of NLRP3 inflammasome in peripheral nerve contributes to chemotherapy-induced neuropathic pain (Jia et al. Mol Pain. 2017; 13: 1-11).

NLRP3 has also been shown to be required for the efficient control of viral, bacterial, fungal, and helminth pathogen infections (Strowig et al., Nature, 481: 278-286, 2012).

Accordingly, examples of diseases, disorders or conditions which may be responsive to NLRP3 inhibition and which may be treated or prevented in accordance with the fifth, sixth, seventh, eighth, ninth or tenth aspect of the present invention include:

(i) inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity;

(ii) auto-immune diseases such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barré syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjögren's syndrome, systemic sclerosis a systemic connective tissue disorder, Takayasu's arteritis, temporal arteritis, warm autoimmune hemolytic anemia, Wegener's granulomatosis, alopecia universalis, Behçet's disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, vitiligo or vulvodynia;
(iii) cancer including lung cancer, pancreatic cancer, gastric cancer, myelodysplastic syndrome, leukaemia including acute lymphocytic leukaemia (ALL) and acute myeloid leukaemia (AML), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour;
(iv) infections including viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxviruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from *schistosoma*, roundworms, tapeworms or flukes) and prion infections;
(v) central nervous system diseases such as Parkinson's disease, Alzheimer's disease, dementia, motor neuron disease, Huntington's disease, cerebral malaria, brain injury from pneumococcal meningitis, intracranial aneurysms, traumatic brain injury, and amyotrophic lateral sclerosis;
(vi) metabolic diseases such as type 2 diabetes (T2D), atherosclerosis, obesity, gout, and pseudo-gout;
(vii) cardiovascular diseases such as hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, and pericarditis including Dressler's syndrome;
(viii) respiratory diseases including chronic obstructive pulmonary disorder (COPD), asthma such as allergic asthma and steroid-resistant asthma, asbestosis, silicosis, nanoparticle induced inflammation, cystic fibrosis and idiopathic pulmonary fibrosis;
(ix) liver diseases including non-alcoholic fatty liver disease (NAFLD) and non-alcoholic steatohepatitis (NASH) including advanced fibrosis stages F3 and F4, alcoholic fatty liver disease (AFLD), and alcoholic steatohepatitis (ASH);
(x) renal diseases including chronic kidney disease, oxalate nephropathy, nephrocalcinosis, glomerulonephritis, and diabetic nephropathy;
(xi) ocular diseases including those of the ocular epithelium, age-related macular degeneration (AMD) (dry and wet), uveitis, corneal infection, diabetic retinopathy, optic nerve damage, dry eye, and glaucoma;
(xii) skin diseases including dermatitis such as contact dermatitis and atopic dermatitis, contact hypersensitivity, sunburn, skin lesions, hidradenitis suppurativa (HS), other cyst-causing skin diseases, and acne conglobata;
(xiii) lymphatic conditions such as lymphangitis and Castleman's disease;
(xiv) psychological disorders such as depression and psychological stress;
(xv) graft versus host disease;
(xvi) allodynia including mechanical allodynia; and
(xvii) any disease where an individual has been determined to carry a germline or somatic non-silent mutation in NLRP3.

In one embodiment, the disease, disorder or condition is selected from:
(i) cancer;
(ii) an infection;
(iii) a central nervous system disease;
(iv) a cardiovascular disease;
(v) a liver disease;
(vi) an ocular diseases; or
(vii) a skin disease.

More typically, the disease, disorder or condition is selected from:
(i) cancer;
(ii) an infection;
(iii) a central nervous system disease; or
(iv) a cardiovascular disease.

In one embodiment, the disease, disorder or condition is selected from:
(i) acne conglobata;
(ii) atopic dermatitis;
(iii) Alzheimer's disease;
(iv) amyotrophic lateral sclerosis;
(v) age-related macular degeneration (AMD);
(vi) anaplastic thyroid cancer;
(vii) cryopyrin-associated periodic syndromes (CAPS);
(viii) contact dermatitis;
(ix) cystic fibrosis;
(x) congestive heart failure;
(xi) chronic kidney disease;
(xii) Crohn's disease;
(xiii) familial cold autoinflammatory syndrome (FCAS);
(xiv) Huntington's disease;
(xv) heart failure;

(xvi) heart failure with preserved ejection fraction;
(xvii) ischemic reperfusion injury;
(xviii) juvenile idiopathic arthritis;
(xix) myocardial infarction;
(xx) macrophage activation syndrome;
(xxi) myelodysplastic syndrome;
(xxii) multiple myeloma;
(xxiii) motor neuron disease;
(xxiv) multiple sclerosis;
(xxv) Muckle-Wells syndrome;
(xxvi) non-alcoholic steatohepatitis (NASH);
(xxvii) neonatal-onset multisystem inflammatory disease (NOMID);
(xxviii) Parkinson's disease;
(xxix) systemic juvenile idiopathic arthritis;
(xxx) systemic lupus erythematosus;
(xxxi) traumatic brain injury;
(xxxii) transient ischemic attack; and
(xxxiii) ulcerative colitis.

In a further typical embodiment of the invention, the disease, disorder or condition is inflammation. Examples of inflammation that may be treated or prevented in accordance with the fifth, sixth, seventh, eighth, ninth or tenth aspect of the present invention include inflammatory responses occurring in connection with, or as a result of:
(i) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;
(ii) a joint condition such as osteoarthritis, systemic juvenile idiopathic arthritis, adult-onset Still's disease, relapsing polychondritis, rheumatoid arthritis, juvenile chronic arthritis, gout, or a seronegative spondyloarthropathy (e.g. ankylosing spondylitis, psoriatic arthritis or Reiter's disease);
(iii) a muscular condition such as polymyositis or myasthenia gravis;
(iv) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);
(v) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;
(vi) a vascular condition such as atherosclerosis, Behcet's disease, vasculitides, or wegener's granulomatosis;
(vii) an autoimmune condition such as systemic lupus erythematosus, Sjogren's syndrome, systemic sclerosis, Hashimoto's thyroiditis, type I diabetes, idiopathic thrombocytopenia purpura, or Graves disease;
(viii) an ocular condition such as uveitis, allergic conjunctivitis, or vernal conjunctivitis;
(ix) a nervous condition such as multiple sclerosis or encephalomyelitis;
(x) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium* intracellulare, Pneumocystis carinii pneumonia, orchitis/epidydimitis, legionella, Lyme disease, influenza A, epstein-barr virus, viral encephalitis/aseptic meningitis, or pelvic inflammatory disease;
(xi) a renal condition such as mesangial proliferative glomerulonephritis, nephrotic syndrome, nephritis, glomerular nephritis, acute renal failure, uremia, or nephritic syndrome;
(xii) a lymphatic condition such as Castleman's disease;
(xiii) a condition of, or involving, the immune system, such as hyper IgE syndrome, lepromatous leprosy, familial hemophagocytic lymphohistiocytosis, or graft versus host disease;
(xiv) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;
(xv) a cancer, including those cancers listed above;
(xvi) a burn, wound, trauma, haemorrhage or stroke;
(xvii) radiation exposure; and/or
(xviii) obesity; and/or
(xix) pain such as inflammatory hyperalgesia.

In one embodiment of the fifth, sixth, seventh, eighth, ninth or tenth aspect of the present invention, the disease, disorder or condition is an autoinflammatory disease such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Tumour Necrosis Factor (TNF) Receptor-Associated Periodic Syndrome (TRAPS), hyperimmunoglobulinemia D and periodic fever syndrome (HIDS), deficiency of interleukin 1 receptor antagonist (DIRA), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

Examples of diseases, disorders or conditions which may be responsive to NLRP3 inhibition and which may be treated or prevented in accordance with the fifth, sixth, seventh, eighth, ninth or tenth aspect of the present invention are listed above. Some of these diseases, disorders or conditions are substantially or entirely mediated by NLRP3 inflammasome activity, and NLRP3-induced IL-1β and/or IL-18. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), neonatal onset multisystem inflammatory disease (NOMID), familial Mediterranean fever (FMF), pyogenic arthritis, pyoderma gangrenosum and acne syndrome (PAPA), hyperimmunoglobulinemia D and periodic fever syndrome (HIDS), Tumour Necrosis Factor (TNF) Receptor-Associated Periodic Syndrome (TRAPS), systemic juvenile idiopathic arthritis, adult-onset Still's disease (AOSD), relapsing polychondritis, Schnitzler's syndrome, Sweet's syndrome, Behcet's disease, anti-synthetase syndrome, deficiency of interleukin 1 receptor antagonist (DIRA), and haploinsufficiency of A20 (HA20).

Moreover, some of the diseases, disorders or conditions mentioned above arise due to mutations in NLRP3, in particular, resulting in increased NLRP3 activity. As a result, such diseases, disorders or conditions may be particularly responsive to NLRP3 inhibition and may be particularly suitable for treatment or prevention in accordance with the fifth, sixth, seventh, eighth, ninth or tenth aspect of the present invention. Examples of such diseases, disorders or conditions include cryopyrin-associated periodic syndromes (CAPS), Muckle-Wells syndrome (MWS), familial cold autoinflammatory syndrome (FCAS), and neonatal onset multisystem inflammatory disease (NOMID).

In one embodiment of the fifth, sixth, seventh, eighth, ninth or tenth aspect of the invention, the disease, disorder or condition is not a metabolic disease such as diabetes, or a disease that is treatable with an estrogen-related receptor-α (ERR-α) modulator, or a disease that is treatable with a muscle stimulant.

An eleventh aspect of the invention provides a method of inhibiting NLRP3, the method comprising the use of a compound of the first or second aspect of the invention, or a pharmaceutically acceptable salt, solvate or prodrug of the third aspect of the invention, or a pharmaceutical composition of the fourth aspect of the invention, to inhibit NLRP3.

In one embodiment of the eleventh aspect of the present invention, the method comprises the use of a compound of the first or second aspect of the invention, or a pharmaceutically acceptable salt, solvate or prodrug of the third aspect of the invention, or a pharmaceutical composition of the fourth aspect of the invention, in combination with one or more further active agents.

In one embodiment of the eleventh aspect of the present invention, the method is performed ex vivo or in vitro, for example in order to analyse the effect on cells of NLRP3 inhibition.

In another embodiment of the eleventh aspect of the present invention, the method is performed in vivo. For example, the method may comprise the step of administering an effective amount of a compound of the first or second aspect, or a pharmaceutically acceptable salt, solvate or prodrug of the third aspect, or a pharmaceutical composition of the fourth aspect, to thereby inhibit NLRP3. In one embodiment, the method further comprises the step of co-administering an effective amount of one or more further active agents. Typically, the administration is to a subject in need thereof.

Alternately, the method of the eleventh aspect of the invention may be a method of inhibiting NLRP3 in a non-human animal subject, the method comprising the steps of administering the compound, salt, solvate, prodrug or pharmaceutical composition to the non-human animal subject and optionally subsequently mutilating or sacrificing the non-human animal subject. Typically, such a method further comprises the step of analysing one or more tissue or fluid samples from the optionally mutilated or sacrificed non-human animal subject. In one embodiment, the method further comprises the step of co-administering an effective amount of one or more further active agents.

A twelfth aspect of the invention provides a compound of the first or second aspect of the invention, or a pharmaceutically acceptable salt, solvate or prodrug of the third aspect of the invention, or a pharmaceutical composition of the fourth aspect of the invention, for use in the inhibition of NLRP3. Typically, the use comprises the administration of the compound, salt, solvate, prodrug or pharmaceutical composition to a subject. In one embodiment, the compound, salt, solvate, prodrug or pharmaceutical composition is co-administered with one or more further active agents.

A thirteenth aspect of the invention provides the use of a compound of the first or second aspect of the invention, or a pharmaceutically effective salt, solvate or prodrug of the third aspect of the invention, in the manufacture of a medicament for the inhibition of NLRP3. Typically, the inhibition comprises the administration of the compound, salt, solvate, prodrug or medicament to a subject. In one embodiment, the compound, salt, solvate, prodrug or medicament is co-administered with one or more further active agents.

In any embodiment of any of the fifth to thirteenth aspects of the present invention that comprises the use or co-administration of one or more further active agents, the one or more further active agents may comprise for example one, two or three different further active agents.

The one or more further active agents may be used or administered prior to, simultaneously with, sequentially with or subsequent to each other and/or to the compound of the first or second aspect of the invention, the pharmaceutically acceptable salt, solvate or prodrug of the third aspect of the invention, or the pharmaceutical composition of the fourth aspect of the invention. Where the one or more further active agents are administered simultaneously with the compound of the first or second aspect of the invention, or the pharmaceutically acceptable salt, solvate or prodrug of the third aspect of the invention, a pharmaceutical composition of the fourth aspect of the invention may be administered wherein the pharmaceutical composition additionally comprises the one or more further active agents.

In one embodiment of any of the fifth to thirteenth aspects of the present invention that comprises the use or co-administration of one or more further active agents, the one or more further active agents are selected from:
(i) chemotherapeutic agents;
(ii) antibodies;
(iii) alkylating agents;
(iv) anti-metabolites;
(v) anti-angiogenic agents;
(vi) plant alkaloids and/or terpenoids;
(vii) topoisomerase inhibitors;
(viii) mTOR inhibitors;
(ix) stilbenoids;
(x) STING agonists;
(xi) cancer vaccines;
(xii) immunomodulatory agents;
(xiii) antibiotics;
(xiv) anti-fungal agents;
(xv) anti-helminthic agents; and/or
(xvi) other active agents.

It will be appreciated that these general embodiments defined according to broad categories of active agents are not mutually exclusive. In this regard any particular active agent may be categorized according to more than one of the above general embodiments. A non-limiting example is urelumab which is an antibody that is an immunomodulatory agent for the treatment of cancer.

In some embodiments, the one or more chemotherapeutic agents are selected from abiraterone acetate, altretamine, amsacrine, anhydrovinblastine, auristatin, azathioprine, adriamycin, bexarotene, bicalutamide, BMS 184476, bleomycin, N,N-dimethyl-L-valyl-L-valyl-N-methyl-L-valyl-L-prolyl-L-proline-t-butylamide, cisplatin, carboplatin, carboplatin cyclophosphamide, chlorambucil, cachectin, cemadotin, cyclophosphamide, carmustine, cryptophycin, cytarabine, docetaxel, doxetaxel, doxorubicin, dacarbazine (DTIC), dactinomycin, daunorubicin, decitabine, dolastatin, etoposide, etoposide phosphate, enzalutamide (MDV3100), 5-fluorouracil, fludarabine, flutamide, gemcitabine, hydroxyurea and hydroxyureataxanes, idarubicin, ifosfamide, irinotecan, leucovorin, lonidamine, lomustine (CCNU), larotaxel (RPR109881), mechlorethamine, mercaptopurine, methotrexate, mitomycin C, mitoxantrone, melphalan, mivobulin, 3',4'-didehydro-4'-deoxy-8'-norvincaleukoblastine, nilutamide, oxaliplatin, onapristone, prednimustine, procarbazine, paclitaxel, platinum-containing anti-cancer agents, 2,3,4,5,6-pentafluoro-N-(3-fluoro-4-methoxyphenyl)benzene sulphonamide, prednimustine, procarbazine, rhizoxin, sertenef, streptozocin, stramustine phosphate, tretinoin, tasonermin, taxol, topotecan, tamoxifen, teniposide, taxane, tegafur/uracil, vincristine, vinblastine, vinorelbine, vindesine, vindesine sulfate, and/or vinflunine.

Alternatively or in addition, the one or more chemotherapeutic agents may be selected from CD59 complement fragment, fibronectin fragment, gro-beta (CXCL2), heparinases, heparin hexasaccharide fragment, human chorionic gonadotropin (hCG), interferon alpha, interferon beta, interferon gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1(TSP-1), transforming growth factor-beta (TGF-β), vasculostatin, vasostatin (calreticulin fragment), and/or cytokines (including interleukins, such as interleukin-2 (IL-2), or IL-10).

In some embodiments, the one or more antibodies may comprise one or more monoclonal antibodies. In some embodiments, the one or more antibodies are selected from abciximab, adalimumab, alemtuzumab, atlizumab, basiliximab, belimumab, bevacizumab, bretuximab vedotin, canakinumab, cetuximab, ceertolizumab pegol, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumuab, ranibizumab, rituximab, tocilizumab, tositumomab, and/or trastuzumab.

In some embodiments, the one or more alkylating agents may comprise an agent capable of alkylating nucleophilic functional groups under conditions present in cells, including, for example, cancer cells. In some embodiments, the one or more alkylating agents are selected from cisplatin, carboplatin, mechlorethamine, cyclophosphamide, chlorambucil, ifosfamide and/or oxaliplatin. In some embodiments, the alkylating agent may function by impairing cell function by forming covalent bonds with amino, carboxyl, sulfhydryl, and/or phosphate groups in biologically important molecules. In some embodiments, the alkylating agent may function by modifying a cell's DNA.

In some embodiments, the one or more anti-metabolites may comprise an agent capable of affecting or preventing RNA or DNA synthesis. In some embodiments, the one or more anti-metabolites are selected from azathioprine and/or mercaptopurine.

In some embodiments, the one or more anti-angiogenic agents are selected from endostatin, angiogenin inhibitors, angiostatin, angioarrestin, angiostatin (plasminogen fragment), basement-membrane collagen-derived anti-angiogenic factors (tumstatin, canstatin, or arrestin), anti-angiogenic antithrombin III, and/or cartilage-derived inhibitor (CDI).

In some embodiments, the one or more plant alkaloids and/or terpenoids may prevent microtubule function. In some embodiments, the one or more plant alkaloids and/or terpenoids are selected from a vinca alkaloid, a podophyllotoxin and/or a taxane. In some embodiments, the one or more vinca alkaloids may be derived from the Madagascar periwinkle, Catharanthus roseus (formerly known as Vinca rosea), and may be selected from vincristine, vinblastine, vinorelbine and/or vindesine. In some embodiments, the one or more taxanes are selected from taxol, paclitaxel, docetaxel and/or ortataxel. In some embodiments, the one or more podophyllotoxins are selected from an etoposide and/or teniposide.

In some embodiments, the one or more topoisomerase inhibitors are selected from a type I topoisomerase inhibitor and/or a type II topoisomerase inhibitor, and may interfere with transcription and/or replication of DNA by interfering with DNA supercoiling. In some embodiments, the one or more type I topoisomerase inhibitors may comprise a camptothecin, which may be selected from exatecan, irinotecan, lurtotecan, topotecan, BNP 1350, CKD 602, DB 67 (AR67) and/or ST 1481. In some embodiments, the one or more type II topoisomerase inhibitors may comprise an epipodophyllotoxin, which may be selected from an amsacrine, etoposid, etoposide phosphate and/or teniposide.

In some embodiments, the one or more mTOR (mammalian target of rapamycin, also known as the mechanistic target of rapamycin) inhibitors are selected from rapamycin, everolimus, temsirolimus and/or deforolimus.

In some embodiments, the one or more stilbenoids are selected from resveratrol, piceatannol, pinosylvin, pterostilbene, alpha-viniferin, ampelopsin A, ampelopsin E, diptoindonesin C, diptoindonesin F, epsilon-vinferin, flexuosol A, gnetin H, hemsleyanol D, hopeaphenol, trans-diptoindonesin B, astringin, piceid and/or diptoindonesin A.

In some embodiments, the one or more STING (Stimulator of interferon genes, also known as transmembrane protein (TMEM) 173) agonists may comprise cyclic di-nucleotides, such as cAMP, cGMP, and cGAMP, and/or modified cyclic di-nucleotides that may include one or more of the following modification features: 2'-O/3'-O linkage, phosphorothioate linkage, adenine and/or guanine analogue, and/or 2'-OH modification (e.g. protection of the 2'-OH with a methyl group or replacement of the 2'-OH by —F or —$N_3$).

In some embodiments, the one or more cancer vaccines are selected from an HPV vaccine, a hepatitis B vaccine, Oncophage, and/or Provenge.

In some embodiments, the one or more immunomodulatory agents may comprise an immune checkpoint inhibitor. The immune checkpoint inhibitor may target an immune checkpoint receptor, or combination of receptors comprising, for example, CTLA-4, PD-1, PD-L1, PD-L2, T cell immunoglobulin and mucin 3 (TIM3 or HAVCR2), galectin 9, phosphatidylserine, lymphocyte activation gene 3 protein (LAG3), MHC class I, MHC class II, 4-1BB, 4-1BBL, OX40, OX40L, GITR, GITRL, CD27, CD70, TNFRSF25, TL1A, CD40, CD40L, HVEM, LIGHT, BTLA, CD160, CD80, CD244, CD48, ICOS, ICOSL, B7-H3, B7-H4, VISTA, TMIGD2, HHLA2, TMIGD2, a butyrophilin (including BTNL2), a Siglec family member, TIGIT, PVR, a killer-cell immunoglobulin-like receptor, an ILT, a leukocyte immunoglobulin-like receptor, NKG2D, NKG2A, MICA, MICB, CD28, CD86, SIRPA, CD47, VEGF, neuropilin, CD30. CD39, CD73, CXCR4, and/or CXCL12.

In some embodiments, the immune checkpoint inhibitor is selected from urelumab, PF-05082566, MEDI6469, TRX518, varlilumab, CP-870893, pembrolizumab (PD1), nivolumab (PD1), atezolizumab (formerly MPDL3280A) (PD-L1), MEDI4736 (PD-L1), avelumab (PD-L1), PDR001 (PD1), BMS-986016, MGA271, lirilumab, IPH2201, emactuzumab, INCB024360, galunisertib, ulocuplumab, BKT140, bavituximab, CC-90002, bevacizumab, and/or MNRP1685A.

In some embodiments, the one or more antibiotics are selected from amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, ticarcillin, calvulanate, ampicillin, subbactam, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanamide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and/or teixobactin.

In some embodiments, the one or more antibiotics may comprise one or more cytotoxic antibiotics. In some embodiments, the one or more cytotoxic antibiotics are selected from an actinomycin, an anthracenedione, an anthracycline, thalidomide, dichloroacetic acid, nicotinic acid, 2-deoxyglucose, and/or chlofazimine. In some embodiments, the one or more actinomycins are selected from actinomycin D, bacitracin, colistin (polymyxin E) and/or polymyxin B. In some embodiments, the one or more antracenediones are selected from mitoxantrone and/or pixantrone. In some embodiments, the one or more anthracyclines are selected from bleomycin, doxorubicin (Adriamycin), daunorubicin (daunomycin), epirubicin, idarubicin, mitomycin, plicamycin and/or valrubicin.

In some embodiments, the one or more anti-fungal agents are selected from bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and/or balsam of Peru.

In some embodiments, the one or more anti-helminthic agents are selected from benzimidazoles (including albendazole, mebendazole, thiabendazole, fenbendazole, triclabendazole, and flubendazole), abamectin, diethylcarbamazine, ivermectin, suramin, pyrantel pamoate, levamisole, salicylanilides (including niclosamide and oxyclozanide), and/or nitazoxanide.

In some embodiments, other active agents are selected from growth inhibitory agents, anti-inflammatory agents (including nonsteroidal anti-inflammatory agents), anti-psoriatic agents (including anthralin and its derivatives), vitamins and vitamin-derivatives (including retinoinds, and VDR receptor ligands), corticosteroids, ion channel blockers (including potassium channel blockers), immune system regulators (including cyclosporin, FK 506, and glucocorticoids), lutenizing hormone releasing hormone agonists (such as leuprolidine, goserelin, triptorelin, histrelin, bicalutamide, flutamide and/or nilutamide), and/or hormones (including estrogen).

Unless stated otherwise, in any of the fifth to thirteenth aspects of the invention, the subject may be any human or other animal. Typically, the subject is a mammal, more typically a human or a domesticated mammal such as a cow, pig, lamb, sheep, goat, horse, cat, dog, rabbit, mouse etc. Most typically, the subject is a human.

Any of the medicaments employed in the present invention can be administered by oral, parenteral (including intravenous, subcutaneous, intramuscular, intradermal, intratracheal, intraperitoneal, intraarticular, intracranial and epidural), airway (aerosol), rectal, vaginal, ocular or topical (including transdermal, buccal, mucosal, sublingual and topical ocular) administration.

Typically, the mode of administration selected is that most appropriate to the disorder, disease or condition to be treated or prevented. Where one or more further active agents are administered, the mode of administration may be the same as or different to the mode of administration of the compound, salt, solvate, prodrug or pharmaceutical composition of the invention.

For oral administration, the compounds, salts, solvates or prodrugs of the present invention will generally be provided in the form of tablets, capsules, hard or soft gelatine capsules, caplets, troches or lozenges, as a powder or granules, or as an aqueous solution, suspension or dispersion.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose. Corn starch and alginic acid are suitable disintegrating agents. Binding agents may include starch and gelatine. The lubricating agent, if present, may be magnesium stearate, stearic acid or talc. If desired, the tablets may be coated with a material, such as glyceryl monostearate or glyceryl distearate, to delay absorption in the gastrointestinal tract. Tablets may also be effervescent and/or dissolving tablets.

Capsules for oral use include hard gelatine capsules in which the active ingredient is mixed with a solid diluent, and soft gelatine capsules wherein the active ingredient is mixed with water or an oil such as peanut oil, liquid paraffin or olive oil.

Powders or granules for oral use may be provided in sachets or tubs. Aqueous solutions, suspensions or dispersions may be prepared by the addition of water to powders, granules or tablets.

Any form suitable for oral administration may optionally include sweetening agents such as sugar, flavouring agents, colouring agents and/or preservatives.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For parenteral use, the compounds, salts, solvates or prodrugs of the present invention will generally be provided in a sterile aqueous solution or suspension, buffered to an appropriate pH and isotonicity. Suitable aqueous vehicles include Ringer's solution and isotonic sodium chloride or glucose. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate. The compounds of the invention may also be presented as liposome formulations.

For ocular administration, the compounds, salts, solvates or prodrugs of the invention will generally be provided in a form suitable for topical administration, e.g. as eye drops. Suitable forms may include ophthalmic solutions, gel-forming solutions, sterile powders for reconstitution, ophthalmic suspensions, ophthalmic ointments, ophthalmic emulsions, ophthalmic gels and ocular inserts. Alternatively, the compounds, salts, solvates or prodrugs of the invention may be provided in a form suitable for other types of ocular administration, for example as intraocular preparations (including as irrigating solutions, as intraocular, intravitreal or juxtascleral injection formulations, or as intravitreal implants), as packs or corneal shields, as intracameral, subconjunctival or retrobulbar injection formulations, or as iontophoresis formulations.

For transdermal and other topical administration, the compounds, salts, solvates or prodrugs of the invention will generally be provided in the form of ointments, cataplasms (poultices), pastes, powders, dressings, creams, plasters or patches. Suitable suspensions and solutions can be used in inhalers for airway (aerosol) administration.

The dose of the compounds, salts, solvates or prodrugs of the present invention will, of course, vary with the disorder, disease or condition to be treated or prevented. In general, a suitable dose will be in the range of 0.01 to 500 mg per kilogram body weight of the recipient per day. The desired dose may be presented at an appropriate interval such as once every other day, once a day, twice a day, three times a day or four times a day. The desired dose may be administered in unit dosage form, for example, containing 1 mg to 50 g of active ingredient per unit dosage form.

For the avoidance of doubt, insofar as is practicable any embodiment of a given aspect of the present invention may occur in combination with any other embodiment of the same aspect of the present invention. In addition, insofar as is practicable it is to be understood that any preferred, typical or optional embodiment of any aspect of the present invention should also be considered as a preferred, typical or optional embodiment of any other aspect of the present invention.

EXAMPLES—COMPOUND SYNTHESIS

All solvents, reagents and compounds were purchased and used without further purification unless stated otherwise.

Abbreviations

2-MeTHF 2-methyltetrahydrofuran
$Ac_2O$ acetic anhydride
AcOH acetic acid
aq aqueous
Boc tert-butyloxycarbonyl
br broad
Cbz carboxybenzyl
CDI 1,1-carbonyl-diimidazole
conc concentrated
d doublet
DABCO 1,4-diazabicyclo[2.2.2]octane
DCE 1,2-dichloroethane, also called ethylene dichloride
DCM dichloromethane
DIPEA N,N-diisopropylethylamine, also called Hünig's base
DMA dimethylacetamide
DMAP 4-dimethylaminopyridine, also called N,N-dimethylpyridin-4-amine
DME dimethoxyethane
DMF N,N-dimethylformamide
DMSO dimethyl sulfoxide
eq or equiv equivalent
(ES+) electrospray ionization, positive mode
Et ethyl
EtOAc ethyl acetate
EtOH ethanol
h hour(s)
HATU 1-[bis(dimethylamino)methylene]-1H-1,2,3-triazolo[4,5-b]pyridinium 3-oxid hexafluorophosphate
HPLC high performance liquid chromatography
LC liquid chromatography
m multiplet
m-CPBA 3-chloroperoxybenzoic acid
Me methyl
MeCN acetonitrile
MeOH methanol
(M+H)+ protonated molecular ion
MHz megahertz
min minute(s)
MS mass spectrometry
Ms mesyl, also called methanesulfonyl
MsCl mesyl chloride, also called methanesulfonyl chloride
MTBE methyl tert-butyl ether, also called tert-butyl methyl ether
m/z mass-to-charge ratio
NaO$^t$Bu sodium tert-butoxide
NBS 1-bromopyrrolidine-2,5-dione, also called N-bromosuccinimide
NCS 1-chloropyrrolidine-2,5-dione, also called N-chlorosuccinimide
NMP N-methylpyrrolidine
NMR nuclear magnetic resonance (spectroscopy)
Pd(dba)$_3$ tris(dibenzylideneacetone) dipalladium(0)

Pd(dppf)Cl₂ [1,1'-bis(diphenylphosphino)ferrocene] dichloropalladium(II)
PE petroleum ether
Ph phenyl
PMB p-methoxybenzyl, also called 4-methoxybenzyl
prep-HPLC preparative high performance liquid chromatography
prep-TLC preparative thin layer chromatography
PTSA p-toluenesulfonic acid
q quartet
RP reversed phase
RT room temperature
s singlet
Sept septuplet
sat saturated
SCX solid supported cation exchange (resin)
t triplet
T3P propylphosphonic anhydride
TBME tert-butyl methyl ether, also called methyl tert-butyl ether
TEA triethylamine
TFA 2,2,2-trifluoroacetic acid
THF tetrahydrofuran
TLC thin layer chromatography
wt % weight percent or percent by weight Experimental Methods Analytical Methods NMR spectra were run on Bruker 400 MHz spectrometers using ICON-NMR, under TopSpin program control. Spectra were measured at 298 K, unless indicated otherwise, and were referenced relative to the solvent resonance.

LC-MS Methods: Using SHIMADZU LCMS-2020, Agilent 1200 LC/G1956A MSD and Agilent 1200\G6110A, Agilent 1200 LC and Agilent 6110 MSD. Mobile Phase: A: 0.025% NH₃.H₂O in water (v/v); B: acetonitrile. Column: Kinetex EVO C18 2.1X30 mm, 5 μm.

Reversed Phase HPLC Purification Method

Automated reversed phase column chromatography was carried out using a Gilson GX-281 system driven by a Gilson-322 pump module, Gilson-156 UV photometer detection unit and Gilson-281 fraction collector. Detection wavelength: 220 and 254 nm.

Alternatively, automated reversed phase column chromatography was carried out using a Gilson GX-215 system driven by a LC-20AP pump module, SPD-20A UV photometer detection unit and Gilson-215 fraction collector. Detection wavelength: 220 and 254 nm.

Synthesis of Intermediates

Intermediate L1:
1-iso-Propyl-1H-pyrazole-3-sulfinamide

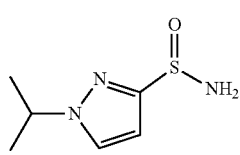

Step A: 1-iso-Propyl-1H-pyrazole-3-sulfonyl chloride

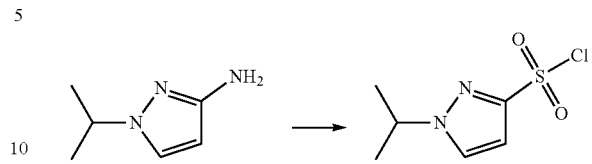

A solution of 1-isopropyl-1H-pyrazol-3-amine (11 g, 70.30 mmol, 1 eq) in MeCN (400 mL) at 0° C. was treated with a solution of concentrated HCl (80 mL) in H₂O (35 mL) followed with aqueous solution of NaNO₂ (5.82 g, 84.36 mmol, 1.2 eq) in H₂O (25 mL) slowly. The resulting solution was stirred at 0° C. for 40 minutes. AcOH (30 mL), CuCl₂ (4.73 g, 35.15 mmol, 0.5 eq) and CuCl (348.00 mg, 3.52 mmol, 84.06 μL, 0.05 eq) were sequentially added to the above mixture and purged with SO₂ gas for 20 minutes at 0° C. The resulting reaction mixture was stirred at 0° C. to 10° C. for 1 hour. The reaction mixture was concentrated in vacuo. The residue was diluted with water (200 mL) and extracted with EtOAc (3×300 mL). The combined organic layers were washed with brine (2×200 mL), dried over anhydrous Na₂SO₄, filtered and concentrated in vacuo. The residue was purified by column chromatography (SiO₂, PE:EtOAc=30:1 to 5:1) to afford the title compound (5.1 g, 24.44 mmol, 35% yield, 100% purity) as a yellow oil.

¹H NMR (CDCl₃): δ 7.57 (d, 1H), 6.88 (d, 1H), 4.67-4.64 (m, 1H) and 1.59 (d, 6H).

LCMS: m/z 209 (M+H)⁺ (ES⁺).

Step B: Sodium 1-iso-propyl-1H-pyrazole-3-sulfinate

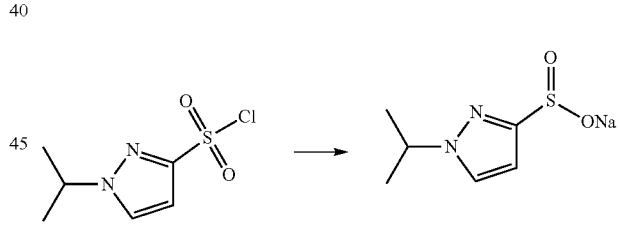

A solution of Na₂SO₃ (4-35 g, 34.50 mmol, 2 eq) in H₂O (12 mL) was stirred at 20° C. for 10 minutes and Na₂CO₃ (3.66 g, 34-50 mmol, 2 eq) was added with stirring. The resulting mixture was stirred at 50° C. for 10 minutes, 1-iso-propyl-1H-pyrazole-3-sulfonyl chloride (3.6 g, 17.25 mmol, 1 eq) was added drop-wise and the resulting mixture was stirred at 50° C. for 2 hours. The reaction mixture was concentrated in vacuo and the residue was re-dissolved in EtOH (24 ml). The suspension was stirred at 20° C. for 10 minutes. The suspension was filtered and the filtrate was evaporated to afford a white solid. The white solid was triturated with EtOAc (20 ml) for 10 minutes and then filtered to afford the title compound (2.4 g, 11.62 mmol, 68% yield, 95% purity) as a white solid.

¹H NMR (DMSO-d₆): δ 7.58 (d, 1H), 6.17 (d, 1H), 4.46-4.43 (m, 1H) and 1.37 (d, 6H).

LCMS: m/z 197 (M+H)⁺ (ES⁺).

Step C: 1-iso-Propyl-1H-pyrazole-3-sulfinamide

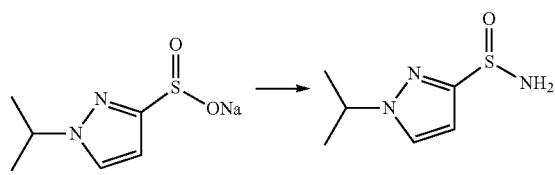

Oxalyl chloride (3.11 g, 24.46 mmol, 2.14 mL, 2 eq) was added drop-wise to a solution of sodium 1-iso-propyl-1H-pyrazole-3-sulfinate (2.4 g, 12.23 mmol, 1 eq) in THF (15 mL) at 0° C. After stirring for 1 hour at 20° C., the reaction mixture was added into a solution of aqueous ammonia (15 mL, 25%) at 0° C. and then the mixture was stirred at 20° C. for 1 hour. The reaction mixture was evaporated in vacuo and DCM (20 mL) was added to the residue. The mixture was stirred for 20 minutes at 20° C., and then filtered. The filtrate was concentrated under reduced pressure to afford the title compound (1.2 g, 6.23 mmol, 51% yield, ca. 90% purity) as yellow oil.

$^1$H NMR (DMSO-$d_6$): δ 7.87 (d, 1H), 6.54 (d, 1H), 6.24 (s, 2H), 4.57-4.50 (m, 1H) and 1.43 (d, 6H).

LCMS: m/z 196 (M+Na)$^+$ (ES$^+$).

Intermediate L2: 1-((R)-2-Hydroxypropyl)-1H-pyrazole-3-sulfinamide

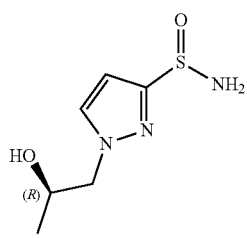

Step A: Lithium 1-(tetrahydro-2H-pyran-2-yl)-1H-pyrazole-5-sulfinate

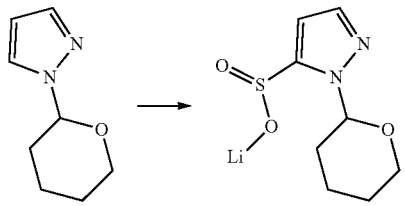

To a solution of 1-(tetrahydro-2H-pyran-2-yl)-1H-pyrazole (38 g, 249.68 mmol, 1 eq) in THF (450 mL) was added n-BuLi (2.5 M, 104.87 mL, 1.05 eq) at −78° C. Then the mixture was stirred for 1.5 hours. The mixture was purged with SO$_2$ for 0.1 hour. Then the mixture was warmed to 25° C. and concentrated in vacuo. The residue was recrystallised from MTBE (1 L) to give the title compound (53 g, 96% yield) as a white solid.

$^1$H NMR (DMSO-$d_6$): δ 7.25 (d, 1H), 6.09 (d, 1H), 5.99 (dd, 1H), 3.97-3.87 (m, 1H), 3.53-3.47 (m, 1H), 2.22-2.18 (m, 1H), 2.01-1.92 (m, 1H), 1.78-1.72 (m, 1H) and 1.53-1.43 (m, 3H).

Step B: N,N-Bis(4-methoxybenzyl)-1H-pyrazole-5-sulfinamide

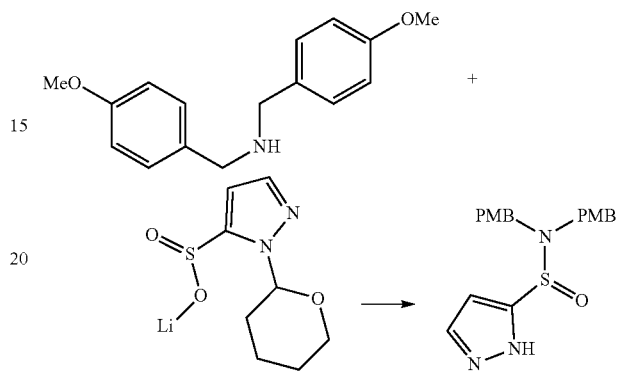

To a solution of lithium 1-(tetrahydro-2H-pyran-2-yl)-1H-pyrazole-5-sulfinate (53 g, 238.53 mmol, 1 eq) in THF (600 mL) was added oxalyl chloride (60.55 g, 477.07 mmol, 41.76 mL, 2 eq) at 0° C. Then the mixture was warmed to 25° C., stirred for 1 hour and then concentrated in vacuo. The residue was dissolved in DCM (600 mL). To the resulting mixture was added TEA (72.41 g, 715.60 mmol, 99.60 mL, 3 eq) followed by bis(4-methoxybenzyl)amine (61.38 g, 238.53 mmol, 1 eq) at 25° C. The mixture was stirred for 1 hour and then concentrated in vacuo. The residue was purified by column chromatography (SiO$_2$, PE:EtOAc=1:1 to 1:3) to give the title compound (54 g, 59% yield, 97% purity on LCMS) as a light yellow oil.

$^1$H NMR (CDCl$_3$): δ 7.77 (d, 1H), 7.06 (d, 4H), 6.77-6.72 (m, 4H), 6.51 (d, 1H), 4.03 (s, 4H) and 3.72 (s, 6H).

LCMS: m/z 372.2 (M+H)$^+$ (ES$^+$).

Step C: 1-((R)-2-Hydroxypropyl)-N,N-bis(4-methoxybenzyl)-1H-pyrazole-3-sulfinamide

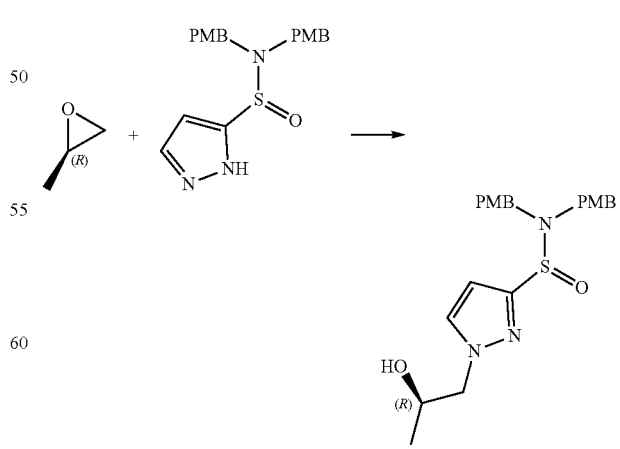

To a solution of N,N-bis(4-methoxybenzyl)-1H-pyrazole-5-sulfinamide (10 g, 26.92 mmol, 1 eq) in DMF (200 mL)

was added (R)-2-methyloxirane (3.13 g, 53.84 mmol, 3.77 mL, 2 eq) follow by K$_2$CO$_3$ (13.39 g, 96.92 mmol, 3.6 eq). The mixture was heated to 50° C. and stirred for 12 hours. Then the reaction mixture was cooled to 25° C. and diluted with H$_2$O (1 L) and extracted with EtOAc (3×200 mL). The combined organic layers were washed with brine (200 mL), dried over Na$_2$SO$_4$, filtered and concentrated under reduced pressure. The residue was purified by column chromatography (SiO$_2$, PE:EtOAc=1:1 to 0:1) to give the title compound (7.2 g, 62% yield, 100% purity on LCMS) as a light yellow oil.

$^1$H NMR (CDCl$_3$): δ 7.51 (t, 1H), 7.16 (dd, 4H), 6.83 (d, 4H), 6.72 (t, 1H), 4.29-4.20 (m, 2H), 4.17-4.06 (m, 5H), 3.80 (s, 6H) and 1.25-1.19 (m, 3H).

LCMS: m/z 430.2 (M+H)$^+$ (ES$^+$).

Step D: Methyl 1-((R)-2-hydroxypropyl)-1H-pyrazole-3-sulfinate

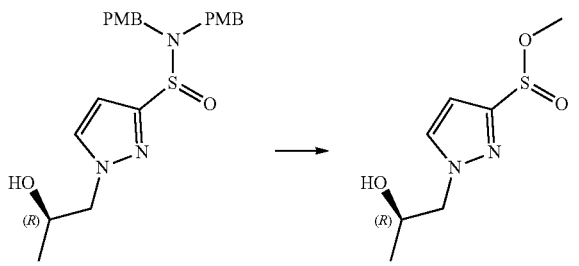

To a solution of 1-((R)-2-hydroxypropyl)-N,N-bis(4-methoxybenzyl)-1H-pyrazole-3-sulfinamide (6 g, 13.97 mmol, 1 eq) in MeOH (100 mL) was added TFA (1.59 g, 13.97 mmol, 1.03 mL, 1 eq). The mixture was stirred at 25° C. for 2 hours and then concentrated in vacuo. The residue was purified by reversed phase flash chromatography (0.05% NH$_3$.H$_2$O in water/MeCN) to give the title compound (2.8 g, 97% yield, 99% purity on LCMS) as a colourless oil.

$^1$H NMR (CDCl$_3$): δ 7.57 (d, 1H), 6.74 (s, 1H), 4.29-4.24 (m, 2H), 4.12-4.07 (m, 1H), 3.74-3.72 (m, 1H), 3.66 (s, 3H) and 1.25 (d, 3H).

LCMS: m/z 227.1 (M+Na)$^+$ (ES$^+$).

Step E: Sodium (R)-1-(2-hydroxypropyl)-1H-pyrazole-3-sulfinate

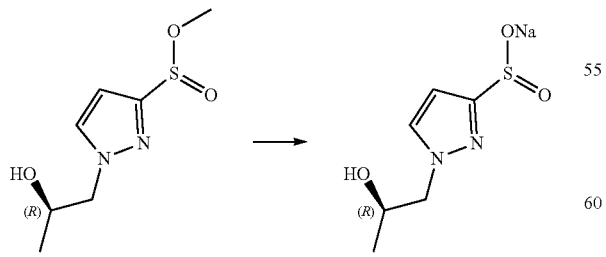

To a solution of methyl 1-((R)-2-hydroxypropyl)-1H-pyrazole-3-sulfinate (3.1 g, 15.18 mmol, 1 eq) in MeOH (40 mL) was added an aqueous NaOH solution (1 M, 62.00 mL, 4.08 eq) and then the mixture was stirred at 25° C. for 1 hour. The mixture was concentrated in vacuo to give the title compound (3.2 g, crude), which was used directly for the next step.

LCMS: m/z 191.1 (M−Na+2H)$^+$ (ES$^+$).

Step F: 1-((R)-2-Hydroxypropyl)-1H-pyrazole-3-sulfinic chloride

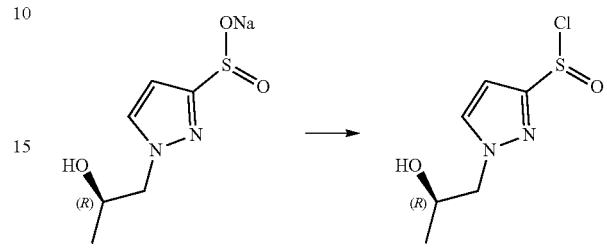

To a solution of sodium (R)-1-(2-hydroxypropyl)-1H-pyrazole-3-sulfinate (3.2 g, 15.08 mmol, 1 eq) in THF (50 mL) was added (COCl)$_2$ (7.66 g, 60.32 mmol, 5.28 mL, 4 eq) at 0° C., then the mixture was warmed to 25° C. and stirred for 1 hour. The reaction mixture was used directly for the next step.

Step G: 1-((R)-2-Hydroxypropyl)-1H-pyrazole-3-sulfinamide

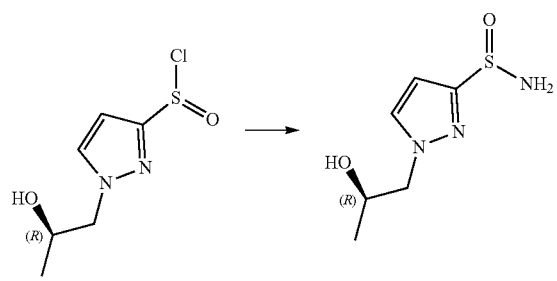

A solution of THF (40 mL) was purged with NH$_3$ at −78° C. for 0.1 hour. Then a solution of 1-((R)-2-hydroxypropyl)-1H-pyrazole-3-sulfinic chloride (3.5 g, crude) in THF (so mL) was added to the above mixture at 0° C. The resulting mixture was stirred at 0° C. for 0.1 hour and then concentrated in vacuo. The residue was purified by reversed phase flash chromatography (0.05% NH$_3$.H$_2$O in water/MeCN) to give the title compound (0.7 g, 17% yield, 75% purity on LCMS) as a colourless oil.

$^1$H NMR (CDCl$_3$): δ 7.55 (dd, 1H), 6.66-6.63 (m, 1H), 4.71 (d, 2H), 4.27-4.21 (m, 2H), 4.09-4.03 (m, 1H) and 1.24 (d, 3H).

LCMS: m/z 212.1 (M+Na)$^+$ (ES$^+$).

Intermediate L3: tert-Butyl ethyl(3-sulfinamoylpropyl)carbamate

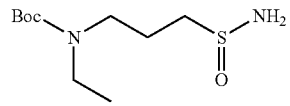

Step A: 3-(Ethylamino)propan-1-ol

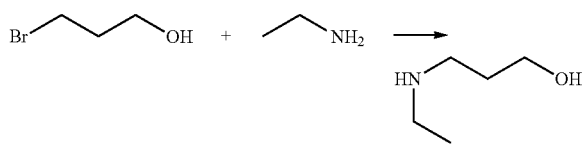

A mixture of 3-bromopropan-1-ol (77 g, 553.99 mmol, 50.00 mL, 1 eq) and ethanamine (74.93 g, 1.66 mol, 108.75 mL, 3 eq) in H₂O (200 mL) was stirred at 25° C. for 20 hours. Then the reaction mixture was concentrated in vacuo to reduce to 200 mL. To the above mixture was added K₂CO₃ (76.57, 553.99 mmol, 1 eq). The reaction mixture was stirred at 25° C. for 0.5 hour and then concentrated in vacuo. The residue was treated with MeOH (500 mL). The filtrate was concentrated in vacuo to give the title compound (60 g, crude) as a yellow oil.

$^1$H NMR (CDCl₃): δ 3.82 (t, 2H), 2.89 (t, 2H), 2.66 (q, 2H), 1.73-1.68 (m, 2H) and 1.10 (t, 3H).

Step B: tert-Butyl ethyl(3-hydroxypropyl)carbamate

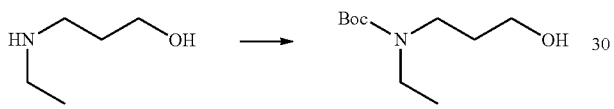

To a mixture of 3-(ethylamino)propan-1-ol (60 g, 581.61 mmol, 1 eq) and TEA (117.71 g, 1.16 mol, 161.91 mL, 2 eq) in DCM (300 mL) were added dropwise Boc₂O (139.63 g, 639.77 mmol, 146.98 mL, 1.1 eq) and DMAP (710 mg, 5.82 mmol, 0.01 eq) at 0° C. Then the reaction mixture was warmed to 25° C. and stirred for 12 hours. The mixture was quenched with water (200 mL) and extracted with DCM (2×200 mL). The combined organic phases were washed with brine (100 mL), dried over anhydrous Na₂SO₄, filtered and concentrated in vacuo. The residue was purified by column chromatography (SiO₂, PE:EtOAc=50:1 to 2:1) to give the title compound (22 g, 15% yield, 82.0% purity on LCMS) as a yellow oil.

$^1$H NMR (CDCl₃): δ 3.93 (br s, 1H), 3.58-3.54 (m, 2H), 3.40-3.36 (m, 2H), 3.28-3.24 (m, 2H), 1.70-1.62 (m, 2H), 1.47 (s, 9H) and 1.12 (t, 3H).

LCMS: m/z 204.1 (M+H)⁺ (ES⁺).

Step C: 3-((tert-Butoxycarbonyl)(ethyl)amino)propyl methanesulfonate

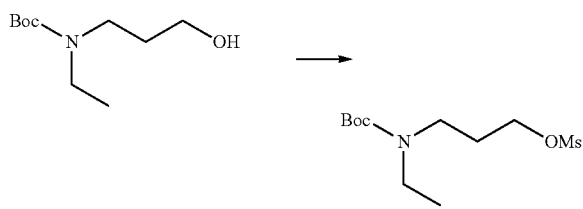

To a mixture of tert-butyl ethyl(3-hydroxypropyl)carbamate (22 g, 108.23 mmol, 1 eq) and TEA (21.9 g, 216.45 mmol, 30.13 mL, 2 eq) in DCM (150 mL) was added dropwise MsCl (15.45 g, 134.87 mmol, 10.44 mL, 1.25 eq) at 0° C. Then the reaction mixture was warmed to 25° C. and stirred for 1.5 hours. The mixture was quenched with water (200 mL) and extracted with DCM (2×200 mL). The combined organic phases were washed with brine (200 mL), dried over anhydrous Na₂SO₄, filtered and concentrated in vacuo to give the title compound (35 g, crude) as a brown oil, which was used directly in the next step without further purification.

$^1$H NMR (CDCl₃): δ 4.26 (t, 2H), 3.31 (t, 2H), 3.29-3.23 (m, 2H), 3.03 (s, 3H), 2.00-1.95 (m, 2H), 1.46 (s, 9H) and 1.12 (t, 3H).

Step D: S-(3-((tert-Butoxycarbonyl)(ethyl)amino)propyl) ethanethioate

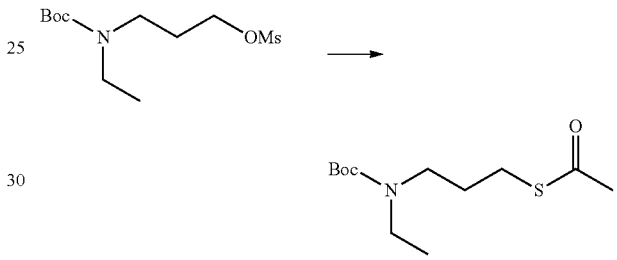

To a mixture of 3-((tert-butoxycarbonyl)(ethyl)amino)propyl methanesulfonate (35 g, 124.39 mmol, 1 eq) in MeCN (200 mL) was added potassium ethanethioate (17.02 g, 149.03 mmol, 1.2 eq) in one portion at 25° C. under nitrogen. Then the reaction mixture was stirred for 12 hours. The mixture was diluted with EtOAc (300 mL) and quenched with water (200 mL), then extracted with EtOAc (2×200 mL). The combined organic phases were washed with brine (100 mL), dried over anhydrous Na₂SO₄, filtered and concentrated in vacuo. The residue was purified by column chromatography (SiO₂, PE:EtOAc=1:0 to 10:1) to give the title compound (30.5 g, 94% yield) as a yellow oil.

$^1$H NMR (CDCl₃): δ 3.29-3.20 (m, 4H), 2.86 (t, 2H), 2.34 (s, 3H), 1.81 (q, 2H), 1.46 (s, 9H) and 1.10 (t, 3H).

Step E: tert-Butyl ethyl(3-mercaptopropyl)carbamate and di-tert-butyl (disulfanediylbis(propane-3,1-diyl))bis(ethylcarbamate)

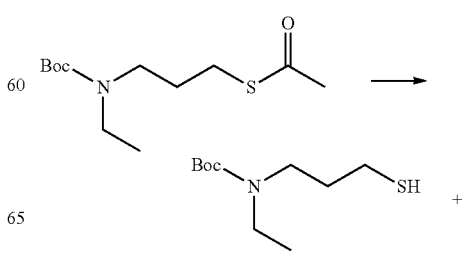

-continued

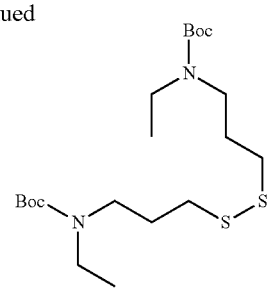

To a mixture of S-(3-((tert-butoxycarbonyl)(ethyl)amino)propyl) ethanethioate (30.5 g, 116.69 mmol, 1 eq) in MeOH (150 mL) was added an aqueous NaOH solution (1 M, 175.03 mL, 1.5 eq) in one portion. Then the mixture was heated to 70° C. and stirred for 2 hours. The mixture was quenched with water (200 mL) and extracted with EtOAc (3×200 mL). The combined organic phases were washed with brine (100 mL), dried over anhydrous $Na_2SO_4$, filtered and concentrated in vacuo to give a mixture of the title compounds tert-butyl ethyl(3-mercaptopropyl)carbamate (minor) and di-tert-butyl (disulfanediylbis(propane-3,1-diyl))bis(ethylcarbamate) (major) (26.6 g, 52% yield) as a green oil.

$^1$H NMR ($CDCl_3$): δ 3.31-3.22 (m, 8H), 2.67-2.50 (m, 4H), 1.90-1.81 (m, 4H), 1.46 (s, 18H) and 1.26 (t, 6H).

LCMS: m/z 459.4 (M+Na)$^+$ (ES$^+$).

Step F: Methyl 3-((tert-butoxycarbonyl)(ethyl)amino)propane-1-sulfinate

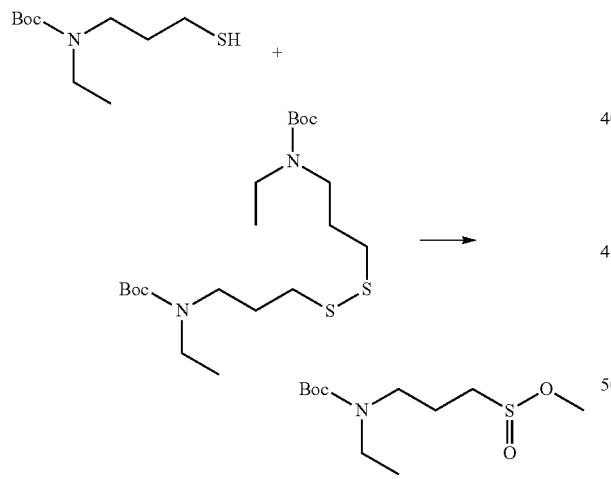

To a mixture of tert-butyl ethyl(3-mercaptopropyl)carbamate and di-tert-butyl (disulfanediylbis(propane-3,1-diyl))bis(ethylcarbamate) (20 g, 45.80 mmol, 1 eq) in MeOH (200 mL) was added NBS (24.46 g, 137.40 mmol, 3 eq) in one portion. Then the reaction mixture was stirred at 25° C. for 1 hour. The mixture was quenched with water (200 mL) and extracted with EtOAc (3×200 mL). The combined organic phases were washed with brine (100 mL), dried over anhydrous $Na_2SO_4$, filtered and concentrated in vacuo. The residue was purified by column chromatography ($SiO_2$, PE:EtOAc=20:1 to 5:1) to give the title compound (12.6 g, 97% yield, 94.0% purity on LCMS) as a yellow oil.

$^1$H NMR ($CDCl_3$): δ 3.78 (s, 3H), 3.34-3.30 (m, 2H), 3.25-3.20 (m, 2H), 2.76-2.70 (m, 2H), 1.95-1.91 (m, 2H), 1.47 (s, 9H) and 1.11 (t, 3H).

LCMS: m/z 166.0 (M-Boc)$^+$ (ES$^+$).

Step G: Sodium 3-((tert-butoxycarbonyl)(ethyl)amino)propane-1-sulfinate

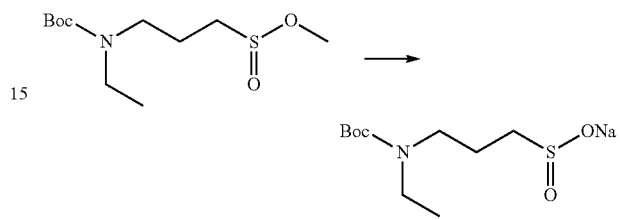

To a mixture of methyl 3-((tert-butoxycarbonyl)(ethyl)amino)propane-1-sulfinate (12.6 g, 47.48 mmol, 1 eq) in MeOH (150 mL) was added an aqueous NaOH solution (1 M, 72.65 mL, 1.53 eq) in one portion. Then the reaction mixture was stirred at 25° C. for 0.5 hour. The mixture was concentrated in vacuo. The residue was purified by reversed phase flash chromatography (0.05% $NH_3.H_2O$ in water/MeCN) to give the title compound (10.5 g, 81% yield) as a white solid.

$^1$H NMR (DMSO-$d_6$): δ 3.14-3.10 (m, 4H), 1.79-1.75 (m, 2H), 1.61-1.59 (m, 2H), 1.38 (s, 9H) and 1.10-1.00 (m, 3H).

Step H: tert-Butyl ethyl(3-sulfinamoylpropyl)carbamate

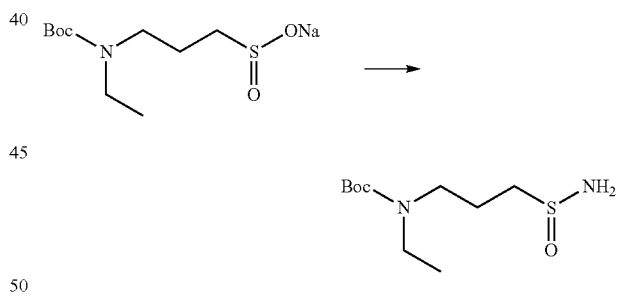

To a mixture of sodium 3-((tert-butoxycarbonyl)(ethyl)amino)propane-1-sulfinate (6.5 g, 23.78 mmol, 1 eq) in THF (200 mL) at 0° C. was added dropwise (COCl)$_2$ (7.70 g, 60.64 mmol, 5.31 mL, 2.55 eq). Then the reaction mixture was warmed to 25° C. and stirred for 2 hours. The reaction mixture was poured into a saturated solution of $NH_3$ in THF (100 mL) at −78° C. The resulting mixture was stirred at 25° C. for another 1 hour. Then the mixture was filtered and the filtrate was concentrated in vacuo. The residue was purified by column chromatography ($SiO_2$, PE:EtOAc=50:1 to 1:1 and EtOAc:MeOH=50:1) to give the title compound (5.2 g, 87% yield) as a yellow oil.

$^1$H NMR ($CDCl_3$): δ 4.10-3.99 (m, 2H), 3.45-3.22 (m, 4H), 2.81-2.70 (m, 2H), 1.96-1.92 (m, 2H), 1.47 (s, 9H) and 1.11 (t, 3H).

Intermediate L4: tert-Butyl 3-sulfinamoylazetidine-1-carboxylate

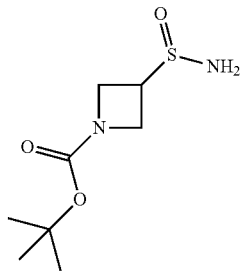

Step A: tert-Butyl 3-mercaptoazetidine-1-carboxylate

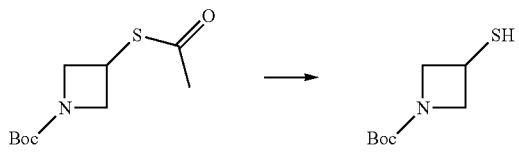

To a solution of tert-butyl 3-(acetylthio)azetidine-1-carboxylate (18 g, 77.82 mmol, 1 eq) in MeOH (70 mL), THF (70 mL) and H$_2$O (35 mL) was added LiOH.H$_2$O (3.27 g, 77.82 mmol, 1 eq). The mixture was stirred at 70° C. for 2 hours. Then the reaction mixture was poured into water and extracted with EtOAc (3×200 mL). The combined organic layers were dried over Na$_2$SO$_4$, filtered and concentrated in vacuo to give the title compound (14 g, 73.97 mmol, 95% yield) as a light yellow oil, which was used in the next step without further purification.

$^1$H NMR (CDCl$_3$): δ 4.35-431 (m, 2H), 3.80-3.76 (m, 2H), 3.70-3.64 (m, 1H) and 1.43 (s, 9H).

Step B: tert-Butyl 3-(methoxysulfinyl)azetidine-1-carboxylate

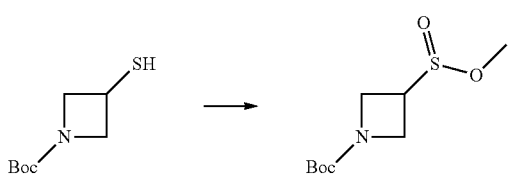

To a solution of tert-butyl 3-mercaptoazetidine-1-carboxylate (6 g, 31.70 mmol, 1 eq) in MeOH (120 mL) was added NBS (11.28 g, 63.40 mmol, 2 eq). The reaction mixture was stirred at 25° C. for 10 minutes. The reaction mixture was quenched with a saturated aqueous Na$_2$SO$_3$ solution (200 mL) and then extracted with EtOAc (3×200 mL). The combined organic layers were dried over Na$_2$SO$_4$, filtered and concentrated in vacuo. The residue was purified by reversed phase flash chromatography (0.1% NH$_3$.H$_2$O/MeCN) to give the title compound (5 g, 21.25 mmol, 67% yield) as a light yellow oil.

$^1$H NMR (CDCl$_3$): δ 4.32-4.28 (m, 1H), 4.12-4.07 (m, 3H), 3.81 (s, 3H), 3.64-3.61 (m, 1H) and 1.44 (s, 9H).

LCMS: m/z 258.1 (M+Na)$^+$ (ES$^+$).

Step C: 1-(tert-Butoxycarbonyl)azetidine-3-sulfinic acid

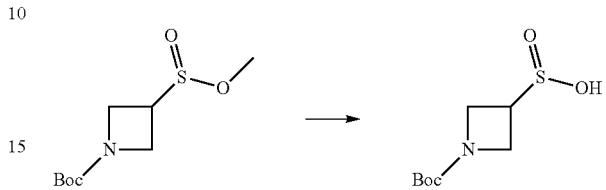

To a solution of tert-butyl 3-(methoxysulfinyl)azetidine-1-carboxylate (1 g, 4.25 mmol, 1 eq) in MeOH (10 mL) was added an aqueous NaOH solution (1 M, 6.50 mL, 1.53 eq). The reaction mixture was stirred at 25° C. for 1 hour. The reaction mixture was adjusted with 1 N HCl to pH=7 and then the mixture was purified by reversed phase flash chromatography (0.1% NH$_3$.H$_2$O/MeCN) to give the title compound (1 g, crude) as a yellow oil.

$^1$H NMR (DMSO-d$_6$): δ 3.84-3.81 (m, 2H), 3.68-3.65 (m, 2H), 2.73-2.68 (m, 1H) and 1.37 (s, 9H).

Step D: tert-Butyl 3-sulfinamoylazetidine-1-carboxylate

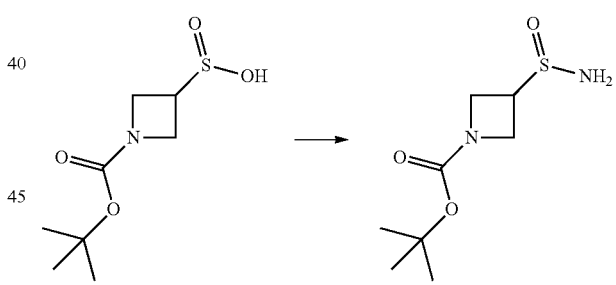

To a solution of 1-(tert-butoxycarbonyl)azetidine-3-sulfinic acid (1 g, 4.52 mmol, 1 eq) in DCM (20 mL) was added oxalyl dichloride (1.15 g, 9.04 mmol, 791.19 μL, 2 eq). The mixture was stirred at 20° C. for 2 hours. Then the mixture was added at −78° C. into NH$_3$/THF, which had been prepared by bubbling NH$_3$ into THF (20 mL) at −78° C. for 10 minutes. The reaction mixture was stirred at 25° C. for another 50 minutes. Then the reaction mixture was filtered and the filtrate was concentrated in vacuo. The residue was purified by column chromatography (SiO$_2$, PE:EtOAc=1:1 to 0:1) to give the title compound (490 mg, 49% yield) as a colourless oil.

$^1$H NMR (DMSO-d$_6$): δ 5.85 (br s, 2H), 4.08-3.99 (m, 3H), 3.78-3.74 (m, 1H), 3.62-3.58 (m, 1H) and 1.38 (s, 9H).

Intermediate L5: 1-(2-Hydroxyethyl)-1H-pyrazole-3-sulfinamide

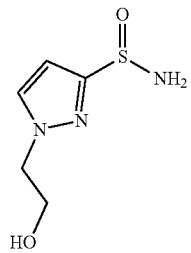

Step A: 1-(2-Hydroxyethyl)-N,N-bis(4-methoxybenzyl)-1H-pyrazole-3-sulfinamide

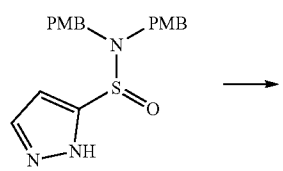

To a solution of N,N-bis(4-methoxybenzyl)-1H-pyrazole-5-sulfinamide (15 g, 40.38 mmol, 1 eq) and $K_2CO_3$ (16.74 g, 121.15 mmol, 3 eq) in DMF (150 mL) was added 2-bromoethanol (10.09 g, 80.76 mmol, 5.73 mL, 2 eq). Then the mixture was heated to 70° C. and stirred for 2 hours. The reaction mixture was quenched with $H_2O$ (500 mL) at 25° C. and extracted with EtOAc (3×300 mL). The combined organic layers were washed with brine (200 mL), dried over $Na_2SO_4$, filtered and concentrated under reduced pressure. The residue was purified by column chromatography ($SiO_2$, PE:EtOAc=1:0 to 0:1) to give the title compound (11 g, 66% yield) as a colourless oil.

$^1$H NMR (CDCl$_3$): δ 7.54 (d, 1H), 7.19-7.16 (m, 4H), 6.89-6.84 (m, 4H), 6.71 (d, 1H), 4.34-4.31 (m, 2H), 4.16-4.12 (m, 4H), 4.05 (t, 2H) and 3.80 (s, 6H).

LCMS: m/z 416.1 (M+H)$^+$ (ES$^+$).

Step B: Methyl 1-(2-hydroxyethyl)-1H-pyrazole-3-sulfinate

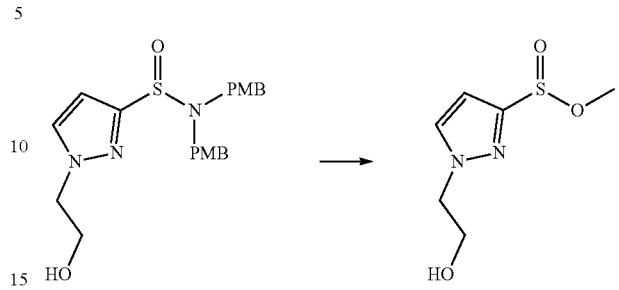

To a solution of 1-(2-hydroxyethyl)-N,N-bis(4-methoxybenzyl)-1H-pyrazole-3-sulfinamide (8.8 g, 21.18 mmol, 1 eq) in MeOH (100 mL) was added TFA (2.41 g, 21.18 mmol, 1.57 mL, 1 eq). The mixture was stirred at 25° C. for 2 hours and then concentrated in vacuo. The residue was purified by reversed phase flash chromatography (0.05% $NH_3.H_2O$ in water/MeCN) to give the title compound (3.5 g, 87% yield) as a colourless oil.

$^1$H NMR (CDCl$_3$): δ 7.59 (d, 1H), 6.73 (d, 1H), 4.41-4.30 (m, 2H), 4.08-4.01 (m, 2H) and 3.66 (s, 3H).

LCMS: m/z 213.1 (M+Na)$^+$ (ES$^+$).

Step C: 1-(2-Hydroxyethyl)-1H-pyrazole-3-sulfinic acid

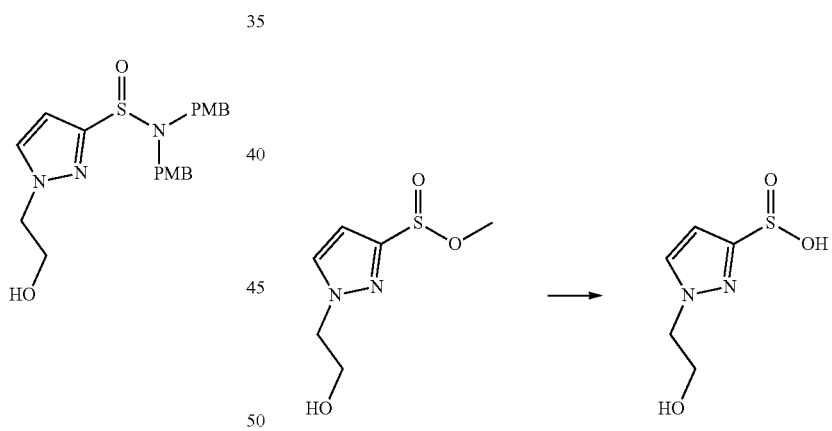

To a solution of methyl 1-(2-hydroxyethyl)-1H-pyrazole-3-sulfinate (3.8 g, 19.98 mmol, 1 eq) in MeOH (100 mL) was added an aqueous NaOH solution (1 M, 39.95 mL, 2 eq) and the mixture was stirred at 25° C. for 1 hour. Then the mixture was concentrated in vacuo. The residue was purified by reversed phase flash chromatography (neutral condition; MeCN/$H_2O$) to give the title compound (3.5 g, 99% yield, 100% purity on LCMS) as a white solid.

$^1$H NMR (DMSO-d$_6$): δ 7.51 (d, 1H), 7.20 (br s, 1H), 6.15 (d, 1H), 4.90 (br s, 1H), 4.08 (t, 2H) and 3.75-3.68 (m, 2H).

LCMS: m/z 199.0 (M+Na)$^+$ (ES$^+$).

Step D: 1-(2-Hydroxyethyl)-1H-pyrazole-3-sulfinic chloride

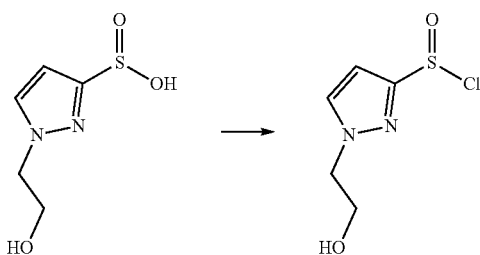 [SMILES: O=S(O)c1ccn(CCO)n1 ; O=S(Cl)c1ccn(CCO)n1]

To a solution of 1-(2-hydroxyethyl)-1H-pyrazole-3-sulfinic acid (0.65 g, 3.69 mmol, 1 eq) in THF (40 mL) was added SOCl$_2$ (878 mg, 7.38 mmol, 535.24 µL, 2 eq). Then the mixture was stirred at 25° C. for 1 hour. The reaction mixture was concentrated in vacuo to give the title compound (0.72 g, crude) as light yellow oil, which was used for the next step.

Step E: 1-(2-Hydroxyethyl)-1H-pyrazole-3-sulfinamide

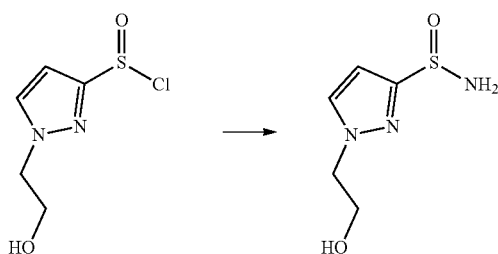 [SMILES: O=S(Cl)c1ccn(CCO)n1 ; NS(=O)c1ccn(CCO)n1]

A solution of THF (40 mL) was purged with NH$_3$ (15 psi) at −78° C. and stirred for 0.1 hour. Then 1-(2-hydroxyethyl)-1H-pyrazole-3-sulfinic chloride (0.71 g, 3.65 mmol, 1 eq) was added and the resulting mixture was stirred for 0.1 hour. The mixture was concentrated in vacuo. The residue was purified by reversed phase flash chromatography (neutral condition; MeCN/H$_2$O) to give the title compound (0.23 g, 31% yield, 88% purity on LCMS) as a white solid.

$^1$H NMR (DMSO-d$_6$): δ 7.80 (d, 1H), 6.53 (d, 1H), 6.26 (br s, 2H), 4.94 (t, 1H), 4.17 (t, 2H) and 3.75-3.71 (m, 2H).

LCMS: m/z 198.1 (M+Na)$^+$ (ES$^+$).

Intermediate L6: 4-Chloro-isopropyl-1H-pyrazole-3-sulfinamide

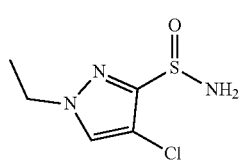

Step A: 4-Chloro-1-isopropyl-1H-pyrazol-3-amine

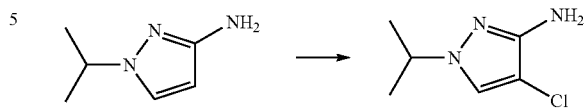

To a solution of 1-isopropyl-1H-pyrazol-3-amine (34.8 g, 278.02 mmol, 1 eq) in THF (400 mL) was added NCS (40.84 g, 305.82 mmol, 1.1 eq) at 20° C. The mixture was stirred at 20° C. for 5 hours and then concentrated in vacuo. The residue was diluted with water (500 mL) and extracted with EtOAc (3×500 mL). The combined organic layers were dried over Na$_2$SO$_4$, filtered and concentrated in vacuo. The residue was purified by column chromatography (SiO$_2$, PE:EtOAc=5:1 to 2:1) to give the title compound (33 g, 74% yield) as a brown oil.

$^1$H NMR (CDCl$_3$): δ 7.17 (s, 1H), 4.21-4.16 (m, 1H), 3.67 (br s, 2H) and 1.39 (dd, 6H).

LCMS: m/z 160.1 (M+H)$^+$ (ES$^+$).

Step B: 4-Chloro-1-isopropyl-1H-pyrazole-3-sulfonyl chloride

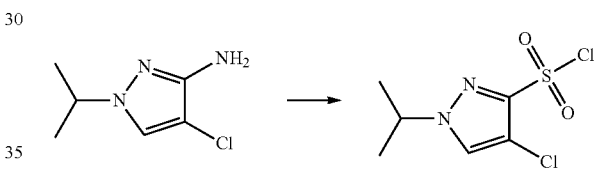

To a solution of 4-chloro-1-isopropyl-1H-pyrazol-3-amine (28 g, 175.42 mmol, 1 eq) in MeCN (600 mL) at 0° C. was added an aqueous HCl solution (60 mL, 6 M), followed by an aqueous solution of NaNO$_2$ (14.52 g, 210.50 mmol, 1.2 eq) in H$_2$O (60 mL) slowly. The resulting mixture was stirred at 0° C. for 40 minutes. Then AcOH (6 mL), CuCl$_2$ (11.79 g, 87.71 mmol, 0.5 eq) and CuCl (868 mg, 8.77 mmol, 209.74 µL, 0.05 eq) were added. Then SO$_2$ gas (15 psi) was bubbled into the resulting mixture at 0° C. for 5 minutes. Then the reaction mixture was concentrated in vacuo. The residue was diluted with water (400 mL) and extracted with EtOAc (3×400 mL). The combined organic layers were dried over Na$_2$SO$_4$, filtered and concentrated in vacuo. The residue was purified by column chromatography (SiO$_2$, PE:EtOAc=10:1 to 3:1) to give the title compound (8.18 g, 19% yield) as a yellow oil.

$^1$H NMR (CDCl$_3$): δ 7.60 (s, 1H), 4.64-4.56 (m, 1H) and 1.57 (d, 6H).

Step C: Sodium 4-chloro-1-isopropyl-1H-pyrazole-3-sulfinate

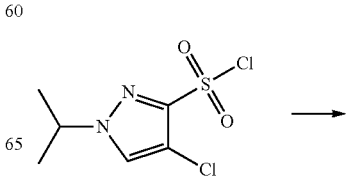

92

Intermediate L7: 5-(1-Hydroxyethyl)-1-methyl-1H-pyrazole-3-sulfinamide

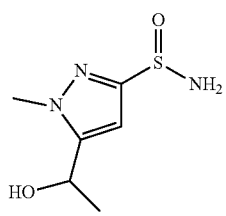

Step A: tert-Butyl (1-methyl-1H-pyrazol-3-yl)carbamate

To a solution of 1-methyl-1H-pyrazol-3-amine (40 g, 411.87 mmol, 1 eq) in THF (400 mL) was added a solution of NaOH (18.12 g, 453.06 mmol, 1.1 eq) in H$_2$O (400 mL) and Boc$_2$O (107.87 g, 494.24 mmol, 113.54 mL, 1.2 eq). The reaction mixture was stirred at 25° C. for 12 hours. Then the reaction mixture was diluted with H$_2$O (500 mL) and extracted with EtOAc (3×500 mL). The combined organic layers were washed with brine (2×200 mL), dried over Na$_2$SO$_4$, filtered and concentrated under reduced pressure. The residue was triturated with MTBE (200 mL) to give the title compound (36 g, 44% yield, 100% purity on LCMS) as a white solid.

$^1$H NMR (CDCl$_3$): δ 8.59 (br s, 1H), 7.19 (d, 1H), 6.45 (s, 1H), 3.81 (s, 3H) and 1.50 (s, 9H).

LCMS: m/z 220.1 (M+Na)$^+$ (ES$^+$).

Step B: tert-Butyl (5-(1-hydroxyethyl)-1-methyl-1H-pyrazol-3-yl)carbamate

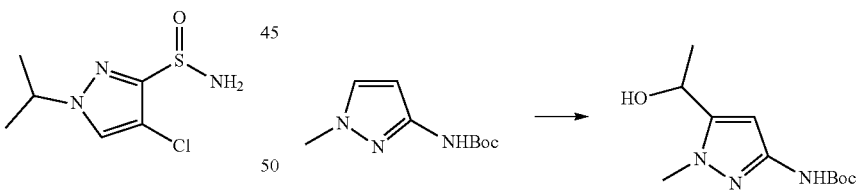

A solution of tert-butyl (1-methyl-1H-pyrazol-3-yl)carbamate (18 g, 91.26 mmol, 1 eq) in THF (400 mL) was cooled to −75° C. Then n-BuLi (2.5 M, 80.31 mL, 2.2 eq) was added dropwise into the mixture at −75° C. The reaction mixture was stirred at −75° C. for 1 hour. Then CH$_3$CHO (8.04 g, 182.52 mmol, 2 eq) was added. The resulting mixture was warmed to 25° C. and stirred at 25° C. for 1 hour. The reaction mixture was quenched with H$_2$O (500 mL) at 25° C. and extracted with EtOAc (3×500 mL). The combined organic layers were washed with brine (2×200 mL), dried over Na$_2$SO$_4$, filtered and concentrated under reduced pressure. The residue was purified by column chromatography (SiO$_2$, PE:EtOAc=10:1 to 0:1) to give the title compound (11 g, 22% yield, 90% purity on HNMR) as a white solid.

91

-continued

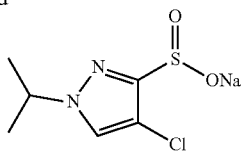

A solution of Na$_2$SO$_3$ (8.48 g, 67.29 mmol, 2 eq) in H$_2$O (25 mL) was stirred at 20° C. for 10 minutes. Na$_2$CO$_3$ (7.13 g, 67.29 mmol, 2 eq) was added and the resulting mixture stirred at 50° C. for 10 minutes. 4-Chloro-1-isopropyl-H-pyrazole-3-sulfonyl chloride (8.18 g, 33.65 mmol, 1 eq) was added dropwise and the resulting mixture was stirred at 50° C. for 2 hours. Then the reaction mixture was concentrated in vacuo. The residue was treated with EtOH (40 mL) and the mixture was stirred at 20° C. for 10 minutes. Then the suspension was filtered and the filtrate was concentrated in vacuo to afford a white solid. The white solid was treated with EtOAc (40 mL) for 10 minutes. Then the mixture was filtered. The filter cake was collected to give the title compound (4.6 g, 59% yield) as a yellow solid.

$^1$H NMR (DMSO-d$_6$): δ 7.81 (s, 1H), 4.46-4.39 (m, 1H) and 1.36 (d, 6H).

LCMS: m/z 191.0 (M−ONa)$^+$ (ES$^+$).

Step D: 4-Chloro-1-isopropyl-1H-pyrazole-3-sulfinamide

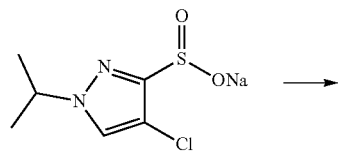

To a solution of sodium 4-chloro-1-isopropyl-1H-pyrazole-3-sulfinate (2.5 g, 10.84 mmol, 1 eq) in THF (40 mL) was added (COCl)$_2$ (2.75 g, 21.68 mmol, 1.90 mL, 2 eq) at 0° C. After stirring at 20° C. for 1 hour, the reaction mixture was added into an aqueous NH$_3$.H$_2$O solution (40 mL) at 0° C. The mixture was stirred at 20° C. for 1 hour and then concentrated in vacuo. The residue was purified by reversed phase flash chromatography (0.1% NH$_3$.H$_2$O/MeCN) to give the title compound (0.47 g, 21% yield, 100% purity on LCMS) as a white solid.

$^1$H NMR (DMSO-d$_6$): δ 8.17 (s, 1H), 6.37 (s, 2H), 4.54-4.47 (m, 1H) and 1.40 (d, 6H).

LCMS: m/z 230.0 (M+Na)$^+$ (ES$^+$).

¹H NMR (CDCl₃): δ 8.07 (s, 1H), 6.41 (s, 1H), 4.83-4.81 (m, 1H), 3.78 (s, 3H), 1.56 (d, 3H) and 1.47 (s, 9H).
LCMS: 264.1 m/z (M+Na)⁺ (ES⁺).

Step C:
1-(3-Amino-1-methyl-1H-pyrazol-5-yl)ethanol

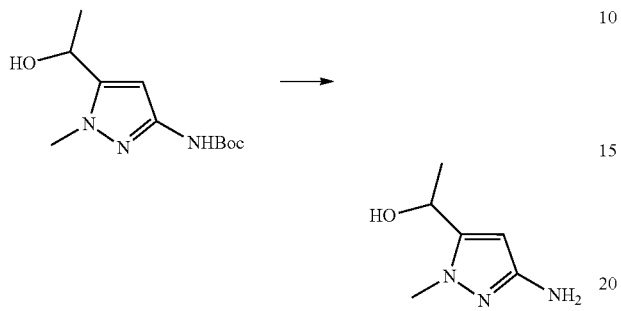

To a solution of tert-butyl (5-(1-hydroxyethyl)-1-methyl-1H-pyrazol-3-yl)carbamate (27 g, 111.90 mmol, 1 eq) in DCM (50 mL) was added HCl/EtOAc (4 M, 720.00 mL, 25.74 eq). The reaction mixture was stirred at 25° C. for 12 hours and then concentrated in vacuo to give the title compound (25 g, crude, HCl salt), which was used in the next step directly without further purification.
LCMS: 142.2 m/z (M+H)⁺ (ES⁺).

Step D:
5-(1-Hydroxyethyl)-1-methyl-1H-pyrazole-3-sulfonyl chloride

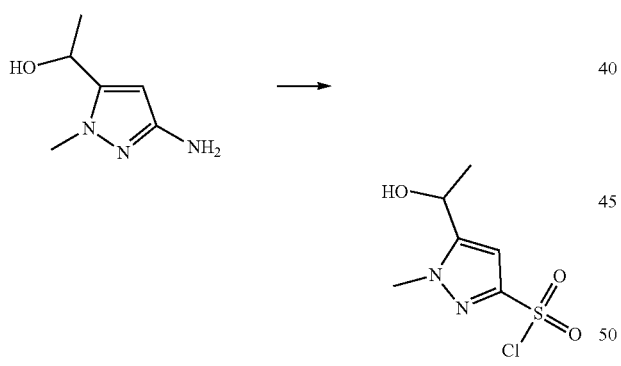

A solution of 1-(3-amino-1-methyl-1H-pyrazol-5-yl)ethanol (25 g, 177.09 mmol, 1 eq) in MeCN (500 mL) at 0° C. was treated with concentrated HCl (so mL) and H₂O (so mL). Then an aqueous solution of NaNO₂ (14.66 g, 212.51 mmol, 1.2 eq) in H₂O (50 mL) was added slowly. The resulting mixture was stirred at 0° C. for 40 minutes. AcOH (50 mL), CuCl (877 mg, 8.85 mmol, 211.74 µL, 0.05 eq) and CuCl₂ (11.91 g, 88.55 mmol, 0.5 eq) were added into the reaction mixture. Then SO₂ gas (15 psi) was bubbled into the mixture for 20 minutes at 0° C. The reaction mixture was stirred at 25° C. for 1 hour. Then the reaction mixture was diluted with H₂O (300 mL) and extracted with EtOAc (2×500 mL). The combined organic layers were washed with brine (200 mL), dried over Na₂SO₄, filtered and concentrated under reduced pressure. The residue was purified by column chromatography (SiO₂, PE:EtOAc=30:1 to 1:1) to give the title compound (7 g, crude) as a yellow oil.
¹H NMR (CDCl₃): δ 6.77 (s, 1H), 5.04-493 (m, 1H), 4.06 (s, 3H), and 1.65 (d, 3H).

Step E: Sodium 5-(1-hydroxyethyl)-1-methyl-1H-pyrazole-3-sulfinate

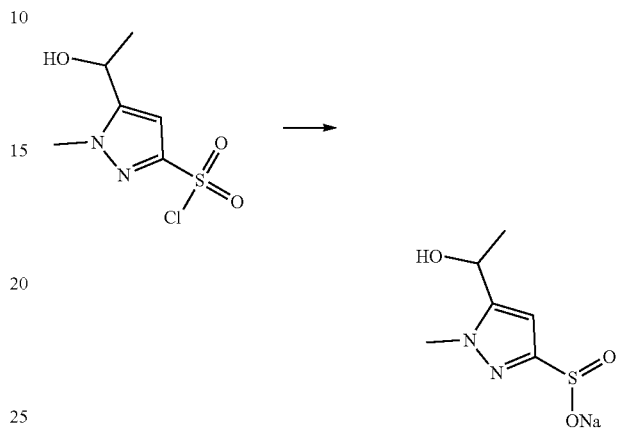

A solution of Na₂SO₃ (7.85 g, 62.32 mmol, 2 eq), Na₂CO₃ (6.60 g, 62.32 mmol, 2 eq) in H₂O (70 mL) was stirred at 20° C. for 10 minutes. Then the mixture was warmed to 50° C. for another 10 minutes. To the solution was added 5-(1-hydroxyethyl)-1-methyl-1H-pyrazole-3-sulfonyl chloride (7 g, 31.16 mmol, 1 eq). The reaction mixture was stirred at 50° C. for 1 hour and then concentrated in vacuo. The residue was treated with MeOH (2×50 mL) and filtered. The filtrate was concentrated in vacuo. The residue was triturated with EtOAc (2×30 mL) to give the title compound (5.4 g, 79% yield, 97% purity on LCMS) as a white solid.
¹H NMR (DMSO-d₆): δ 6.10 (s, 1H), 4.77-4.72 (m, 1H), 3.76 (s, 3H), and 1.38 (d, 3H).
LCMS: m/z 213.1 (M+H)⁺ (ES⁺).

Step F: 5-(1-Hydroxyethyl)-1-methyl-1H-pyrazole-3-sulfinamide

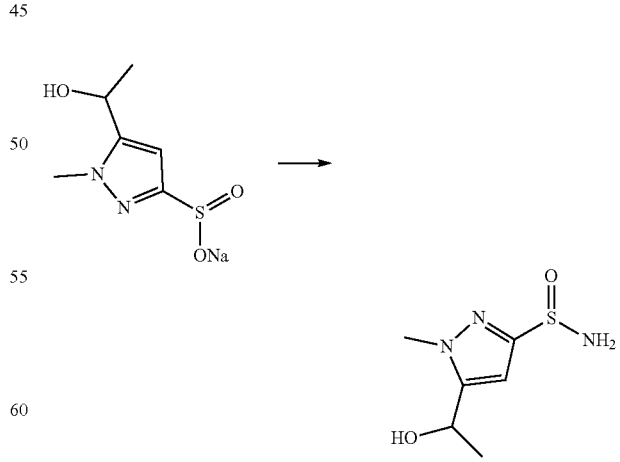

To a solution of sodium 5-(1-hydroxyethyl)-1-methyl-1H-pyrazole-3-sulfinate (3 g, 14-14 mmol, 1 eq) in THF (10 mL) was added oxalyl chloride (3.59 g, 28.27 mmol, 2.48 mL, 2 eq). The reaction mixture was stirred at 25° C. for 2 hours.

Then the reaction mixture was added dropwise into a solution of $NH_3$ in THF, which had been prepared by bubbling $NH_3$ gas (15 psi) into THF (10 mL) at −70° C. for 10 minutes. The resulting mixture was stirred at 25° C. for 1 hour and then concentrated in vacuo. The residue was purified by reversed phase flash chromatography (water (0.05% $NH_3.H_2O$)-MeCN) to give the title compound (2.5 g, 39% yield, 83% purity on LCMS) as a yellow oil.

$^1$H NMR (DMSO-$d_6$): δ 6.48 (s, 1H), 6.23 (br s, 2H), 4.86-4.76 (m, 1H), 3.85 (s, 3H), and 1.43-1.37 (m, 3H).

LCMS: m/z 212.1 (M+Na)$^+$ (ES$^+$).

Intermediate L8: 5-(Azetidin-1-ylmethyl)-1-methyl-1H-pyrazole-3-sulfinamide

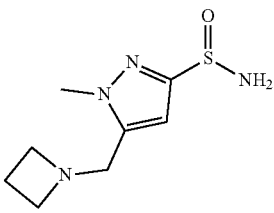

Step A: tert-Butyl (1-methyl-1H-pyrazol-3-yl)carbamate

To a solution of 1-methyl-1H-pyrazol-3-amine (50 g, 514.84 mmol, 1 eq) in THF (500 mL) was added a solution of NaOH (22.65 g, 566.32 mmol, 1.1 eq) in $H_2O$ (500 mL) at 20° C. Then $Boc_2O$ (112.36 g, 514.84 mmol, 118.28 mL, 1 eq) was added at 0° C. The reaction mixture was stirred at 20° C. for 24 hours and then concentrated in vacuo to remove THF. The aqueous solution was extracted with EtOAc (3×300 mL). The combined organic layers were concentrated in vacuo. The residue was purified by column chromatography ($SiO_2$, PE:EtOAc=10:1 to 2:1) to give the title compound (67 g, 66% yield) as a white solid.

$^1$H NMR (CDCl$_3$): δ 8.42 (br s, 1H), 7.20 (d, 1H), 6.45 (s, 1H), 3.81 (s, 3H) and 1.51 (s, 9H).

Step B: tert-Butyl(5-formyl-1-methyl-1H-pyrazol-3-yl)carbamate

n-BuLi (2.5 M, 133.85 mL, 2 eq) was added dropwise to a stirred solution of tert-butyl (1-methyl-1H-pyrazol-3-yl)carbamate (33 g, 167-31 mmol, 1 eq) in THF (1 L) at −75° C. under $N_2$. The reaction mixture was stirred at −75° C. for 1 hour. Then a solution of DMF (18.34 g, 250.97 mmol, 19.31 mL, 1.5 eq) in THF (100 mL) was added dropwise whilst maintaining the temperature below −65° C. The resulting mixture was stirred at −65° C. for 1 hour. The reaction mixture was quenched with water (500 mL) and concentrated in vacuo to remove THF. The aqueous layer was extracted with EtOAc (3×400 mL). The combined organic layers were dried over $Na_2SO_4$, filtered and concentrated in vacuo. The residue was purified by column chromatography ($SiO_2$, PE:EtOAc=1:0 to 15:1) to give the title compound (32 g, crude) as a white solid.

$^1$H NMR (CDCl$_3$): δ 9.44 (s, 1H), 6.94 (s, 1H), 6.77 (s, 1H), 3.74 (s, 3H) and 1.19 (s, 9H).

Step C: tert-Butyl (5-(hydroxymethyl)-1-methyl-1H-pyrazol-3-yl)carbamate

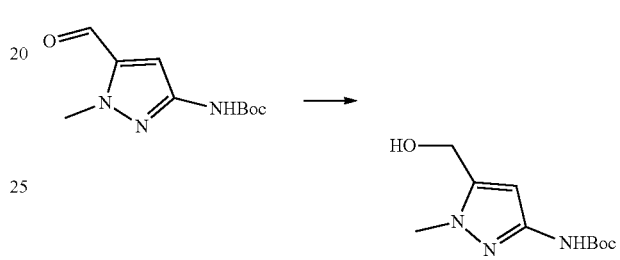

To a solution of tert-butyl (5-formyl-1-methyl-1H-pyrazol-3-yl)carbamate (32 g, 71.03 mmol, 1 eq) in MeOH (200 mL) was added $NaBH_4$ (2.69 g, 71.03 mmol, 1 eq) at 0° C. The reaction mixture was stirred at 20° C. for 1 hour. The reaction mixture was quenched with water (100 mL) and concentrated in vacuo to remove MeOH. The aqueous layer was diluted with water (100 mL) and extracted with EtOAc (3×10 mL). The combined organic layers were dried over $Na_2SO_4$, filtered and concentrated in vacuo. The residue was purified by column chromatography ($SiO_2$, PE:EtOAc=15:1 to 1:1) to give the title compound (15 g, 79% yield, 85% purity on LCMS) as a white solid.

$^1$H NMR (CDCl$_3$): δ 7.99 (s, 1H), 6.38 (s, 1H), 4.58 (s, 2H), 3.78 (s, 3H) and 1.50 (s, 9H).

LCMS: m/z 250.2 (M+Na)$^+$ (ES$^+$).

Step D: (3-Amino-1-methyl-1H-pyrazol-5-yl)methanol

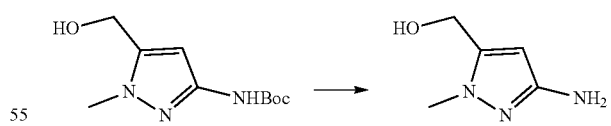

To a solution of tert-butyl (5-(hydroxymethyl)-1-methyl-1H-pyrazol-3-yl)carbamate (32 g, 140.81 mmol, 1 eq) in DCM (300 mL) was added HCl/dioxane (4 M, 250 mL, 7.10 eq) at 0° C. The reaction mixture was stirred at 20° C. for 18 hours and then concentrated in vacuo to give the title compound (23 g, 99.8% yield, HCl salt) as a white solid, which was used in next step without further purification.

$^1$H NMR (CD$_3$OD-$d_4$): δ 6.06 (s, 1H), 4.60 (s, 2H) and 3.81 (s, 3H).

LCMS: m/z 128.2 (M+H)$^+$ (ES$^+$).

Step E: 5-(Hydroxymethyl)-1-methyl-1H-pyrazole-3-sulfonyl chloride

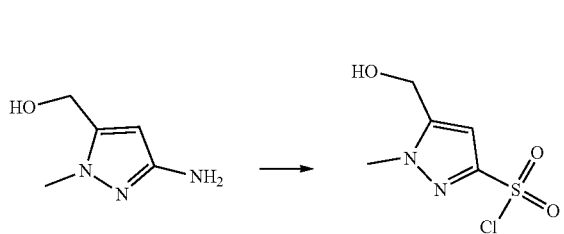

A solution of (3-amino-1-methyl-1H-pyrazol-5-yl)methanol (22.90 g, 140 mmol, 1 eq, HCl) in MeCN (500 mL) at 0° C. was treated with hydrochloric acid (100 mL, 6 M). Then a solution of $NaNO_2$ (11.59 g, 168.00 mmol, 1.2 eq) in $H_2O$ (50 mL) was added slowly. The resulting mixture was stirred at 0° C. for 40 minutes. AcOH (50 mL), $CuCl_2$ (9.41 g, 70.00 mmol, 0.5 eq) and CuCl (693 mg, 7.00 mmol, 167.39 µL, 0.05 eq) were added. Then $SO_2$ gas (15 psi) was bubbled into the mixture at 0° C. for 5 minutes. The reaction mixture was concentrated in vacuo to remove most of MeCN. The aqueous layer was diluted with water (300 mL) and extracted with EtOAc (3×400 mL). The combined organic layers were dried over $Na_2SO_4$, filtered and concentrated in vacuo. The residue was purified by column chromatography ($SiO_2$, PE:EtOAc=10:1 to 1:1) to give the title compound (14 g, 28% yield, 60% purity on HNMR) as a yellow oil. 20 $^1$H NMR ($CDCl_3$): δ 6.78 (s, 1H), 4.73 (s, 2H) and 4.03 (s, 3H).

Step F: Sodium 5-(hydroxymethyl)-1-methyl-1H-pyrazole-3-sulfinate

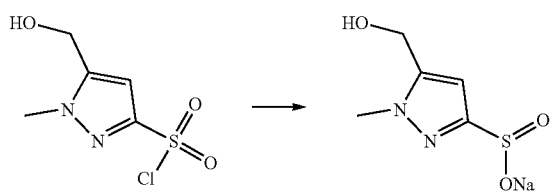

A solution of $Na_2SO_3$ (10.05 g, 79.76 mmol, 2 eq) and $Na_2CO_3$ (8.45 g, 79.76 mmol, 2 eq) in $H_2O$ (60 mL) was stirred at 50° C. for 10 minutes. Then 5-(hydroxymethyl)-1-methyl-1H-pyrazole-3-sulfonyl chloride (14 g, 39.88 mmol, 1 eq) was added dropwise. The resulting mixture was stirred at 50° C. for another 2 hours and then concentrated in vacuo. The residue was treated with MeOH (100 mL) and the mixture was stirred for 30 minutes. The suspension was filtered and the filtrate was concentrated in vacuo. The residue was triturated with EtOAc (80 mL) to give the title compound (7.8 g, 99% yield) as a white solid.

$^1$H NMR (DMSO-$d_6$): δ 6.10 (s, 1H), 4.42 (s, 2H) and 3.73 (s, 3H).

Step G: 5-(Hydroxymethyl)-1-methyl-1H-pyrazole-3-sulfinamide

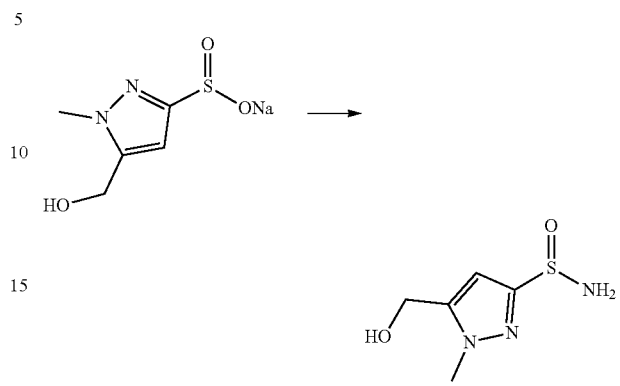

To a solution of sodium 5-(hydroxymethyl)-1-methyl-1H-pyrazole-3-sulfinate (3 g, 15.14 mmol, 1 eq) in THF (50 mL) was added oxalyl chloride (3.84 g, 30.28 mmol, 2.65 mL, 2 eq) at 0° C. After stirring for 1 hour at 20° C., the reaction mixture was added into an aqueous $NH_3.H_2O$ solution (50 mL, 25%) at 0° C. The reaction mixture was stirred at 20° C. for 1 hour and then concentrated in vacuo. The residue was purified by reversed phase flash chromatography (water (0.05% $NH_3.H_2O$)-MeCN) to give the title compound (900 mg, 33% yield, 96% purity on LCMS) as colourless gum.

$^1$H NMR (DMSO-$d_6$): δ 6.47 (s, 1H), 6.21 (s, 2H), 5.38 (t, 1H), 4.50 (d, 2H) and 3.81 (s, 3H).

LCMS: m/z 198.1 (M+Na)$^+$ (ES$^+$).

Step H: 5-(Chloromethyl)-1-methyl-1H-pyrazole-3-sulfinamide

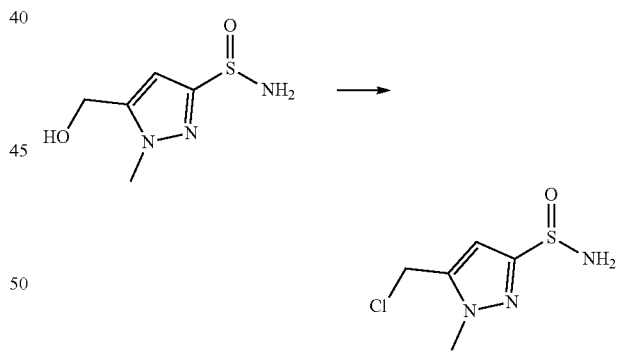

To a solution of 5-(hydroxymethyl)-1-methyl-1H-pyrazole-3-sulfinamide (800 mg, 4.57 mmol, 1 eq) and $Et_3N$ (924 mg, 9.13 mmol, 1.27 mL, 2 eq) in DMF (6 mL) was added methanesulfonyl chloride (523 mg, 4.57 mmol, 353.40 µL, 1 eq) at 0° C. The reaction mixture was stirred at 20° C. for 3 hours. The reaction mixture was diluted with MeOH (2 mL) and filtered. The filtrate was purified by reversed phase flash chromatography (water (0.05% $NH_3.H_2O$)-MeCN) to give the title compound (350 mg, 37% yield, 94% purity on LCMS) as a white solid.

$^1$H NMR (DMSO-$d_6$): δ 6.65 (s, 1H), 6.33 (s, 2H), 4.96 (s, 2H) and 3.88 (s, 3H).

LCMS: m/z 216.0 (M+Na)$^+$ (ES$^+$).

Step I: 5-(Azetidin-1-ylmethyl)-1-methyl-1H-pyrazole-3-sulfinamide

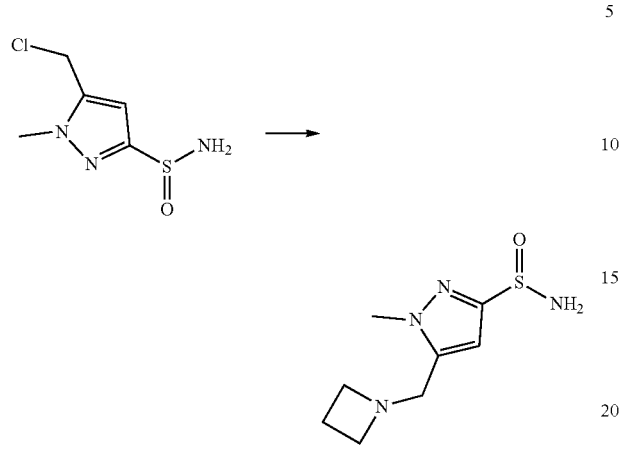

To a solution of 5-(chloromethyl)-1-methyl-1H-pyrazole-3-sulfinamide (350 mg, 1.81 mmol, 1 eq) in THF (5 mL) was added azetidine (413 mg, 7.23 mmol, 487.89 μL, 4 eq). The mixture was stirred at 50° C. for 2 hours and then concentrated in vacuo. The residue was purified by reversed phase flash chromatography (water (0.05% $NH_3.H_2O$)-MeCN) to give the title compound (280 mg, 59% yield, 81% purity on LCMS) as colourless gum.

$^1$H NMR (DMSO-$d_6$): δ 6.42 (s, 1H), 6.21 (s, 2H), 3.79 (s, 3H), 3.56 (s, 2H), 3.16-3.11 (m, 4H) and 2.01-1.97 (m, 2H).

LCMS: m/z 215.2 (M+H)$^+$ (ES$^+$).

Intermediate R1: 4-Isocyanato-1,2,3,5,6,7-hexahydro-s-indacene

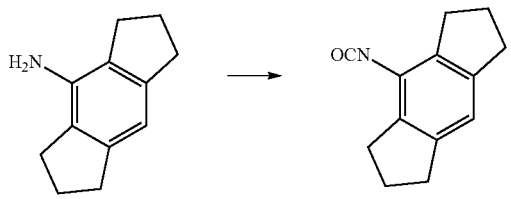

To a solution of phosgene (4.45 mL, 20% weight in toluene, 8.4 mmol) in EtOAc (90 mL) was added dropwise a solution of 1,2,3,5,6,7-hexahydro-s-indacen-4-amine (589 mg, 3.4 mmol) in EtOAc (45 mL) at ambient temperature. The resulting reaction mixture was then heated to reflux for 3 hours and upon cooling was filtered and concentrated in vacuo to afford the title compound as a brown oil (756 mg, 100% yield). The crude product was used directly without further purification.

$^1$H NMR (CDCl$_3$): δ 6.8 (s, 1H), 2.89 (m, 8H) and 2.09 (m, 4H).

Intermediate R2: 4-(4-Isocyanato-2,3-dihydro-1H-inden-5-yl)-2-methoxypyridine

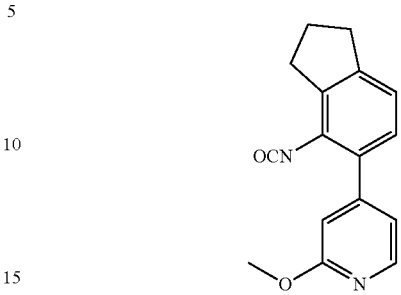

Step A: 4-Nitro-2,3-dihydro-1H-indene

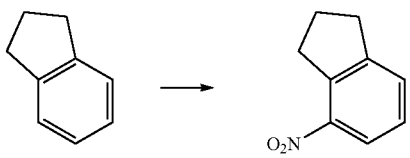 [SMILES: c1ccc2c(c1)CCC2 ; O=[N+]([O-])c1cccc2c1CCC2]

To a mixture of 2,3-dihydro-1H-indene (60 g, 507.72 mmol, 62.50 mL, 1 eq) in $H_2SO_4$ (30 mL) was added a mixture of $HNO_3$ (50 mL, 60% purity) and $H_2SO_4$ (50 mL) dropwise at 0° C. over a period of 3.5 hours. The reaction mixture was stirred at 0° C. for 0.5 hour. Then the reaction mixture was poured into ice water (600 mL) and extracted with EtOAc (2×400 mL). The combined organic layers were washed with water (500 mL), saturated aqueous $NaHCO_3$ solution (500 mL) and brine (2×500 mL). The organic layer was dried over anhydrous $Na_2SO_4$, filtered and concentrated in vacuo. The residue was purified by column chromatography (SiO$_2$, PE:EtOAc=1:0 to 100:1) to give the title compound (55 g, 66% yield) as a colourless oil.

$^1$H NMR (CDCl$_3$): δ 7.98 (d, 1H), 7.51 (d, 1H), 7.30 (t, 1H), 3.41 (t, 2H), 302 (t, 2H) and 2.22-2.20 (m, 2H).

Step B: 2,3-Dihydro-1H-inden-4-amine

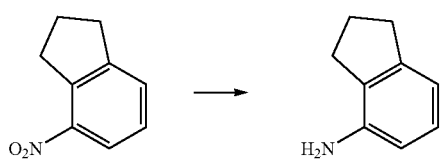 [SMILES: O=[N+]([O-])c1cccc2c1CCC2 ; Nc1cccc2c1CCC2]

To a solution of 4-nitro-2,3-dihydro-1H-indene (55 g, 337.07 mmol, 1 eq) in MeOH (500 mL) was added Pd/C (5 g, 10% purity) under $N_2$. The suspension was degassed in vacuo and purged with $H_2$ several times. The reaction mixture was stirred at 20° C. for 12 hours under $H_2$ (50 psi), filtered and the filtrate was concentrated in vacuo. The residue was purified by column chromatography (SiO$_2$, PE:EtOAc=1:0 to 100:4) to give the title compound (19.82 g, 43% yield, 96.4% purity on LCMS) as a brown oil.

$^1$H NMR (CDCl$_3$): δ 7.01 (t, 1H), 6.71 (d, 1H), 6.51 (d, 1H), 3.57 (br s, 2H), 2.93 (t, 2H), 2.75 (t, 2H) and 2.16-2.08 (m, 2H).

Step C: N-(2,3-Dihydro-1H-inden-4-yl)acetamide

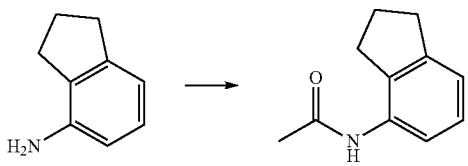

To a solution of 2,3-dihydro-1H-inden-4-amine (19.8 g, 148.66 mmol, 1 eq) and TEA (19.56 g, 193.26 mmol, 26.90 mL, 1.3 eq) in DCM (300 mL) was added dropwise Ac$_2$O (17.45 g, 170.96 mmol, 16.01 mL, 1.15 eq) over 0.1 hour at 0° C. Then the reaction mixture was warmed to 16° C. and stirred for 1.4 hours. The mixture was poured into water (500 mL) and extracted with DCM (2×300 mL). The combined organic phases were washed with brine (2×500 mL), dried over anhydrous Na$_2$SO$_4$, filtered and concentrated in vacuo to give the title compound (25.74 g, 96% yield, 96.7% purity on LCMS) as a white solid.

$^1$H NMR (CDCl$_3$): δ 7.70 (d, 1H), 7.15 (t, 1H), 7.02 (d, 1H), 2.95 (t, 2H), 2.81 (t, 2H), 2.18 (s, 3H) and 2.15-2.08 (m, 2H).

LCMS: m/z 176.2 (M+H)$^+$ (ES$^+$).

Step D: N-(5-Bromo-2,3-dihydro-1H-inden-4-yl)acetamide

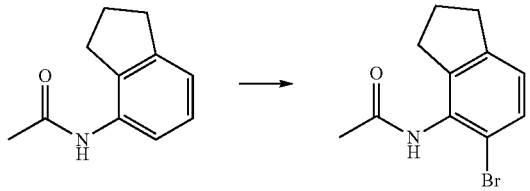

A mixture of N-(2,3-dihydro-1H-inden-4-yl)acetamide (34.6 g, 197.46 mmol, 1 eq), PTSA (18.70 g, 108.60 mmol, 0.55 eq) and Pd(OAc)$_2$ (2.22 g, 9.87 mmol, 0.05 eq) were suspended in toluene (400 mL) and stirred at 20° C. for 0.5 hour under air atmosphere. Then NBS (38.66 g, 217.20 mmol, 1.1 eq) was added into the reaction mixture. The reaction mixture was stirred at 20° C. for 2 hours and then poured into water (500 mL) and extracted with EtOAc (2×500 mL). The combined organic phases were washed with brine (2×500 mL), dried over anhydrous Na$_2$SO$_4$, filtered and concentrated in vacuo. The residue was purified by column chromatography (SiO$_2$, PE:EtOAc=10:1 to 2:1) to give the title compound (13.9 g, 27% yield, 98.1% purity on LCMS) as a white solid.

$^1$H NMR (CDCl$_3$): δ 7.33 (d, 1H), 7.16 (s, 1H), 6.98 (d, 1H), 2.92-2.83 (m, 4H), 2.21 (s, 3H) and 2.10-2.02 (m, 2H).

LCMS: m/z 254.1 (M+H)$^+$ (ES$^+$).

Step E: 5-Bromo-2,3-dihydro-1H-inden-4-amine

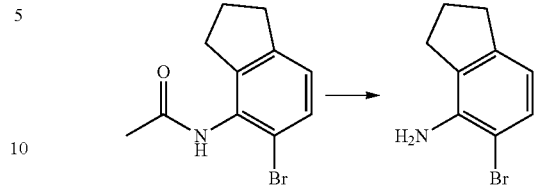

A mixture of N-(5-bromo-2,3-dihydro-1H-inden-4-yl)acetamide (45.68 g, 179.76 mmol, 1 eq) in EtOH (200 mL) and concentrated HCl (300 mL, 36%) was stirred at 80° C. for 36 hours. Then the reaction mixture was cooled to 0° C. in an ice bath and some solid was precipitated. The suspension was filtered. The filter cake was washed with ice water (50 mL) and dried in vacuo to give the title compound (34.1 g, 72% yield, 94.1% purity on LCMS, HCl salt) as a grey solid.

$^1$H NMR (DMSO-d$_6$): δ 7.67 (br s, 2H), 7.24 (d, 1H), 6.69 (d, 1H), 2.85 (t, 2H), 2.79 (t, 2H) and 2.04-1.96 (m, 2H).

LCMS: m/z 212.0 (M+H)$^+$ (ES$^+$).

Step F: 5-(2-Methoxypyridin-4-yl)-2,3-dihydro-1H-inden-4-amine

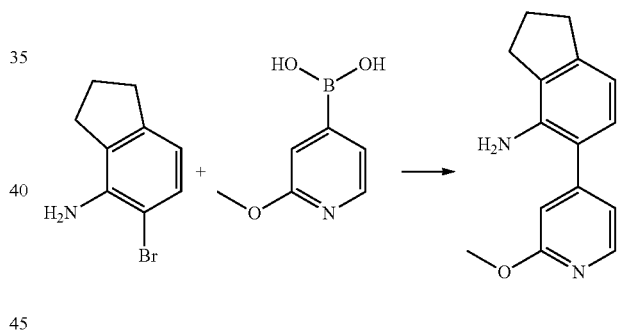

A solution of (2-methoxypyridin-4-yl)boronic acid (25.11 g, 164.15 mmol, 1.2 eq), 5-bromo-2,3-dihydro-1H-inden-4-amine (34 g, 136.80 mmol, 1 eq, HCl salt) and K$_2$CO$_3$ (60.50 g, 437.74 mmol, 3.2 eq) in dioxane (500 mL) and H$_2$O (100 mL) was degassed with nitrogen for 15 minutes before Pd(dppf)Cl$_2$·CH$_2$Cl$_2$ (6 g, 7.35 mmol, 0.053 eq) was added. The reaction mixture was heated to 80° C. for 12 hours under N$_2$. The mixture was poured into water (500 mL) and extracted with EtOAc (2×500 mL). The combined organic phases were washed with brine (2×700 mL), dried over anhydrous Na$_2$SO$_4$, filtered and concentrated in vacuo. The residue was purified by flash silica gel column chromatography (SiO$_2$, EtOAc:PE=0:1 to 1:10) to give the title compound (27.4 g, 79% yield, 95% purity on LCMS) as a white solid.

$^1$H NMR (CDCl$_3$): δ 8.22 (d, 1H), 7.03-7.00 (m, 1H), 6.99 (d, 1H), 6.87 (s, 1H), 6.77 (d, 1H), 3.99 (s, 3H), 3.77 (br s, 2H), 2.97 (t, 2H), 2.77 (t, 2H) and 2.21-2.13 (m, 2H).

LCMS: m/z 241.2 (M+H)$^+$ (ES$^+$).

LCMS: m/z 134.2 (M+H)$^+$ (ES$^+$).

Step G: 4-(4-Isocyanato-2,3-dihydro-1H-inden-5-yl)-2-methoxypyridine

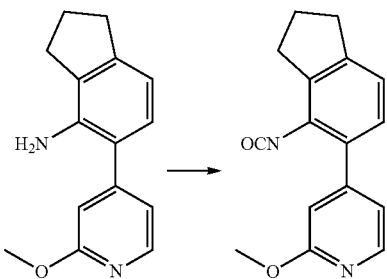

To a solution of 5-(2-methoxypyridin-4-yl)-2,3-dihydro-1H-inden-4-amine (11 g, 45.78 mmol, 1 eq) and TEA (5.10 g, 50-35 mmol, 7.01 mL, 1.1 eq) in THF (275 mL) was added in portions bis(trichloromethyl) carbonate (4.93 g, 16.61 mmol, 0.36 eq) at 0° C. Then the reaction mixture was stirred at 16° C. for 0.5 hour. The reaction mixture was filtered and the filter cake was washed with THF (2 L). The filtrate was concentrated in vacuo to give the title compound (9.04 g, 74% yield) as a light yellow solid.

$^1$H NMR (CDCl$_3$): δ 8.28 (d, 1H), 7.20-7.16 (m, 3H), 7.02 (s, 1H), 4.16 (s, 3H), 3.04-2.99 (m, 4H) and 2.23-2.15 (m, 2H).

Intermediate R3: 4-(5-Fluoro-2-isocyanato-3-isopropylphenyl)picolinonitrile

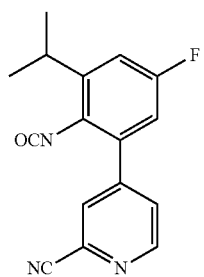

Step A: 4-Fluoro-2-(prop-1-en-2-yl)aniline

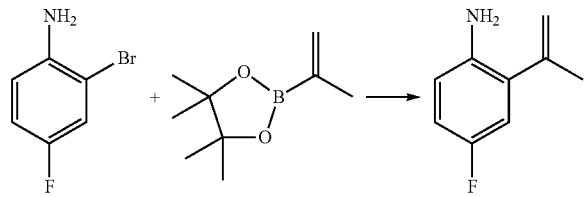

To a mixture of 2-bromo-4-fluoroaniline (39 g, 205.25 mmol, 1 eq), 4,4,5,5-tetramethyl-2-(prop-1-en-2-yl)-1,3,2-dioxaborolane (36.21 g, 215.51 mmol, 1.05 eq) and K$_2$CO$_3$ (70.92 g, 513.12 mmol, 2.5 eq) in dioxane (200 mL) and H$_2$O (40 mL) was added Pd(dppf)Cl$_2$ (7-51 g, 10.26 mmol, 0.05 eq) under N$_2$ atmosphere. Then the reaction mixture was stirred at 80° C. for 5 hours. The reaction mixture was quenched by addition of H$_2$O (600 mL) and extracted with EtOAc (2×500 mL). The combined organic layers were washed with brine (2×600 mL), dried over anhydrous Na$_2$SO$_4$, filtered and concentrated under reduced pressure. The residue was purified by column chromatography (SiO$_2$, PE:EtOAc=1:0 to 100:1) to give the title compound (27 g, 77% yield, 89% purity on LCMS) as a yellow oil.

$^1$H NMR (CDCl$_3$): δ 6.81-6.76 (m, 2H), 6.66-6.62 (m, 1H), 5.38 (s, 1H), 5.08 (s, 1H), 3.69 (br s, 2H) and 1.25 (s, 3H).

LCMS: m/z 152.2 (M+H)$^+$ (ES$^+$).

Step B: 4-Fluoro-2-isopropylaniline

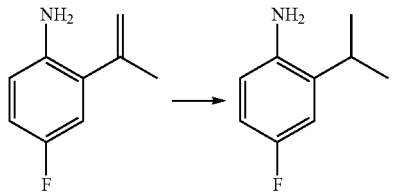

To a solution of 4-fluoro-2-(prop-1-en-2-yl)aniline (21 g, 138.91 mmol, 1 eq) in MeOH (300 mL) was added Pd/C (2.1 g, 178.59 mmol, 10% purity) under N$_2$ atmosphere. The reaction mixture was degassed in vacuo and purged with H$_2$ several times. Then the reaction mixture was stirred at 25° C. for 12 hours under H$_2$ (50 psi), filtered and the filtrate was concentrated in vacuo to give the title compound (20 g, crude) as a yellow oil.

$^1$H NMR (CDCl$_3$): δ 6.86 (dd, 1H), 6.75-6.72 (m, 1H), 6.63-6.61 (m, 1H), 3.50 (br s, 2H), 2.95-2.84 (m, 1H) and 1.25 (d, 6H).

LCMS: m/z 154.2 (M+H)$^+$ (ES$^+$).

Step C: 2-Bromo-4-fluoro-6-isopropylaniline

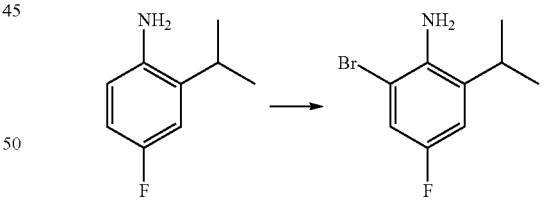

To a solution of 4-fluoro-2-isopropylaniline (20 g, 130.55 mmol, 1 eq) in toluene (250 mL) was added NBS (23.24 g, 130.55 mmol, 1 eq) at 25° C. The reaction mixture was stirred at 25° C. for 10 minutes. Then the reaction mixture was poured into H$_2$O (300 mL) and extracted with EtOAc (2×250 mL). The organic phases were washed with brine (2×400 mL), dried over anhydrous Na$_2$SO$_4$, filtered and concentrated in vacuo. The residue was purified by column chromatography (SiO$_2$, eluting with PE) to give the title compound (30 g, 99% yield) as a black brown oil.

$^1$H NMR (CDCl$_3$): δ 6.99 (dd, 1H), 6.78 (dd, 1H), 3.91 (br s, 2H), 2.88-2.71 (m, 1H) and 1.17 (d, 6H).

LCMS: m/z 232.1 (M+H)$^+$ (ES$^+$).

Step D: 4-(2-Amino-5-fluoro-3-isopropylphenyl)picolinonitrile

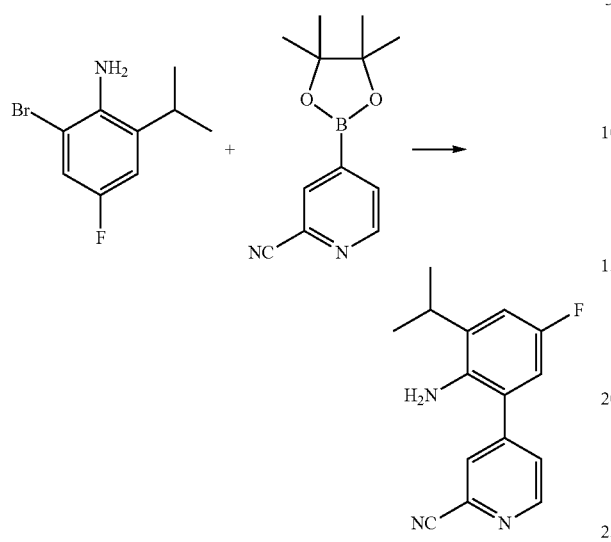

To a solution of 2-bromo-4-fluoro-6-isopropylaniline (3.6 g, 15.51 mmol, 1 eq) and 4-(4,4,5,5-tetramethyl-1,3,2-dioxaborolan-2-yl)picolinonitrile (3.60 g, 15.67 mmol, 1.01 eq) in dioxane (90 mL) and H$_2$O (9 mL) was added Na$_2$CO$_3$ (4.11 g, 38.78 mmol, 2.5 eq). Then Pd(dppf)Cl$_2$ (1.13 g, 1.55 mmol, 0.1 eq) was added under N$_2$ atmosphere. The resulting mixture was stirred at 80° C. for 2 hours under nitrogen and then concentrated in vacuo. The residue was purified by column chromatography (SiO$_2$, PE:EtOAc=20:1 to 5:1) and then triturated with PE (10 mL) to give the title compound (2.65 g, 65% yield, 97% purity on LCMS) as a yellow solid.

$^1$HNMR (CDCl$_3$): δ 8.79 (d, 1H), 7.86 (d, 1H), 7.65 (dd, 1H), 6.99 (dd, 1H), 6.70 (dd, 1H), 3.63 (br s, 2H), 2.98-2.87 (m, 1H) and 1.30 (d, 6H).

LCMS: m/z 256.2 (M+H)$^+$ (ES$^+$).

Step E: 4-(5-Fluoro-2-isocyanato-3-isopropylphenyl)picolinonitrile

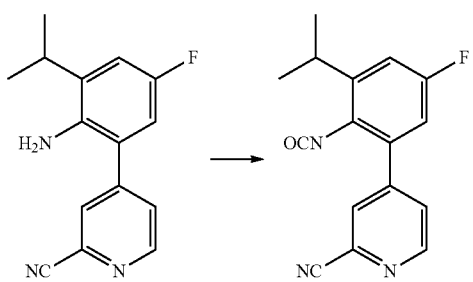

To a solution of 4-(2-amino-5-fluoro-3-isopropylphenyl)picolinonitrile (1 g, 3.92 mmol, 1 eq) in THF (40 mL) was added TEA (793 mg, 7.83 mmol, 1.09 mL, 2 eq). Then triphosgene (465 mg, 1.57 mmol, 0.4 eq) was added in portions at 5° C. The mixture was stirred at 70° C. for 1 hour. Then the mixture was diluted with EtOAc (200 mL) and filtered through silica gel. The filtrate was concentrated in vacuo to give the title compound (1.2 g, crude) as a yellow solid, which was used directly in the next step.

Intermediate R4: 4-(5-Fluoro-2-isocyanato-3-isopropylphenyl)-2-methoxypyridine

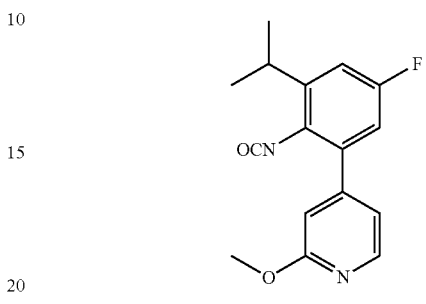

Step A: 4-Fluoro-2-isopropyl-6-(2-methoxypyridin-4-yl)aniline

To a solution of 2-bromo-4-fluoro-6-isopropylaniline (12 g, 51.70 mmol, 1 eq) in dioxane (240 mL) and H$_2$O (48 mL) was added (2-methoxypyridin-4-yl)boronic acid (9.49 g, 62.04 mmol, 1.2 eq) and Na$_2$CO$_3$ (13.70 g, 129.26 mmol, 2.5 eq). The reaction mixture was purged with N$_2$ three times. Then Pd(dppf)Cl$_2$ (3.78 g, 5.17 mmol, 0.1 eq) was added under N$_2$. The resulting mixture was heated at 80° C. for 2 hours. Then the reaction mixture was quenched with H$_2$O (800 mL) and extracted with EtOAc (2×600 mL). The combined organic layers were washed with brine (2×800 mL), dried over anhydrous Na$_2$SO$_4$, filtered and concentrated under reduced pressure. The residue was purified by column chromatography (SiO$_2$, PE:EtOAc=70:1 to 10:1) and then triturated with hexane (100 mL) to give the title compound (10.05 g, 72% yield, 96% purity on LCMS).

1H NMR (CDCl$_3$): δ 8.24 (d, 1H), 6.97 (d, 1H), 6.93 (d, 1H), 6.83 (s, 1H), 6.73-6.70 (m, 1H), 3.99 (s, 3H), 3.66 (br s, 2H), 2.97-2.89 (m, 1H) and 1.29 (dd, 6H).

LCMS: m/z 261.1 (M+H)$^+$ (ES$^+$).

Step B: 4-(5-Fluoro-2-isocyanato-3-isopropylphenyl)-2-methoxypyridine

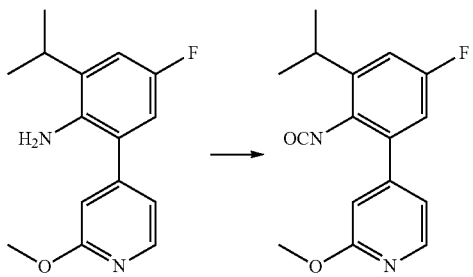

To a solution of 4-fluoro-2-isopropyl-6-(2-methoxypyridin-4-yl)aniline (1 g, 3.84 mmol, 1 eq) in THF (40 mL) was added TEA (777 mg, 7.68 mmol, 1.07 mL, 2 eq). Then triphosgene (456 mg, 1.54 mmol, 0.4 eq) was added in portions at 5° C. The mixture was stirred at 70° C. for 1 hour. Then the mixture was diluted with EtOAc (200 mL) and filtered through silica gel. The filtrate was concentrated in vacuo to give the title compound (1.1 g, crude) as yellow oil, which was used directly in the next step.

Intermediate R5:
5-Fluoro-2-isocyanato-1,3-diisopropylbenzene

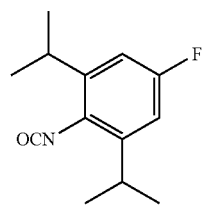

Step A: 4-Fluoro-2,6-di(prop-1-en-2-yl)aniline

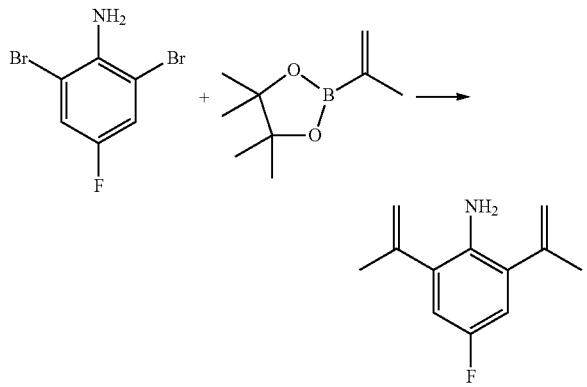

To a solution of 2,6-dibromo-4-fluoroaniline (32.96 g, 122.58 mmol, 1 eq) in dioxane (400 mL) and H$_2$O (40 mL) was added 4,4,5,5-tetramethyl-2-(prop-1-en-2-yl)-1,3,2-dioxaborolane (55 g, 327.30 mmol, 2.67 eq), Pd(dppf)Cl$_2$ (4.48 g, 6.13 mmol, 0.05 eq) and Cs$_2$CO$_3$ (79.88 g, 245.17 mmol, 2 eq) under N$_2$. The reaction mixture was stirred at 100° C. for 3 hours. Then the reaction mixture was diluted with H$_2$O (500 mL) and extracted with EtOAc (3×1 L). The combined organic layers were washed with brine (3×200 mL), dried over Na$_2$SO$_4$, filtered and concentrated under reduced pressure. The residue was purified by column chromatography (SiO$_2$, eluting with PE) to give the title compound (25 g, crude) as a blue oil.

$^1$H NMR (CDCl$_3$): δ 6.66 (d, 2H), 5.34-5.32 (m, 2H), 5.10-5.08 (m, 2H), 3.85 (br s, 2H) and 2.08 (s, 6H).

LCMS: m/z 192.2 (M+H)$^+$ (ES$^+$).

Step B: 4-Fluoro-2,6-diisopropylaniline

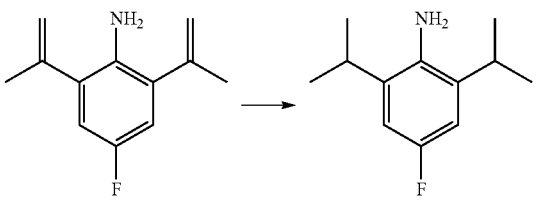

To a solution of 4-fluoro-2,6-di(prop-1-en-2-yl)aniline (25 g, 130.72 mmol, 1 eq) in MeOH (400 mL) was added Pd/C (3 g, 10% purity) under N$_2$. The suspension was degassed in vacuo and purged with H$_2$ several times. The reaction mixture was stirred at 25° C. for 12 hours under H$_2$ (50 psi). Then the reaction mixture was filtered and the filtrate was concentrated in vacuo. The residue was purified by column chromatography (SiO$_2$, eluting with PE) to give the title compound (13 g, 50% yield, 98% purity on LCMS) as a yellow oil.

$^1$H NMR (CDCl$_3$): δ 6.78 (d, 2H), 4.42 (br s, 2H), 3.04-2.93 (m, 2H) and 1.26 (d, 12H).

LCMS: m/z 196.1 (M+H)$^+$ (ES$^+$).

Step C:
5-Fluoro-2-isocyanato-1,3-diisopropylbenzene

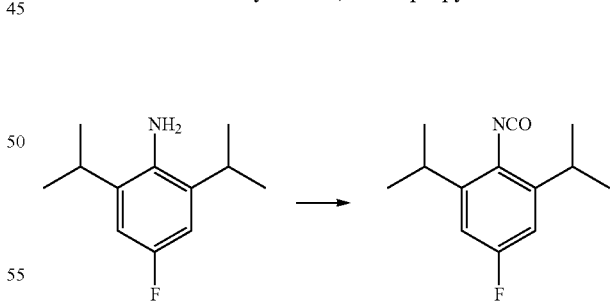

To a solution of 4-fluoro-2,6-diisopropylaniline (540 mg, 2.77 mmol, 1 eq) and TEA (560 mg, 5.53 mmol, 769.80 μL, 2 eq) in THF (15 mL) was added triphosgene (279 mg, 940.21 μmol, 0.34 eq) at 0° C. The reaction mixture was stirred at 70° C. for 1 hour. Then the suspension was filtered and the filtrate was concentrated in vacuo to give the title compound (540 mg, 88% yield) as a brown oil, which was used directly in next step.

Intermediate R6: 4-(7-Fluoro-4-isocyanato-2,3-dihydro-1H-inden-5-yl)pyridine

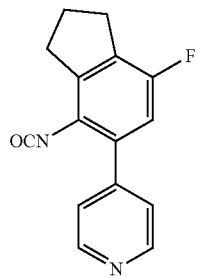

Step A:
7-Fluoro-4-nitro-2,3-dihydro-1H-inden-1-one

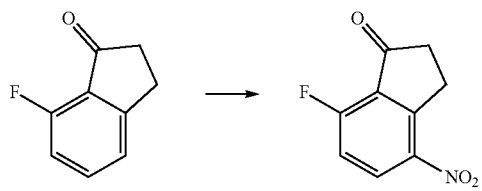 [SMILES: O=C1CCc2cccc(F)c21 ; O=C1CCc2c([N+](=O)[O-])ccc(F)c21]

To a mixture of 7-fluoro-2,3-dihydro-1H-inden-1-one (9.5 g, 63.27 mmol, 1 eq) in H$_2$SO$_4$ (100 mL) was added dropwise a solution of HNO$_3$ (7.51 g, 82.25 mmol, 5.37 mL, 69% purity, 1.3 eq) in H$_2$SO$_4$ (20 mL) at −15° C. Then the reaction mixture was stirred at 0° C. for 0.5 hour. The mixture was quenched with water (500 mL) at 0° C. and then extracted with EtOAc (3×300 mL). The combined organic phases were dried over anhydrous Na$_2$SO$_4$, filtered and concentrated in vacuo. The residue was purified by column chromatography (SiO$_2$, PE:EtOAc=10:1 to 3:1) to give the title compound (11.4 g, 92% yield) as a yellow solid.

$^1$H NMR (CDCl$_3$): δ 8.51 (dd, 1H), 7.22 (t, 1H), 3.69-3.65 (m, 2H) and 2.88-2.82 (m, 2H).

Step B: 7-Fluoro-4-nitro-2,3-dihydro-1H-inden-1-ol

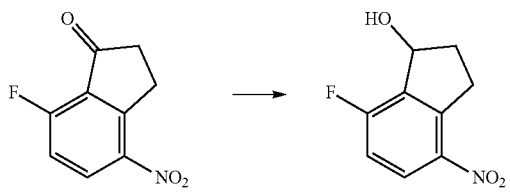 [SMILES: O=C1CCc2c([N+](=O)[O-])ccc(F)c21 ; O=[N+]([O-])c1ccc(F)c2c1CCC2O]

To a mixture of 7-fluoro-4-nitro-2,3-dihydro-1H-inden-1-one (30 g, 153-73 mmol, 1 eq) in EtOH (450 mL) was added NaBH$_4$ (11.63 g, 307.46 mmol, 2 eq) in portions. Then the reaction mixture was stirred at 15° C. for 1 hour. The mixture was poured into water (500 mL) and extracted with DCM (2×200 mL). The combined organic phases were washed with brine (200 mL), dried over anhydrous Na$_2$SO$_4$, filtered and concentrated in vacuo to give the title compound (30 g, crude) as brown oil.

$^1$H NMR (CDCl$_3$): δ 8.21 (dd, 1H), 7.08 (t, 1H), 5.59-5.56 (m, 1H), 3.66-3.59 (m, 1H), 3.44-3.39 (m, 1H), 2.56-2.51 (m, 1H) and 2.22-2.17 (m, 2H).

Step C: 4-Fluoro-7-nitro-2,3-dihydro-1H-indene

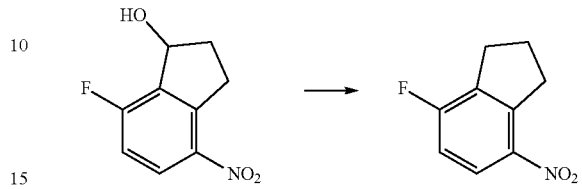

To a mixture of 7-fluoro-4-nitro-2,3-dihydro-1H-inden-1-ol (4.5 g, 22.82 mmol, 1 eq) in TFA (20 mL) was added Et$_3$SiH (7.96 g, 68.47 mmol, 10.94 mL, 3 eq) in one portion. Then the reaction mixture was stirred at 25° C. for 12 hours. The mixture was quenched with water (100 mL) and extracted with EtOAc (3×100 mL). The combined organic layers were washed with saturated aqueous NaHCO$_3$ solution (2×100 mL) dried over anhydrous Na$_2$SO$_4$, filtered and concentrated in vacuo to give the title compound (5 g, crude) as brown oil.

$^1$H NMR (CDCl$_3$): δ 8.06 (dd, 1H), 7.01 (t, 1H), 3.46 (t, 2H), 3.04 (t, 2H) and 2.25-2.20 (m, 2H).

Step D: 7-Fluoro-2,3-dihydro-1H-inden-4-amine

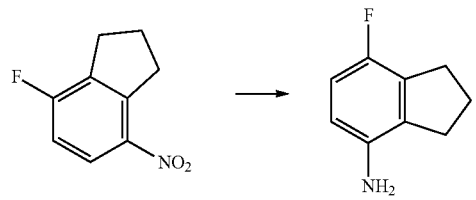

To a mixture of 4-fluoro-7-nitro-2,3-dihydro-1H-indene (5 g, 27.60 mmol, 1 eq) in MeOH (50 mL) was added Pd/C (0.5 g, 10% purity) at 25° C. under N$_2$. Then the reaction mixture was stirred at 25° C. for 12 hours under H$_2$ (15 psi). The mixture was filtered and the filtrate was concentrated in vacuo. The residue was purified by column chromatography (SiO$_2$, PE:EtOAc=50:1 to 10:1) to give the title compound (1.8 g, 43% yield) as a brown solid.

$^1$H NMR (CDCl$_3$): δ 6.69 (t, 1H), 6.44 (dd, 1H), 3.47 (br s, 2H), 2.95 (t, 2H), 2.75 (t, 2H) and 2.19-2.11 (m, 2H).

Step E:
5-Bromo-7-fluoro-2,3-dihydro-1H-inden-4-amine

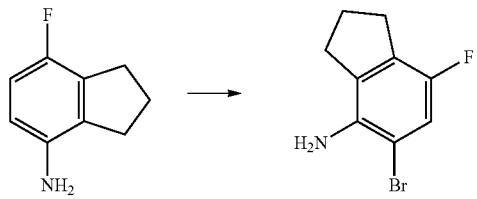 [SMILES: Nc1ccc(F)c2c1CCC2 ; Nc1c(Br)cc(F)c2c1CCC2]

To a solution of 7-fluoro-2,3-dihydro-1H-inden-4-amine (8.3 g, 54-90 mmol, 1 eq) in toluene (100 mL) was added NBS (10.26 g, 57.65 mmol, 1.05 eq) in one portion at 25° C. The reaction mixture turned dark brown immediately and then the mixture was stirred at 25° C. for 30 minutes. The reaction mixture was quenched with saturated aqueous Na$_2$SO$_3$ solution (200 mL) and extracted with EtOAc (2×100 mL). The combined organic phases were washed with brine (100 mL), dried over anhydrous Na$_2$SO$_4$, filtered and concentrated in vacuo. The residue was purified by column chromatography (SiO$_2$, PE:EtOAc=1:0 to 20:1) to give the title compound (8.51 g, 67% yield) as a brown solid.

$^1$H NMR (CDCl$_3$): δ 6.99 (d, 1H), 3.81 (br s, 2H), 2.92 (t, 2H), 2.78 (t, 2H) and 2.21-2.13 (m, 2H).

Step F: 7-Fluoro-5-(pyridin-4-yl)-2,3-dihydro-1H-inden-4-amine

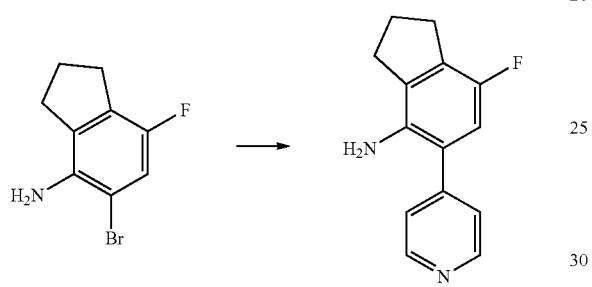

To a mixture of 5-bromo-7-fluoro-2,3-dihydro-1H-inden-4-amine (3.5 g, 15.21 mmol, 1 eq) and pyridin-4-ylboronic acid (1.96 g, 15.97 mmol, 1.05 eq) in dioxane (50 mL) and H$_2$O (5 mL) was added K$_2$CO$_3$ (6.31 g, 45.64 mmol, 3 eq) and Pd(dppf)Cl$_2$ (1.11 g, 1.52 mmol, 0.1 eq) in one portion under N$_2$. Then the reaction mixture was heated to 80° C. for 12 hours. The reaction mixture was filtered. The filtrate was diluted with water (50 mL) and extracted with EtOAc (3×100 mL). The combined organic phases were washed with brine (100 mL), dried over anhydrous Na$_2$SO$_4$, filtered and concentrated in vacuo. The residue was purified by column chromatography (SiO$_2$, PE:EtOAc=10:1 to 2:1) to give the title compound (1.7 g, 45% yield, 91.0% purity on HPLC) as a brown solid.

$^1$H NMR (CDCl$_3$): δ 8.68 (dd, 2H), 7.40 (dd, 2H), 6.72 (d, 1H), 3.76 (br s, 2H), 3.01 (t, 2H), 2.80 (t, 2H) and 2.26-2.18 (m, 2H).

Step G: 4-(7-Fluoro-4-isocyanato-2,3-dihydro-1H-inden-5-yl)pyridine

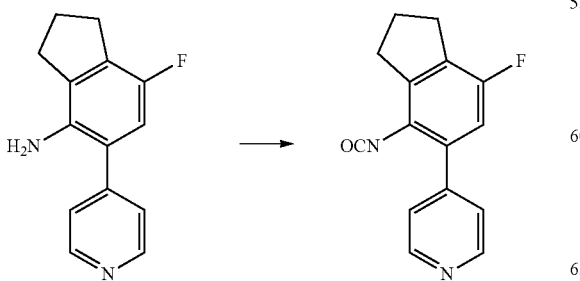

To a solution of 7-fluoro-5-(pyridin-4-yl)-2,3-dihydro-1H-inden-4-amine (400 mg, 1.75 mmol, 1 eq) and TEA (355 mg, 3.50 mmol, 487.82 μL, 2 eq) in THF (30 mL) was added bis(trichloromethyl) carbonate (208 mg, 700.94 μmol, 0.4 eq) at 0° C. The reaction mixture was stirred at 70° C. for 30 minutes. Then the reaction mixture was filtered through a pad of silica gel and the filter cake was washed with THF (20 mL). The filtrate was concentrated in vacuo to a reduced volume of 10 mL, which was used directly in the next step.

PREPARATION OF EXAMPLES

Examples 1 and 2: N-((1,2,3,5,6,7-Hexahydro-s-indacen-4-yl)carbamoyl)-1-iso-propyl-1H-pyrazole-3-sulfonimidamide and 4-chloro-N-((1,2,3,5,6,7-hexahydro-s-indacen-4-yl)carbamoyl)-1-iso-propyl-1H-pyrazole-3-sulfonimidamide

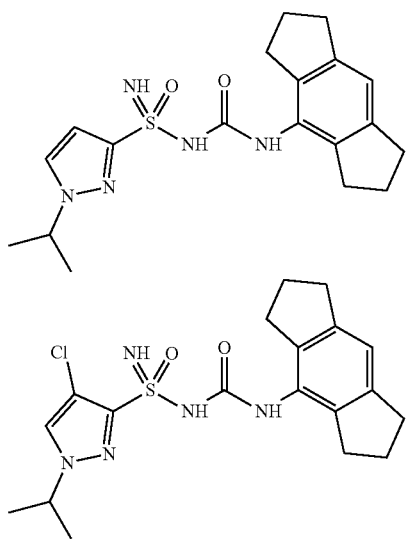

Step A: N-((1,2,3,5,6,7-Hexahydro-s-indacen-4-yl)carbamoyl)-1-iso-propyl-1H-pyrazole-3-sulfinamide

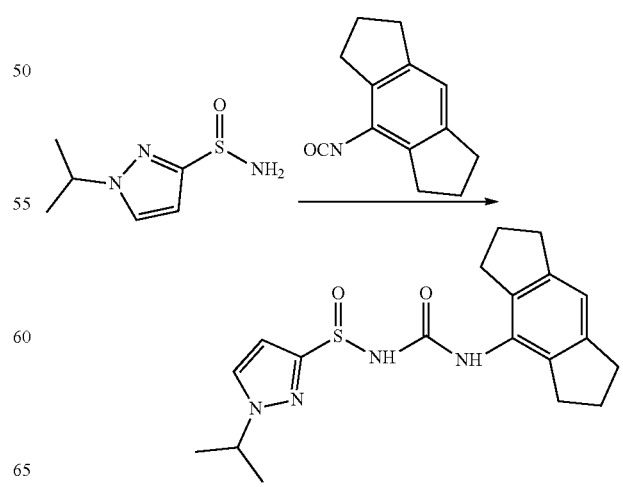

To a solution of 1-iso-propyl-1H-pyrazole-3-sulfinamide (intermediate L1) (950 mg, 5.48 mmol, 1 equiv.) in THF (20 mL) was added sodium methoxide (296.26 mg, 5.48 mmol, 1 eq) at 20° C. After stirring for 30 minutes, 4-isocyanato-1,2,3,5,6,7-hexahydro-s-indacene (intermediate R1) (1.09 g, 5.48 mmol, 1 eq) was added and the mixture was stirred at 70° C. for 1 hour. The reaction mixture was concentrated in vacuo and the residue was purified by column chromatography (SiO$_2$, DCM:MeOH=50:1 to 20:1) to afford the title compound (1.1 g, 2.51 mmol, 46% yield, ca. 85% purity) as a white solid.

$^1$H NMR (DMSO-d$_6$): δ 9.63 (s, 1H), 8.24 (s, 1H), 8.05 (d, 1H), 6.96 (s, 1H), 6.76 (d, 1H), 4.66-4.59 (m, 1H), 2.84-2.73 (m, 4H), 2.71-2.69 (m, 4H), 2.02-1.97 (m, 4H) and 1.45 (d, 6H).

LCMS: m/z 373 (M+H)$^+$ (ES$^+$).

Step B: N-((1,2,3,5,6,7-Hexahydro-s-indacen-4-yl)carbamoyl)-1-iso-propyl-1H-pyrazole-3-sulfonimidamide and 4-chloro-N-((1,2,3,5,6,7-hexahydro-s-indacen-4-yl)carbamoyl)-1-iso-propyl-1H-pyrazole-3-sulfonimidamide

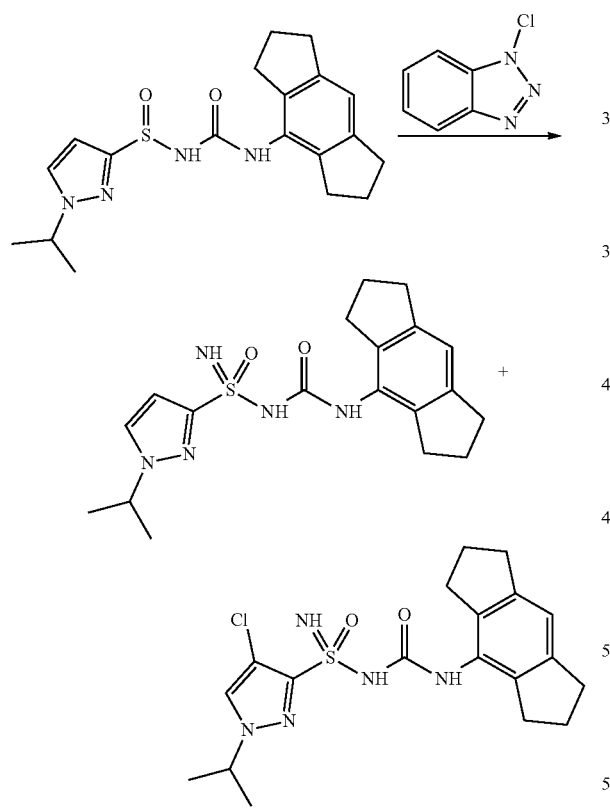

N-((1,2,3,5,6,7-hexahydro-s-indacen-4-yl)carbamoyl)-1-iso-propyl-1H-pyrazole-3-sulfinamide (100 mg, 268.47 µmol, 1 eq) was suspended in THF (1 mL) under nitrogen and treated with 1-chlorobenzotriazole (37.11 mg, 241.62 µmol, 0.9 eq) in a single portion. The mixture became a homogeneous yellow solution after 10 minutes and was stirred for another 20 minutes at 20° C. This solution was added drop-wise over 10 minutes at −70° C. to a solution of ammonia in THF (5 mL), which had been prepared by bubbling NH$_3$ gas into THF (5 mL) at −70° C. for 5 minutes. After being stirred for 15 minutes, the mixture was warmed to 20° C. and allowed to stir for 2 hours. The reaction mixture was concentrated in vacuo and the residue was purified by prep-TLC (SiO$_2$, DCM:MeOH=10:1) to give a yellow solid, which was further purified by prep-HPLC (neutral conditions—column: Phenomenex Gemini C18 250 mm*50 mm*10 µm; mobile phase: [A: water (10 mM NH$_4$HCO$_3$); B: MeCN]; B %: 32%-62%, 10 min) to afford N-((1,2,3,5,6,7-hexahydro-s-indacen-4-yl)carbamoyl)-1-iso-propyl-1H-pyrazole-3-sulfonimidamide (example 1) (1.3 mg, 3.35 µmol, 1% yield) as a white solid and 4-chloro-N-((1,2,3,5,6,7-hexahydro-s-indacen-4-yl)carbamoyl)-1-iso-propyl-1H-pyrazole-3-sulfonimidamid (example 2) (3.5 mg, 8.29 µmol, 3% yield), also as a white solid.

Example 1: N-((1,2,3,5,6,7-Hexahydro-s-indacen-4-yl)carbamoyl)-1-iso-propyl-1H-pyrazole-3-sulfonimidamide $^1$H NMR (DMSO-d$_6$): δ 8.27 (br s, 1H), 7.91 (d, 1H), 7.42 (br s, 2H), 6.85 (s, 1H), 6.60 (d, 1H), 4.60-4.55 (m, 1H), 2.84-2.73 (m, 4H), 2.71-2.69 (m, 4H), 1.93-1.90 (m, 4H) and 1.45 (d, 6H).

LCMS: m/z 388 (M+H)$^+$ (ES$^+$).

Example 2: 4-Chloro-N-((1,2,3,5,6,7-hexahydro-s-indacen-4-yl)carbamoyl)-1-iso-propyl-1H-pyrazole-3-sulfonimidamide $^1$H NMR (DMSO-d$_6$): δ 8.36 (br s, 1H), 7.91 (d, 1H), 7.38 (br s, 2H), 6.60 (d, 1H), 4.59-4.55 (m, 1H), 2.83-2.75 (m, 8H), 2.00-1.94 (m, 4H) and 1.43 (d, 6H).

LCMS: m/z 422 (M+H)$^+$ (ES$^+$).

Example 3: N-((1,2,3,5,6,7-Hexahydro-s-indacen-4-yl)carbamoyl)-1-((R)-2-hydroxypropyl)-1H-pyrazole-3-sulfonimidamide

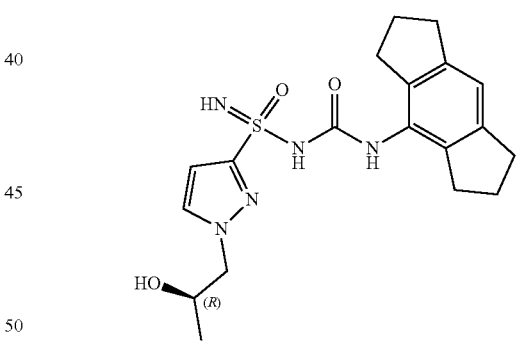

Step A: N-((1,2,3,5,6,7-Hexahydro-s-indacen-4-yl)carbamoyl)-1-((R)-2-hydroxypropyl)-1H-pyrazole-3-sulfinamide

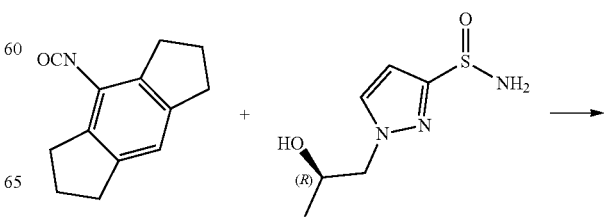

-continued

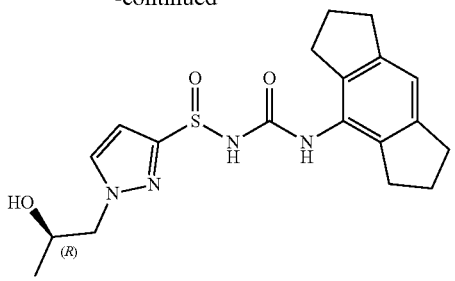

To a solution of 1-((R)-2-hydroxypropyl)-1H-pyrazole-3-sulfinamide (intermediate L2) (0.6 g, 3.17 mmol, 1 eq) in THF (20 mL) was added NaOMe (171 mg, 3.17 mmol, 1 eq) and the mixture was stirred at 25° C. for 0.5 hour. Then 4-isocyanato-1,2,3,5,6,7-hexahydro-s-indacene (intermediate R1) (631 mg, 3.17 mmol, 1 eq) was added and the resulting mixture was heated to 70° C. for 2 hours. Then the reaction mixture was concentrated in vacuo. The residue was purified by prep-HPLC (column: Phenomenex Gemini 150 mm×*25 mm*10 µm; mobile phase: [A: water (0.04% $NH_3.H_2O$+10 mM $NH_4HCO_3$); B: MeCN]; B %: 18%-48%, 11 min) to give the title compound (0.075 g, 5% yield, 82% purity on LCMS) as a white solid.

$^1$H NMR (DMSO-$d_6$): δ 9.47 (br s, 1H), 8.29 (d, 1H), 7.93 (d, 1H), 6.95 (s, 1H), 6.75 (d, 1H), 4.98 (dd, 1H), 4.24-3.97 (m, 3H), 2.82 (t, 4H), 2.74-2.66 (m, 4H), 1.99-1.94 (m, 4H) and 1.08 (dd, 3H).

LCMS: m/z 411.1 (M+Na)$^+$ (ES$^+$).

Step B: N-((1,2,3,5,6,7-Hexahydro-s-indacen-4-yl)carbamoyl)-1-((R)-2-hydroxypropyl)-1H-pyrazole-3-sulfonimidamide

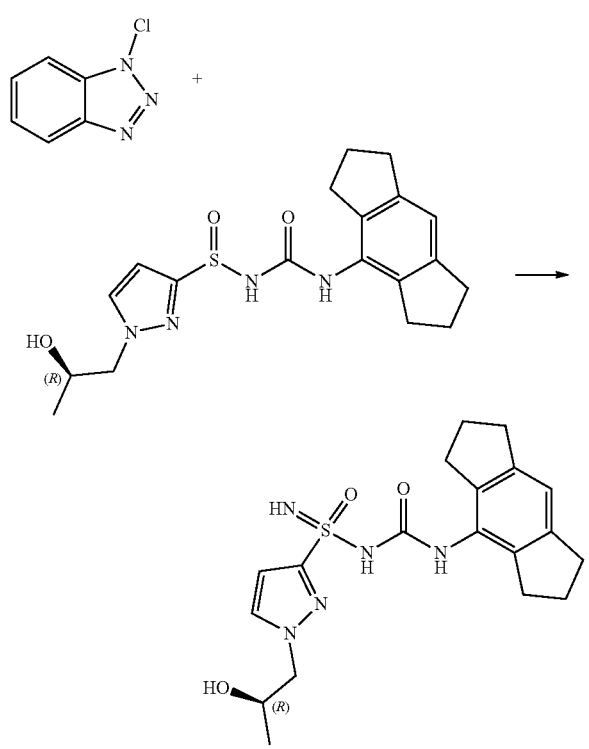

To a solution of N-((1,2,3,5,6,7-hexahydro-s-indacen-4-yl)carbamoyl)-1-((R)-2-hydroxypropyl)-1H-pyrazole-3-sulfinamide (0.07 g, 180.19 µmol, 1 eq) in THF (5 mL) was added 1-chloro-1H-benzo[d][1,2,3]triazole (25 mg, 162.17 mol, 0.9 eq) under $N_2$ atmosphere. Then the mixture was stirred for 0.5 hour. This solution was added dropwise over 10 minutes to a saturated ammonia solution of THF (5 mL) at −70° C., which had been prepared by bubbling $NH_3$ gas into THF (5 mL) at −70° C. for 5 minutes. After stirring for 25 minutes, the mixture was warmed to 25° C. for 2 hours. Then the mixture was concentrated in vacuo. The residue was purified by prep-HPLC (column: Phenomenex Gemini 150 mm*25 mm*10 µm; mobile phase: [A: water (0.04% $NH_3.H_2O$+10 mM $NH_4HCO_3$); B: MeCN]; B %: 22%-52%, 11 min) to give the title compound (0.0148 g, 20% yield, 100% purity on LCMS) as a white solid.

$^1$H NMR (CD$_3$OD): δ 7.74 (s, 1H), 6.92 (s, 1H), 6.76 (s, 1H), 4.24-4.08 (m, 3H), 2.92-2.79 (m, 8H), 2.10-2.00 (m, 4H) and 1.20 (dd, 3H).

LCMS: m/z 404.2 (M+H)$^+$ (ES$^+$).

Example 4: tert-Butylethyl(3-(N-((1,2,3,5,6,7-hexahydro-s-indacen-4-yl)carbamoyl) sulfinimidoyl)propyl)carbamate

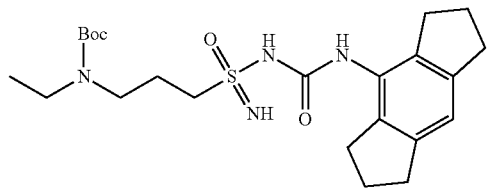 [SMILES: CCN(CCCS(=N)(=O)NC(=O)Nc1c2c(cc3c1CCC3)CCC2)C(=O)OC(C)(C)C]

Step A: tert-Butylethyl(3-(N-((1,2,3,5,6,7-hexahydro-s-indacen-4-yl)carbamoyl) sulfinamoyl)propyl)carbamate

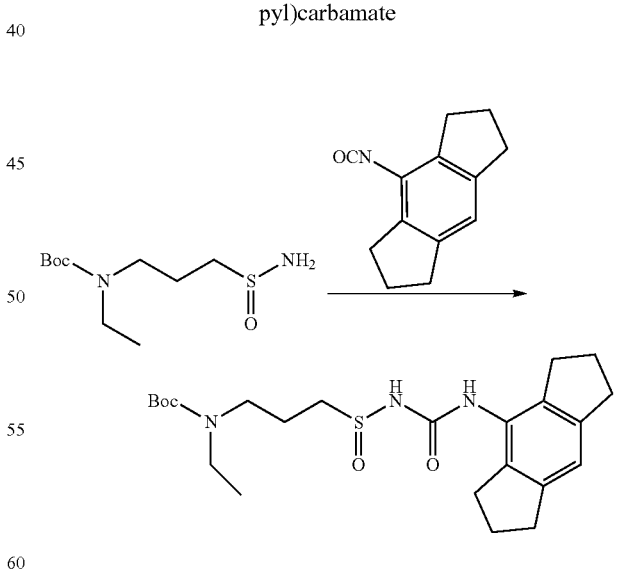

To a solution of tert-butyl ethyl(3-sulfinamoylpropyl)carbamate (intermediate L3) (5.8 g, 23.17 mmol, 1 eq) in THF (60 mL) was added NaOMe (1.50 g, 27.80 mmol, 1.2 eq) in one portion at 25° C. The reaction mixture was stirred for 10 minutes. Then 4-isocyanato-1,2,3,5,6,7-hexahydro-s-indacene (intermediate R1) (4.62 g, 23.17 mmol, 1 eq) was added and the reaction mixture was stirred at 25° C. for 50 minutes under nitrogen. The mixture was concentrated in vacuo. The residue was diluted with EtOAc (300 mL) and water (100 mL). The two layers were separated and the aqueous layer was extracted with EtOAc (2×100 mL). The combined organic phases were washed with brine (100 mL), dried over anhydrous $Na_2SO_4$, filtered and concentrated in vacuo. The residue was purified by trituration with a mixture of PE and EtOAc (20:1, 500 mL) to give the title compound (5.9 g, 57% yield) as a white solid.

$^1$H NMR (DMSO-$d_6$): δ 8.83-8.81 (m, 1H), 8.32-8.28 (m, 1H), 6.94 (s, 1H), 3.27 (t, 2H), 3.20-3.16 (m, 2H), 2.89-2.83 (m, 2H), 2.80 (t, 4H), 2.69 (t, 4H), 1.99-1.94 (m, 4H), 1.81-1.75 (m, 2H), 1.40 (s, 9H) and 1.04 (t, 3H).

Step B: tert-Butylethyl(3-(N-((1,2,3,5,6,7-hexa-hydro-s-indacen-4-yl)carbamoyl) sulfinimidoyl)propyl)carbamate

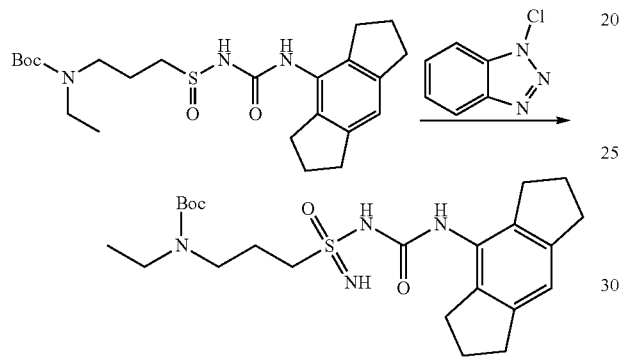

To a solution of tert-butyl ethyl(3-(N-((1,2,3,5,6,7-hexahydro-s-indacen-4-yl)carbamoyl)sulfinamoyl)propyl)carbamate (0.5 g, 1.11 mmol, 1 eq) in THF (5 mL) was added 1-chloro-1H-benzo[d][1,2,3]triazole (154 mg, 1.00 mmol, 0.9 eq) in one portion under nitrogen. The mixture became homogeneous and turned yellow after 10 minutes and then was stirred for another 20 minutes. This solution was added dropwise over 10 minutes to a solution of ammonia in THF (5 mL) at −70° C., which had been prepared by $NH_3$ gas bubbling into THF (5 mL) at −65° C. for 5 minutes. After stirring for 15 minutes, the mixture was warmed to 20° C. for 2 hours. Then the mixture was concentrated in vacuo. The residue was purified by silica gel chromatography (EtOAc:MeOH=50:1 to 20:1) to give the title compound (0.55 g, 99% yield, 92.9% purity on LCMS) as a white solid.

$^1$H NMR (DMSO-$d_6$): δ 6.87 (s, 1H), 3.24 (t, 2H), 3.17-3.14 (m, 2H), 2.80-2.65 (m, 10H), 1.99-1.89 (m, 6H), 1.39 (s, 9H) and 1.05-1.01 (m, 3H).

LCMS: m/z 465.2 (M+H)$^+$ (ES$^+$).

Example 5: 3-(Ethylamino)-N-((1,2,3,5,6,7-hexa-hydro-s-indacen-4-yl)carbamoyl) propane-1-sulfo-nimidamide

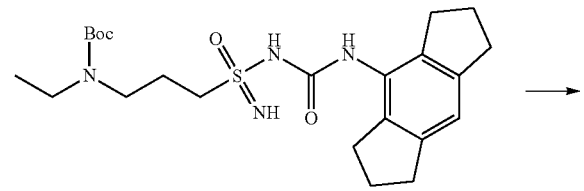

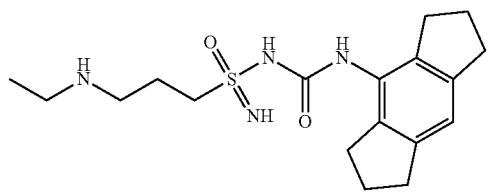

To a solution of tert-butyl ethyl(3-(N-((1,2,3,5,6,7-hexahydro-s-indacen-4-yl) carbamoyl)sulfamimidoyl)propyl) carbamate (example 4) (0.5 g, 1.08 mmol, 1 eq) in DCM (10 mL) was added TFA (3.08 g, 27.01 mmol, 2 mL, 25.10 eq) in one portion. Then the reaction mixture was stirred at 25° C. for 0.5 hour. The mixture was concentrated in vacuo to give the title compound (0.5 g, crude, TFA salt) as a yellow oil.

$^1$H NMR (DMSO-$d_6$): δ 8.42-837 (m, 1H), 7.08-7.06 (m, 1H), 6.88 (s, 1H), 3.53-350 (m, 2H), 3.07-3.04 (m, 2H), 2.96-2.92 (m, 2H), 2.79 (t, 4H), 2.72 (t, 4H), 2.05-2.01 (m, 2H), 1.98-1.93 (m, 4H) and 1.18-1.14 (m, 3H).

LCMS: m/z 365.2 (M+H)$^+$ (ES$^+$).

Example 6: 3-(Diethylamino)-N-((1,2,3,5,6,7-hexa-hydro-s-indacen-4-yl)carbamoyl) propane-1-sulfo-nimidamide

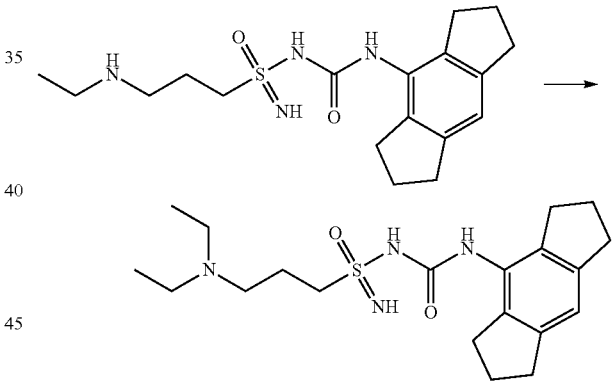

To a solution of 3-(ethylamino)-N-((1,2,3,5,6,7-hexahydro-s-indacen-4-yl)carbamoyl) propane-1-sulfonimid-amide (example 5) (0.4 g, 835.90 μmol, 1 eq, TFA salt) and TEA (727 mg, 7.18 mmol, 1 mL, 8.59 eq) in DMF (4 mL) was added iodoethane (156 mg, 1.00 mmol, 80.23 μL, 1.2 eq) in one portion. Then the reaction mixture was stirred at 25° C. for 12 hours. The mixture was concentrated in vacuo. The residue was purified by prep-HPLC (column: Phenomenex Gemini 150 mm*25 mm*10 μm; mobile phase: [A: water (0.05% $NH_4HCO_3$); B: MeCN]; B %: 25%-55%, 10 min) to give the title compound (30.88 mg, 9% yield, 98.6% purity on LCMS) as a white solid.

$^1$H NMR (DMSO-$d_6$): δ 8.19 (br s, 1H), 6.86 (s, 1H), 6.80 (br s, 1H), 3.46-3.40 (m, 2H), 2.78 (q, 4H), 2.71-2.66 (m, 4H), 2.47-2.41 (m, 6H), 1.97-1.89 (m, 4H), 1.83-1.76 (m, 2H) and 0.93 (t, 6H).

LCMS: m/z 393.2 (M+H)$^+$ (ES$^+$).

Example 7: N-((1,2,3,5,6,7-Hexahydro-s-indacen-4-yl)carbamoyl)-1-isopropyl-azetidine-3-sulfonimidamide

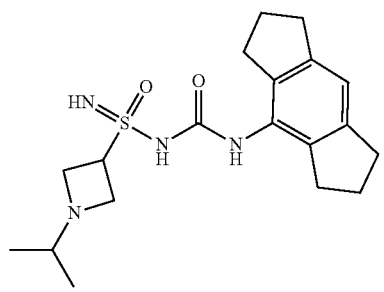 [SMILES: CC(C)N1CC(S(=N)(=O)NC(=O)Nc2c3c(cc4c2CCC4)CCC3)C1]

Step A: tert-Butyl 3-(N-((1,2,3,5,6,7-hexahydro-s-indacen-4-yl)carbamoyl)sulfinamoyl) azetidine-1-carboxylate

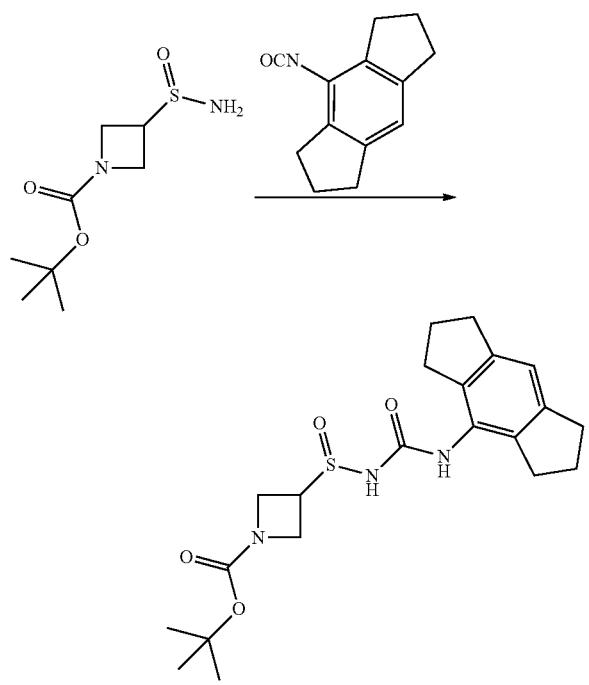

To a solution of tert-butyl 3-sulfinamoylazetidine-1-carboxylate (intermediate L4) (1.35 g, 6.13 mmol, 1 eq) in THF (40 mL) was added NaOMe (397 mg, 7.35 mmol, 1.2 eq) and the resulting mixture was stirred for 10 minutes. To this reaction mixture was added 4-isocyanato-1,2,3,5,6,7-hexahydro-s-indacene (intermediate R1) (1.22 g, 6.13 mmol, 1 eq). The mixture was stirred at 70° C. for 50 minutes. Then the reaction mixture was poured into water (100 mL) and extracted with EtOAc (3×200 mL). The combined organic layers were dried over Na₂SO₄, filtered and concentrated in vacuo. The residue was redissolved in MeOH and the mixture was stirred for another 10 minutes. Then the mixture was filtered and the filter cake was concentrated in vacuo to give 1.4 g of the title compound. The filtrate was concentrated in vacuo and the residue was purified by column chromatography (SiO₂, PE:EtOAc=3:1 to 0:1) to give a further 500 mg of the title compound. The title compound (1.9 g, 74% yield, 100% purity on LCMS) was obtained as a white solid.

¹H NMR (DMSO-d₆): δ 9.28 (s, 1H), 8.19 (s, 1H), 6.96 (s, 1H), 4.18-4.11 (m, 3H), 3.99-3.96 (m, 1H), 3.85-3.82 (m, 1H), 2.84-2.67 (m, 8H), 2.02-1.96 (m, 4H) and 1.40 (s, 9H).

LCMS: m/z 420.2 (M+H)⁺ (ES⁺).

Step B: N-((1,2,3,5,6,7-Hexahydro-s-indacen-4-yl)carbamoyl)azetidine-3-sulfinamide

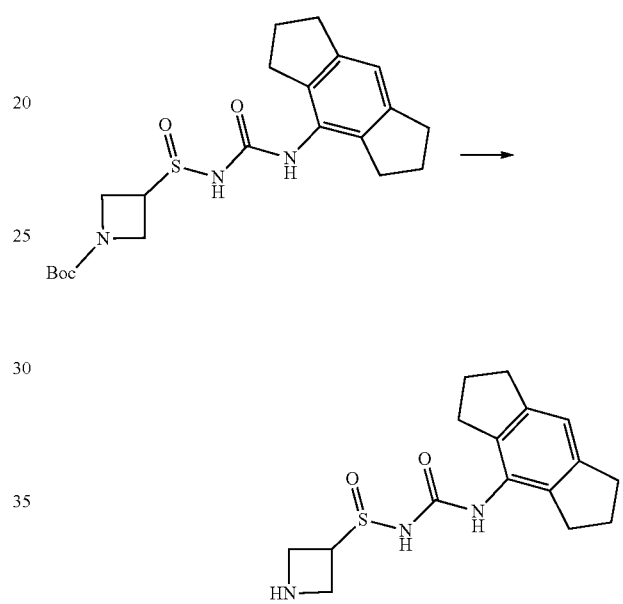

To a solution of tert-butyl 3-(N-((1,2,3,5,6,7-hexahydro-s-indacen-4-yl)carbamoyl) sulfinamoyl)azetidine-1-carboxylate (640 mg, 1.53 mmol) in DCM (10 mL) was added TFA (4.62 g, 40.52 mmol, 3 mL, 26.56 eq). The mixture was stirred at 25° C. for 1 hour. Then the reaction mixture was concentrated in vacuo to give the title compound (661 mg, TFA salt), which was used in the next step without further purification.

LCMS: m/z 320.2 (M+H)⁺ (ES⁺).

Step C: N-((1,2,3,5,6,7-Hexahydro-s-indacen-4-yl)carbamoyl)-1-isopropylazetidine-3-sulfinamide

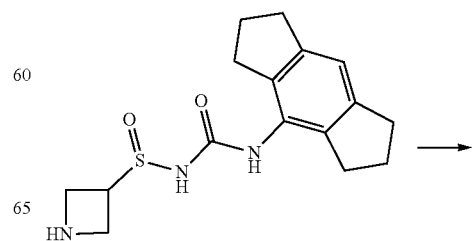

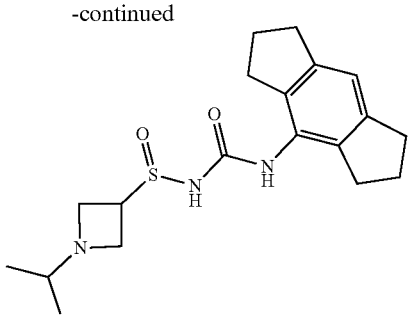

To a solution of N-((1,2,3,5,6,7-hexahydro-s-indacen-4-yl)carbamoyl)azetidine-3-sulfinamide (661 mg, 1.52 mmol, 1 eq, TFA salt) in DMF (5 mL) was added TEA (1.54 g, 15.25 mmol, 2.12 mL, 10 eq) and 2-iodopropane (337 mg, 1.98 mmol, 198.24 μL, 1.3 eq). The mixture was stirred at 50° C. for 2 hours. Then the reaction mixture was purified by reversed phase flash chromatography (0.1% NH$_3$.H$_2$O/MeCN) to give the title compound (80 mg, 14% yield, 96.3% purity on LCMS) as a white solid.

$^1$H NMR (DMSO-d$_6$): δ 8.29 (s, 1H), 6.96 (s, 1H), 3.79-3.75 (m, 1H), 3.40-3.37 (m, 3H), 3.09-3.06 (m, 1H), 2.82 (t, 4H), 2.70 (t, 4H), 2.32-2.29 (m, 1H), 2.02-1.96 (m, 4H) and 0.89-0.82 (m, 6H).

LCMS: m/z 362.2 (M+H)$^+$ (ES$^+$).

Step D: N-((1,2,3,5,6,7-Hexahydro-s-indacen-4-yl)carbamoyl)-1-isopropylazetidine-3-sulfonimidamide

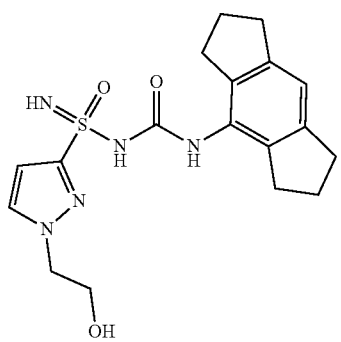 [SMILES: N=S(=O)(NC(=O)Nc1c2c(cc3c1CCC3)CCC2)c1ccn(CCO)n1]

To a solution of N-((1,2,3,5,6,7-hexahydro-s-indacen-4-yl)carbamoyl)-1-isopropylazetidine-3-sulfinamide (210 mg, 580.91 μmol, 1 eq) in THF (10 mL) was added 1-chloro-1H-benzo[d][1,2,3]triazole (80 mg, 522.82 μmol, 0.9 eq) at 20° C. The mixture was stirred at 20° C. for 30 minutes. NH$_3$ was bubbled into THF (30 mL) at −78° C. for 10 minutes and the above reaction mixture was added into the NH$_3$/THF solution over 10 minutes at −70° C. The resulting mixture was stirred at 20° C. for another 130 minutes and then concentrated in vacuo. The residue was purified by prep-HPLC (column: Phenomenex Gemini 150 mm*25 mm*10 μm; mobile phase: [A: water (0.05% NH$_4$HCO$_3$); B: MeCN]; B %: 26%-56%, 10 min) to give the title compound (39.99 mg, 18% yield, 97.1% purity on LCMS) as a white solid.

$^1$H NMR (DMSO-d$_6$): δ 8.25 (br s, 1H), 7.05 (br s, 2H), 6.87 (s, 1H), 4.34-4.26 (m, 1H), 3.48-3.42 (m, 2H), 3.27-3.23 (m, 2H), 2.79 (t, 4H), 2.70 (t, 4H), 2.35-2.31 (m, 1H), 1.98-1.90 (m, 4H) and 0.83 (d, 6H).

Example 8: N-((1,2,3,5,6,7-Hexahydro-s-indacen-4-yl)carbamoyl)-1-(2-hydroxyethyl)-1H-pyrazole-3-sulfonimidamide

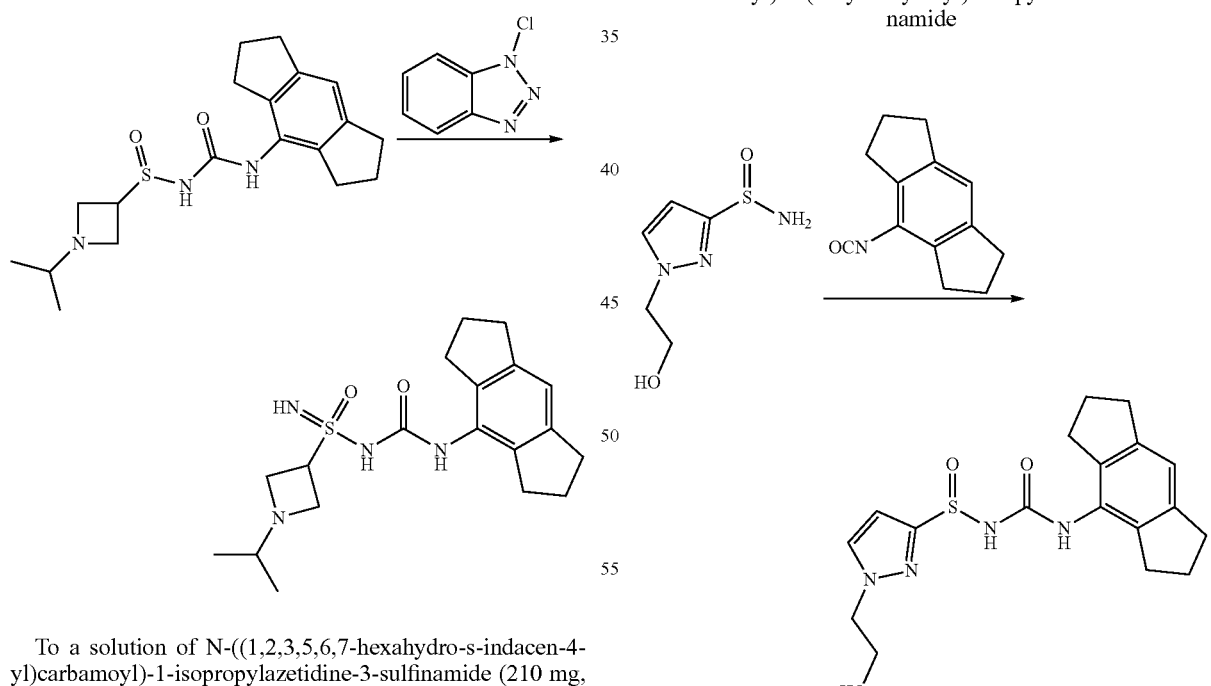

Step A: N-((1,2,3,5,6,7-Hexahydro-s-indacen-4-yl)carbamoyl)-1-(2-hydroxyethyl)-1H-pyrazole-3-sulfinamide To a solution of 1-(2-hydroxyethyl)-1H-pyrazole-3-sulfinamide (intermediate L5) (0.9 g, 5.14 mmol, 1 eq) in THF (50 mL) was added t-BuONa (148 mg, 1.54 mmol, 0.3 eq) at 25° C. and stirred for 0.5 hour. 4-Isocyanato-1,2,3,5,6,7-hexahydro-s-indacene (intermediate R1) (1.02 g, 5.14 mmol, 1 eq) was added and the mixture was heated to 70°

C. and stirred for another 21.5 hours. Then the mixture was concentrated in vacuo. The residue was purified by reversed phase flash chromatography (basic condition, 0.05% NH₃.H₂O in water/MeCN) to give the title compound (0.58 g, 30% yield, 98% purity on LCMS) as a light yellow solid.

$^1$H NMR (DMSO-$d_6$): δ 7.91 (s, 1H), 6.93 (s, 1H), 6.70 (s, 1H), 4.99 (br s, 1H), 4.23 (t, 2H), 3.78-3.73 (m, 2H), 2.81 (t, 4H), 2.74-2.69 (m, 4H) and 2.01-1.95 (m, 4H).

LCMS: m/z 375.3 (M+H)⁺ (ES⁺).

Step B: N-((1,2,3,5,6,7-Hexahydro-s-indacen-4-yl) carbamoyl)-1-(2-hydroxyethyl)-1H-pyrazole-3-sulfonimidamide

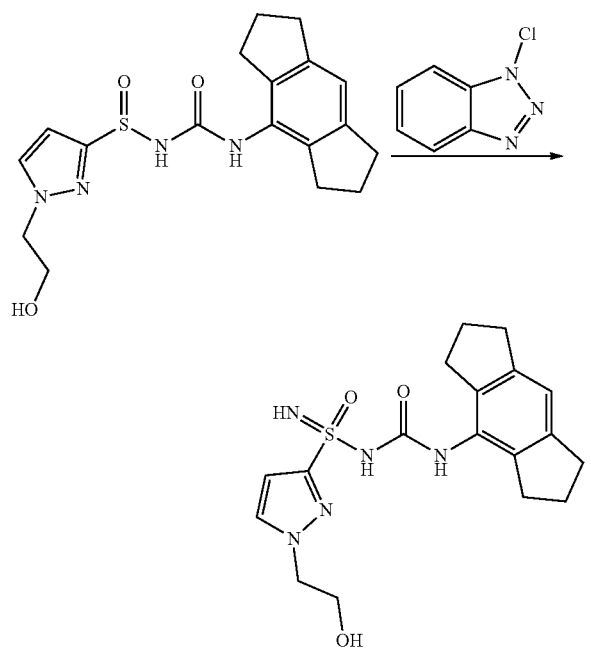

To a solution of N-((1,2,3,5,6,7-hexahydro-s-indacen-4-yl)carbamoyl)-1-(2-hydroxyethyl)-1H-pyrazole-3-sulfinamide (0.25 g, 667.63 μmol, 1 eq) in THF (5 mL) was added 1-chloro-1H-benzo[d][1,2,3]triazole (102 mg, 667.63 μmol, 1 eq) under N₂ atmosphere. Then the mixture was stirred for 0.5 hour. This solution was added dropwise over 10 minutes at −70° C. to a saturated solution of ammonia in THF (5 mL), which had been prepared by bubbling NH₃ gas into THF (5 mL) at −70° C. for 5 minutes. After stirring for 25 minutes, the mixture was warmed to 25° C. for 2 hours. Then the mixture was concentrated in vacuo. The residue was purified by prep-TLC (DCM:MeOH=10:1) and then purified by prep-HPLC (column: Phenomenex Gemini 150 mm*25 mm*10 μm; mobile phase: [A: water (0.04% NH₃.H₂O+10 mM NH₄HCO₃); B: MeCN]; B %: 16%-46%, 10 min) to give the title compound (0.02 g, 8% yield, 100% purity on LCMS) as a white solid.

$^1$H NMR (DMSO-$d_6$): δ 8.31 (br s, 1H), 7.84 (d, 1H), 7.41 (br s, 2H), 6.86 (s, 1H), 6.61 (s, 1H), 5.00 (t, 1H), 4.21 (t, 2H), 3.78-3.73 (m, 2H), 2.77 (t, 4H), 2.68 (t, 4H) and 1.97-1.89 (m, 4H).

LCMS: m/z 390.2 (M+H)⁺ (ES⁺).

Example A: 2-(3-(N-((1,2,3,5,6,7-Hexahydro-s-indacen-4-yl)carbamoyl) sulfamimidoyl)-1H-pyrazol-1-yl)ethyl methanesulfonate

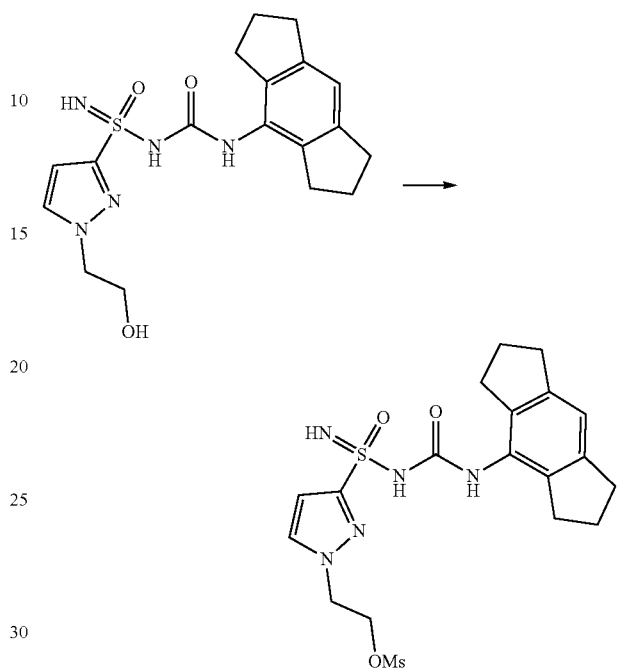

To a solution of N-((1,2,3,5,6,7-hexahydro-s-indacen-4-yl)carbamoyl)-1-(2-hydroxyethyl)-1H-pyrazole-3-sulfonimidamide (example 8) (0.02 g, 51.35 μmol, 1 eq) in THF (2 mL) was added MsCl (6 mg, 51.35 μmol, 3.97 μL, 1 eq) followed by TEA (16 mg, 154.06 μmol, 21.44 μL, 3 eq). Then the mixture was stirred at 25° C. for 6 hours. The reaction mixture was diluted with H₂O (10 mL) and extracted with EtOAc (2×10 mL). The combined organic layers were washed with brine (10 mL), dried over Na₂SO₄, filtered and concentrated under reduced pressure to give the title compound (0.024 g, 59% yield, 59% purity on LCMS) as a white solid, which was used to prepare the compound of example 10 without further purification.

LCMS: m/z 468.1 (M+H)⁺ (ES⁺).

Example 10: 1-(2-(Dimethylamino)ethyl)-N-((1,2,3,5,6,7-hexahydro-s-indacen-4-yl)carbamoyl)-1H-pyrazole-3-sulfonimidamide

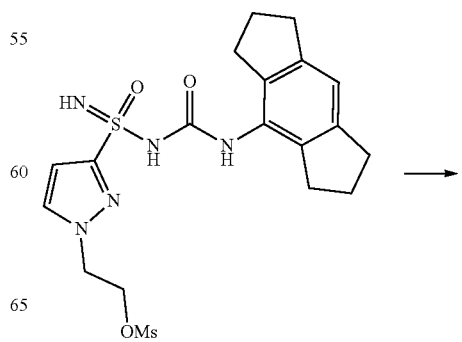

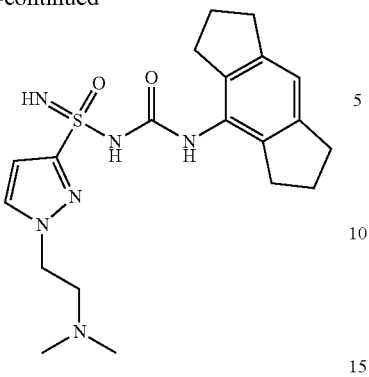

To a solution of 2-(3-(N-((1,2,3,5,6,7-hexahydro-s-indacen-4-yl)carbamoyl) sulfamimidoyl)-1H-pyrazol-1-yl) ethyl methanesulfonate (example 9) (0.2 g with 51% purity, 218.15 μmol, 1 eq) in THF (1 mL) was added dimethylamine (2 M, 10.2 mL, 93.51 eq). The mixture was heated to 60° C. for 12 hours. Then the reaction mixture was concentrated in vacuo. The residue was purified by prep-HPLC (column: Phenomenex Gemini 150 mm*25 mm*10 μm; mobile phase: [A: water (0.225% HCOOH); B: MeCN]; B %: 8%-38%, 10 min) to give the title compound (0.85 mg, 1% yield, 95% purity on LCMS, HCOOH salt) as a white solid.

$^1$H NMR (CDCl$_3$): δ 7.53 (d, 1H), 6.91 (s, 1H), 6.69 (s, 1H), 6.56 (br s, 1H), 4.29 (t, 2H), 2.86 (t, 2H), 2.79 (t, 4H), 2.74-2.70 (m, 4H), 2.78 (s, 6H) and 1.98-1.93 (m, 4H).

LCMS: m/z 417.2 (M+H)$^+$ (ES$^+$).

Example 11: 4-Chloro-1-isopropyl-N-((5-(2-methoxypyridin-4-yl)-2,3-dihydro-1H-inden-4-yl)carbamoyl)-1H-pyrazole-3-sulfonimidamide Step A: 4-Chloro-1-isopropyl-N-((5-(2-methoxypyridin-4-yl)-2,3-dihydro-1H-inden-4-yl)carbamoyl)-1H-pyrazole-3-sulfinamide

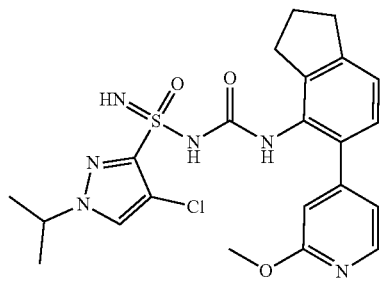 [SMILES: COc1cc(-c2ccc3c(c2NC(=O)NS(=N)(=O)c2nn(C(C)C)cc2Cl)CCC3)ccn1]

To a solution of 4-chloro-1-isopropyl-1H-pyrazole-3-sulfinamide (intermediate L6) (150 mg, 722.26 μmol, 1 eq) in THF (2 mL) was added t-BuONa (69 mg, 722.26 μmol, 1 eq). The mixture was stirred at 20° C. for 10 minutes. Then 4-(4-isocyanato-2,3-dihydro-1H-inden-5-yl)-2-methoxypyridine (intermediate R2) (192 mg, 722.26 μmol, 1 eq) was added. The mixture was stirred at 20° C. for 20 minutes and then concentrated in vacuo. The residue was purified by reversed phase flash chromatography (0.1% NH$_3$.H$_2$O/ MeCN) to give the title compound (290 mg, 83% yield, 98% purity on LCMS) as a white solid.

$^1$H NMR (CD$_3$OD): δ 8.11 (d, 1H), 8.00 (s, 1H), 7.27 (d, 1H), 7.16 (d, 1H), 6.96-6.94 (m, 1H), 6.79 (s, 1H), 4.61-4.53 (m, 1H), 3.90 (s, 3H), 3.01 (t, 2H), 2.92 (t, 2H), 2.17-2.09 (m, 2H) and 1.50 (d, 6H).

LCMS: m/z 474.2 (M+H)$^+$ (ES$^+$).

Step B: 4-Chloro-1-isopropyl-N-((5-(2-methoxypyridin-4-yl)-2,3-dihydro-1H-inden-4-yl)carbamoyl)-1H-pyrazole-3-sulfonimidamide

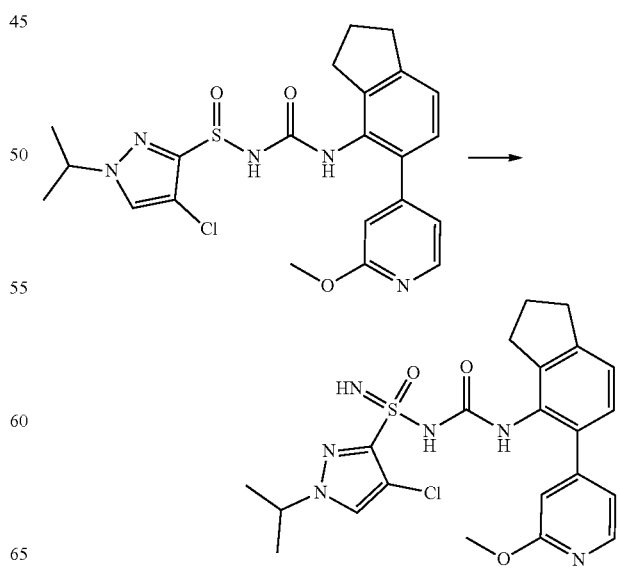

4-Chloro-1-isopropyl-N-((5-(2-methoxypyridin-4-yl)-2,3-dihydro-1H-inden-4-yl)carbamoyl)-1H-pyrazole-3-sulfinamide (200 mg, 421.96 μmol, 1 eq) was dissolved in THF (4 mL) under nitrogen. Then 1-chloro-1H-benzo[d][1,2,3]triazole (58 mg, 379.77 μmol, 0.9 eq) was added in one portion. The resulting mixture was stirred for 30 minutes. The reaction mixture was added dropwise over 10 minutes at −70° C. to a solution of ammonia in THF (10 mL), which had been prepared by bubbling NH₃ gas (15 psi) into THF (10 mL) at −70° C. for 5 minutes. After stirring for 15 minutes, the mixture was warmed to 20° C. for 2 hours and then concentrated in vacuo. The residue was purified by prep-TLC (DCM:MeOH=10:1) and then purified by prep-HPLC (column: Phenomenex Gemini 150 mm*25 mm*10 μm; mobile phase: [A: water (10 mM NH₄HCO₃); B: MeCN]; B %: 32%-62%, 10 min) to give the title compound (61.15 mg, 30% yield, 100% purity on LCMS) as a white solid.

¹H NMR (DMSO-d₆): δ 8.19 (s, 2H), 8.10 (d, 1H), 7.36 (br s, 2H), 7.15 (d, 1H), 7.08 (d, 1H), 6.95 (d, 1H), 6.77 (s, 1H), 4.55-4.47 (m, 1H), 3.87 (s, 3H), 2.90 (t, 2H), 2.75-2.67 (m, 2H), 2.01-1.94 (m, 2H) and 1.41 (d, 6H).

LCMS: m/z 489.2 (M+H)⁺ (ES⁺).

Example 12: 4-Chloro-N-((2-(2-cyanopyridin-4-yl)-4-fluoro-6-isopropylphenyl) carbamoyl)-1-isopropyl-1H-pyrazole-3-sulfonimidamide

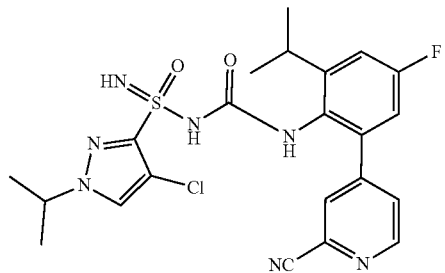 [SMILES: CC(C)c1cc(F)cc(-c2ccnc(C#N)c2)c1NC(=O)NS(=N)(=O)c1nn(C(C)C)cc1Cl]

Step A: 4-Chloro-N-((2-(2-cyanopyridin-4-yl)-4-fluoro-6-isopropylphenyl)carbamoyl)-1-isopropyl-1H-pyrazole-3-sulfinamide

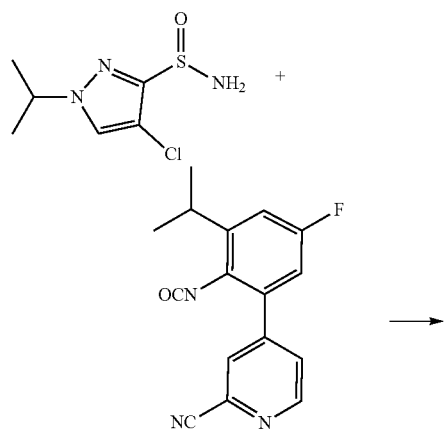

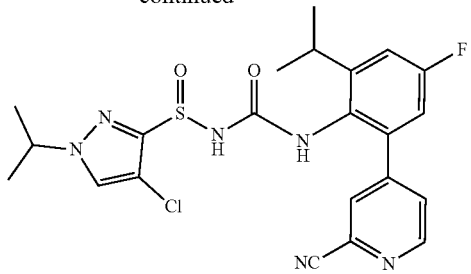

To a solution of 4-chloro-1-isopropyl-1H-pyrazole-3-sulfinamide (intermediate L6) (150 mg, 722.26 μmol, 1 eq) in THF (2 mL) was added t-BuONa (69 mg, 722.26 μmol, 1 eq). The mixture was stirred at 20° C. for 10 minutes. Then 4-(5-fluoro-2-isocyanato-3-isopropylphenyl)picolinonitrile (intermediate R3) (203 mg, 722.26 μmol, 1 eq) was added. The mixture was stirred at 20° C. for 20 minutes and then concentrated in vacuo. The residue was purified by reversed phase flash chromatography (0.1% NH₃.H₂O/MeCN) to give the title compound (320 mg, 70% yield, 77% purity on LCMS) as a yellow solid.

¹H NMR (CD₃OD): δ 8.73 (d, 1H), 8.02 (s, 1H), 7.90 (s, 1H), 7.70-7.68 (m, 1H), 7.29 (dd, 1H), 7.10 (dd, 1H), 4.64-4.57 (m, 1H), 3.28-3.24 (m, 1H), 1.52 (dd, 6H) and 1.29-1.26 (m, 6H).

LCMS: m/z 489.2 (M+H)⁺ (ES⁺).

Step B: 4-Chloro-N-((2-(2-cyanopyridin-4-yl)-4-fluoro-6-isopropylphenyl)carbamoyl)-1-isopropyl-1H-pyrazole-3-sulfonimidamide

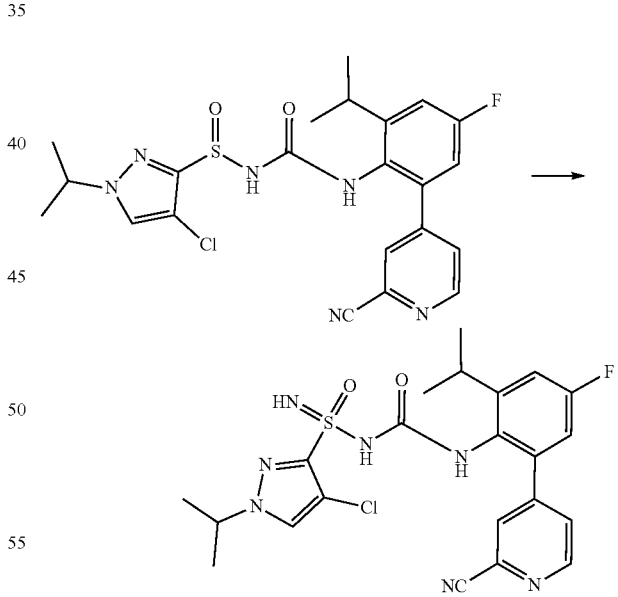

4-Chloro-N-((2-(2-cyanopyridin-4-yl)-4-fluoro-6-isopropylphenyl)carbamoyl)-1-isopropyl-1H-pyrazole-3-sulfinamide (200 mg, 409.03 μmol, 1 eq) was dissolved in THF (4 mL) under nitrogen. Then 1-chloro-1H-benzo[d][1,2,3]triazole (57 mg, 368.12 μmol, 0.9 eq) was added in one portion. The resulting mixture was stirred for 30 minutes. The mixture was added dropwise over 10 minutes at −70° C. to a solution of ammonia in THF (6 mL), which had been prepared by bubbling NH₃ gas (15 psi) into THF (10 mL) at −70° C. for 5 minutes. After stirring for 15 minutes, the mixture was warmed to 20° C., stirred for 2 hours and then concentrated in vacuo. The residue was purified by prep-TLC (DCM:MeOH=10:1) and then purified by prep-HPLC (column: Waters Xbridge 150 mm*50 mm*10 μm; mobile phase: [A: water (1 mM NH₄HCO₃); B: MeCN]; B %: 30%-60%, 11.5 min) to give the title compound (41.11 mg, 20% yield, 99% purity on LCMS) as a white solid.

¹H NMR (DMSO-d₆): δ 8.70 (d, 1H), 8.38 (s, 1H), 8.15 (s, 1H), 8.01 (s, 1H), 7.69 (d, 1H), 7.23 (dd, 1H), 7.12 (dd, 1H), 6.71 (br s, 2H), 4.51-4.43 (m, 1H), 3.20-3.16 (m, 1H), 1.44-1.38 (m, 6H) and 1.19-1.11 (m, 6H).

LCMS: m/z 504.2 (M+H)⁺ (ES⁺).

Example 13: 4-Chloro-N-((4-fluoro-2-isopropyl-6-(2-methoxypyridin-4-yl)phenyl) carbamoyl)-1-isopropyl-1H-pyrazole-3-sulfonimidamide

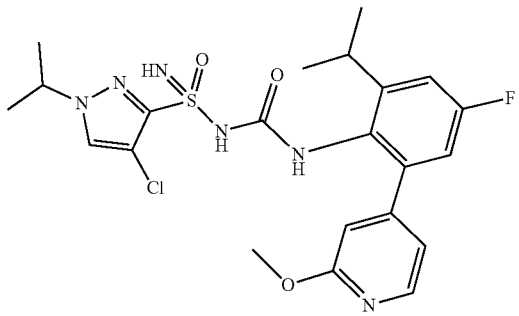 [SMILES: COc1cc(-c2cc(F)cc(C(C)C)c2NC(=O)NS(=N)(=O)c2nn(C(C)C)cc2Cl)ccn1]

Step A: 4-Chloro-N-((4-fluoro-2-isopropyl-6-(2-methoxypyridin-4-yl)phenyl) carbamoyl)-1-isopropyl-1H-pyrazole-3-sulfinamide

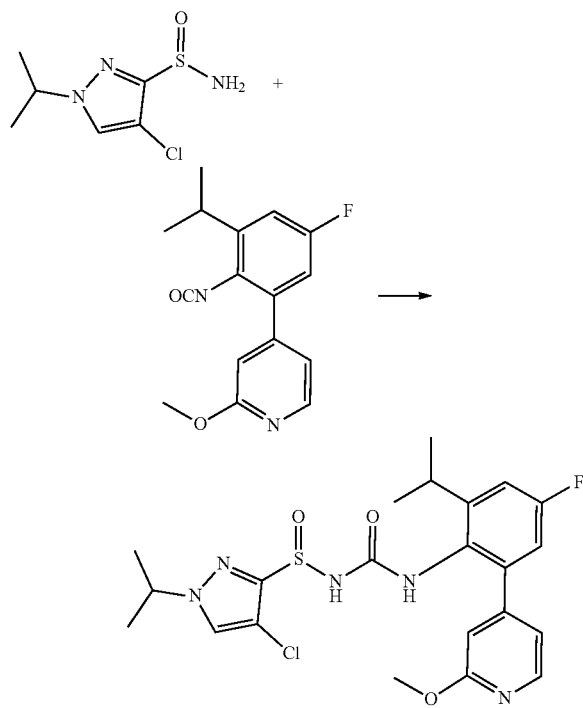

To a solution of 4-chloro-1-isopropyl-1H-pyrazole-3-sulfinamide (intermediate L6) (150 mg, 722.26 μmol, 1 eq) in THF (2 mL) was added t-BuONa (69 mg, 722.26 μmol, 1 eq). The mixture was stirred at 20° C. for 10 minutes. Then 4-(5-fluoro-2-isocyanato-3-isopropylphenyl)-2-methoxypyridine (intermediate R4) (207 mg, 722.26 μmol, 1 eq) was added. The mixture was stirred at 20° C. for 20 minutes and then concentrated in vacuo. The residue was purified by reversed phase flash chromatography (0.1% NH₃.H₂O/MeCN) to give the title compound (300 mg, 74% yield, 88% purity on LCMS) as a white solid.

¹H NMR (CD₃OD): δ 8.12 (d, 1H), 8.00 (s, 1H), 7.20 (dd, 1H), 7.00-6.95 (m, 2H), 6.81 (s, 1H), 4.62-4.55 (m, 1H), 3.90 (s, 3H), 3.24-3.20 (m, 1H), 1.52-1.47 (m, 6H) and 1.29-1.22 (m, 6H).

LCMS: m/z 494.2 (M+H)⁺ (ES⁺).

Step B: 4-Chloro-N-((4-fluoro-2-isopropyl-6-(2-methoxypyridin-4-yl)phenyl) carbamoyl)-1-isopropyl-1H-pyrazole-3-sulfonimidamide

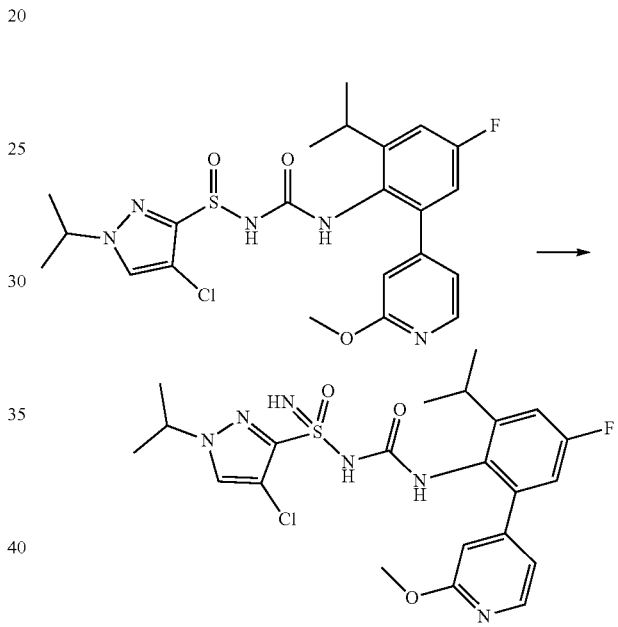

4-Chloro-N-((4-fluoro-2-isopropyl-6-(2-methoxypyridin-4-yl)phenyl)carbamoyl)-1-isopropyl-1H-pyrazole-3-sulfinamide (200 mg, 404.87 μmol, 1 eq) was dissolved in THF (4 mL) under nitrogen. Then 1-chloro-1H-benzo[d][1,2,3]triazole (56 mg, 364.39 μmol, 0.9 eq) was added in one portion. The resulting reaction mixture was stirred for 30 minutes. Then the mixture was added dropwise over 10 minutes at −70° C. to a solution of ammonia in THF (1 mL), which had been prepared by bubbling NH₃ gas (15 psi) into THF (10 mL) at −70° C. for 5 minutes. After stirring for 15 minutes, the reaction mixture was warmed to 20° C., stirred for 2 hours and then concentrated in vacuo. The residue was purified by prep-TLC (DCM:MeOH=10:1) and then purified by prep-HPLC (column: Waters Xbridge 150 mm*50 mm*10 μm; mobile phase: [A: water (10 mM NH₄HCO₃); B: MeCN]; B %: 35%-65%, 11.5 min) to give the title compound (71.14 mg, 35% yield, 100% purity in LCMS) as a white solid.

¹H NMR (DMSO-d₆): δ 8.22-8.10 (m, 3H), 7.54 (br s, 2H), 7.17-7.14 (m, 1H), 7.00-6.80 (m, 2H), 6.78 (m, 1H), 4.53-4.46 (m, 1H), 3.85 (s, 3H), 3.19-3.14 (m, 1H), 1.42-1.33 (m, 6H) and 1.11-1.02 (m, 6H).

LCMS: m/z 509.2 (M+H)⁺ (ES⁺).

Example 14: 1-Isopropyl-N-((5-(2-methoxypyridin-4-yl)-2,3-dihydro-1H-inden-4-yl) carbamoyl)-1H-pyrazole-3-sulfonimidamide

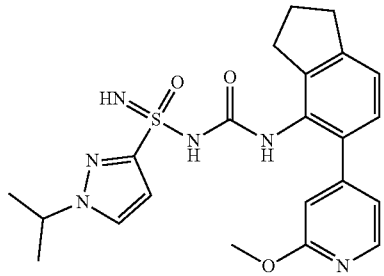 [SMILES: COc1cc(-c2ccc3c(c2NC(=O)NS(=N)(=O)c2ccn(C(C)C)n2)CCC3)ccn1]

Step A: 1-Isopropyl-N-((5-(2-methoxypyridin-4-yl)-2,3-dihydro-1H-inden-4-yl) carbamoyl)-1H-pyrazole-3-sulfinamide

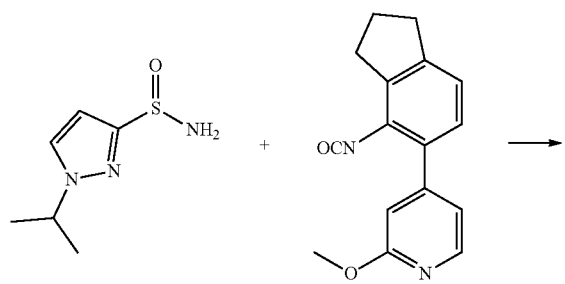

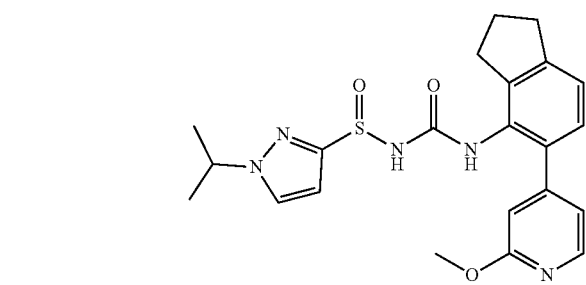

To a solution of 1-iso-propyl-1H-pyrazole-3-sulfinamide (intermediate L1) (100 mg, 577.25 μmol, 1 eq) in THF (6 mL) was added t-BuONa (55 mg, 577.25 μmol, 1 eq) and 4-(4-isocyanato-2,3-dihydro-1H-inden-5-yl)-2-methoxy-pyridine (intermediate R2) (154 mg, 577.25 μmol, 1 eq). The mixture was stirred at 10° C. for 1 hour and then concentrated in vacuo. The residue was purified by reversed phase flash chromatography (0.1% $NH_3 \cdot H_2O$/MeCN) to give the title compound (210 mg, 80% yield, 96.4% purity on LCMS) as a white solid.

$^1$H NMR (DMSO-$d_6$): δ 8.15 (d, 1H), 7.94 (s, 1H), 7.21 (d, 1H), 7.13 (d, 1H), 6.95 (d, 1H), 6.77 (s, 1H), 6.61 (s, 1H), 4.61-4.54 (m, 1H), 3.87 (s, 3H), 2.94 (t, 2H), 2.81 (t, 2H), 2.07-2.00 (m, 2H) and 1.44 (d, 6H).

LCMS: m/z 440.2 (M+H)$^+$ (ES$^+$).

Step B: 1-Isopropyl-N-((5-(2-methoxypyridin-4-yl)-2,3-dihydro-1H-inden-4-yl)-2,3-dihydro-1H-inden-4-yl)carbamoyl)-1H-pyrazole-3-sulfonimidamide

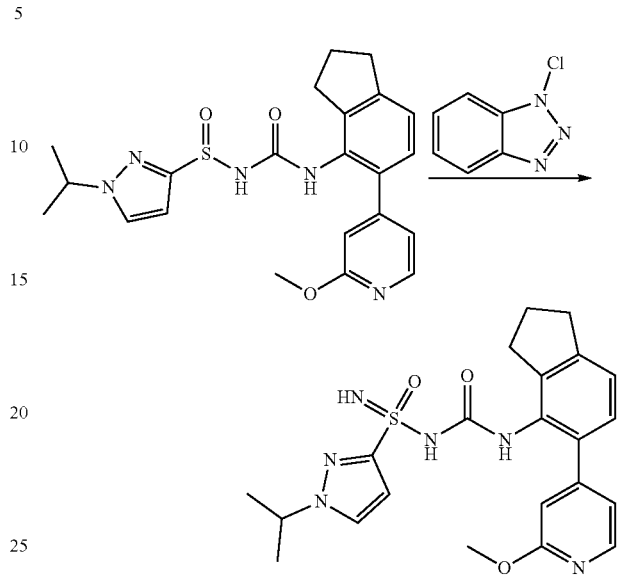

To a solution of 1-isopropyl-N-((5-(2-methoxypyridin-4-yl)-2,3-dihydro-1H-inden-4-yl)carbamoyl)-1H-pyrazole-3-sulfinamide (200 mg, 455.03 μmol, 1 eq) in THF (5 mL) was added 1-chloro-1H-benzo[d][1,2,3]triazole (70 mg, 455.03 μmol, 1 eq) and the mixture was stirred at 10° C. for 30 minutes. $NH_3$ was bubbled into THF (30 mL) at −75° C. for 10 minutes. The above reaction mixture was added into the $NH_3$/THF solution at −75° C. and the resulting mixture was stirred for another 20 minutes. The mixture was slowly warmed to 10° C. and stirred at 10° C. for 1 hour. Then the reaction mixture was concentrated in vacuo. The residue was purified by prep-HPLC (column: Phenomenex Gemini 150 mm*25 mm*10 μm; mobile phase: [A: water (0.05% $NH_4HCO_3$); B: MeCN]; B %: 30%-60%, 12 min) to give the title compound (68.64 mg, 33% yield, 100% purity on LCMS) as a white solid.

$^1$H NMR (DMSO-$d_6$): δ 8.26 (br s, 1H), 8.12 (d, 1H), 7.91 (d, 1H), 7.41 (br s, 2H), 7.16 (d, 1H), 7.09 (d, 1H), 6.95 (d, 1H), 6.77 (s, 1H), 6.51 (s, 1H), 4.64-4.53 (m, 1H), 3.88 (s, 3H), 2.91 (t, 2H), 2.73-2.67 (m, 2H), 2.00-1.95 (m, 2H) and 1.44 (d, 6H).

LCMS: m/z 455.2 (M+H)$^+$ (ES$^+$).

Example 15: N-((2-(2-Cyanopyridin-4-yl)-4-fluoro-6-isopropylphenyl)carbamoyl)-1-isopropyl-1H-pyrazole-3-sulfonimidamide

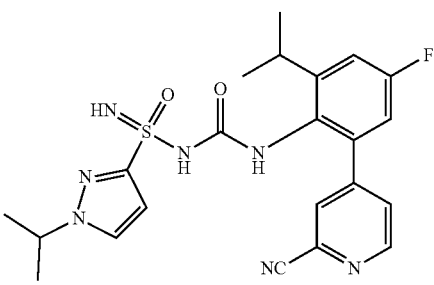 [SMILES: CC(C)c1cc(F)cc(-c2ccnc(C#N)c2)c1NC(=O)NS(=N)(=O)c1ccn(C(C)C)n1]

Step A: N-((2-(2-Cyanopyridin-4-yl)-4-fluoro-6-isopropylphenyl)carbamoyl)-1-isopropyl-1H-pyrazole-3-sulfinamide

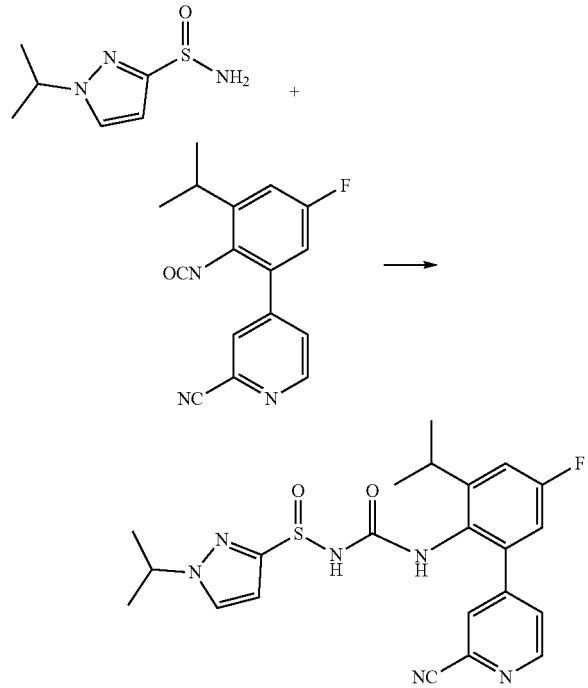

To a solution of 1-iso-propyl-1H-pyrazole-3-sulfinamide (intermediate L1) (100 mg, 577.25 μmol, 1 eq) in THF (5 mL) was added t-BuONa (61 mg, 634.97 μmol, 1.1 eq) and 4-(5-fluoro-2-isocyanato-3-isopropylphenyl)picolinonitrile (intermediate R3) (162 mg, 577.25 μmol, 1 eq). The mixture was stirred at 25° C. for 1 hour and then concentrated in vacuo. The residue was purified by reversed phase flash chromatography (0.1% NH$_3$.H$_2$O/MeCN) to give the title compound (200 mg, 76% yield) as a white solid.

$^1$H NMR (DMSO-d$_6$): δ 8.77 (d, 1H), 8.22 (s, 1H), 8.09 (s, 1H), 8.02 (d, 1H), 7.75-773 (m, 1H), 7.35 (d, 1H), 7.23 (dd, 1H), 6.66 (d, 1H), 4.67-4.51 (m, 1H), 3.17-313 (m, 1H), 1.45 (d, 6H) and 1.20 (dd, 6H).

LCMS: m/z 455.2 (M+H)$^+$ (ES$^+$).

Step B: N-((2-(2-Cyanopyridin-4-yl)-4-fluoro-6-isopropylphenyl)carbamoyl)-1-isopropyl-1H-pyrazole-3-sulfonimidamide

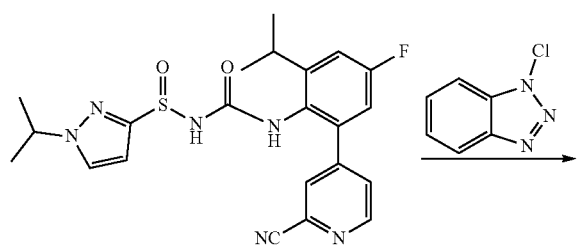

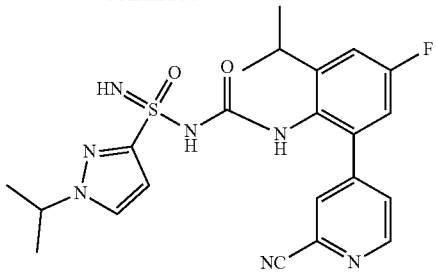

To a solution of N-((2-(2-cyanopyridin-4-yl)-4-fluoro-6-isopropylphenyl)carbamoyl)-1-isopropyl-1H-pyrazole-3-sulfinamide (160 mg, 352.02 μmol, 1 eq) in THF (5 mL) was added 1-chloro-1H-benzo[d][1,2,3]triazole (54 mg, 352.02 μmol, 1 eq) and the mixture was stirred for 30 minutes. The above solution was added into a NH$_3$/THF solution, which had been prepared by bubbling NH$_3$ into THF (30 mL) at −78° C. for 10 minutes. The reaction mixture was stirred at −70 to −60° C. for 30 minutes and then stirred at 25° C. for 3.5 hours. The reaction mixture was concentrated in vacuo. The residue was purified by prep-HPLC (column: Phenomenex Gemini 150 mm*25 mm*10 μm; mobile phase: [A: water (0.05% NH$_4$HCO$_3$); B: MeCN]; B %: 30%-60%, 12 min) to give the title compound (7.76 mg, 5% yield, 100% purity on LCMS) as an off-white solid.

$^1$H NMR (DMSO-d$_6$): δ 8.69 (d, 1H), 7.97 (s, 1H), 7.80 (d, 1H), 7.71 (d, 1H), 7.22-7.17 (m, 3H), 7.08 (dd, 1H), 6.39 (s, 1H), 4.62-4.51 (m, 1H), 3.27-3.21 (m, 1H), 1.46 (d, 6H) and 1.17 (dd, 6H).

LCMS: m/z 470.2 (M+H)$^+$ (ES$^+$).

Example 16: N-((4-Fluoro-2-isopropyl-6-(2-methoxypyridin-4-yl)phenyl)carbamoyl)-1-isopropyl-1H-pyrazole-3-sulfonimidamide

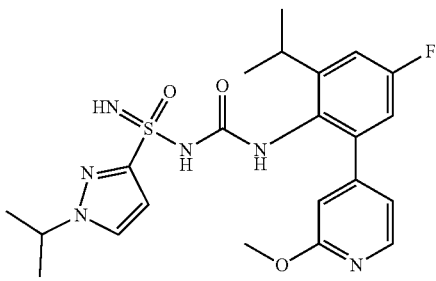 [SMILES: COc1cc(-c2cc(F)cc(C(C)C)c2NC(=O)NS(=N)(=O)c2ccn(C(C)C)n2)ccn1]

Step A: N-((4-Fluoro-2-isopropyl-6-(2-methoxypyridin-4-yl)phenyl)carbamoyl)-1-isopropyl-1H-pyrazole-3-sulfinamide

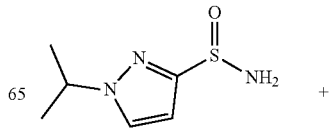

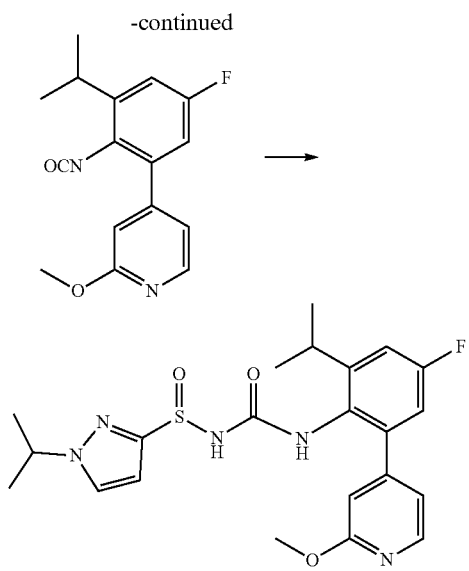

To a solution of 1-iso-propyl-1H-pyrazole-3-sulfinamide (intermediate L1) (100 mg, 577.25 μmol, 1 eq) in THF (6 mL) was added t-BuONa (55 mg, 577.25 μmol, 1 eq) and 4-(5-fluoro-2-isocyanato-3-isopropylphenyl)-2-methoxypyridine (intermediate R4) (165 mg, 577.25 μmol, 1 eq). The mixture was stirred at 10° C. for 1 hour and then concentrated in vacuo. The residue was purified by reversed phase flash chromatography (0.1% NH$_3$.H$_2$O/MeCN) to give the title compound (180 mg, 66% yield, 96.6% purity on LCMS) as a white solid.

$^1$H NMR (DMSO-d$_6$): δ 8.12 (d, 1H), 7.88 (s, 1H), 7.22 (d, 1H), 7.06-7.00 (m, 2H), 6.85 (s, 1H), 6.50 (s, 1H), 4.59-4.51 (m, 1H), 3.86 (s, 3H), 3.20-3.17 (m, 1H), 1.43 (d, 6H) and 1.16 (d, 6H).

LCMS: m/z 460.3 (M+H)$^+$ (ES$^+$).

Step B: N-((4-Fluoro-2-isopropyl-6-(2-methoxypyridin-4-yl)phenyl)carbamoyl)-1-isopropyl-1H-pyrazole-3-sulfonimidamide

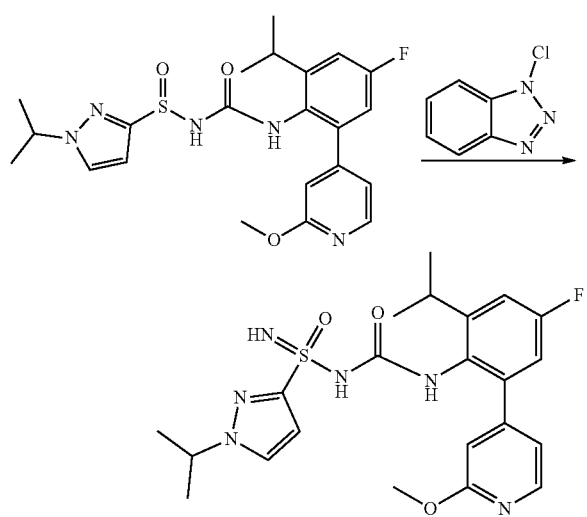

To a solution of N-((4-fluoro-2-isopropyl-6-(2-methoxypyridin-4-yl)phenyl) carbamoyl)-1-isopropyl-1H-pyrazole-3-sulfinamide (160 mg, 348.18 μmol, 1 eq) in THF (5 mL) was added 1-chloro-1H-benzo[d][1,2,3]triazole (53 mg, 348.18 μmol, 1 eq) and the mixture was stirred at 10° C. for 30 minutes. NH$_3$ was bubbled into THF (30 mL) at −75° C. for 10 minutes. The above reaction mixture was added into the NH$_3$/THF solution at −75° C. and stirred another 20 minutes. The mixture was slowly warmed to ° C. and stirred at 10° C. for 1 hour. Then the reaction mixture was concentrated in vacuo. The residue was purified by prep-HPLC (column: Phenomenex Gemini 150 mm*25 mm*10 μm; mobile phase: [A: water (0.05% NH$_4$HCO$_3$); B: MeCN]; B %: 33%-63%, 12 min) to give the title compound (28.24 mg, 17% yield, 99.5% purity on LCMS) as a white solid.

$^1$H NMR (DMSO-d$_6$): δ 8.11 (d, 1H), 8.00 (br s, 1H), 7.82 (d, 1H), 7.15-7.11 (m, 3H), 6.99-6.93 (m, 2H), 6.81 (s, 1H), 6.42 (s, 1H), 4.61-4.52 (m, 1H), 3.91 (s, 3H), 3.25-3.20 (m, 1H), 1.46 (d, 6H) and 1.17-1.09 (m, 6H).

LCMS: m/z 475.2 (M+H)$^+$ (ES$^+$).

Example 17: 1-((R)-2-Hydroxypropyl)-N-((5-(2-methoxypyridin-4-yl)-2,3-dihydro-1H-inden-4-yl)carbamoyl)-1H-pyrazole-3-sulfonimidamide

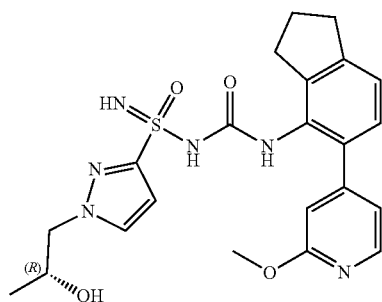

Step A: 1-((R)-2-Hydroxypropyl)-N-((5-(2-methoxypyridin-4-yl)-2,3-dihydro-1H-inden-4-yl)carbamoyl)-1H-pyrazole-3-sulfinamide

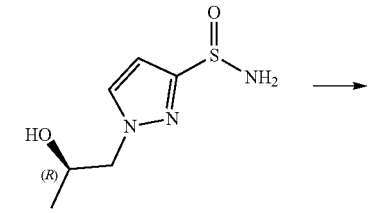

-continued

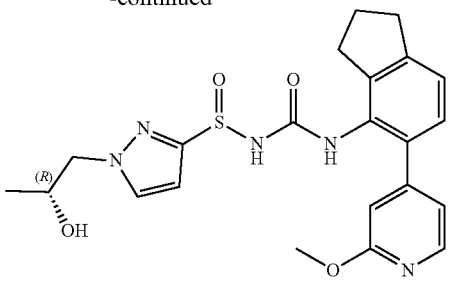

To a solution of 1-((R)-2-hydroxypropyl)-1H-pyrazole-3-sulfinamide (intermediate L2) (0.06 g, 317.07 μmol, 1 eq) in THF (2 mL) was added t-BuONa (37 mg, 380.48 μmol, 1.2 eq) at 25° C. The mixture was stirred for 0.5 hour. Then 4-(4-isocyanato-2,3-dihydro-1H-inden-5-yl)-2-methoxy-pyridine (intermediate R2) (101 mg, 380.48 μmol, 1.2 eq) was added. The mixture was heated to 70° C., stirred for another 0.1 hour and then concentrated in vacuo. The residue was purified by reversed phase flash chromatography (basic condition, 0.1% NH$_3$.H$_2$O in water/MeCN) to give the title compound (0.1 g, 67% yield, 97% purity on LCMS) as a white solid.

$^1$H NMR (CDCl$_3$): δ 7.93 (s, 1H), 7.39 (m, 1H), 7.12-7.08 (m, 1H), 7.03-7.00 (m, 1H), 6.77 (s, 1H), 6.62 (s, 1H), 6.38 (s, 1H), 4.13-3.89 (m, 3H), 3.82 (s, 3H), 2.98-2.61 (m, 4H), 1.99-1.95 (m, 2H) and 1.07-1.04 (m, 3H).

LCMS: m/z 456.2 (M+H)$^+$ (ES$^+$)

Step B: 1-((R)-2-Hydroxypropyl)-N-((5-(2-methoxypyridin-4-yl)-2,3-dihydro-1H-inden-4-yl)carbamoyl)-1H-pyrazole-3-sulfonimidamide

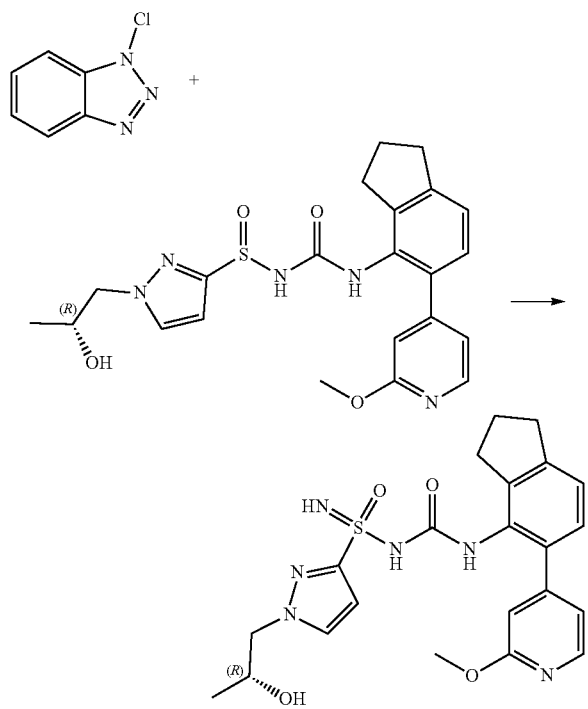

To a solution of 1-((R)-2-hydroxypropyl)-N-((5-(2-methoxypyridin-4-yl)-2,3-dihydro-1H-inden-4-yl)carbam-oyl)-1H-pyrazole-3-sulfinamide (0.1 g, 219.52 μmol, 1 eq) in THF (5 mL) was added 1-chloro-1H-benzo[d][1,2,3]triazole (33.71 mg, 219.52 μmol, 1 eq) under N$_2$ atmosphere. Then the mixture was stirred for 0.5 hour. This solution was added dropwise over 10 minutes at −70° C. to a solution of ammonia in THF (5 mL), which had been prepared by bubbling NH$_3$ gas into THF (5 mL) at −70° C. for 5 minutes. After stirring for 25 minutes, the mixture was warmed to 25° C. for 2 hours and then concentrated in vacuo. The residue was purified by prep-TLC (dichloromethane:methanol=10:1) and then purified by prep-HPLC (column: Phenomenex Gemini 150 mm*25 mm*10 μm; mobile phase: [A: water (0.04% NH$_3$.H$_2$O+10 mM NH$_4$HCO$_3$); B: MeCN]; B %: 18%-48%, 10 min) to give the title compound (9.05 mg, 9% yield, 100% purity on LCMS) as a white solid.

$^1$H NMR (DMSO-d$_6$): δ 8.23 (br s, 1H), 8.12 (d, 1H), 7.79 (d, 1H), 7.34 (br s, 2H), 7.16 (d, 1H), 7.08 (d, 1H), 6.95 (d, 1H), 6.77 (s, 1H), 6.47 (s, 1H), 5.02-5.00 (m, 1H), 4.08 (d, 2H), 4.04-3.96 (m, 1H), 3.88 (s, 3H), 2.91 (t, 2H), 2.78-2.74 (m, 2H), 2.03-1.96 (m, 2H) and 1.05 (dd, 3H).

LCMS: m/z 471.2 (M+H)$^+$ (ES$^+$).

Example 8: N-((2-(2-Cyanopyridin-4-yl)-4-fluoro-6-isopropylphenyl)carbamoyl)-1-((R)-2-hydroxypropyl)-1H-pyrazole-3-sulfonimidamide

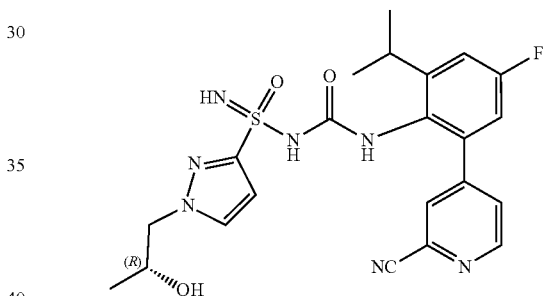

Step A: N-((2-(2-Cyanopyridin-4-yl)-4-fluoro-6-isopropylphenyl)carbamoyl)-1-((R)-2-hydroxypropyl)-1H-pyrazole-3-sulfinamide

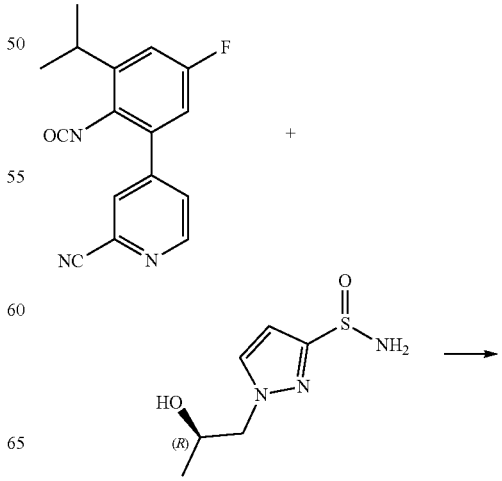

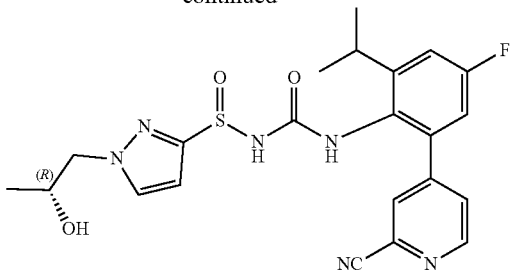

To a solution of 1-((R)-2-hydroxypropyl)-1H-pyrazole-3-sulfinamide (intermediate L2) (0.07 g, 369.91 µmol, 1 eq) in THF (2 mL) was added t-BuONa (43 mg, 443.89 mol, 1.2 eq) at 25° C. The mixture was stirred for 0.5 hour. Then 4-(5-fluoro-2-isocyanato-3-isopropylphenyl)picolinonitrile (intermediate R3) (125 mg, 443.89 mol, 1.2 eq) was added and the resulting mixture was heated to 70° C. and stirred for 0.1 hour. Then the mixture was concentrated in vacuo. The residue was purified by reversed phase flash chromatography (basic condition, 0.1% NH$_3$.H$_2$O in water/MeCN) to give the title compound (0.11 g, 55% yield, 87% purity on LCMS) as a white solid.

$^1$H NMR (CDCl$_3$): δ 8.58 (d, 1H), 8.02-7.85 (m, 1H), 7.68-7.64 (m, 1H), 7.55-7.44 (m, 2H), 7.11 (dd, 1H), 6.85 (d, 1H), 6.49 (s, 1H), 4.18-4.10 (m, 2H), 3.99-3.92 (m, 1H), 3.15-3.10 (m, 1H) and 1.20-1.02 (m, 9H).

LCMS: m/z 471.2 (M+H)$^+$ (ES$^+$).

Step B: N-((2-(2-Cyanopyridin-4-yl)-4-fluoro-6-isopropylphenyl)carbamoyl)-1-((R)-2-hydroxypropyl)-1H-pyrazole-3-sulfonimidamide

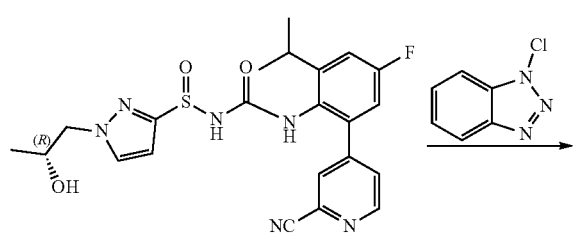

To a solution of N-((2-(2-cyanopyridin-4-yl)-4-fluoro-6-isopropylphenyl)carbamoyl)-1-((R)-2-hydroxypropyl)-1H-pyrazole-3-sulfinamide (0.11 g, 233.78 µmol, 1 eq) in THF (5 mL) was added 1-chloro-1H-benzo[d][1,2,3]triazole (36 mg, 233.78 µmol, 1 eq) under N$_2$ atmosphere. Then the mixture was stirred for 0.5 hour. This mixture was added dropwise over 10 minutes to a solution of ammonia in THF (5 mL) at −70° C. The ammonia solution had been prepared by bubbling NH$_3$ gas into THF (5 mL) at −70° C. for 5 minutes. After stirring at −70° C. for 25 minutes, the mixture was warmed to 25° C. for 2 hours and then concentrated in vacuo. The residue was purified by prep-TLC (dichloromethane:methanol=10:1) and then purified by prep-HPLC (column: Phenomenex Gemini 150 mm*25 mm*10 µm; mobile phase: [A: water (0.04% NH$_3$.H$_2$O+10 mM NH$_4$HCO$_3$); B: MeCN]; B %: 18%-51%, 10 min) to give the title compound (15.84 mg, 14% yield, 99% purity on LCMS) as a white solid.

$^1$H NMR (DMSO-d$_6$): δ 8.72 (d, 1H), 8.36 (br s, 1H), 8.08-7.96 (m, 1H), 7.74 (s, 1H), 7.68 (s, 1H), 7.31 (br s, 2H), 7.24 (d, 1H), 7.15-7.12 (m, 1H), 6.36-6.26 (m, 1H), 4.99 (d, 1H), 4.06 (d, 2H), 3.99-3.92 (m, 1H), 3.19-3.15 (m, 1H) and 1.26-0.93 (m, 9H).

LCMS: m/z 486.2 (M+H)$^+$ (ES$^+$).

Example 19: N-((4-Fluoro-2-isopropyl-6-(2-methoxypyridin-4-yl)phenyl)carbamoyl)-1-((R)-2-hydroxypropyl)-1H-pyrazole-3-sulfonimidamide

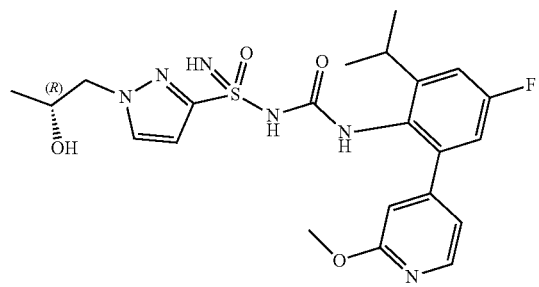

Step A: N-((4-Fluoro-2-isopropyl-6-(2-methoxypyridin-4-yl)phenyl)carbamoyl)-1-((R)-2-hydroxypropyl)-1H-pyrazole-3-sulfinamide

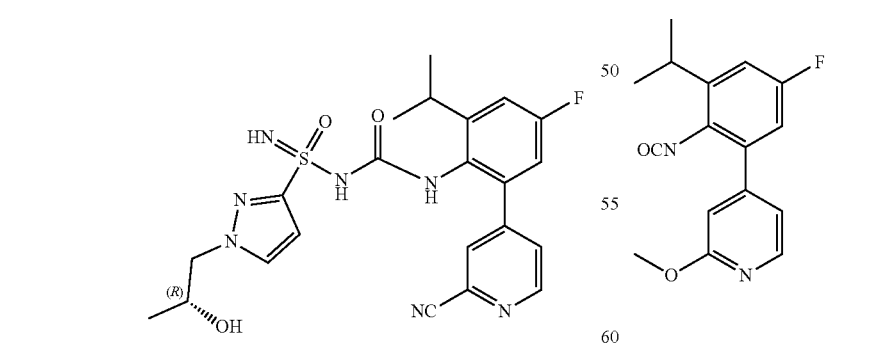

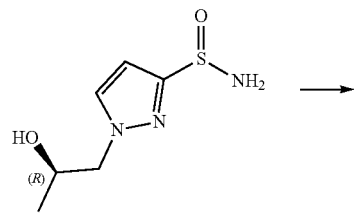

-continued

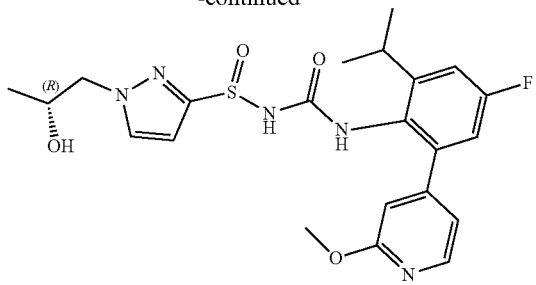

To a solution of 1-((R)-2-hydroxypropyl)-1H-pyrazole-3-sulfinamide (intermediate L2) (0.07 g, 369.91 μmol, 1 eq) in THF (2 mL) was added t-BuONa (43 mg, 443.89 μmol, 1.2 eq) at 25° C. The mixture was stirred for 0.5 hour. Then 4-(5-fluoro-2-isocyanato-3-isopropylphenyl)-2-methoxypyridine (intermediate R4) (127 mg, 443.89 μmol, 1.2 eq) was added. The mixture was heated to 70° C., stirred for another 0.1 hour and then concentrated in vacuo. The residue was purified by reversed phase flash chromatography (basic condition, 0.1% $NH_3.H_2O$ in water/MeCN) to give the title compound (0.09 g, 50% yield, 97% purity on LCMS) as a white solid.

$^1$H NMR ($CDCl_3$): δ 7.89 (s, 1H), 7.66 (br s, 1H), 7.46 (s, 1H), 7.05 (d, 1H), 6.84-6.80 (m, 2H), 6.63 (s, 1H), 6.46-6.41 (m, 1H), 4.12-4.00 (m, 2H), 3.99-3.66 (m, 4H), 3.19-3.12 (m, 1H) and 1.25-1.04 (m, 9H).

LCMS: m/z 476.2 $(M+H)^+$ $(ES^+)$.

Step B: N-((4-Fluoro-2-isopropyl-6-(2-methoxypyridin-4-yl)phenyl)carbamoyl)-1-((R)-2-hydroxypropyl)-1H-pyrazole-3-sulfonimidamide

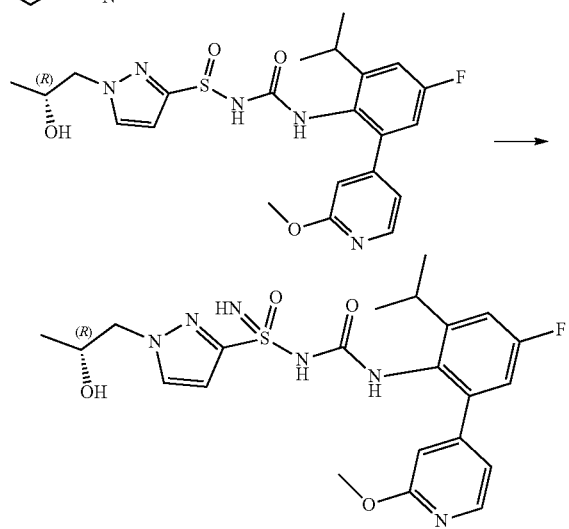

To a solution of N-((4-fluoro-2-isopropyl-6-(2-methoxypyridin-4-yl)phenyl) carbamoyl)-1-((R)-2-hydroxypropyl)-1H-pyrazole-3-sulfinamide (0.09 g, 189.26 μmol, 1 eq) in THF (5 mL) was added 1-chloro-1H-benzo[d][1,2,3]triazole (29 mg, 189.26 μmol, 1 eq) under $N_2$ atmosphere. Then the mixture was stirred for 0.5 hour. This solution was added dropwise over 10 minutes at −70° C. to a solution of ammonia in THF (5 mL), which had been prepared by bubbling $NH_3$ gas into THF (5 mL) at −70° C. for 5 minutes. After stirring for 25 minutes, the mixture was warmed to 25° C. for 2 hours and then concentrated in vacuo. The residue was purified by prep-TLC (dichloromethane:methanol=10:1) and then purified by prep-HPLC (column: Phenomenex Gemini 150 mm*25 mm*10 μm; mobile phase: [A: water (0.04% $NH_3.H_2O$+10 mM $NH_4HCO_3$); B: MeCN]; B %: 23%-53%, 10 min) to give the title compound (4.45 mg, 5% yield, 100% purity on LCMS) as a white solid.

$^1$H NMR (DMSO-$d_6$): δ 8.11 (d, 1H), 7.95 (br s, 1H), 7.74 (d, 1H), 7.23 (br s, 2H), 7.13 (dd, 1H), 6.98 (d, 1H), 6.94 (dd, 1H), 6.81 (s, 1H), 6.41 (s, 1H), 4.72 (d, 1H), 4.10-4.08 (m, 2H), 4.05-3.99 (m, 1H), 3.91 (s, 3H), 3.25-3.19 (m, 1H), 1.19-1.14 (m, 6H) and 1.08 (d, 3H).

LCMS: m/z 491.2 $(M+H)^+$ $(ES^+)$.

Example 20: N-((1,2,3,5,6,7-Hexahydro-s-indacen-4-yl)carbamoyl)-5-(1-hydroxyethyl)-1-methyl-1H-pyrazole-3-sulfonimidamide

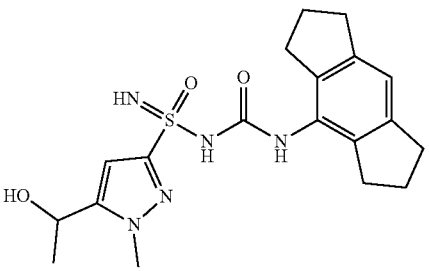 [SMILES: CC(O)c1cc(S(=N)(=O)NC(=O)Nc2c3c(cc4c2CCC4)CCC3)nn1C]

Step A: N-((1,2,3,5,6,7-Hexahydro-s-indacen-4-yl)carbamoyl)-5-(1-hydroxyethyl)-1-methyl-1H-pyrazole-3-sulfinamide

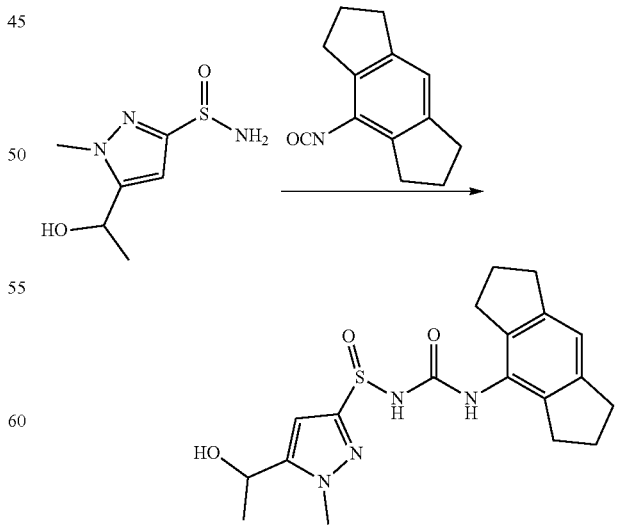

To a solution of 5-(1-hydroxyethyl)-1-methyl-1H-pyrazole-3-sulfinamide (intermediate L7) (855 mg, 4.52 mmol, 1 eq) in THF (10 mL) was added t-BuONa (434 mg, 4.52 mmol, 1 eq). The reaction mixture was stirred at 20° C. for 10 minutes. To the above mixture was added 4-isocyanato-1,2,3,5,6,7-hexahydro-s-indacene (intermediate R1) (900 mg, 4.52 mmol, 1 eq). The resulting mixture was stirred at 20° C. for 1 hour and then concentrated in vacuo. The residue was purified by reversed phase flash chromatography (water (0.05% NH$_3$.H$_2$O)-MeCN) to give the title compound (450 mg, 26% yield) as a yellow solid.

$^1$H NMR (DMSO-d$_6$): δ 9.19 (br s, 1H), 6.90 (s, 1H), 6.71 (s, 1H), 5.47-5.46 (m, 1H), 4.86-4.83 (m, 1H), 3.88 (s, 3H), 2.80 (t, 4H), 2.71 (t, 4H), 1.98-1.96 (m, 4H) and 1.46-1.43 (m, 3H).

LCMS: m/z 389.2 (M+H)$^+$ (ES$^+$).

Step B: N-((1,2,3,5,6,7-Hexahydro-s-indacen-4-yl)carbamoyl)-5-(1-hydroxyethyl)-1-methyl-1H-pyrazole-3-sulfonimidamide

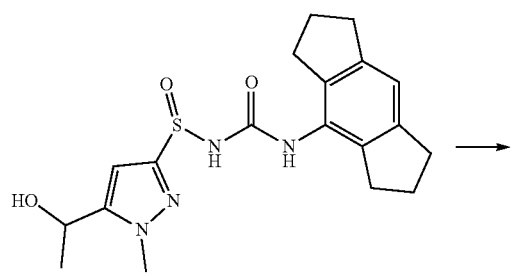

To a solution of N-((1,2,3,5,6,7-hexahydro-s-indacen-4-yl)carbamoyl)-5-(1-hydroxyethyl)-1-methyl-1H-pyrazole-3-sulfinamide (310 mg, 797.98 μmol, 1 eq) in THF (6 mL) was added 1-chloro-1H-benzo[d][1,2,3]triazole (110 mg, 718.18 μmol, 0.9 eq). The mixture was stirred at 20° C. for 30 minutes. Then the mixture was added dropwise over 10 minutes at −70° C. to a saturated solution of ammonia in THF (10 mL), which had been prepared by bubbling NH$_3$ gas (15 psi) into THF (10 mL) at −70° C. for 5 minutes. After stirring for 15 minutes, the mixture was warmed to 20° C. for 2 hours and then concentrated in vacuo. The residue was purified by reversed phase flash chromatography (water (0.05% NH$_3$.H$_2$O)-MeCN) to give the title compound (113 mg, 35% yield) as a white solid.

$^1$H NMR (DMSO-d$_6$): δ 8.28 (br s, 1H), 7.39 (br s, 2H), 6.86 (s, 1H), 6.53 (s, 1H), 5.49 (d, 1H), 4.87-4.83 (m, 1H), 3.88 (s, 3H), 2.78 (t, 4H), 2.69-2.65 (m, 4H), 1.97-1.92 (m, 4H) and 1.42 (d, 3H).

LCMS: m/z 404.2 (M+H)$^+$ (ES$^+$).

Example 21: 5-(1-Chloroethyl)-N-((1,2,3,5,6,7-hexahydro-s-indacen-4-yl)carbamoyl)-1-methyl-1H-pyrazole-3-sulfonimidamide

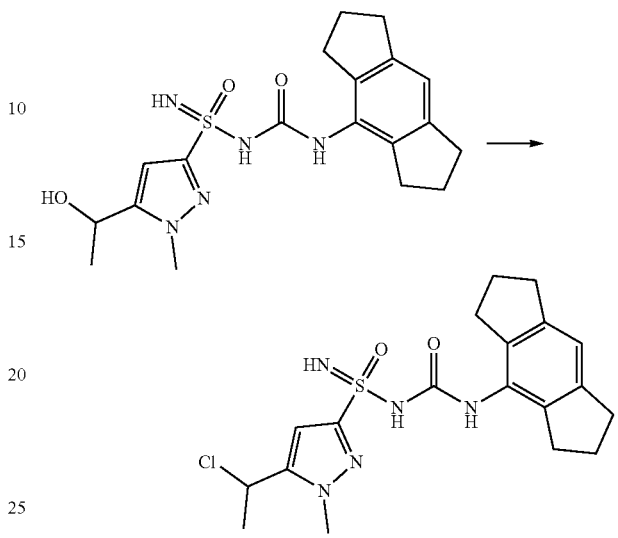

To a solution of N-((1,2,3,5,6,7-hexahydro-s-indacen-4-yl)carbamoyl)-5-(1-hydroxyethyl)-1-methyl-1H-pyrazole-3-sulfonimidamide (example 20) (80 mg, 198.27 μmol, 1 eq) in THF (2 mL) was added SOCl$_2$ (35 mg, 297.40 μmol, 21.57 μL, 1.5 eq) at 0° C. The reaction mixture was stirred at 0° C. for 1 hour and then concentrated in vacuo to give the title compound (95 mg, crude) as a yellow solid, which was used to prepare the compound of example 22 without further purification.

LCMS: m/z 422.2 (M+H)$^+$ (ES$^+$).

Example 22: 5-(1-(Azetidin-1-yl)ethyl)-N-((1,2,3,5,6,7-hexahydro-s-indacen-4-yl)carbamoyl)-1-methyl-1H-pyrazole-3-sulfonimidamide

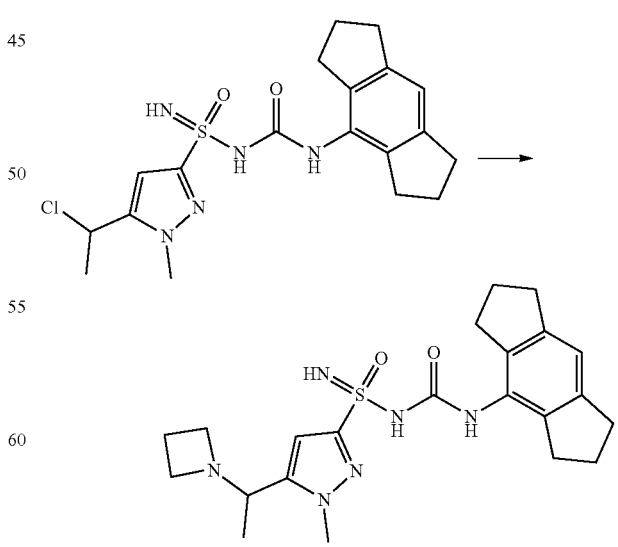

To a solution of 5-(1-chloroethyl)-N-((1,2,3,5,6,7-hexahydro-s-indacen-4-yl)carbamoyl)-1-methyl-1H-pyrazole-3- sulfonimidamide (example 21) (84 mg, 198.27 μmol, 1 eq) in THF (2 mL) was added azetidine (68 mg, 1.19 mmol, 80.28 μL, 6 eq). The reaction mixture was stirred at 35° C. for 7 hours and then concentrated in vacuo. The residue was purified by prep-HPLC (column: Phenomenex Gemini 150 mm*25 mm*10 μm; mobile phase: [A: water (10 mM NH₄HCO₃); B: MeCN]; B %: 25%-55%, 11 min) to give the title compound (13.9 mg, 16% yield, 98% purity on LCMS) as a white solid.

¹H NMR (DMSO-d₆): δ 8.30 (br s, 1H), 7.23 (br s, 2H), 6.86 (s, 1H), 6.48 (s, 1H), 3.90 (s, 3H), 3.62-3.60 (m, 1H), 3.11-3.06 (m, 4H), 2.77 (t, 4H), 2.67 (t, 4H), 1.94-1.90 (m, 6H) and 1.12 (d, 3H).

LCMS: m/z 443.3 (M+H)⁺ (ES⁺).

Example 23: 5-(Azetidin-1-ylmethyl)-N-((4-fluoro-2,6-diisopropylphenyl) carbamoyl)-1-methyl-1H-pyrazole-3-sulfonimidamide

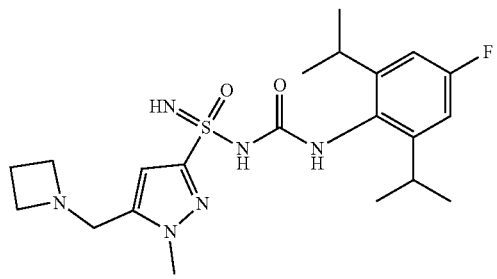 [SMILES: CC(C)c1cc(F)cc(C(C)C)c1NC(=O)NS(=N)(=O)c1cc(CN2CCC2)n(C)n1]

Step A: 5-(Azetidin-1-ylmethyl)-N-((4-fluoro-2,6-diisopropylphenyl)carbamoyl)-1-methyl-1H-pyrazole-3-sulfinamide

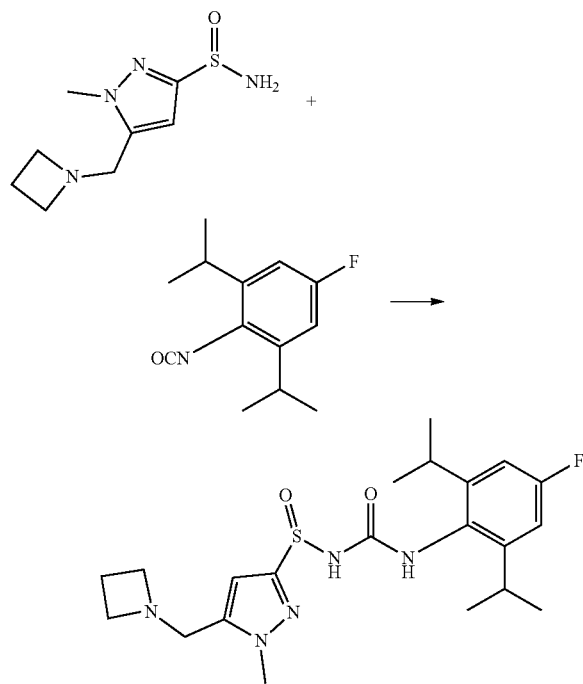

To a solution of 5-(azetidin-1-ylmethyl)-1-methyl-1H-pyrazole-3-sulfinamide (intermediate L8) (270 mg, 1.02 mmol, 1 eq) in THF (5 mL) was added t-BuONa (98 mg, 1.02 mmol, 1 eq). The mixture was stirred at 20° C. for 10 minutes. Then 5-fluoro-2-isocyanato-1,3-diisopropylbenzene (intermediate R5) (226 mg, 1.02 mmol, 1 eq) was added. The resulting mixture was stirred at 20° C. for 20 minutes and then concentrated in vacuo. The residue was purified by reversed phase flash chromatography (water (0.05% NH₃.H₂O)-MeCN) to give the title compound (250 mg, 50% yield, 89% purity on LCMS) as a white solid.

¹H NMR (DMSO-d₆): δ 6.88 (d, 2H), 6.41 (s, 1H), 3.85 (s, 3H), 3.58 (s, 2H), 3.26-3.16 (m, 6H), 2.07-2.02 (m, 2H) and 1.16-1.13 (m, 12H).

LCMS: m/z 458.2 (M+Na)⁺ (ES⁺).

Step B: 5-(Azetidin-1-ylmethyl)-N-((4-fluoro-2,6-diisopropylphenyl)carbamoyl)-1-methyl-1H-pyrazole-3-sulfonimidamide

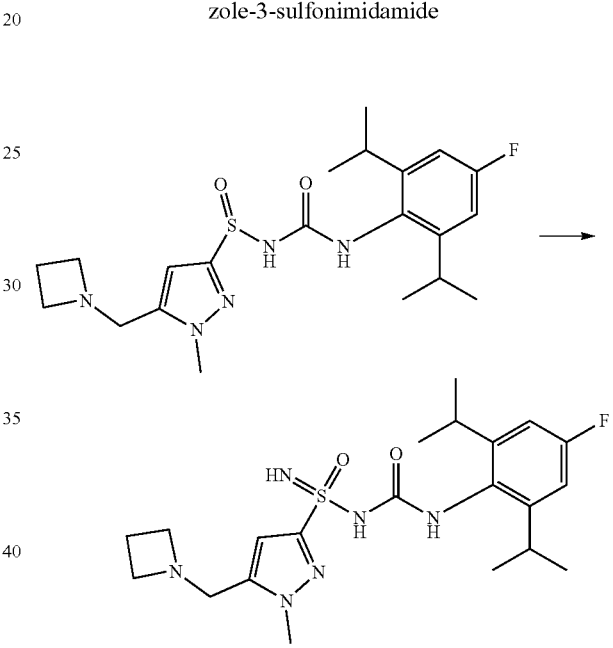

To a solution of 5-(azetidin-1-ylmethyl)-N-((4-fluoro-2,6-diisopropylphenyl) carbamoyl)-1-methyl-1H-pyrazole-3-sulfinamide (170 mg, 390.30 μmol, 1 eq) in THF (2 mL) was added 1-chloro-1H-benzo[d][1,2,3]triazole (54 mg, 351.27 μmol, 0.9 eq). The reaction mixture was stirred at 20° C. for 30 minutes. Then the above mixture was added dropwise over 10 minutes at −70° C. to a saturated solution of ammonia in THF (5 mL), which had been prepared by bubbling NH₃ gas (15 psi) into THF (10 mL) at −70° C. for 5 minutes. After stirring for 15 minutes, the reaction mixture was warmed to 20° C. for 2 hours and then concentrated in vacuo. The residue was purified by prep-TLC (DCM:MeOH=10:1) and then purified by prep-HPLC (column: Phenomenex Gemini 150 mm*25 mm*10 μm; mobile phase: [A: water (10 mM NH₄HCO₃); B: MeCN]; B %: 25%-55%, 11 min) to give the title compound (12.2 mg, 7% yield, 100% purity on LCMS) as a white solid.

¹H NMR (DMSO-d₆): δ 7.82 (br s, 1H), 7.19 (br s, 2H), 6.82 (d, 2H), 6.47 (s, 1H), 3.83 (s, 3H), 3.57 (s, 2H), 3.20-3.16 (m, 6H), 2.03-1.99 (m, 2H) and 1.12-1.09 (m, 12H).

LCMS: m/z 451.1 (M+H)⁺ (ES⁺).

Example 24: N-((7-Fluoro-5-(pyridin-4-yl)-2,3-di-hydro-1H-inden-4-yl)carbamoyl)-1-isopropyl-1H-pyrazole-3-sulfonimidamide

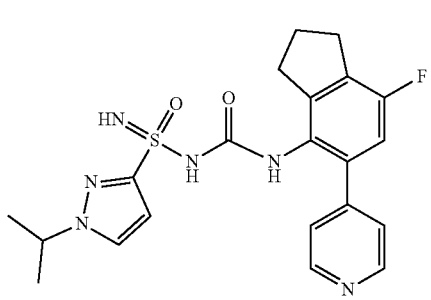 [SMILES: CC(C)n1ccc(S(=N)(=O)NC(=O)Nc2c(-c3ccncc3)cc(F)c3c2CCC3)n1]

Step A: N-((7-Fluoro-5-(pyridin-4-yl)-2,3-dihydro-1H-inden-4-yl)carbamoyl)-1-isopropyl-1H-pyrazole-3-sulfinamide

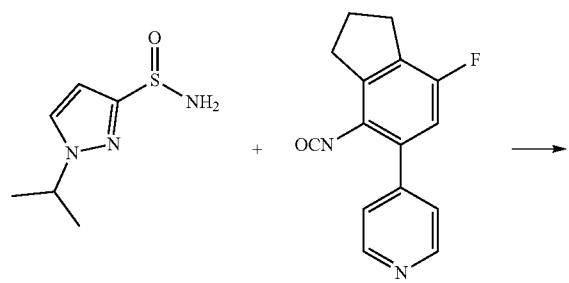

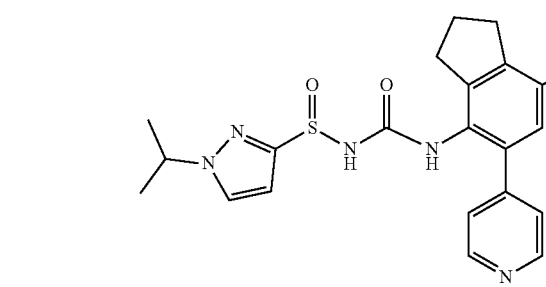

To a solution of 1-iso-propyl-1H-pyrazole-3-sulfinamide (intermediate L1) (100 mg, 577.25 μmol, 1 eq) in THF (6 mL) was added t-BuONa (55 mg, 577.25 μmol, 1 eq) and 4-(7-fluoro-4-isocyanato-2,3-dihydro-1H-inden-5-yl)pyridine (intermediate R6) (147 mg, 577.25 μmol, 1 eq). The reaction mixture was stirred at 10° C. for 1.5 hours and then concentrated in vacuo. The residue was purified by reversed phase flash chromatography (0.1% NH$_3$.H$_2$O/MeCN) to give the title compound (170 mg, yield 68%, 98.9% purity on LCMS) as an off-white solid.

$^1$H NMR (DMSO-d$_6$): δ 9.68 (br s, 1H), 8.61 (d, 2H), 8.00 (d, 1H), 7.37 (d, 2H), 7.07 (d, 1H), 6.67 (d, 1H), 4.64-4.55 (m, 1H), 3.00 (t, 2H), 2.86 (t, 2H), 2.15-2.07 (m, 2H) and 1.45 (d, 6H).

LCMS: m/z 428.2 (M+H)$^+$ (ES$^+$).

Step B: N-((7-Fluoro-5-(pyridin-4-yl)-2,3-dihydro-1H-inden-4-yl)carbamoyl)-1-isopropyl-H-pyrazole-3-sulfonimidamide

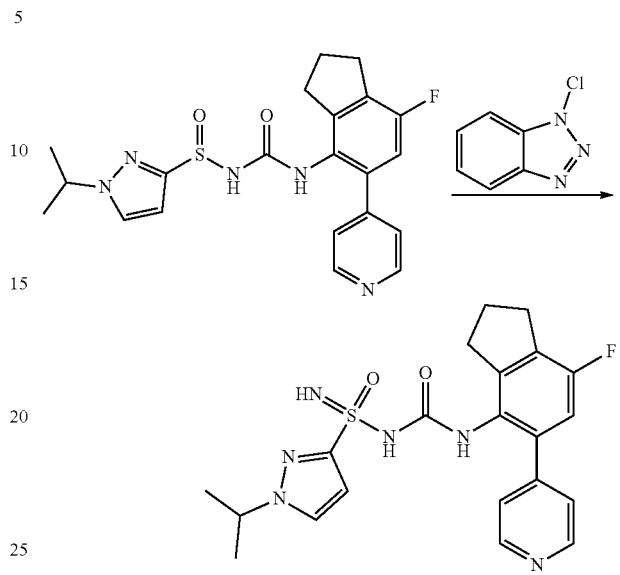

To a solution of N-((7-fluoro-5-(pyridin-4-yl)-2,3-di-hydro-1H-inden-4-yl)carbamoyl)-1-isopropyl-1H-pyrazole-3-sulfinamide (160 mg, 374.27 μmol, 1 eq) in THF (5 mL) was added 1-chloro-1H-benzo[d][1,2,3]triazole (57 mg, 374.27 μmol, 1 eq). The reaction mixture was stirred at 10° C. for 30 minutes. Then the reaction mixture was added at −75° C. into a NH$_3$/THF solution, which had been prepared by bubbling NH$_3$ into THF (30 mL) at −75° C. for 10 minutes. Then the reaction mixture was stirred for another 20 minutes, slowly warmed to 10° C., stirred at 10° C. for 1 hour and then concentrated in vacuo. The residue was purified prep-TLC (SiO$_2$, DCM:MeOH=1:0 to 10:1) and then purified by prep-HPLC (column: Phenomenex Gemini 150 mm*25 mm*10 μm; mobile phase: [A: water (0.05% NH$_4$HCO$_3$ v/v); B: MeCN]; B %: 23%-53%, 10 min) to give the title compound (28.09 mg, yield 17%, 100% purity on LCMS) as a white solid.

1H NMR (DMSO-d$_6$): δ 8.57-8.54 (m, 2H), 8.27 (br s, 1H), 7.91 (d, 1H), 7.41-7.36 (m, 4H), 6.98 (d, 1H), 6.50 (s, 1H), 4.64-4.53 (m, 1H), 2.95 (t, 2H), 2.81-2.77 (m, 2H), 2.09-2.02 (m, 2H) and 1.46-1.41 (m, 6H).

LCMS: m/z 443.2 (M+H)$^+$ (ES$^+$).

Example 25: N-((7-Fluoro-5-(pyridin-4-yl)-2,3-di-hydro-1H-inden-4-yl)carbamoyl)-1-((R)-2-hydroxy-propyl)-1H-pyrazole-3-sulfonimidamide

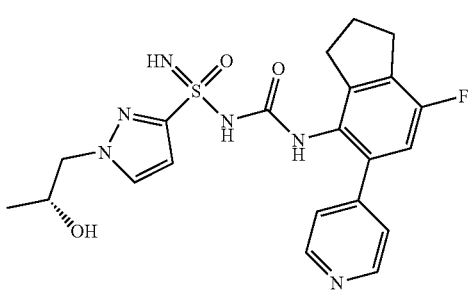 [SMILES: C[C@@H](O)Cn1ccc(S(=N)(=O)NC(=O)Nc2c(-c3ccncc3)cc(F)c3c2CCC3)n1]

Step A: N-((7-Fluoro-5-(pyridin-4-yl)-2,3-dihydro-1H-inden-4-yl)carbamoyl)-1-((R)-2-hydroxypropyl)-1H-pyrazole-3-sulfinamide

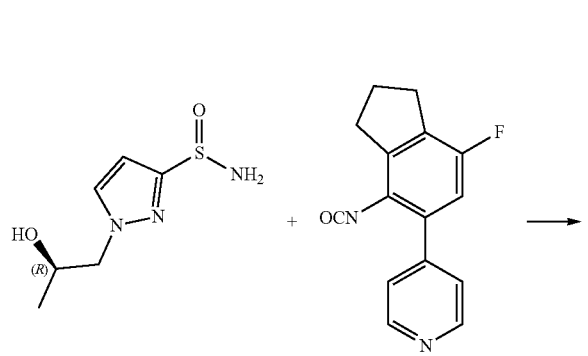

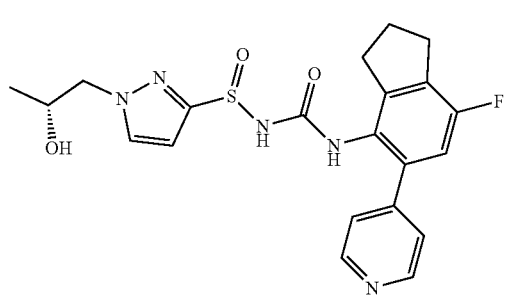

A solution of 1-((R)-2-hydroxypropyl)-1H-pyrazole-3-sulfinamide (intermediate L2) (160 mg, 845.51 µmol, 1 eq) and t-BuONa (81 mg, 845.51 µmol, 1 eq) in THF (3 mL) was stirred at 25° C. for 10 minutes. Then 4-(7-fluoro-4-isocyanato-2,3-dihydro-1H-inden-5-yl)pyridine (intermediate R6) (215 mg, 845.51 µmol, 1 eq) was added. The resulting mixture was stirred at 25° C. for 10 minutes and then concentrated in vacuo. The residue was purified by reversed phase flash chromatography (0.05% NH$_3$.H$_2$O, H$_2$O/MeCN) to give the title compound (150 mg, 40% yield, 99% purity on LCMS) as a red solid.

$^1$H NMR (DMSO-d$_6$): δ 8.54 (d, 2H), 7.70 (s, 1H), 7.41 (d, 2H), 6.98 (d, 1H), 6.42 (s, 1H), 4.95 (br s, 1H), 4.06-3.94 (m, 3H), 2.96 (t, 2H), 2.87 (t, 2H), 2.10-2.04 (m, 2H) and 1.04 (d, 3H).

LCMS: m/z 444.3 (M+H)$^+$ (ES$^+$).

Step B: N-((7-Fluoro-5-(pyridin-4-yl)-2,3-dihydro-1H-inden-4-yl)carbamoyl)-1-((R)-2-hydroxypropyl)-1H-pyrazole-3-sulfonimidamide

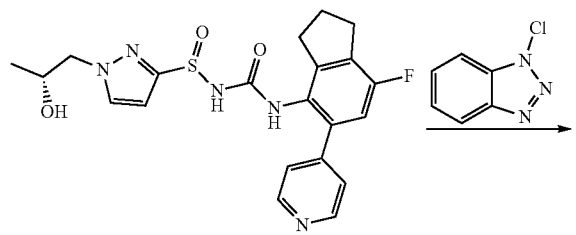

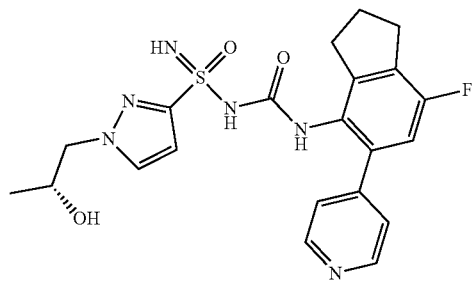

To a solution of N-((7-fluoro-5-(pyridin-4-yl)-2,3-dihydro-1H-inden-4-yl)carbamoyl)-1-((R)-2-hydroxypropyl)-1H-pyrazole-3-sulfinamide (150 mg, 338.22 µmol, 1 eq) in THF (2 mL) was added 1-chloro-1H-benzo[d][1,2,3]triazole (47 mg, 304.40 µmol, 0.9 eq). The reaction mixture was stirred at 20° C. for 30 minutes. Then the reaction mixture was added dropwise over 10 minutes at −70° C. to a saturated solution of ammonia in THF (8 mL), which had been prepared by bubbling NH$_3$ gas (15 psi) into THF (10 mL) at −70° C. for 5 minutes. After stirring for 15 minutes, the reaction mixture was warmed to 20° C., stirred for 2 hours and then concentrated in vacuo. The residue was purified by prep-TLC (DCM:MeOH=10:1) and then further purified by prep-HPLC (column: Waters Xbridge 150 mm*25 mm*5 µm; mobile phase: [A: water (0.05% ammonia hydroxide v/v); B: MeCN]; B %: 10%-30%, 8 min) to give the title compound (27.61 mg, 18% yield, 99% purity on LCMS) as a white solid.

$^1$H NMR (DMSO-d$_6$): δ 8.55 (d, 2H), 8.28 (br s, 1H), 7.79 (s, 1H), 7.49-7.30 (m, 4H), 6.98 (d, 1H), 6.47 (s, 1H), 5.02 (s, 1H), 4.08-4.00 (m, 2H), 3.99-3.95 (m, 1H), 2.94 (t, 2H), 2.88-2.70 (m, 2H), 2.07-2.01 (m, 2H) and 1.05 (dd, 3H).

LCMS: m/z 459.2 (M+H)$^+$ (ES$^+$).

Example 26: 4-Chloro-N-((7-fluoro-5-(pyridin-4-yl)-2,3-dihydro-1H-inden-4-yl)carbamoyl)-1-isopropyl-1H-pyrazole-3-sulfonimidamide

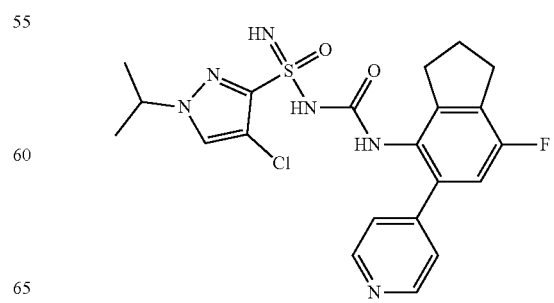

151

Step A: 4-Chloro-N-((7-fluoro-5-(pyridin-4-yl)-2,3-dihydro-1H-inden-4-yl)carbamoyl)-1-isopropyl-1H-pyrazole-3-sulfinamide

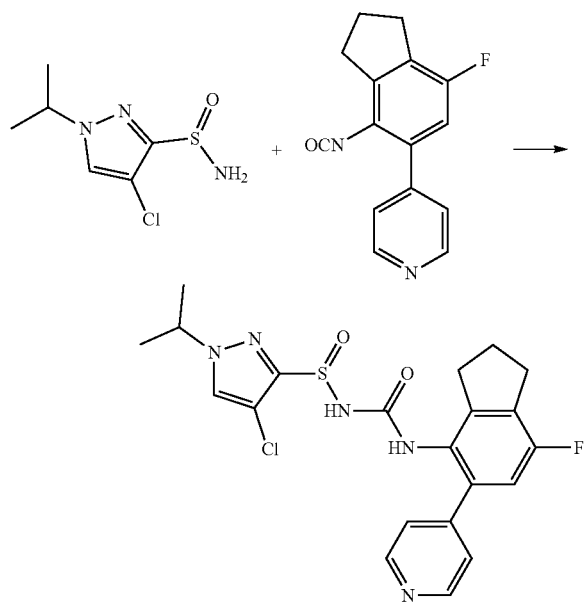

To a solution of 4-chloro-1-isopropyl-1H-pyrazole-3-sulfinamide (intermediate L6) (150 mg, 722.26 μmol, 1 eq) in THF (3 mL) was added t-BuONa (69 mg, 722.26 μmol, 1 eq). The mixture was stirred at 20° C. for 10 minutes. To the above mixture was added a solution of 4-(7-fluoro-4-isocyanato-2,3-dihydro-1H-inden-5-yl)pyridine (intermediate R6) (184 mg, 722.26 μmol, 1 eq) in THF (2 mL). The resulting mixture was stirred at 20° C. for 20 minutes and then concentrated in vacuo. The residue was purified by reversed phase flash chromatography (water (0.05% $NH_3.H_2O$)-MeCN) to give the title compound (260 mg, 76% yield, 97% purity on LCMS) as a yellow solid.

$^1$H NMR (DMSO-$d_6$): δ 9.87 (br s, 1H), 8.59 (d, 2H), 8.33-8.30 (m, 2H), 7.37 (dd, 2H), 7.08 (d, 1H), 4.61-4.53 (m, 1H), 2.99 (t, 2H), 2.85 (t, 2H), 2.13-2.09 (m, 2H) and 1.44 (d, 6H).

LCMS: m/z 462.2 (M+H)$^+$ (ES$^+$).

Step B: 4-Chloro-N-((7-fluoro-5-(pyridin-4-yl)-2,3-dihydro-1H-inden-4-yl)carbamoyl)-1-isopropyl-1H-pyrazole-3-sulfonimidamide

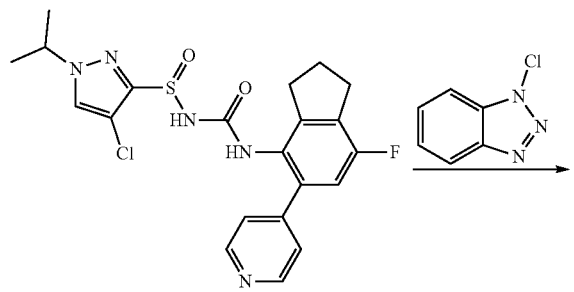

152

-continued

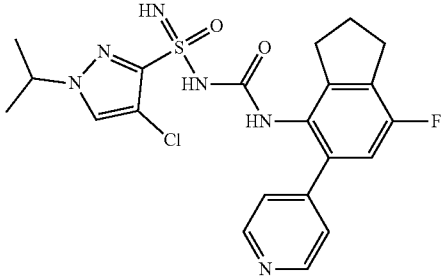 [SMILES: CC(C)n1cc(Cl)c(S(=N)(=O)NC(=O)Nc2c(-c3ccncc3)cc(F)c3c2CCC3)n1]

To a solution of 4-chloro-N-((7-fluoro-5-(pyridin-4-yl)-2,3-dihydro-1H-inden-4-yl)carbamoyl)-1-isopropyl-1H-pyrazole-3-sulfinamide (200 mg, 432.96 μmol, 1 eq) in THF (2 mL) was added 1-chloro-1H-benzo[d][1,2,3]triazole (60 mg, 389.66 μmol, 0.9 eq). The mixture was stirred at 20° C. for 30 minutes. Then the reaction mixture was added dropwise over 10 minutes at −70° C. to a saturated solution of ammonia in THF (8 mL), which had been prepared by bubbling NH$_3$ gas (15 psi) into THF (10 mL) at −70° C. for 5 minutes. After stirring for 15 minutes, the reaction mixture was warmed to 20° C. for 2 hours and then concentrated in vacuo. The residue was purified by prep-TLC (DCM:MeOH=10:1) and then further purified by prep-HPLC (column: Xtimate C18 250 mm*50 mm*10 μm; mobile phase: [A: water (0.05% ammonia hydroxide v/v); B: MeCN]; B %: 5%-35%, 10 min) to give the title compound (33.6 mg, 16% yield, 99% purity on LCMS) as a white solid.

$^1$H NMR (DMSO-$d_6$): δ 8.56-8.53 (m, 2H), 8.24 (br s, 1H), 8.19 (s, 1H), 7.43 (br s, 2H), 7.38 (d, 2H), 6.99 (d, 1H), 4.53-4.47 (m, 1H), 2.95 (t, 2H), 2.85-2.75 (m, 2H), 2.07-2.02 (m, 2H) and 1.42 (d, 6H).

LCMS: m/z 477.2 (M+H)$^+$ (ES$^+$).

Examples 27 and 28: (R)-1-Isopropyl-N-((5-(2-methoxypyridin-4-yl)-2,3-dihydro-1H-inden-4-yl)carbamoyl)-1H-pyrazole-3-sulfonimidamide and (S)-1-Isopropyl-N-((5-(2-methoxypyridin-4-yl)-2,3-dihydro-1H-inden-4-yl) carbamoyl)-1H-pyrazole-3-sulfonimidamide

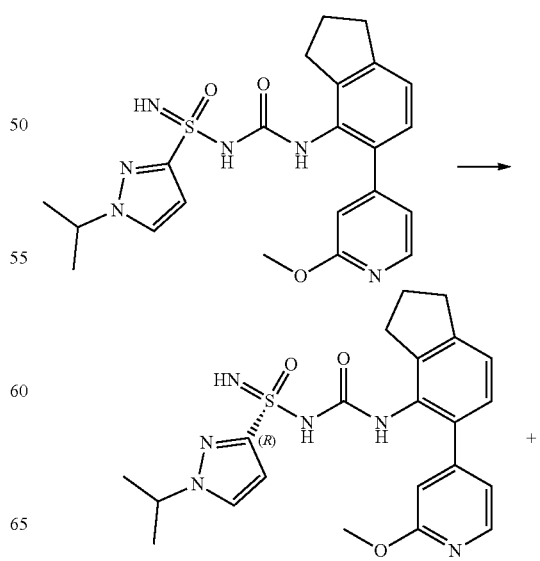

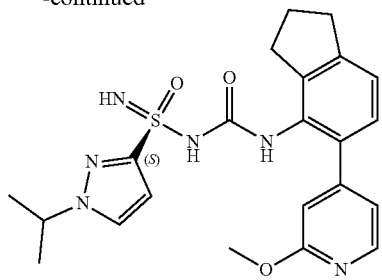

Racemic 1-isopropyl-N-((5-(2-methoxypyridin-4-yl)-2,3-dihydro-1H-inden-4-yl) carbamoyl)-1H-pyrazole-3-sulfonimidamide (example 14) (24.9 mg) was separated by preparative chiral HPLC (Gilson, basic (0.1% ammonium bicarbonate), Chiralpak® IC (Daicel Ltd.) column (2×25 cm), flow rate 15 mL/min eluting with 40% MeCN in 10 mM aqueous ammonium bicarbonate (isocratic)) to afford (R)-1-isopropyl-N-((5-(2-methoxypyridin-4-yl)-2,3-dihydro-1H-inden-4-yl) carbamoyl)-1H-pyrazole-3-sulfonimidamide (example 27) (9.3 mg, 37% yield) as a white solid and (S)-1-isopropyl-N-((5-(2-methoxypyridin-4-yl)-2,3-dihydro-1H-inden-4-yl) carbamoyl)-1H-pyrazole-3-sulfonimidamide (example 28) (9.0 mg, 36% yield), also as a white solid.

Example 27: (R)-1-Isopropyl-N-((5-(2-methoxypyridin-4-yl)-2,3-dihydro-1H-inden-4-yl) carbamoyl)-1H-pyrazole-3-sulfonimidamide $^1$H NMR (500 MHz, DMSO-d6) δ 8.20 (s, 1H), 8.11 (d, J=5.3 Hz, 1H), 7.89 (d, J=2.3 Hz, 1H), 7.16 (d, J=7.6 Hz, 1H), 7.08 (d, J=7.6 Hz, 1H), 6.94 (dd, J=5.2, 1.5 Hz, 1H), 6.77 (s, 1H), 6.49 (d, J=2.3 Hz, 1H), 5-79 (br s, 2H), 4.58 (sept, J=6.7 Hz, 1H), 3.87 (s, 3H), 2.90 (t, J=7.5 Hz, 2H), 2.80-2.68 (m, 2H), 1.97 (p, J=7.6 Hz, 2H), 1.44 (d, J=6.7 Hz, 6H).

LCMS; m/z 455.2 (M+H)$^+$ (ES$^+$).

Example 28: (S)-1-Isopropyl-N-((5-(2-methoxypyridin-4-yl)-2,3-dihydro-1H-inden-4-yl) carbamoyl)-1H-pyrazole-3-sulfonimidamide $^1$H NMR (500 MHz, DMSO-d6) δ 8.20 (s, 1H), 8.11 (d, J=5.3 Hz, 1H), 7.89 (d, J=2.3 Hz, 1H), 7.16 (d, J=7.6 Hz, 1H), 7.08 (d, J=7.6 Hz, 1H), 6.94 (dd, J=5.2, 1.5 Hz, 1H), 6.77 (s, 1H), 6.49 (d, J=2.3 Hz, 1H), 5.79 (br s, 2H), 4.58 (sept, J=6.7 Hz, 1H), 3.87 (s, 3H), 2.90 (t, J=7.5 Hz, 2H), 2.80-2.68 (m, 2H), 1.97 (p, J=7.6 Hz, 2H), 1.44 (d, J=6.7 Hz, 6H).

LCMS; m/z 455.2 (M+H)$^+$ (ES$^+$); 453.1 (M−H)$^-$ (ES$^-$).

Examples—Biological Studies

NLRP3 and Pyroptosis

It is well established that the activation of NLRP3 leads to cell pyroptosis and this feature plays an important part in the manifestation of clinical disease (Yan-gang Liu et al., Cell Death & Disease, 2017, 8(2), e2579; Alexander Wree et al., Hepatology, 2014, 59(3), 898-910; Alex Baldwin et al., Journal of Medicinal Chemistry, 2016, 59(5), 1691-1710; Ema Ozaki et al., Journal of Inflammation Research, 2015, 8, 15-27; Zhen Xie & Gang Zhao, Neuroimmunology Neuroinflammation, 2014, 1(2), 60-65; Mattia Cocco et al., Journal of Medicinal Chemistry, 2014, 57(24), 10366-10382; T. Satoh et al., Cell Death & Disease, 2013, 4, e644). Therefore, it is anticipated that inhibitors of NLRP3 will block pyroptosis, as well as the release of pro-inflammatory cytokines (e.g. IL-1β) from the cell.

THP-1 Cells: Culture and Preparation

THP-1 cells (ATCC #TIB-202) were grown in RPMI containing L-glutamine (Gibco #11835) supplemented with 1 mM sodium pyruvate (Sigma #S8636) and penicillin (100 units/ml)/streptomycin (0.1 mg/ml) (Sigma #P4333) in 10% Fetal Bovine Serum (FBS) (Sigma #F0804). The cells were routinely passaged and grown to confluency (~10$^6$ cells/ml). On the day of the experiment, THP-1 cells were harvested and resuspended into RPMI medium (without FBS). The cells were then counted and viability (>90%) checked by Trypan blue (Sigma #T8154). Appropriate dilutions were made to give a concentration of 625,000 cells/ml. To this diluted cell solution was added LPS (Sigma #L4524) to give a 1 μg/ml Final Assay Concentration (FAC). 40 μl of the final preparation was aliquoted into each well of a 96-well plate. The plate thus prepared was used for compound screening.

THP-1 Cells Pyroptosis Assay

The following method step-by-step assay was followed for compound screening.
1. Seed THP-1 cells (25,000 cells/well) containing 1.0 μg/ml LPS in 40 μl of RPMI medium (without FBS) in 96-well, black walled, clear bottom cell culture plates coated with poly-D-lysine (VWR #734-0317)
2. Add 5 μl compound (8 points half-log dilution, with 10 μM top dose) or vehicle (DMSO 0.1% FAC) to the appropriate wells
3. Incubate for 3 hrs at 37° C. in 5% CO$_2$
4. Add 5 μl nigericin (Sigma #N7143) (FAC 5 μM) to all wells
5. Incubate for 1 hr at 37° C. and 5% CO$_2$
6. At the end of the incubation period, spin plates at 300×g for 3 mins and remove supernatant
7. Then add 50 μl of resazurin (Sigma #R7017) (FAC 100 μM resazurin in RPMI medium without FBS) and incubate plates for a further 1-2 hrs at 37° C. and 5% CO$_2$
8. Plates were read in an Envision reader at Ex 560 nm and Em 590 nm
9. IC$_{50}$ data is fitted to a non-linear regression equation (log inhibitor vs response-variable slope 4-parameters)

96-Well Plate Map

|   | 1 | 2 | 3 | 4 | 5 | 6 | 7 | 8 | 9 | 10 | 11 | 12 |
|---|---|---|---|---|---|---|---|---|---|---|---|---|
| A | High | Comp 1 | Comp 2 | Comp 3 | Comp 4 | Comp 5 | Comp 6 | Comp 7 | Comp 8 | Comp 9 | Comp 10 | Low |
| B | High | Comp 1 | Comp 2 | Comp 3 | Comp 4 | Comp 5 | Comp 6 | Comp 7 | Comp 8 | Comp 9 | Comp 10 | Low |
| C | High | Comp 1 | Comp 2 | Comp 3 | Comp 4 | Comp 5 | Comp 6 | Comp 7 | Comp 8 | Comp 9 | Comp 10 | Low |
| D | High | Comp 1 | Comp 2 | Comp 3 | Comp 4 | Comp 5 | Comp 6 | Comp 7 | Comp 8 | Comp 9 | Comp 10 | Low |
| E | High | Comp 1 | Comp 2 | Comp 3 | Comp 4 | Comp 5 | Comp 6 | Comp 7 | Comp 8 | Comp 9 | Comp 10 | Low |
| F | High | Comp 1 | Comp 2 | Comp 3 | Comp 4 | Comp 5 | Comp 6 | Comp 7 | Comp 8 | Comp 9 | Comp 10 | Low |

| | 1 | 2 | 3 | 4 | 5 | 6 | 7 | 8 | 9 | 10 | 11 | 12 |
|---|---|---|---|---|---|---|---|---|---|---|---|---|
| G | High | Comp 1 | Comp 2 | Comp 3 | Comp 4 | Comp 5 | Comp 6 | Comp 7 | Comp 8 | Comp 9 | Comp 10 | Low |
| H | High | Comp 1 | Comp 2 | Comp 3 | Comp 4 | Comp 5 | Comp 6 | Comp 7 | Comp 8 | Comp 9 | Comp 10 | Low |

High MCC950 (10 uM)
Low Drug free control
Compound 8-point half-log dilution

The results of the pyroptosis assay performed are summarised in Table 1 below as THP $IC_{50}$.

Human Whole Blood IL1β Release Assay

For systemic delivery, the ability to inhibit NLRP3 when the compounds are present within the bloodstream is of great importance. For this reason, the NLRP3 inhibitory activity of a number of compounds in human whole blood was investigated in accordance with the following protocol.

Human whole blood in Li-heparin tubes was obtained from healthy donors from a volunteer donor panel.

1. Plate out 80 μl of whole blood containing 1 μg/ml of LPS in 96-well, clear bottom cell culture plate (Corning #3585)
2. Add 10 μl compound (8 points half-log dilution with 10 μM top dose) or vehicle (DMSO 0.1% FAC) to the appropriate wells
3. Incubate for 3 hrs at 37° C., 5% $CO_2$
4. Add 10 μl nigericin (Sigma #N7143) (10 μM FAC) to all wells
5. Incubate for 1 hr at 37° C., 5% $CO_2$
6. At the end of the incubation period, spin plates at 300×g for 5 mins to pellet cells and remove 20 μl of supernatant and add to 96-well v-bottom plates for IL-1β analysis (note: these plates containing the supernatants can be stored at −80° C. to be analysed at a later date)
7. IL-1β was measured according to the manufacturer protocol (Perkin Elmer-AlphaLisa IL-1 Kit AL220F-5000)
8. $IC_{50}$ data is fitted to a non-linear regression equation (log inhibitor vs response-variable slope 4-parameters)

The results of the human whole blood assay are summarised in Table 1 below as HWB $IC_{50}$.

TABLE 1

NLRP3 inhibitory activity (≤0.1 μm = '+++++', ≤0.5 μm = '++++', ≤1 μm = '+++', ≤5 μm = '++', ≤10 μm = '+', not determined = 'ND')

| Example No | Structure | THP $IC_{50}$ | HWB $IC_{50}$ |
|---|---|---|---|
| 1 | 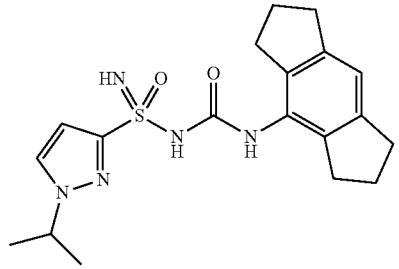 [SMILES: CC(C)n1ccc(S(=N)(=O)NC(=O)Nc2c3c(cc4c2CCC4)CCC3)n1] | ++++ | ++ |
| 2 | 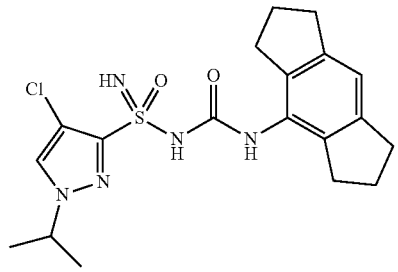 [SMILES: CC(C)n1cc(Cl)c(S(=N)(=O)NC(=O)Nc2c3c(cc4c2CCC4)CCC3)n1] | +++++ | ++ |

TABLE 1-continued

NLRP3 inhibitory activity (≤0.1 μm = '+++++', ≤0.5 μm = '++++', ≤1 μm = '+++', ≤5 μm = '++', ≤10 μm = '+', not determined = 'ND')

| Example No | Structure | THP IC$_{50}$ | HWB IC$_{50}$ |
|---|---|---|---|
| 3 | 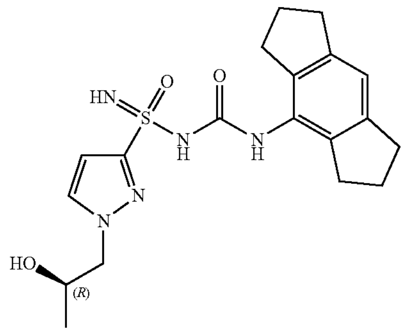 | +++++ | ++++ |
| 6 | 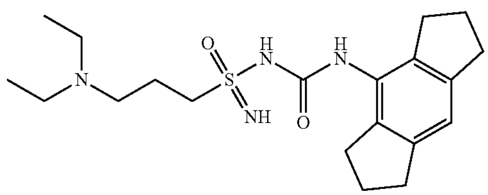 [SMILES: CCN(CC)CCCS(=N)(=O)NC(=O)Nc1c2c(cc3c1CCC3)CCC2] | + | ND |
| 7 | 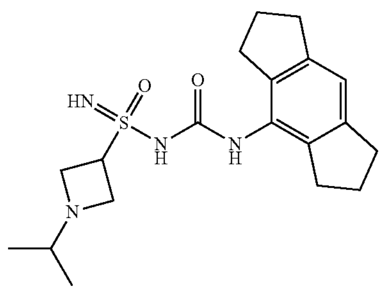 [SMILES: CC(C)N1CC(S(=N)(=O)NC(=O)Nc2c3c(cc4c2CCC4)CCC3)C1] | ++ | ++ |
| 10 | 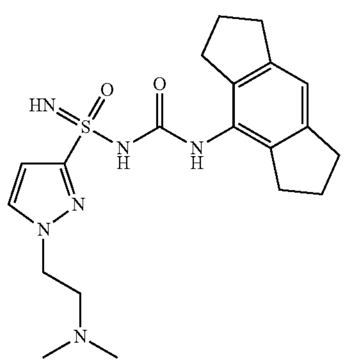 [SMILES: CN(C)CCn1ccc(S(=N)(=O)NC(=O)Nc2c3c(cc4c2CCC4)CCC3)n1] | ++++ | ++++ |
| 11 | 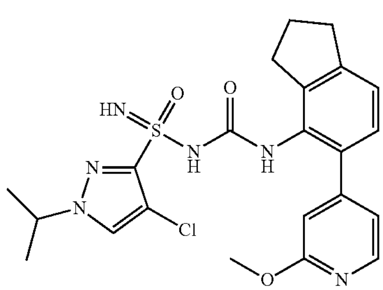 [SMILES: COc1cc(-c2ccc3c(c2NC(=O)NS(=N)(=O)c2nn(C(C)C)cc2Cl)CCC3)ccn1] | +++++ | +++ |

TABLE 1-continued
NLRP3 inhibitory activity (≤0.1 μm = '+++++', ≤0.5 μm = '++++', ≤1 μm = '+++', ≤5 μm = '++', ≤10 μm = '+', not determined = 'ND')
| Example No | Structure | THP IC$_{50}$ | HWB IC$_{50}$ |
|---|---|---|---|
| 12 | 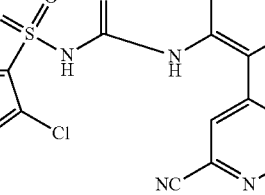 | +++++ | ++++ |
| 13 | 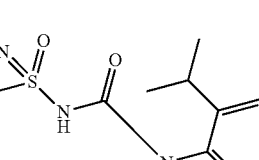 | +++++ | +++ |
| 14 | 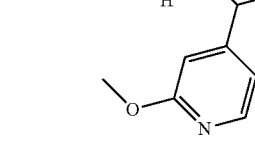 | +++++ | ++++ |
| 15 | 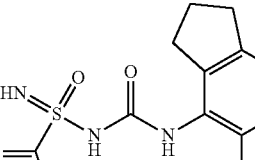 | +++ | +++ |
| 16 | 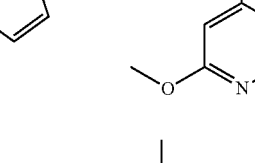 | +++++ | +++ |

TABLE 1-continued

NLRP3 inhibitory activity (≤0.1 μm = '+++++', ≤0.5 μm = '++++', ≤1 μm = '+++', ≤5 μm = '++', ≤10 μm = '+', not determined = 'ND')

| Example No | Structure | THP IC$_{50}$ | HWB IC$_{50}$ |
|---|---|---|---|
| 17 | 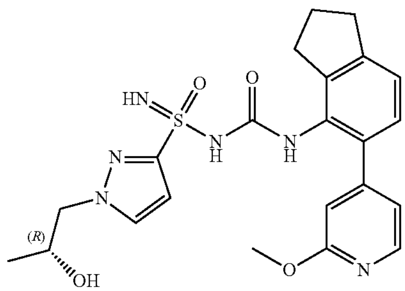 | +++++ | ++++ |
| 18 | 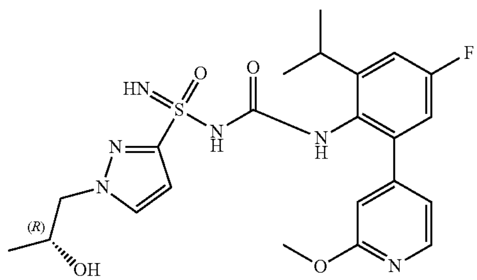 | ++++ | ++++ |
| 19 | 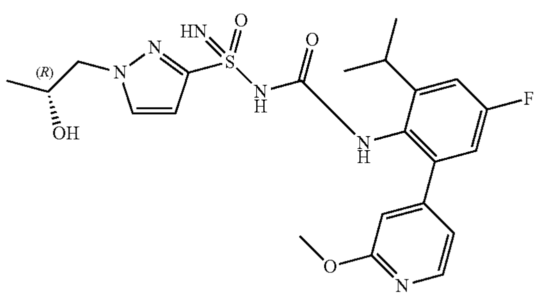 | +++++ | +++ |
| 22 | 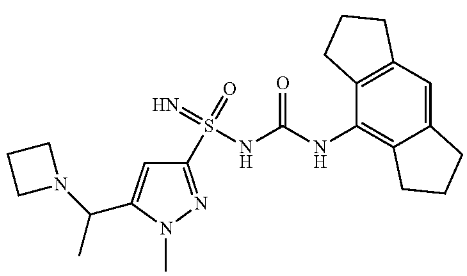 [SMILES: CC(c1cc(S(=N)(=O)NC(=O)Nc2c3c(cc4c2CCC4)CCC3)nn1C)N1CCC1] | +++++ | ++++ |
| 23 | 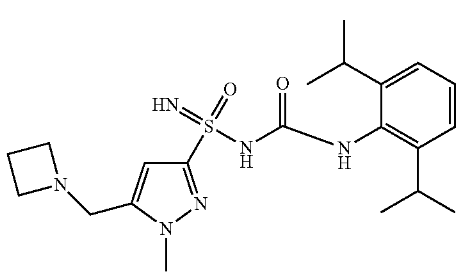 [SMILES: CC(C)c1cccc(C(C)C)c1NC(=O)NS(=N)(=O)c1cc(CN2CCC2)n(C)n1] | +++++ | ++ |

TABLE 1-continued

NLRP3 inhibitory activity (≤0.1 μm = '+++++', ≤0.5 μm = '++++', ≤1 μm = '+++', ≤5 μm = '++', ≤10 μm = '+', not determined = 'ND')

| Example No | Structure | THP IC$_{50}$ | HWB IC$_{50}$ |
|---|---|---|---|
| 24 | 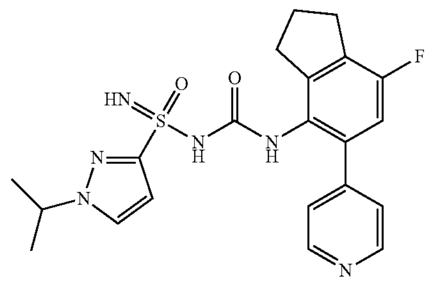 [SMILES: CC(C)n1ccc(S(=N)(=O)NC(=O)Nc2c(-c3ccncc3)cc(F)c3c2CCC3)n1] | +++++ | ++++ |
| 25 | 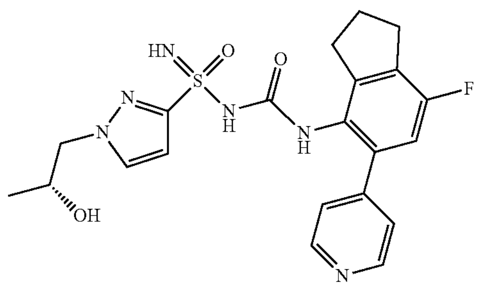 [SMILES: C[C@@H](O)Cn1ccc(S(=N)(=O)NC(=O)Nc2c(-c3ccncc3)cc(F)c3c2CCC3)n1] | +++++ | ++++ |
| 26 | 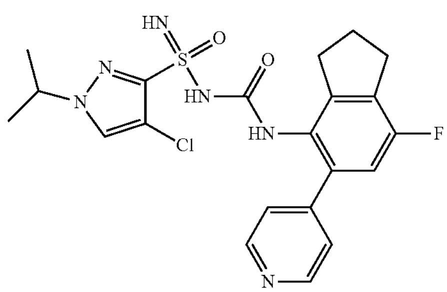 [SMILES: CC(C)n1cc(Cl)c(S(=N)(=O)NC(=O)Nc2c(-c3ccncc3)cc(F)c3c2CCC3)n1] | +++++ | ++++ |
| 27 | 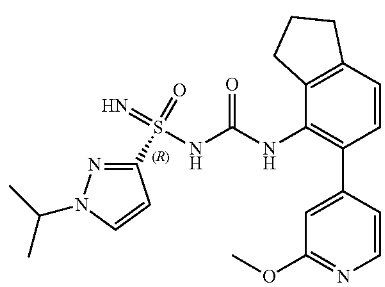 | +++++ | ++++ |
| 28 | 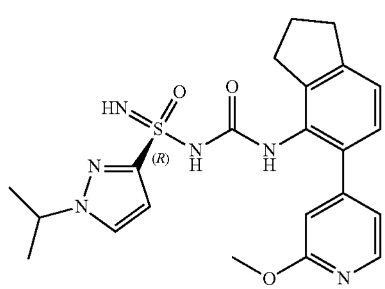 | +++ | ++ |

PK Protocol

Pharmacokinetic parameters were determined in male Sprague Dawley rats (Vital River Laboratory Animal Technology Co Ltd, Beijing, China, 7-9 weeks old). Animals were individually housed during the study and maintained under a 12 h light/dark cycle. Animals had free access to food and water.

For intravenous administration, compounds were formulated as a solution in DMSO:PBS [10:90] in 2 mL/kg dosing volume and administered via tail vein.

Serial blood samples (about 200 μL) were taken from each animal at each of 8 time-points post dose (0.083, 0.25, 0.5, 1, 2, 4, 8 and 24 h). Samples were held on ice for no longer than 30 minutes before centrifugation (5,696 rpm (3,000 g) for 15 minutes) for plasma generation. Plasma was frozen on dry ice prior to bioanalysis. PK parameters were generated from LC-MS/MS data using Phoenix WinNonlin 6.3 software.

TABLE 2

PK data (intravenous administration)

| Example No | Dose (mg/kg) | AUC (ng•hr/mL) | $T_{1/2}$ (hr) | $V_{dss}$ (L/kg) | Cl (mL/min/kg) |
|---|---|---|---|---|---|
| 3 | 1 | 2248.6 | 2.7 | 0.75 | 7.4 |
| 11 | 1 | 2718.2 | 1.0 | 0.45 | 6.1 |
| 14 | 1 | 1738.5 | 0.9 | 0.34 | 9.6 |

As is evident from the results presented in Table 1, surprisingly in spite of the structural differences versus the prior art compounds, the compounds of the invention show high levels of NLRP3 inhibitory activity in the pyroptosis assay and in the human whole blood assay.

As is evident from the results presented in Table 2, the compounds of the invention show advantageous pharmacokinetic properties, for example half-life $T_{1/2}$, area under the curve AUC, clearance Cl and/or bioavailability, compared to the prior art compounds.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A compound of formula (I):

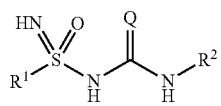

Formula (I)

or a pharmaceutically acceptable salt or solvate thereof, wherein:

Q is selected from O or S;

$R^1$ is a 4- to 10-membered cyclic group, wherein the cyclic group may optionally be substituted with one, two or three substituents independently selected from —$NO_2$, —OH, —$OR^\beta$, —SH, —$SR^\beta$, —$SOR^\beta$, —$SO_2H$, —$SO_2NH_2$, —$SO_2NHR^\beta$, —$SO_2N(R^\beta)_2$, —$R^\alpha$—SH, —$R^\alpha$—$SR^\beta$, —$R^\alpha$—$SOR^\beta$, —$R^\alpha$—$SO_2H$, —$R^\alpha$—$SO_2R^\beta$, —$R^\alpha$—$SO_2NH_2$, —$R^\alpha$—$SO_2NHR^\beta$, —$R^\alpha$—$SO_2N(R^\beta)_2$, —$NH_2$, —$NHR^\beta$, —$N(R^\beta)_2$, —$R^\alpha$—$NH_2$, —$R^\alpha$—$NHR^\beta$, —CHO, —$COR^\beta$, —COOH, —$COOR^\beta$, —$OCOR^\beta$, —$R^\alpha$—CHO, —$R^\alpha$—$COR^\beta$, —$R^\alpha$—COOH, —$R^\alpha$—$COOR^\beta$, —$R^\alpha$—$OCOR^\beta$, $C_2$-$C_6$ alkenyl or $C_2$-$C_6$ alkynyl; wherein the $C_2$-$C_6$ alkenyl or $C_2$-$C_6$ alkynyl may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —C≡CH, oxo (=O), or 4- to 6-membered heterocyclic group;

each —$R^\alpha$— is independently selected from an alkylene, alkenylene or alkynylene group, wherein the alkylene, alkenylene or alkynylene group contains from 1 to 6 atoms in its backbone, wherein one or more carbon atoms in the backbone of the alkylene, alkenylene or alkynylene group may optionally be replaced by one or more heteroatoms N, O or S, and wherein the alkylene, alkenylene or alkynylene group may optionally be substituted with one or more halo and/or —$R^\beta$ groups;

each —$R^\beta$ is independently selected from a $C_1$-$C_6$ alkyl, $C_2$-$C_6$ alkenyl, $C_2$-$C_6$ alkynyl or $C_2$-$C_6$ cyclic group, and wherein any —$R^\beta$ may optionally be substituted with one or more $C_1$-$C_4$ alkyl, $C_1$-$C_4$ haloalkyl, $C_3$-$C_7$ cycloalkyl, —O($C_1$-$C_4$ alkyl), —O($C_1$-$C_4$ haloalkyl), —O($C_3$-$C_7$ cycloalkyl), halo, —OH, —$NH_2$, —CN, —C≡CH, oxo (=O), or 4- to 6-membered heterocyclic group; and $R^2$ is a cyclic group substituted at the α-position, wherein $R^2$ may optionally be further substituted.

2. The compound or the pharmaceutically acceptable salt or solvate thereof as claimed in claim 1, wherein $R^1$ is a cycloalkyl, cycloalkenyl, non-aromatic heterocyclic, aryl or heteroaryl group, all of which may optionally be substituted as defined in claim 1.

3. The compound or the pharmaceutically acceptable salt or solvate thereof as claimed in claim 1, wherein $R^2$ is an aryl or a heteroaryl group, wherein the aryl or the heteroaryl group is substituted at the α-position, and wherein $R^2$ may optionally be further substituted.

4. The compound or the pharmaceutically acceptable salt or solvate thereof as claimed in claim 3, wherein $R^2$ is an aryl or a heteroaryl group, wherein the aryl or the heteroaryl group is substituted at the α and α' positions, and wherein $R^2$ may optionally be further substituted.

5. The compound or the pharmaceutically acceptable salt or solvate thereof as claimed in claim 4, wherein $R^2$ is a fused aryl or a fused heteroaryl group, wherein a first cycloalkyl, cycloalkenyl, non-aromatic heterocyclic, aryl or heteroaryl ring is fused to the aryl or heteroaryl group across the α, β positions and a second cycloalkyl, cycloalkenyl, non-aromatic heterocyclic, aryl or heteroaryl ring is fused to the aryl or heteroaryl group across the α', β' positions, and wherein $R^2$ may optionally be further substituted.

6. The compound or the pharmaceutically acceptable salt or solvate thereof as claimed in claim 1, wherein $R^2$ is a cyclic group substituted at the α-position with a monovalent heterocyclic group or a monovalent aromatic group, wherein a ring atom of the heterocyclic or aromatic group is directly attached to the α-ring atom of the cyclic group, wherein the heterocyclic or aromatic group may optionally be substituted, and wherein the cyclic group may optionally be further substituted.

7. The compound or the pharmaceutically acceptable salt or solvate thereof as claimed in claim 1, wherein $R^2$ is a cyclic group substituted at the α and α' positions, wherein $R^2$ may optionally be further substituted.

8. The compound or the pharmaceutically acceptable salt or solvate thereof as claimed in claim 1, wherein Q is O.

9. A compound selected from the group consisting of:
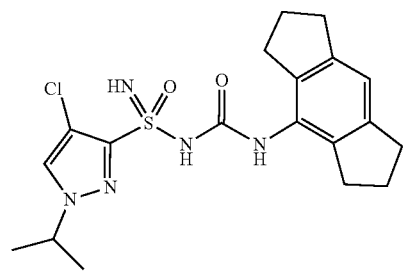
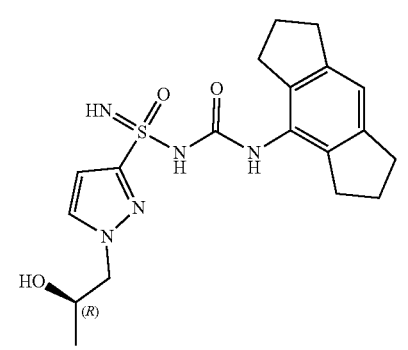
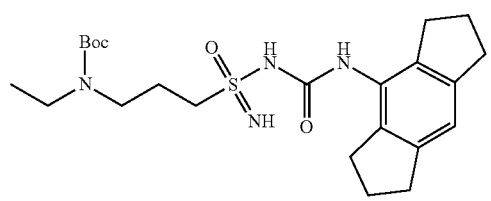
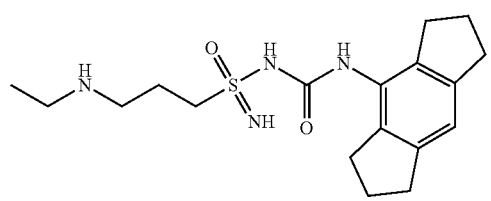
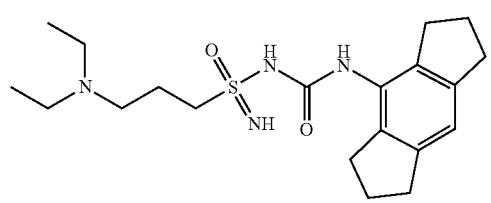
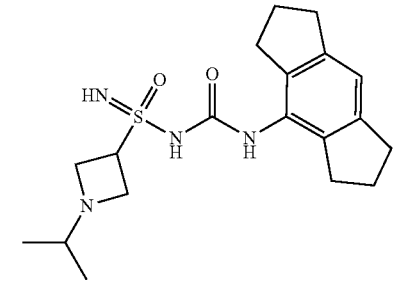
-continued
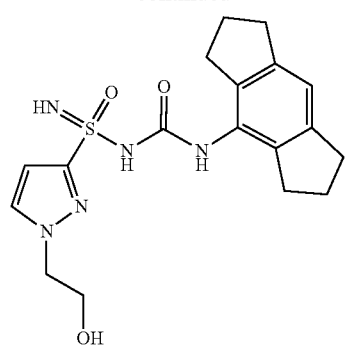
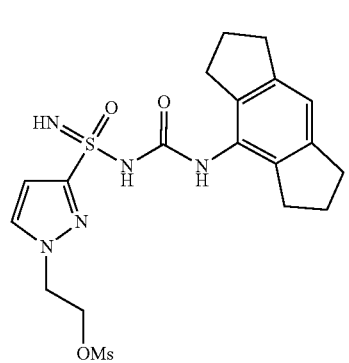
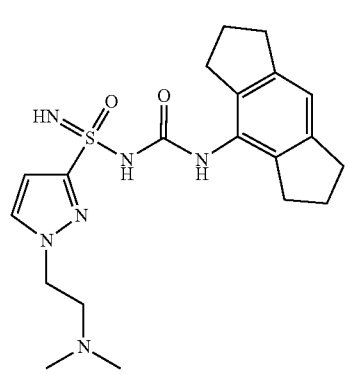
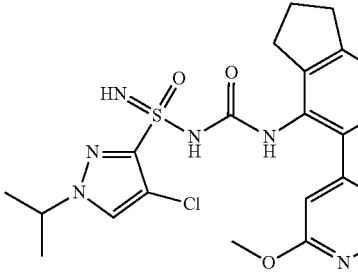
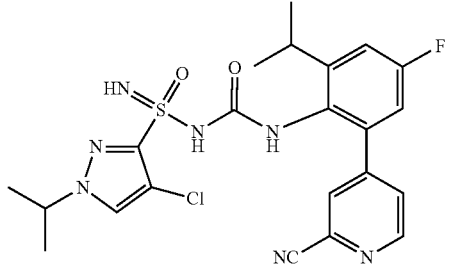

169
-continued
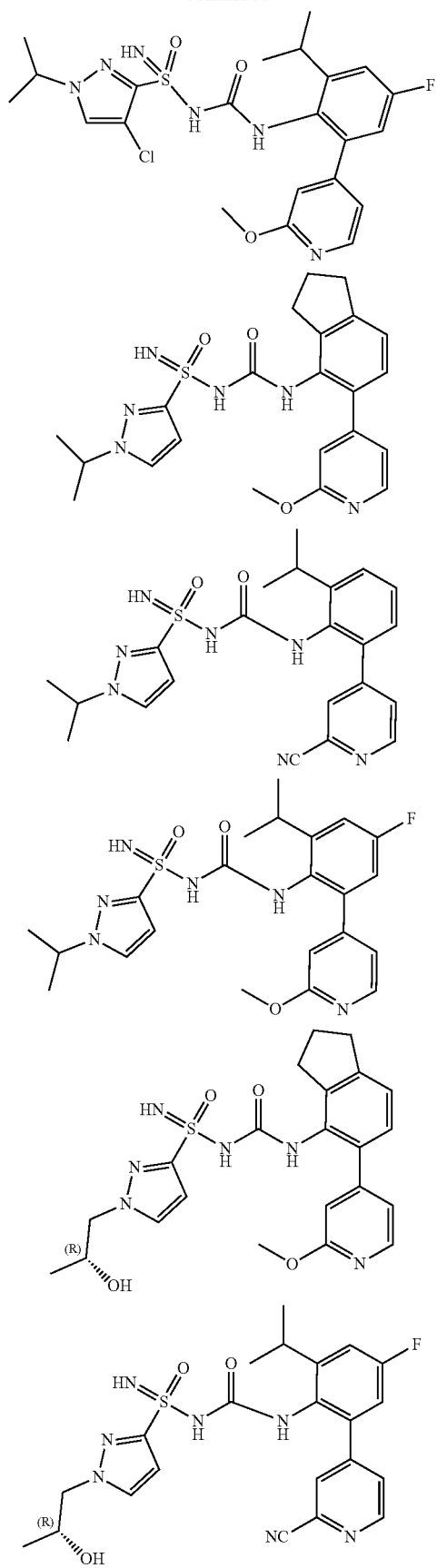
170
-continued
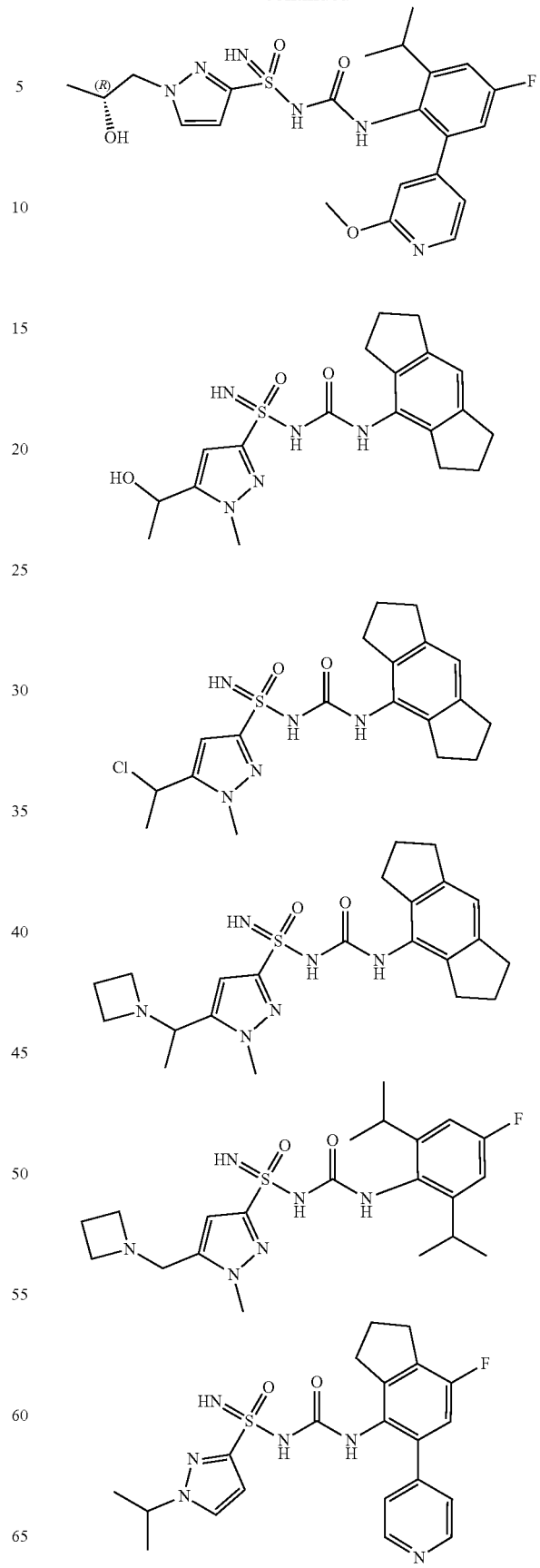

-continued

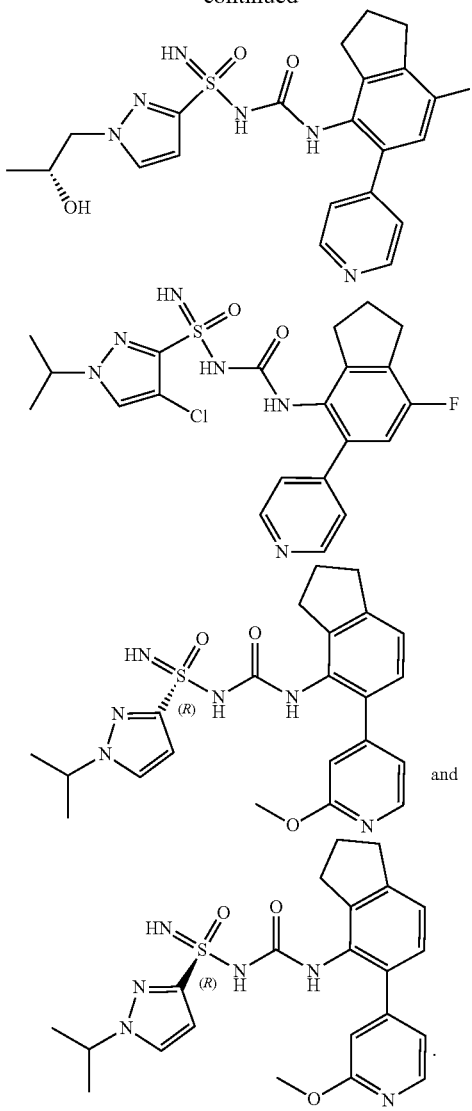

or a pharmaceutically acceptable salt or solvate thereof.

10. A pharmaceutical composition comprising the compound or the pharmaceutically acceptable salt or solvate thereof as claimed in claim 1, and a pharmaceutically acceptable excipient.

11. A method of treating, delaying onset of or reducing risk of a disease, disorder or condition in a subject, the method comprising a step of administering an effective amount of the compound or the pharmaceutically acceptable salt or solvate thereof as claimed in claim 1 to the subject, thereby treating, delaying onset of or reducing risk of the disease, disorder or condition, optionally wherein the disease, disorder or condition is responsive to NLRP3 inhibition.

12. The method as claimed in claim 11, wherein the disease, disorder or condition is selected from:
 (i) inflammation;
 (ii) an auto-immune disease;
 (iii) cancer;
 (iv) an infection;
 (v) a central nervous system disease;
 (vi) a metabolic disease;
 (vii) a cardiovascular disease;
 (viii) a respiratory disease;
 (ix) a liver disease;
 (x) a renal disease;
 (xi) an ocular disease;
 (xii) a skin disease;
 (xiii) a lymphatic condition;
 (xiv) a psychological disorder;
 (xv) graft versus host disease;
 (xvi) allodynia; and
 (xvii) any disease where an individual has been determined to carry a germline or somatic non-silent mutation in NLRP3.

13. The method as claimed in claim 11, wherein the disease, disorder or condition is selected from:
 (i) cryopyrin-associated periodic syndromes (CAPS);
 (ii) Muckle-Wells syndrome (MWS);
 (iii) familial cold autoinflammatory syndrome (FCAS);
 (iv) neonatal onset multisystem inflammatory disease (NOMID);
 (v) familial Mediterranean fever (FMF);
 (vi) pyogenic arthritis, pyoderma gangrenosum and acne syndrome (PAPA);
 (vii) hyperimmunoglobulinemia D and periodic fever syndrome (HIDS);
 (viii) Tumour Necrosis Factor (TNF) Receptor-Associated Periodic Syndrome (TRAPS);
 (ix) systemic juvenile idiopathic arthritis;
 (x) adult-onset Still's disease (AOSD);
 (xi) relapsing polychondritis;
 (xii) Schnitzler's syndrome;
 (xiii) Sweet's syndrome;
 (xiv) Behcet's disease;
 (xv) anti-synthetase syndrome;
 (xvi) deficiency of interleukin 1 receptor antagonist (DIRA); and
 (xvii) haploinsufficiency of A20 (HA20).

14. The method as claimed in claim 11, wherein the compound or the pharmaceutically acceptable salt or solvate thereof is administered as a pharmaceutical composition further comprising a pharmaceutically acceptable excipient.

15. A method of inhibiting NLRP3 in a subject, comprising administering the compound or the pharmaceutically acceptable salt or solvate thereof as claimed in claim 1 to the subject thereby inhibiting NLRP3.

16. A method of analysing inhibition of NLRP3 or an effect of inhibition of NLRP3 by a compound, comprising contacting a cell or non-human animal with the compound or the pharmaceutically acceptable salt or solvate thereof as claimed in claim 1, and analysing inhibition of NLRP3 or an effect of inhibition of NLRP3 in the cell or non-human animal by the compound.

* * * * *

UNITED STATES PATENT AND TRADEMARK OFFICE
CERTIFICATE OF CORRECTION

PATENT NO.        : 11,623,922 B2
APPLICATION NO.   : 16/753239
DATED             : April 11, 2023
INVENTOR(S)       : David Miller et al.

Page 1 of 1

It is certified that error appears in the above-identified patent and that said Letters Patent is hereby corrected as shown below:

In the Claims

In Column 171, Lines 33-43, Claim 9, delete "

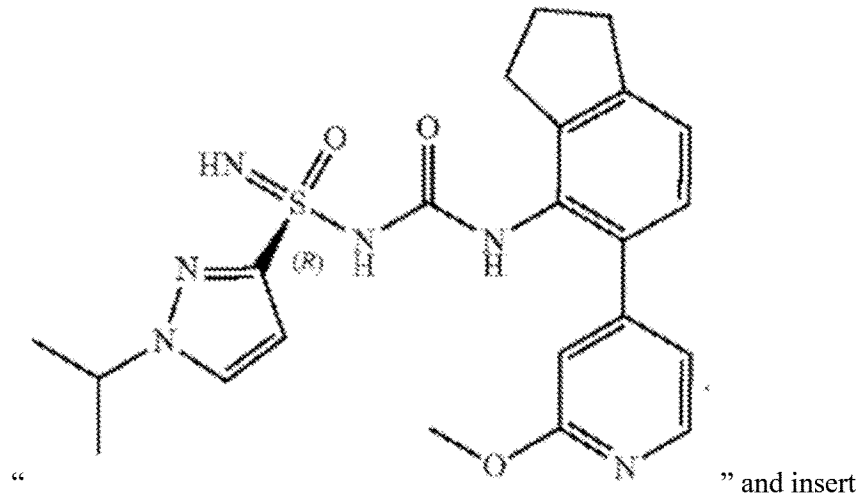

" and insert

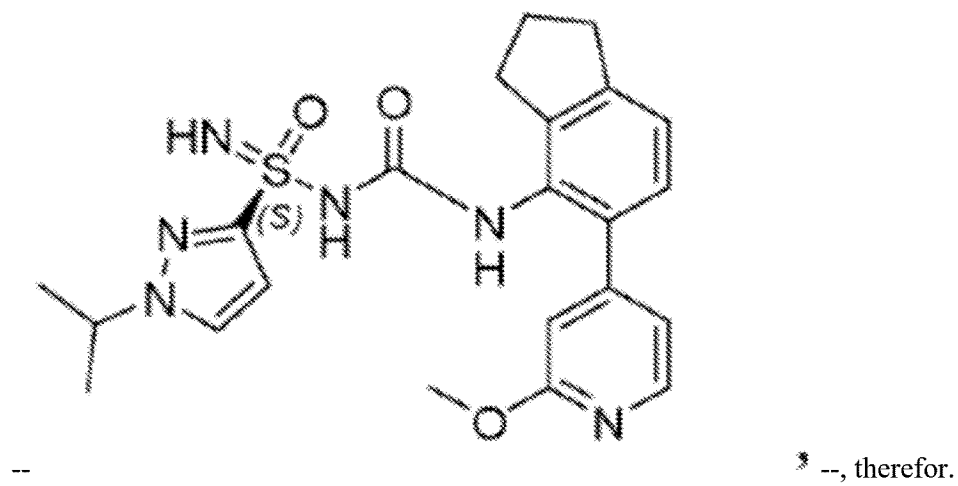

--, therefor.

Signed and Sealed this
Twelfth Day of November, 2024

Katherine Kelly Vidal
*Director of the United States Patent and Trademark Office*